US012599747B2

(12) United States Patent
Moisa et al.

(10) Patent No.: US 12,599,747 B2
(45) Date of Patent: Apr. 14, 2026

(54) MEDICAL DEVICE SYSTEMS AND METHODS INCLUDING SAFETY RELEASE, LUMEN FLUID-PROVIDING MECHANISMS, OR BOTH

(71) Applicant: KARDIUM INC., Burnaby (CA)

(72) Inventors: Saar Moisa, Vancouver (CA); Julie Elizabeth O'Keane, Vancouver (CA); Ian Garben, Burnaby (CA); Peter Josiah Hawes, Burnaby (CA)

(73) Assignee: KARDIUM INC., Burnaby (CA)

( * ) Notice: Subject to any disclaimer, the term of this patent is extended or adjusted under 35 U.S.C. 154(b) by 1248 days.

(21) Appl. No.: 17/474,149

(22) Filed: Sep. 14, 2021

(65) Prior Publication Data

US 2021/0402139 A1     Dec. 30, 2021

Related U.S. Application Data

(63) Continuation of application No. 15/332,318, filed on Oct. 24, 2016, now Pat. No. 11,147,947.

(Continued)

(51) Int. Cl.
*A61M 25/00*     (2006.01)
*A61B 5/00*     (2006.01)
(Continued)

(52) U.S. Cl.
CPC ....... *A61M 25/0043* (2013.01); *A61B 5/0036* (2018.08); *A61B 18/1492* (2013.01);
(Continued)

(58) Field of Classification Search
CPC .......... A61M 25/0147; A61M 25/0136; A61M 2025/0161; A61M 2025/0163;
(Continued)

(56) References Cited

U.S. PATENT DOCUMENTS 4,403,985 A     9/1983  Boretos
4,717,381 A     1/1988  Papantonakos
(Continued)

FOREIGN PATENT DOCUMENTS

WO     2015089649 A1     6/2015

OTHER PUBLICATIONS

Office Action issued in U.S. Appl. No. 15/332,318 mailed Feb. 26, 2020.

(Continued)

*Primary Examiner* — Joseph A Stoklosa
*Assistant Examiner* — Brian M Antiskay
(74) *Attorney, Agent, or Firm* — ROSSI, KIMMS & McDOWELL LLP

(57)     ABSTRACT

A medical device system may include a catheter sheath and a catheter shaft sized for delivery through a lumen of the catheter sheath. The catheter shaft may be coupled to an end effector at or adjacent a distal end of the catheter shaft. The catheter shaft may include a lumen and a control element. The control element may be coupled to the end effector and may reside within the lumen of the catheter shaft. Physical access may be provided to the control element, to allow the control element to be severed to facilitate removal of the end effector from a bodily cavity. The control element may include a lumen and a control cable therein. A liquid entry port may be provided in the lumen of the control element toward a distal end of the control element to allow expedited provision of fluid to a distal portion of the control element.

22 Claims, 37 Drawing Sheets

Related U.S. Application Data

(60) Provisional application No. 62/251,818, filed on Nov. 6, 2015.

(51) Int. Cl.

| | |
|---|---|
| *A61B 18/14* | (2006.01) |
| *A61M 25/01* | (2006.01) |
| *A61M 25/10* | (2013.01) |
| *A61M 31/00* | (2006.01) |
| *A61N 1/05* | (2006.01) |
| *A61N 1/362* | (2006.01) |
| *A61B 5/287* | (2021.01) |
| *A61B 17/00* | (2006.01) |
| *A61B 18/00* | (2006.01) |
| *A61B 18/02* | (2006.01) |

(52) U.S. Cl.
CPC .... *A61M 25/0026* (2013.01); *A61M 25/0113* (2013.01); *A61M 25/0147* (2013.01); *A61M 25/1018* (2013.01); *A61N 1/056* (2013.01); *A61N 1/362* (2013.01); *A61B 5/287* (2021.01); *A61B 5/6858* (2013.01); *A61B 2017/00367* (2013.01); *A61B 2018/0016* (2013.01); *A61B 2018/00196* (2013.01); *A61B 2018/00267* (2013.01); *A61B 2018/00351* (2013.01); *A61B 2018/00357* (2013.01); *A61B 2018/00577* (2013.01); *A61B 2018/00791* (2013.01); *A61B 2018/00839* (2013.01); *A61B 2018/00875* (2013.01); *A61B 18/02* (2013.01); *A61B 2218/002* (2013.01); *A61M 2210/125* (2013.01)

(58) Field of Classification Search
CPC ........ A61M 2210/125; A61M 25/0071; A61M 25/0133; A61M 2025/0024; A61B 18/1492; A61B 2018/00351; A61B 5/287; A61B 2017/003; A61B 2018/00839; A61B 5/283; A61B 5/6852; A61B 2018/1407; A61B 2018/1467; A61B 2018/00267; A61B 2218/002; A61B 5/6869; A61B 2090/0814
USPC ................ 600/372–374, 377, 381, 434–435, 600/508–509; 604/95.04, 105–106, 604/110–111
See application file for complete search history.

(56) References Cited

U.S. PATENT DOCUMENTS

| | | | | |
|---|---|---|---|---|
| 4,769,006 | A | 9/1988 | Papantonakos | |
| 4,802,487 | A | 2/1989 | Martin | |
| 5,221,267 | A * | 6/1993 | Folden .................. | A61M 1/285 604/905 |
| 5,389,104 | A * | 2/1995 | Hahnen .............. | A61B 17/1608 606/174 |
| 5,817,057 | A | 10/1998 | Berenstein | |
| 6,203,525 | B1 * | 3/2001 | Whayne ........... | A61M 25/0043 604/95.01 |
| 6,522,930 | B1 | 2/2003 | Schaer | |
| 7,662,143 | B2 | 2/2010 | Carrison | |
| 9,452,016 | B2 | 9/2016 | Moisa | |
| 2007/0043351 | A1 | 2/2007 | Fleischman | |
| 2008/0249519 | A1 | 10/2008 | Goldman | |
| 2009/0012515 | A1 * | 1/2009 | Hoenig ................ | A61B 18/203 604/20 |
| 2010/0022943 | A1 | 1/2010 | Mauch | |
| 2010/0185197 | A1 * | 7/2010 | Sakao ................ | A61B 18/1445 606/51 |
| 2010/0249505 | A1 | 9/2010 | Shoham | |
| 2011/0071506 | A1 | 3/2011 | Gardner | |
| 2011/0082494 | A1 * | 4/2011 | Kerr ..................... | A61B 17/285 606/205 |
| 2013/0197497 | A1 | 8/2013 | Wittenberger | |
| 2013/0304065 | A1 | 11/2013 | Lopes | |
| 2013/0304181 | A1 | 11/2013 | Green | |
| 2014/0046298 | A1 | 2/2014 | Fischell | |
| 2014/0114307 | A1 * | 4/2014 | Moisa ................ | A61B 18/1492 606/41 |
| 2014/0236131 | A1 * | 8/2014 | Taniguchi .............. | A61B 17/29 606/1 |
| 2015/0051599 | A1 * | 2/2015 | Joseph ............... | A61B 18/1442 606/41 |
| 2015/0088074 | A1 * | 3/2015 | Steinmetz ............ | A61M 25/01 604/173 |
| 2016/0038321 | A1 | 2/2016 | Shumer | |

OTHER PUBLICATIONS

Amendment filed in U.S. Appl. No. 15/332,318 on May 26, 2020.
Office Action issued in U.S. Appl. No. 15/332,318 mailed Oct. 30, 2020.
Response After Final Action filed in U.S. Appl. No. 15/332,318 on Dec. 23, 2020.
Notice of Allowance issued in U.S. Appl. No. 15/332,318 mailed Aug. 13, 2021.

* cited by examiner

100

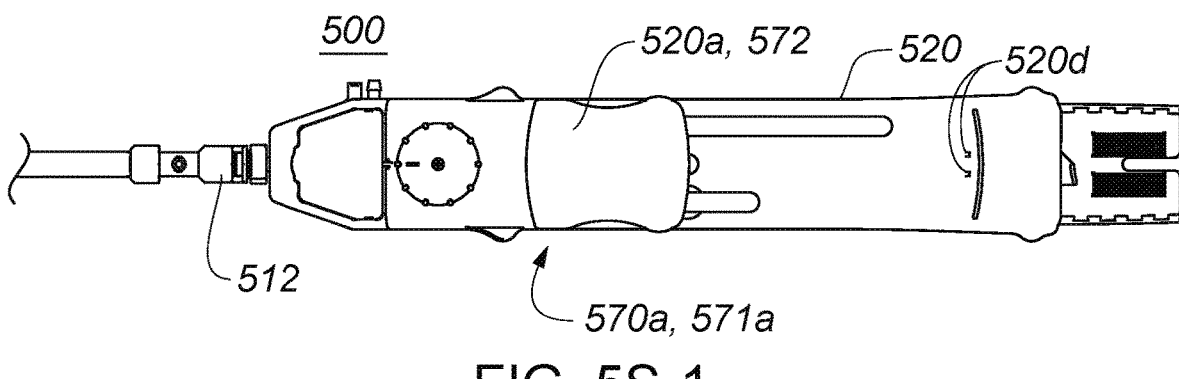
FIG. 5S-1
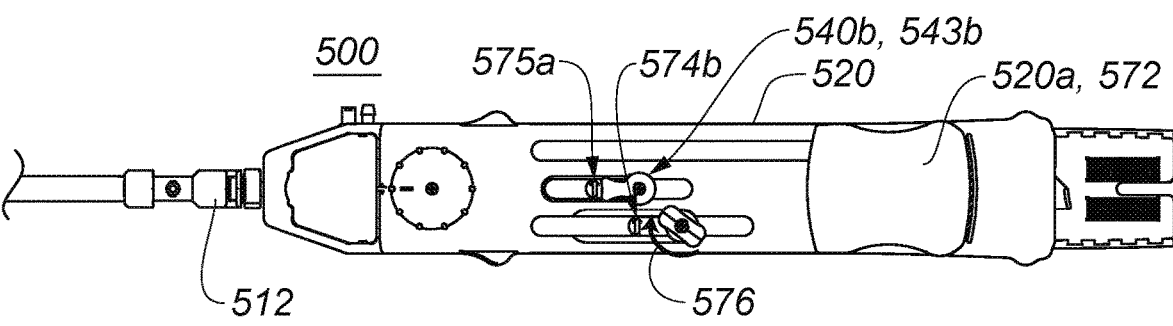
FIG. 5S-2
FIG. 5S-3

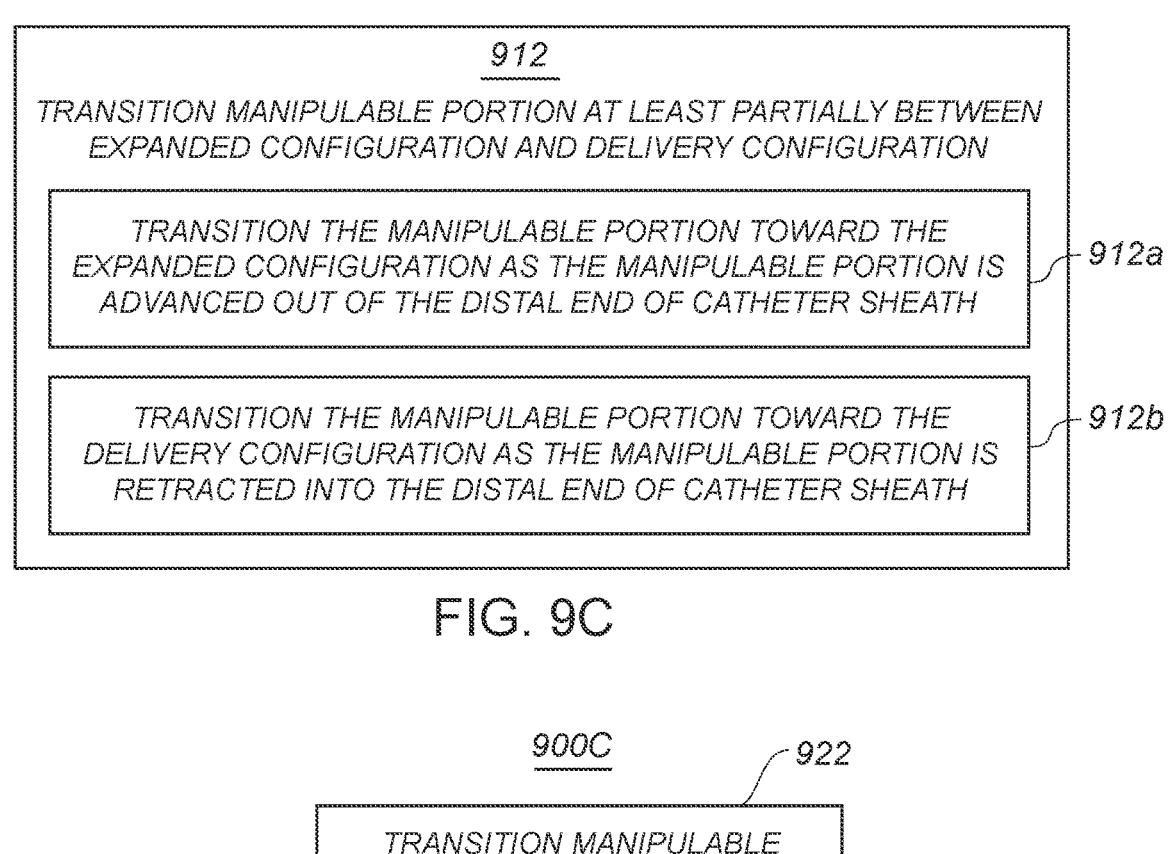

*912*

TRANSITION MANIPULABLE PORTION AT LEAST PARTIALLY BETWEEN
EXPANDED CONFIGURATION AND DELIVERY CONFIGURATION

TRANSITION THE MANIPULABLE PORTION TOWARD THE
EXPANDED CONFIGURATION AS THE MANIPULABLE PORTION IS
ADVANCED OUT OF THE DISTAL END OF CATHETER SHEATH
— 912a

TRANSITION THE MANIPULABLE PORTION TOWARD THE
DELIVERY CONFIGURATION AS THE MANIPULABLE PORTION IS
RETRACTED INTO THE DISTAL END OF CATHETER SHEATH
— 912b

TRANSITION MANIPULABLE
PORTION AT LEAST PARTIALLY
BETWEEN EXPANDED
CONFIGURATION AND
DELIVERY CONFIGURATION

924

CAUSE A CONTROL ELEMENT TO
HAVE A FIRST AMOUNT OF LENGTH
LOCATED OUTSIDE OF DISTAL END
OF CATHETER SHEATH WHEN A
PARTICULAR RELATIVE
POSITIONING EXISTS BETWEEN
THE CATHETER SHEATH AND A
SHAFT RECEIVED IN THE LUMEN
OF THE CATHETER SHEATH
DURING THE TRANSITION TOWARD
THE EXPANDED CONFIGURATION

926

CAUSE A CONTROL ELEMENT TO
HAVE A SECOND AMOUNT OF
LENGTH LOCATED OUTSIDE OF
DISTAL END OF CATHETER SHEATH
WHEN THE PARTICULAR RELATIVE
POSITIONING EXISTS BETWEEN
THE CATHETER SHEATH AND A
SHAFT RECEIVED IN THE LUMEN
OF THE CATHETER SHEATH
DURING THE TRANSITION TOWARD
THE DELIVERY CONFIGURATION

FIG. 9D

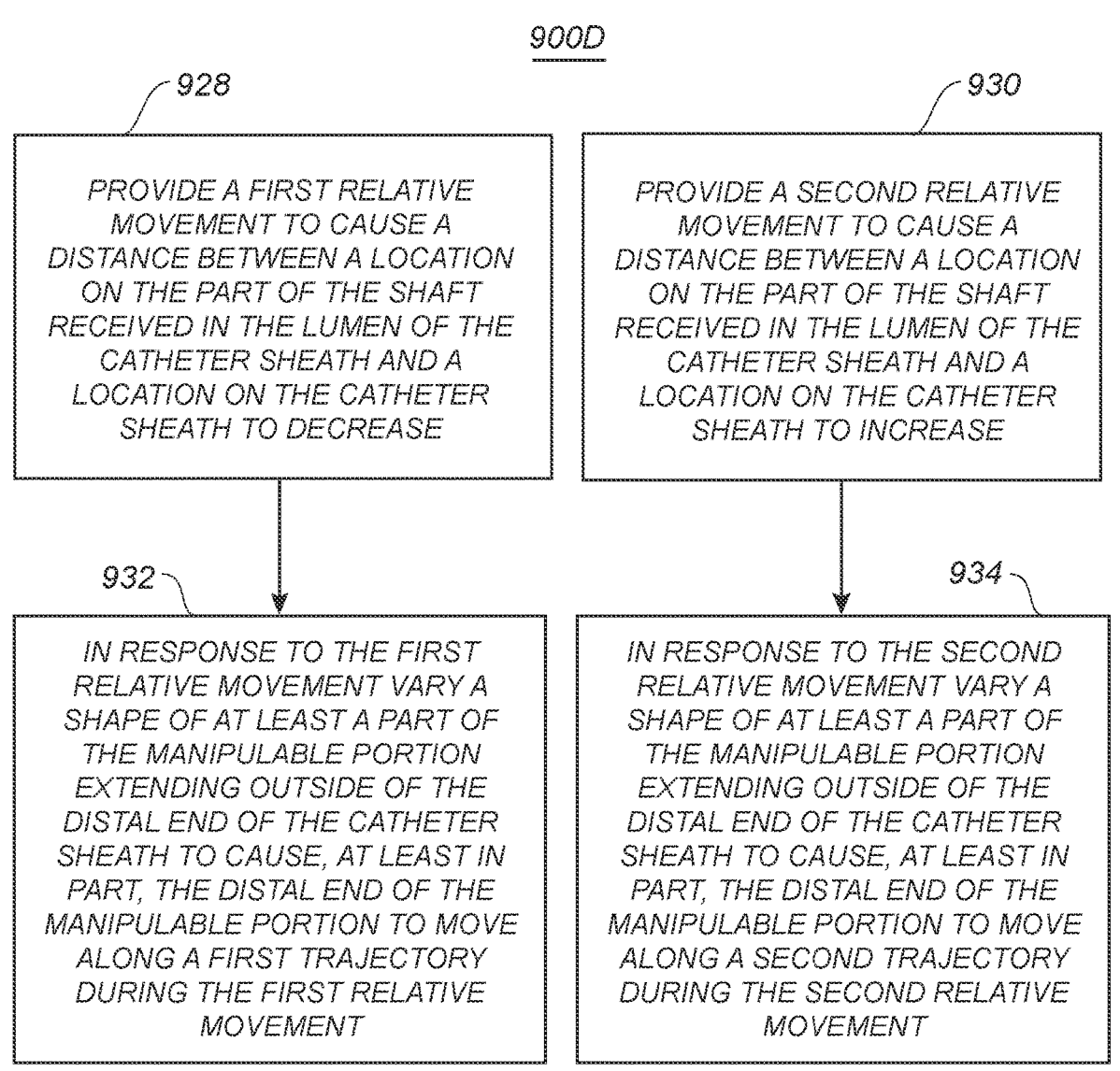

*900D*

*928*

PROVIDE A FIRST RELATIVE MOVEMENT TO CAUSE A DISTANCE BETWEEN A LOCATION ON THE PART OF THE SHAFT RECEIVED IN THE LUMEN OF THE CATHETER SHEATH AND A LOCATION ON THE CATHETER SHEATH TO DECREASE

*930*

PROVIDE A SECOND RELATIVE MOVEMENT TO CAUSE A DISTANCE BETWEEN A LOCATION ON THE PART OF THE SHAFT RECEIVED IN THE LUMEN OF THE CATHETER SHEATH AND A LOCATION ON THE CATHETER SHEATH TO INCREASE

*932*

IN RESPONSE TO THE FIRST RELATIVE MOVEMENT VARY A SHAPE OF AT LEAST A PART OF THE MANIPULABLE PORTION EXTENDING OUTSIDE OF THE DISTAL END OF THE CATHETER SHEATH TO CAUSE, AT LEAST IN PART, THE DISTAL END OF THE MANIPULABLE PORTION TO MOVE ALONG A FIRST TRAJECTORY DURING THE FIRST RELATIVE MOVEMENT

*934*

IN RESPONSE TO THE SECOND RELATIVE MOVEMENT VARY A SHAPE OF AT LEAST A PART OF THE MANIPULABLE PORTION EXTENDING OUTSIDE OF THE DISTAL END OF THE CATHETER SHEATH TO CAUSE, AT LEAST IN PART, THE DISTAL END OF THE MANIPULABLE PORTION TO MOVE ALONG A SECOND TRAJECTORY DURING THE SECOND RELATIVE MOVEMENT

FIG. 9E

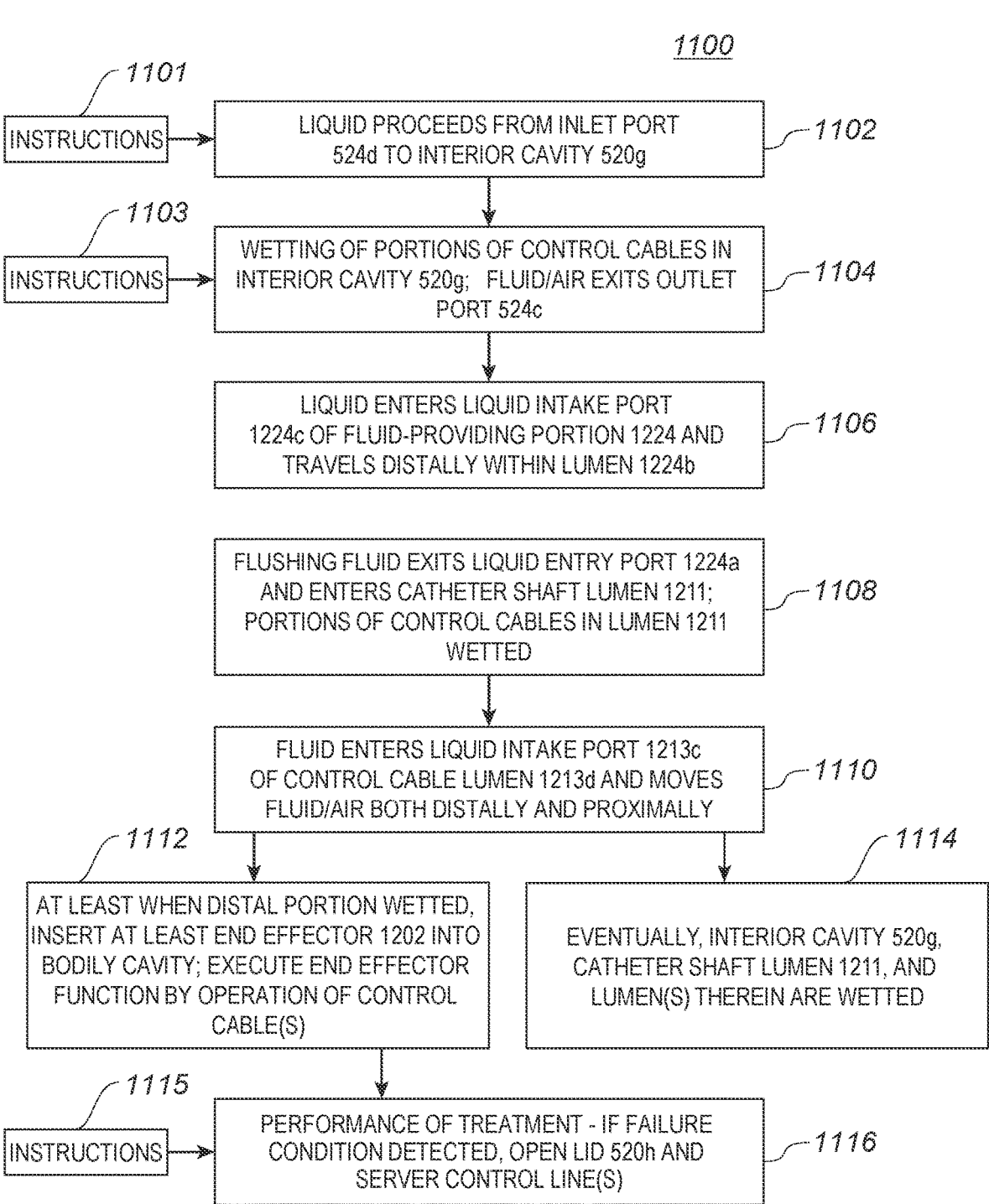

_1100_

1101
INSTRUCTIONS

1102
LIQUID PROCEEDS FROM INLET PORT 524d TO INTERIOR CAVITY 520g

1103
INSTRUCTIONS

1104
WETTING OF PORTIONS OF CONTROL CABLES IN INTERIOR CAVITY 520g;   FLUID/AIR EXITS OUTLET PORT 524c

1106
LIQUID ENTERS LIQUID INTAKE PORT 1224c OF FLUID-PROVIDING PORTION 1224 AND TRAVELS DISTALLY WITHIN LUMEN 1224b

1108
FLUSHING FLUID EXITS LIQUID ENTRY PORT 1224a AND ENTERS CATHETER SHAFT LUMEN 1211; PORTIONS OF CONTROL CABLES IN LUMEN 1211 WETTED

1110
FLUID ENTERS LIQUID INTAKE PORT 1213c OF CONTROL CABLE LUMEN 1213d AND MOVES FLUID/AIR BOTH DISTALLY AND PROXIMALLY

1112
AT LEAST WHEN DISTAL PORTION WETTED, INSERT AT LEAST END EFFECTOR 1202 INTO BODILY CAVITY; EXECUTE END EFFECTOR FUNCTION BY OPERATION OF CONTROL CABLE(S)

1114
EVENTUALLY, INTERIOR CAVITY 520g, CATHETER SHAFT LUMEN 1211, AND LUMEN(S) THEREIN ARE WETTED

1115
INSTRUCTIONS

1116
PERFORMANCE OF TREATMENT - IF FAILURE CONDITION DETECTED, OPEN LID 520h AND SERVER CONTROL LINE(S)

FIG. 11

MEDICAL DEVICE SYSTEMS AND METHODS INCLUDING SAFETY RELEASE, LUMEN FLUID-PROVIDING MECHANISMS, OR BOTH

CROSS-REFERENCE TO RELATED APPLICATIONS

This application is a continuation of U.S. patent application Ser. No. 15/332,318, filed Oct. 24, 2016, now U.S. Pat. No. 11,147,947 issued Oct. 19, 2021, which claims the benefit of U.S. Provisional Application No. 62/251,818, filed Nov. 6, 2015. The entire disclosure of each of the applications cited in this paragraph is hereby incorporated herein by reference.

TECHNICAL FIELD

Some aspects of this disclosure generally are related to medical device systems and methods of operating the medical device systems. The medical device systems may include a catheter sheath and an elongated catheter shaft sized for delivery through a lumen of the catheter sheath. A distal end of the catheter shaft may be coupled to an end effector, and the catheter shaft may include a lumen and a control element. The control element may be coupled to the end effector and may reside within the lumen of the catheter shaft.

BACKGROUND

Cardiac surgery was initially undertaken using highly invasive open procedures. A sternotomy, which is a type of incision in the center of the chest that separates the sternum, was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During various procedures, health care providers create specific patterns of lesions in the left or right atria to block various paths taken by the spurious electrical signals. Such lesions were originally created using incisions, but are now typically created by ablating the tissue with various techniques including radio-frequency (RF) energy, microwave energy, laser energy and cryogenic techniques. The procedure is performed with a high success rate under the direct vision that is provided in open procedures, but is relatively complex to perform intravascularly or percutaneously because of the difficulty in creating the lesions in the correct locations.

In this regard, various problems, potentially leading to severe adverse results, may occur if the lesions are placed incorrectly. It is particularly important to know the position of the various transducers which will be creating the lesions relative to cardiac features such as the pulmonary veins and mitral valve. The continuity, transmurality, and placement of the lesion patterns that are formed can impact the ability to block paths taken within the heart by spurious electrical signals. Other requirements for various ones of the transducers to perform additional functions such as, but not limited to, mapping various anatomical features, mapping electrophysiological activity, sensing tissue characteristics such as impedance and temperature, and tissue stimulation can also complicate the operation of the employed medical device.

Additional complications may arise with these intravascular or percutaneous procedures when fluid is required to be delivered through one or more lumens that may be provided by a percutaneously- or intravascularly-deliverable medical device system. In some cases, at least one of the one or more lumens may have small cross-sections or contain other elements therein that at least partially occlude the lumen. Either or both of these situations may introduce significant fluid drag or resistance which may hinder, restrict, or obstruct a required flow of fluid in the at least one of the one or more lumens. In some cases, it may be required that air or other fluids be flushed out of lumens of various percutaneously- or intravascularly-deliverable medical devices to avoid the risk of such matter causing a potentially harmful embolism in the patient. In this regard, the present inventors of the subject matter of this disclosure recognized that, since a percutaneously- or intravascularly-deliverable medical device typically has quite a long length, such providing of fluid and flushing of air and other fluids may require a relatively long time, especially when a lumen through which the air or other fluid is to be flushed has a small cross-section or contains other elements therein that at least partially occlude the lumen. Extending the time required for these procedures is clearly not desirable. Accordingly, there is a need in the art to safely expedite the process of facilitating the flow of fluid through one or more lumens in a percutaneously- or intravascularly-deliverable medical device.

Some percutaneously- or intravascularly deliverable medical devices typically have an end effector, or manipulable portion, that includes the transducers that are employable in various diagnostic procedures, treatment procedures, or both diagnostic and treatment procedures. Often the end effector or manipulable portion is manipulated within a bodily cavity to position at least some of the transducers in a desired positioning with respect to a particular anatomical structure within the bodily cavity. Such an end effector or manipulable portion typically is controlled by one or more control elements that lead to a control mechanism outside of the patient's body. In this regard, the present inventors of the subject matter of this disclosure recognized that a risk exists to the patient that, if the one or more control elements or the control mechanism fail to operate as intended, it may be difficult to remove the end effector from the patient in some circumstances. Accordingly, there is a need in the art for improved techniques for safe removal of the end effector or manipulable portion from the patient.

SUMMARY

At least the above-discussed needs are addressed and technical solutions are achieved by various embodiments of the present invention. In some embodiments, a medical device system includes an end effector, an enclosure, a catheter shaft extending between the end effector and the enclosure, and a control element operatively coupled to the end effector to selectively enable a particular end effector function of the end effector, the control element spanning at least a portion of an interior of the catheter shaft between the end effector and a portion of the enclosure. A method of operating the medical device system may include, according to some embodiments, inhibiting the particular end effector function at least by severing the control element within a region of the control element located within the enclosure.

According to some embodiments, the severing may include severing the control element within the region of the control element while the region of the control element is submerged in a liquid in an interior cavity of the enclosure. The severing may include severing the control element within the region of the control element while a portion of the control element in an interior cavity of the enclosure is wetted by a liquid.

According to some embodiments, the control element includes a flexible control cable, the control cable spanning at least the portion of the interior of the catheter shaft between the end effector and the portion of the enclosure. In some embodiments, the severing releases tension in the control cable. In some embodiments, the severing includes severing a portion of the control cable while the portion of the control cable is submerged in a liquid in an interior cavity of the enclosure.

In some embodiments, the control element includes a control cable and an elongate member, the elongate member including a first end, a second end, and an elongated portion extending between the first end and the second end. The elongate member may provide at least a control cable lumen extending between the first end and the second end, the control cable lumen including the control cable therein. Each of the control cable lumen and the control cable may span at least the portion of the interior of the catheter shaft between the end effector and the portion of the enclosure. In some embodiments, the severing releases tension in the control cable. In some embodiments, the severing includes severing a portion of the control cable while the portion of the control cable is submerged in a liquid in an interior cavity of the enclosure. In some embodiments, the severing includes severing a portion of the elongate member while the portion of the elongate member is submerged in the liquid in the interior cavity of the enclosure. In some embodiments, a portion of the control cable and a portion of the elongate member are located in an interior cavity of the enclosure, and at least the portion of the elongate member is submerged in a liquid in the interior cavity of the enclosure. In some embodiments, the elongate member and the control cable each extends outwardly from the interior cavity of the enclosure through each of at least two spaced-apart openings provided in at least one wall of the enclosure. The elongate member may be sealed to at least a particular wall of the at least one wall of the enclosure at each of at least one of the at least two spaced-apart openings to restrict an egress of the liquid from the enclosure at the at least one of the at least two spaced-apart openings according to some embodiments. In some embodiments, each particular part of the elongate member that is submerged in the liquid in the interior cavity of the enclosure lacks an inlet in the interior cavity of the enclosure, the inlet suitable to allow an ingress of the liquid from the interior cavity of the enclosure into the control cable lumen. In some embodiments, the method includes wetting the portion of the control cable with the liquid prior to the severing.

According to some embodiments, the severing includes severing the control element within the region of the control element while the region of the control element is submerged in a liquid in an interior cavity of the enclosure. In some embodiments, the enclosure includes an inlet port, and the method includes directing a first portion of the liquid from the inlet port into the interior cavity of the enclosure during the severing. In some embodiments, the enclosure includes an inlet port and an outlet port, and the method includes directing a first portion of the liquid from the inlet port into the interior cavity of the enclosure while expelling a fluid other than the liquid from the outlet port.

In some embodiments, the control element includes a control cable and an elongate member, the elongate member including a first end, a second end, and an elongated portion extending between the first end and the second end, the elongate member providing at least a control cable lumen extending between the first end and the second end, the control cable lumen including the control cable therein. Each of the control cable lumen and the control cable may span at least the portion of the interior of the catheter shaft between the end effector and the portion of the enclosure. In some embodiments, the first end of the elongate member is arranged to be delivered ahead of the second end of the elongate member during percutaneous delivery of at least a portion of the catheter shaft, and the method includes providing a flow of liquid through a portion of the control cable lumen while a portion of the control cable is located in the portion of the control cable lumen, the flow of liquid flowing through the portion of the control cable lumen toward the first end. In some embodiments, the first end of the elongate member is arranged to be delivered ahead of the second end of the elongate member during percutaneous delivery of at least a portion of the catheter shaft, and the method includes providing a flow of liquid through a portion of the control cable lumen while a portion of the control cable is located in the portion of the control cable lumen, an inlet of the flow of liquid into the portion of the control cable lumen located along the elongate member at a location spaced from each of the first end and the second end of the elongate member.

In some embodiments, the method includes opening an enclosure lid that provides access to an interior cavity of the enclosure via an access port made accessible by the opening of the enclosure lid. According to some embodiments, the severing may include severing the control element within the region of the control element located within the enclosure with at least a first tool, the severing occurring at least by passing at least a portion of the at least a first tool through the access port made accessible by the opening of the enclosure lid.

In some embodiments, the method includes opening an enclosure lid that provides access to an interior cavity of the enclosure via an access port made accessible by the opening of the enclosure lid, According to some embodiments, the severing includes severing the control element within the region of the control element with at least a first tool while the region of the control element is submerged in a liquid in the interior cavity of the enclosure.

In some embodiments, the method includes detecting a failure condition, the severing occurring in response to the detected failure condition.

Various methods may include combinations and subsets of those disclosed above or otherwise herein.

In some embodiments, a medical device system includes an end effector, an enclosure, a catheter shaft extending between the end effector and the enclosure, and a control element operatively coupled to the end effector to selectively enable a particular end effector function of the end effector. The control element may span at least a portion of an interior of the catheter shaft between the end effector and a portion of the enclosure. A method of operating the medical device system according to some embodiments may include providing the medical device system in a state in which the particular end effector function is enabled at least by way of an operative coupling between the control element and the end effector; and providing an indicator including instructions to sever a region of the control element located within the enclosure.

In some embodiments, the method may include submerging a portion of the control element in a liquid within an interior cavity of the enclosure. In some embodiments, the method may include providing a second indicator that includes instructions to submerge a portion of the control element in a liquid within an interior cavity of the enclosure. In some embodiments, the method may include providing a second indicator that includes instructions to wet a portion of the control element in a liquid within an interior cavity of the enclosure.

In some embodiments, the control element includes a flexible control cable, the control cable spanning at least the portion of the interior of the catheter shaft between the end effector and the portion of the enclosure. In some embodiments, the particular end effector function may be executed at least in part by increasing tension in the control cable. In some embodiments, the particular end effector function may be executed at least in part by decreasing tension in the control cable.

In some embodiments, the control element includes a control cable and an elongate member, the elongate member including a first end, a second end, and an elongated portion extending between the first end and the second end, the elongate member providing at least a control cable lumen extending between the first end and the second end, the control cable lumen including the control cable therein. Each of the control cable lumen and the control cable may span at least the portion of the interior of the catheter shaft between the end effector and the portion of the enclosure. According to some embodiments, the method may include executing, at least in part, the particular end effector function via a relative repositioning between a portion of the control cable and a portion of the elongate member of the control element. The method may include submerging at least a portion of the control cable and a portion of the elongate member in a liquid in an interior cavity of the enclosure. In some embodiments, the elongate member and the control cable may each extends outwardly from the interior cavity of the enclosure from each of at least two spaced-apart openings provided in at least one wall of the enclosure. In some embodiments, the elongate member may be sealed to at least a particular wall of the at least one wall of the enclosure at each of at least one of the at least two spaced-apart openings to restrict an egress of the liquid from the enclosure at the at least one of the at least two spaced-apart openings. In some embodiments, each particular part of the elongate member that is submerged in the liquid in the interior cavity of the enclosure lacks an inlet in the interior cavity of the enclosure, the inlet suitable to allow an ingress of the liquid from the interior cavity of the enclosure into the control cable lumen. In some embodiments, the method includes wetting the portion of the control cable submerged in the liquid in the interior cavity of the enclosure by the liquid at least before or during an operation of the control element to execute the particular end effector function.

In some embodiments, the method includes submerging a portion of the control element in a liquid within an interior cavity of the enclosure. In some embodiments, the enclosure includes an inlet port, and the method may include directing a first portion of the liquid from the inlet port into the interior cavity of the enclosure at least before or during an initiating operation of the control element to execute the particular end effector function. In some embodiments, the enclosure includes an inlet port and an outlet port, and the method may include directing a first portion of the liquid from the inlet port into the interior cavity of the enclosure while expelling a fluid other than the liquid from the outlet port.

According to some embodiments, the control element may include a control cable and an elongate member, the elongate member including a first end, a second end, and an elongated portion extending between the first end and the second end, the elongate member providing at least a control cable lumen extending between the first end and the second end, the control cable lumen including the control cable therein. Each of the control cable lumen and the control cable may span at least the portion of the interior of the catheter shaft between the end effector and the portion of the enclosure. In at least some embodiments, the first end of the elongate member is arranged to be delivered ahead of the second end of the elongate member during percutaneous delivery of at least a portion of the catheter shaft, and the method may include providing a flow of liquid through a portion of the control cable lumen while a portion of the control cable is located in the portion of the control cable lumen, the flow of liquid flowing through the portion of the control cable lumen toward the first end. In some embodiments, the first end of the elongate member is arranged to be delivered ahead of the second end of the elongate member during percutaneous delivery of at least a portion of the catheter shaft, and the method may include providing a flow of liquid through a portion of the control cable lumen while a portion of the control cable is located in the portion of the control cable lumen, an inlet of the flow of liquid into the portion of the control cable lumen located along elongate member at a location spaced from each of the first end and the second end of the elongate member.

In some embodiments, the method includes submerging a portion of the control element in a liquid within an interior cavity of the enclosure. The method may include opening an enclosure lid providing access to the submerged portion of the control element in the interior cavity of the enclosure via an access port made accessible by the opening of the enclosure lid.

In some embodiments, the indicator may include instructions to open, prior to the severing, an enclosure lid providing access to the region of the control element in the enclosure via an access port made accessible by the opening of the enclosure lid. In some embodiments, the instructions to sever the region of the control element located within the enclosure may include instructions to sever the region of the control element at least by passing at least a portion of at least one tool through the access port made accessible by the opening of the enclosure lid.

In some embodiments, the indicator may include instructions to detect a condition indicating a failure associated with the particular end effector function, and the instructions to sever the region of the control element located within the enclosure may include instructions to sever the region of the control element in response to the detected condition. In some embodiments, the indicator may include instructions to detect a condition indicating a failure associated with the end effector, and the instructions to sever the region of the control element located within the enclosure may include instructions to sever the region of the control element in response to the detected condition.

In some embodiments, the medical device system may include an actuator operatively coupled to the control element to selectively transmit force via the control element to the end effector. The indicator may include instructions to detect a condition indicating a failure associated with the actuator, and the instructions to sever the region of the control element located within the enclosure may include instructions to sever the region of the control element in response to the detected condition according to some embodiments. In some embodiments, the actuator is located in the enclosure.

In some embodiments, the medical device system may include at least one visual representation of the indicator that includes instructions to sever the region of the control element located within the enclosure. In some embodiments, the medical device system includes a memory device system accessible by a data processing device system and storing a processor-accessible file including the indicator instructing severing of the region of the control element located within the enclosure, the processor-accessible file in a format compatible with visual or audible presentation by the data processing device system via an input-output device system communicatively connected to the data processing device system.

Various methods may include combinations and subsets of those disclosed above or otherwise herein.

In some embodiments, a medical device system may be summarized as including an end effector; an enclosure; a catheter shaft extending between the end effector and the enclosure; a control element operatively coupled to the end effector to selectively enable a particular end effector function of the end effector, the control element spanning at least a portion of an interior of the catheter shaft between the end effector and a portion of the enclosure; and an indicator comprising instructions to sever a region of the control element located within the enclosure.

In some embodiments, the medical device system may include a memory device system accessible by a data processing device system and storing a processor-accessible file including the indicator instructing severing of the region of the control element located within the enclosure, the processor-accessible file in a format compatible with visual or audible presentation by the data processing device system via an input-output device system communicatively connected to the data processing device system.

In some embodiments, a medical device system may be summarized as including an end effector; an enclosure; a catheter shaft extending between the end effector and the enclosure; a control element operatively coupled to the end effector to selectively enable a particular end effector function of the end effector, the control element spanning a least a portion of an interior of the catheter shaft between the end effector and a portion of the enclosure; and an enclosure lid, the enclosure lid providing access to an interior cavity of the enclosure via an access port, the access port made accessible by an opening of the enclosure lid, the access port providing physical access to at least a portion of the control element in the interior cavity. An opaque part of the enclosure may be positioned to restrict visual access to at least the portion of the control element in the interior cavity at least when the enclosure lid is closed. The enclosure may include a window including a transparent or translucent material, the window positioned to provide visual access to at least the portion of the control element in the interior cavity at least when the enclosure lid is closed.

In some embodiments, the enclosure lid may include the window. In some embodiments, the medical device system may include a seal arranged between the enclosure and the enclosure lid, the seal configured to restrict liquid flow between the enclosure and the enclosure lid. The seal may include an elastomeric material.

In some embodiments, the medical device system may include one or more ports operatively coupled with the interior cavity to allow for liquid flow therebetween, each of the one or more ports arranged to at least (a) allow an egress of liquid out from the interior cavity, or (b) allow an ingress of liquid into the interior cavity. In some embodiments, the window may be positioned to provide visual access to determine a liquid level in the interior cavity. In some embodiments, a first port of the one or more ports may be located on the enclosure lid. In some embodiments, a second port of the one or more ports may be located on the enclosure.

In some embodiments, the control element may include a flexible control cable. In some embodiments, the control element includes a control cable and an elongate member, the elongate member including a first end, a second end, and an elongated portion extending between the first end and the second end, the elongate member providing at least a control cable lumen extending between the first end and the second end, the control cable lumen including the control cable therein. Each of the control cable lumen and the control cable may span at least the portion of the interior of the catheter shaft between the end effector and the portion of the enclosure according to some embodiments. In some embodiments, the control element is operatively coupled to the end effector to selectively execute, at least in part, a particular end effector function of the end effector in response to a relative repositioning between a portion of the control cable and a portion of the elongate member of the control cable. The portion of the control element may include a portion of the control cable and a portion of the elongate member that are each located in the interior cavity of the enclosure. In some embodiments, the elongate member and the control cable each extends outwardly from the interior cavity of the enclosure from each of at least two spaced-apart openings provided in at least one wall of the enclosure. In some embodiments, the elongate member may be fixedly coupled to at least a particular wall of the at least one wall of the enclosure at each of at least one of the at least two spaced-apart openings. In some embodiments, the elongate member may be sealed to at least a particular wall of the at least one wall of the enclosure at each of at least one of the at least two spaced-apart openings.

Various systems may include combinations and subsets of those disclosed above or otherwise herein.

In some embodiments, a medical device system may be summarized as including an end effector; an enclosure; a catheter shaft extending between the end effector and the enclosure; and an enclosure lid, the enclosure lid providing access to an interior cavity of the enclosure via an access port, the access port made accessible by an opening of the enclosure lid. The medical device system may include one or more ports operatively coupled with the interior cavity to allow for liquid flow therebetween, each of the one or more ports arranged to at least (a) allow an egress of liquid out from the interior cavity, or (b) allow an ingress of liquid into the interior cavity. At least a first port of the one or more ports may be located on the enclosure lid.

In some embodiments, a second port of the one or more ports may be located on the enclosure. In some embodiments, the medical device system includes a seal arranged between the enclosure and the enclosure lid, the seal configured to restrict liquid flow between the enclosure and the enclosure lid. In some embodiments, the seal includes an elastomeric material.

In some embodiments, the medical device system includes a control element operatively coupled to the end effector to selectively execute, at least in part, a particular end effector function of the end effector. The control element may include a flexible control cable. In some embodiments, the control element may include a control cable and an elongate member, the elongate member including a first end, a second end, and an elongated portion extending between the first end and the second end, the elongate member providing at least a control cable lumen extending between the first end and the second end, the control cable lumen including the control cable therein. Each of the control cable lumen and the control cable may span at least a portion of an interior of the catheter shaft between the end effector and a portion of the enclosure. In some embodiments, the control element may be operatively coupled to the end effector to selectively execute, at least in part, a particular end effector function of the end effector in response to a relative repositioning between a portion of the control cable and a portion of the control cable lumen. In some embodiments, the elongate member and the control cable each extends outwardly from the interior cavity of the enclosure from each of at least two spaced-apart locations on or in the enclosure. In some embodiments, the elongate member may be fixedly coupled to at least one wall of the enclosure at each of at least one of the at least two spaced-apart locations on or in the enclosure. In some embodiments, the elongate member may be sealed to at least one wall of the enclosure at each of at least one of the at least two spaced-apart locations.

Various systems may include combinations and subsets of those disclosed above or otherwise herein.

In some embodiments, a medical device system includes a catheter shaft, a control cable lumen within the catheter shaft, and a control cable within the control cable lumen, the control cable lumen provided by a first sleeve including a proximal end and a distal end, the distal end arranged to be percutaneously insertable into a body while the proximal end remains outside of the body. According to some embodiments, a method of operating the medical device system may be summarized as including adding liquid into the catheter shaft via a liquid supply port; and continuing to add the liquid into the catheter shaft via the liquid supply port at least until a sufficient amount of the liquid has been added into the catheter shaft to enter a liquid intake port of the first sleeve leading to the control cable lumen and flush a distal portion of the control cable lumen of a fluid other than the liquid, the distal portion of the control cable lumen extending from the distal end of the first sleeve, and the liquid intake port of the control cable lumen located within the catheter shaft and closer to the distal end of the first sleeve than the proximal end of the first sleeve.

In some embodiments, the method may include continuing to add the liquid into the catheter shaft via the liquid supply port at least until a sufficient amount of the liquid has been added into the catheter shaft to enter the liquid intake port and flush a proximal portion of the control cable lumen of the fluid other than the liquid, the proximal portion of the control cable lumen located closer to the proximal end of the first sleeve than to the distal portion of the control cable lumen.

In some embodiments, the method may include continuing to add the liquid into the catheter shaft via the liquid supply port at least until a sufficient amount of the liquid has been added into the catheter shaft to enter the liquid intake port and flush a proximal portion of the control cable lumen of the fluid other than the liquid, the proximal portion of the control cable lumen extending from and including the proximal end of the first sleeve.

In some embodiments, the liquid intake port may be spaced along the first sleeve from each of the proximal end of the first sleeve and the distal end of the first sleeve. In some embodiments, the liquid supply port may be located closer to the proximal end of the first sleeve than the distal end of the first sleeve. In some embodiments, the catheter shaft includes a first end portion and a second end portion, the first end portion arranged to be percutaneously insertable into the body while the second end portion remains outside of the body, and the liquid supply port is located closer to the second end portion than the first end portion.

In some embodiments, the control cable lumen is a first lumen of at least two lumens within the catheter shaft, and the liquid supply port leads to a second lumen of the at least two lumens other than the first lumen. In some embodiments, the second lumen is provided by a second sleeve including a proximal end and a distal end, the distal end of the second sleeve arranged to be percutaneously insertable into the body while the proximal end of the second sleeve remains outside of the body. The liquid supply port may be located on the second sleeve closer to the proximal end of the second sleeve than to the distal end of the second sleeve according to some embodiments. In some embodiments, each of the first lumen and the second lumen may be provided by a respective tubular member. In some embodiments, the first lumen may be provided by a tubular member located in the second lumen. In some embodiments, the catheter shaft includes a first end portion and a second end portion, the first end portion arranged to be percutaneously insertable into the body while the second end portion remains outside of the body. Each lumen of the at least two lumens includes a respective longitudinal axis extending between the first end portion of the catheter shaft and the second end portion of the catheter shaft. Each lumen of the at least two lumens includes a respective cross-sectional area circumferentially bounded by at least one surface as viewed along the respective longitudinal axis. The respective cross-sectional areas of the first lumen and the second lumen may be different according to some embodiments. In some embodiments, the first lumen includes a first longitudinal axis extending between the proximal end of the first sleeve and the distal end of the first sleeve, and the second lumen includes a second longitudinal axis extending between the proximal end of the second sleeve and the distal end of the second sleeve. In some embodiments, the first lumen includes a first cross-sectional area circumferentially bounded by at least one surface as viewed along the first longitudinal axis, and the second lumen includes a second cross-sectional area circumferentially bounded by at least one surface as viewed along the second longitudinal axis. The second cross-sectional area may be larger than the first cross-sectional area according to some embodiments.

In some embodiments, the control cable lumen is a first lumen of at least two lumens, each lumen of the at least two lumens provided by a respective sleeve. Each respective sleeve includes a respective proximal end and a respective distal end. Each respective distal end may be arranged to be percutaneously insertable into the body while the respective proximal end remains outside of the body. In some embodiments, the adding liquid into the catheter shaft via the liquid supply port provides a flow of the liquid through a second lumen of the at least two lumens toward the respective distal end of the respective sleeve providing the second lumen, the second lumen being other than the first lumen.

In some embodiments, the method may include continuing to add the liquid into the catheter shaft via the liquid supply port at least until a sufficient amount of the liquid has been added into the catheter shaft to enter the liquid intake port and flush a proximal portion of the control cable lumen of the fluid other than the liquid, the proximal portion of the control cable lumen located closer to the proximal end of the first sleeve than to the distal portion of the control cable lumen. In some embodiments, the control cable lumen may be provided by a first lumen of at least two lumens. Each lumen of the at least two lumens may be provided by a respective sleeve, each respective sleeve including a respective proximal end and a respective distal end. Each respective distal end may be arranged to be percutaneously insertable into the body while the respective proximal end remains outside of the body. The adding liquid into the catheter shaft via the liquid supply port may, according to some embodiments, provide a flow of the liquid through a second lumen of the at least two lumens toward the respective distal end of the respective sleeve providing the second lumen, the second lumen other than the first lumen.

In some embodiments, the catheter shaft includes a first end portion and a second end portion, and the first end portion may be arranged to be percutaneously insertable into the body while the second end portion remains outside of the body. In some embodiments, the medical device system includes an end effector located at least proximate the first end portion of the catheter shaft, the control cable operatively coupled to the end effector, and the method may include providing relative movement between a portion of the control cable and a portion of the first sleeve to execute, at least in part, a particular end effector function of the end effector.

In some embodiments, the medical device system includes an end effector and at least one actuator provided in an enclosure, the catheter shaft extending between the end effector and the at least one actuator, and the control cable operatively coupled between the at least one actuator and the end effector to selectively enable a particular end effector function of the end effector, the control cable and the control cable lumen each extending outwardly from an interior cavity provided in the enclosure. According to some embodiments, the adding liquid into the catheter shaft via the liquid supply port may include introducing the liquid into the liquid supply port from the interior cavity.

Various methods may include combinations and subsets of those disclosed above or otherwise herein.

In some embodiments, a medical device system may be summarized as including a catheter shaft; a control element sleeve, at least a portion thereof located within the catheter shaft and providing at least a control cable lumen, the control element sleeve comprising a proximal end and a distal end, the distal end arranged to be percutaneously insertable into a body while the proximal end remains outside of the body; a control cable within the control cable lumen; and a liquid supply port arranged to provide liquid into the catheter shaft. The control element sleeve may include a liquid intake port arranged to receive liquid provided by the liquid supply port and flush at least a distal portion of the control cable lumen of a fluid other than the liquid, the distal portion of the control cable lumen extending from the distal end of the control element sleeve, and the liquid intake port located within the catheter shaft closer to the distal end of the control element sleeve than to the proximal end of the control element sleeve.

In some embodiments, the liquid intake port may be arranged to receive the liquid provided by the liquid supply port and flush a proximal portion of the control cable lumen of the fluid other than the liquid, the proximal portion of the control cable lumen located closer to the proximal end of the control element sleeve than to the distal portion of the control cable lumen. In some embodiments, the liquid intake port may be arranged to receive the liquid provided by the liquid supply port and flush a proximal portion of the control cable lumen of the fluid other than the liquid, the proximal portion of the control cable lumen extending from and including the proximal end of the control element sleeve. In some embodiments the liquid intake port may be spaced along the control element sleeve from each of the proximal end of the control element sleeve and the distal end of the control element sleeve. In some embodiments, the liquid supply port may be located closer to the proximal end of the control element sleeve than the distal end of the control element sleeve. In some embodiments, the catheter shaft includes a first end portion and a second end portion. The first end portion may be arranged to be percutaneously insertable into the body while the second end portion remains outside of the body, and the liquid supply port may be located closer to the second end portion than the first end portion.

In some embodiments, the control cable lumen may be a first lumen of at least two lumens within the catheter shaft, and the liquid supply port leads to a second lumen of the at least two lumens other than the first lumen. In some embodiments, each lumen of the at least two lumens may be provided by a respective sleeve, each respective sleeve including a respective proximal end and a respective distal end, each respective distal end arranged to be percutaneously insertable into the body while the respective proximal end remains outside of the body. The liquid supply port may be located on the respective sleeve providing the second lumen closer to the respective proximal end of the respective sleeve providing the second lumen than the respective distal end of the respective sleeve providing the second lumen according to some embodiments. In some embodiments, each of the first lumen and the second lumen may be provided by a respective tubular member. In some embodiments, the first lumen may be provided by a tubular member located in the second lumen. In some embodiments, the catheter shaft includes a first end portion and a second end portion. The first end portion may be arranged to be percutaneously insertable into the body while the second end portion remains outside of the body. Each lumen of the at least two lumens includes a respective longitudinal axis extending between the first end portion of the catheter shaft and the second end portion of the catheter shaft, and each lumen of the at least two lumens including a respective cross-sectional area circumferentially bounded at least one surface as viewed along the respective longitudinal axis. The cross-sectional areas of the first lumen and the second lumen may be different according to various embodiments.

In some embodiments, each lumen of the at least two lumens is provided by a respective sleeve, each respective sleeve including a respective proximal end and a respective distal end, each respective distal end arranged to be percutaneously insertable into the body while the respective proximal end remains outside of the body, and the liquid supply port is located on the respective sleeve providing the second lumen closer to the respective proximal end of the respective sleeve providing the second lumen than the respective distal end of the respective sleeve providing the second lumen. In some embodiments, the first lumen may include a first longitudinal axis extending between the proximal end and the distal end of the control element sleeve, and the second lumen includes a second longitudinal axis extending between the respective proximal end and the respective distal end of the respective sleeve providing the second lumen. In various embodiments, the first lumen includes a first cross-sectional area circumferentially bounded by at least one surface as viewed along the first longitudinal axis, and the second lumen includes a second cross-sectional area circumferentially bounded by at least one surface as viewed along the second longitudinal axis. The second cross-sectional area is larger than the first cross-sectional area according to some embodiments.

In some embodiments, the control cable lumen is a first lumen of at least two lumens, each lumen of the at least two lumens provided by a respective sleeve, each respective sleeve including a respective proximal end and a respective distal end. Each respective distal end may be arranged to be percutaneously insertable into the body while the respective proximal end remains outside of the body. The liquid supply port may be arranged to provide a flow of the liquid through a second lumen of the at least two lumens toward the respective distal end of the respective sleeve that provides the second lumen, the second lumen other than the first lumen according to some embodiments.

In some embodiments, wherein the liquid intake port is arranged to receive the liquid provided by the liquid supply port and flush a proximal portion of the control cable lumen of the fluid other than the liquid, the proximal portion of the control cable lumen located closer to the proximal end of the control element sleeve than to the distal portion of the control cable lumen. The control cable lumen may be a first lumen of at least two lumens, each lumen of the at least two lumens provided by a respective sleeve, each respective sleeve comprising a respective proximal end and a respective distal end, each respective distal end arranged to be percutaneously insertable into the body while the respective proximal end remains outside of the body. The liquid supply port may be arranged to provide a flow of the liquid through a second lumen of the at least two lumens toward the respective distal end of the respective conduit that provides the second lumen, the second lumen other than the first lumen according to some embodiments.

In some embodiments, the catheter shaft includes a first end portion and a second end portion, the first end portion arranged to be percutaneously insertable into the body while the second end portion remains outside of the body, and the medical device system includes an end effector located at least proximate the first end portion of the catheter shaft. The control element is operatively coupled to the end effector to execute, at least in part, a particular end effector function of the end effector in response to a relative movement between a portion of the control cable and a portion of the control element sleeve according to some embodiments.

In some embodiments, the medical device system may include an end effector and at least one actuator provided in an enclosure, the catheter shaft extending between the end effector and the at least one actuator, and the control cable operatively coupled between the at least one actuator and the end effector to selectively enable a particular end effector function of the end effector. The control cable and the control cable lumen may each extend outwardly from an interior cavity provided in the enclosure, and the liquid supply port may be arranged to receive the liquid from the interior cavity according to some embodiments.

Various systems may include combinations and subsets of those disclosed above or otherwise herein.

In some embodiments, a medical device system may be summarized as including a catheter shaft; two or more conduits, at least one of the two or more conduits located at least in part within the catheter shaft, each conduit of the two or more conduits including a respective proximal end, a respective distal end, and a respective lumen extending between the respective proximal end and the respective distal end, each conduit of the two or more conduits arranged to be deliverable respective distal end ahead of respective proximal end through a bodily opening leading toward a bodily cavity, and the two or more conduits providing at least two lumens. The medical device system may include an end effector arranged to be percutaneously insertable into the bodily cavity; a control element operatively coupled to the end effector to selectively execute, at least in part, a particular end effector function of the end effector in response to movement of at least a portion of the control element; and a liquid supply port arranged to provide liquid into the catheter shaft. A first conduit of the two or more conduits may include a first liquid intake port arranged to receive at least a first part of the liquid provided by the liquid supply port to distribute at least the first part of the liquid through a first lumen of the first conduit at least toward the respective distal end of the first conduit, the first liquid intake port of the first conduit located closer to the respective proximal end of the first conduit than the respective distal end of the first conduit. A second conduit of the two or more conduits may include a second liquid intake port arranged to receive at least a second part of the liquid provided by the liquid supply port to distribute at least the second part of the liquid through a second lumen of the second conduit at least toward the respective proximal end of the second conduit, the second liquid intake port of the second conduit located closer to the respective distal end of the second conduit than the respective proximal end of the second conduit. The at least two lumens include the first lumen and the second lumen, and the at least the portion of the control element is located in at least one of the at least two lumens according to some embodiments.

In some embodiments, the at least the portion of the control element may be located in the first lumen. In some embodiments, the at least the portion of the control element may be located in the second lumen. In some embodiments, the catheter shaft may be provided at least by an elongate tubular member, and each of the first lumen and the second lumen may be provided by a respective elongate tubular member other than the catheter shaft. In some embodiments, the first conduit is located in the second conduit, or the second conduit is located in the first conduit.

In some embodiments, each respective lumen of the two or more conduits includes a respective longitudinal axis extending between the respective proximal end and the respective distal end. Each respective lumen of the two or more conduits includes a respective cross-sectional area circumferentially bounded at least one surface as viewed along the respective longitudinal axis, and the cross-sectional areas of the first lumen and the second lumen are different according to some embodiments.

In some embodiments, each respective lumen of the two or more conduits includes a respective longitudinal axis extending between the respective proximal end and the respective distal end. Each respective lumen of the two or more conduits includes a respective cross-sectional area circumferentially bounded at least one surface as viewed along the respective longitudinal axis, and the respective cross-sectional area of one of first lumen and the second lumen is larger than the respective cross-sectional area of the other of the first lumen and the second lumen according to some embodiments. The at least the portion of the control element may be located in the other of the first lumen and the second lumen according to some embodiments.

In some embodiments, the at least the portion of the control element may include a flexible control cable. In some embodiments, the control element may include a tubular member and a flexible control cable disposed within the tubular member. In some embodiments, the control element may include a Bowden cable. In some embodiments, the control element may include a push-pull rod.

In some embodiments, the at least the portion of the control element is located in the second lumen and the second intake port may be located at a location along the second conduit that is spaced from the respective distal end of the second conduit.

In some embodiments, the catheter shaft includes a first end portion and a second end portion, the first end portion arranged to be deliverable ahead of the second end portion through the bodily opening toward the bodily cavity, and the liquid supply port is located closer to the second end portion than the first end portion. In some embodiments, the medical device system may include at least one actuator, operatively coupled to the control element to selectively effect movement of the at least the portion of the control element. The at least one actuator may be provided at least in part with an enclosure physically coupled to the catheter shaft at a location at least proximate the second end portion, and the liquid supply port may be located within the enclosure according to some embodiments.

In some embodiments, the second liquid intake port of the second lumen may be located within the catheter shaft. In some embodiments, the second liquid intake port of the second lumen may be located within the end effector. In some embodiments, the second liquid intake port may be arranged to receive at least the second part of the liquid provided by the liquid supply port to distribute at least the second part of the liquid through the second lumen at least toward both the respective distal end of the second conduit and the respective proximal end of the second conduit. In some embodiments, the at least the second part of the liquid may include at least some of the at least the first part of the liquid. In some embodiments, the first lumen and the second lumen may be fluidly coupled together to allow for fluid flow therebetween.

In some embodiments, the first liquid intake port may be arranged to receive at least the first part of the liquid and flush at least a distal portion of the first lumen of a fluid other than the liquid, the distal portion of the first lumen extending from the respective distal end of the first conduit. In some embodiments, the second liquid intake port may be arranged to receive at least the second part of the liquid and flush at least a proximal portion of the second lumen of the fluid, the proximal portion of the second lumen extending from the respective proximal end of the second conduit. In some embodiments, the second liquid intake port may be arranged to receive at least the second part of the liquid and flush each of at least a proximal portion of the second lumen and at least a distal portion of the second lumen of the fluid, the proximal portion of the second lumen extending from the respective proximal end of the second conduit, and the distal portion of the second lumen extending from the respective distal end of the second conduit. In some embodiments, the at least the portion of the control element may be located in the second lumen.

In some embodiments, at least part of the control element is arranged to be wetted by the liquid. In some embodiments, at least a part of the control element positioned at least proximate the end effector is arranged to be wetted by the liquid. In some embodiments, the catheter shaft is provided at least by an elongate tubular member, and wherein one of the two or more conduits is provided by the catheter shaft.

Various systems may include combinations and subsets of those disclosed above or otherwise herein.

In some embodiments, a medical device system includes a catheter shaft; two or more conduits including a first conduit and a second conduit, each of at least one of the two or more conduits located at least in part within the catheter shaft, each conduit of the two or more conduits including a respective proximal end, a respective distal end, and a respective lumen extending between the respective proximal end and the respective distal end, each conduit of the two or more conduits arranged to be deliverable respective distal end ahead of respective proximal end through a bodily opening leading toward a bodily cavity, and the two or more conduits providing at least two lumens. The medical device system may include an end effector arranged to be percutaneously insertable into the bodily cavity; a control element operatively coupled to the end effector to selectively execute, at least in part, a particular end effector function of the end effector in response to movement of at least a portion of the control element, the at least the portion of the control element located in at least one of the at least two lumens; and a liquid supply port arranged to provide liquid into the catheter shaft. A method of operating the medical device system may include receiving at least a first part of the liquid at a first liquid intake port of the first conduit and distributing at least the first part of the liquid through a first lumen of the first conduit at least toward the respective distal end of the first conduit, the first liquid intake port located closer to the respective proximal end of the first conduit than the respective distal end of the first conduit. The method may include receiving at least a second part of the liquid at a second liquid intake port of the second conduit and distributing at least the second part of the liquid through a second lumen of the second conduit at least toward the respective proximal end of the second conduit, the second liquid intake port located closer to the respective distal end of the second conduit than the respective proximal end of the second conduit, and the at least two lumens including the first lumen and the second lumen.

Various systems may include combinations and subsets of all the systems summarized above or otherwise described herein.

Various methods may include combinations and subsets of all the methods summarized above or otherwise described herein.

In some embodiments, some or all of any of the systems or devices summarized above or otherwise described herein, or one or more combinations thereof, may be controlled by one or more control methods for executing some or all of the functionality of such systems or devices summarized above or otherwise described herein. In some embodiments, a computer program product may be provided that comprises program code portions for performing some or all of any of such control methods, when the computer program product is executed by a computing device. The computer program product may be stored on one or more computer-readable storage mediums. In some embodiments, each of the one or more computer-readable storage mediums is a non-transitory computer-readable storage medium. In some embodiments, such control methods are implemented or executed in part or in whole by at least one data processing device or system upon configuration thereof by one or more programs executable by the at least one data processing device or system and stored in one or more computer-readable storage mediums. In some embodiments, each of the one or more computer-readable storage mediums is a non-transitory computer-readable storage medium.

BRIEF DESCRIPTION OF THE DRAWINGS

It is to be understood that the attached drawings are for purposes of illustrating aspects of various embodiments and may include elements that are not to scale.

FIG. 5L-1 is a perspective view of an end effector or manipulable portion of the catheter system of FIG. 5A configured in an expanded configuration known as a first fanned configuration, according to some example embodiments.

FIG. 5L-2 is a top plan view of the end effector or manipulable portion configured in the first fanned configuration of FIG. 5L-1, according to some example embodiments.

FIG. 5M-1 is a perspective view of an end effector or manipulable portion of the catheter system of FIG. 5A configured in an expanded configuration known as a second fanned configuration, according to some example embodiments.

FIG. 5M-2 is a top plan view of the end effector or manipulable portion configured in the second fanned configuration of FIG. 5M-1, according to some example embodiments.

FIGS. 5R-1 and 5R-2 are respective top and bottom perspective views of at least a portion of the catheter system of FIG. 5A with various external portions of a housing thereof removed, according to some example embodiments.

Figure 4:
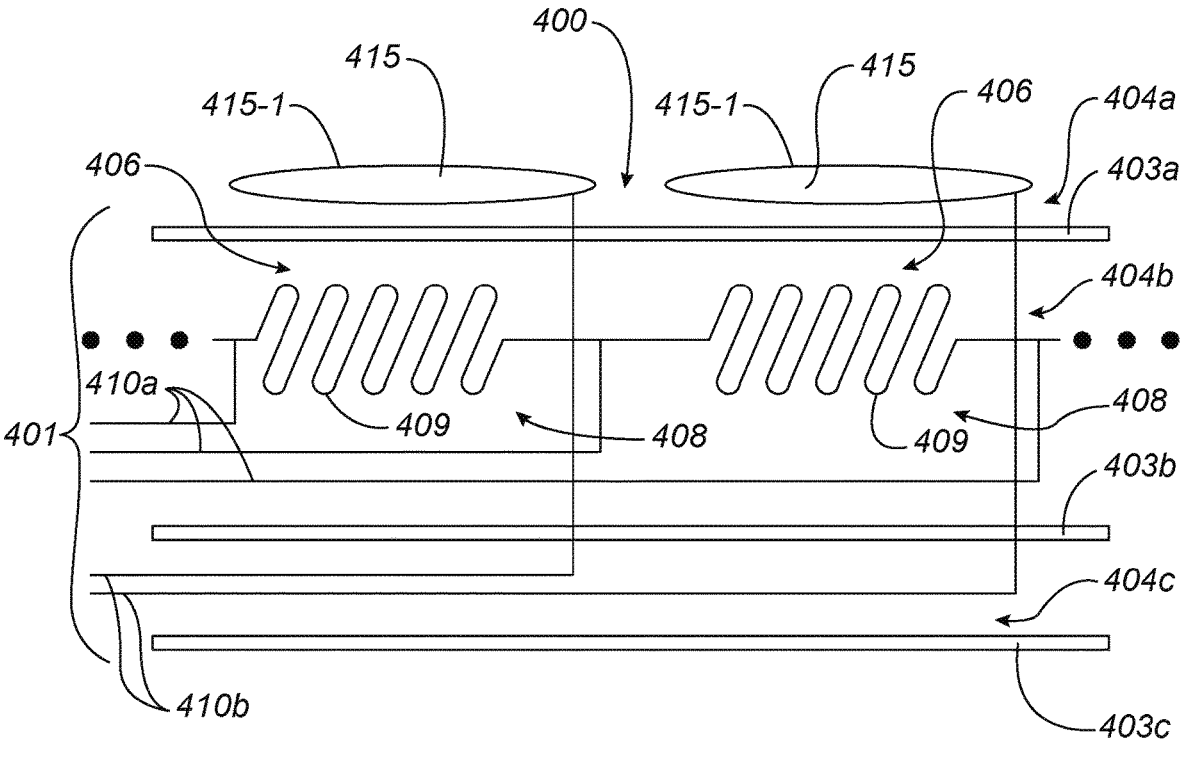
FIG. 4 is a schematic representation of a transducer-based device that includes a flexible circuit structure, according to some example embodiments.
Figure 5A:
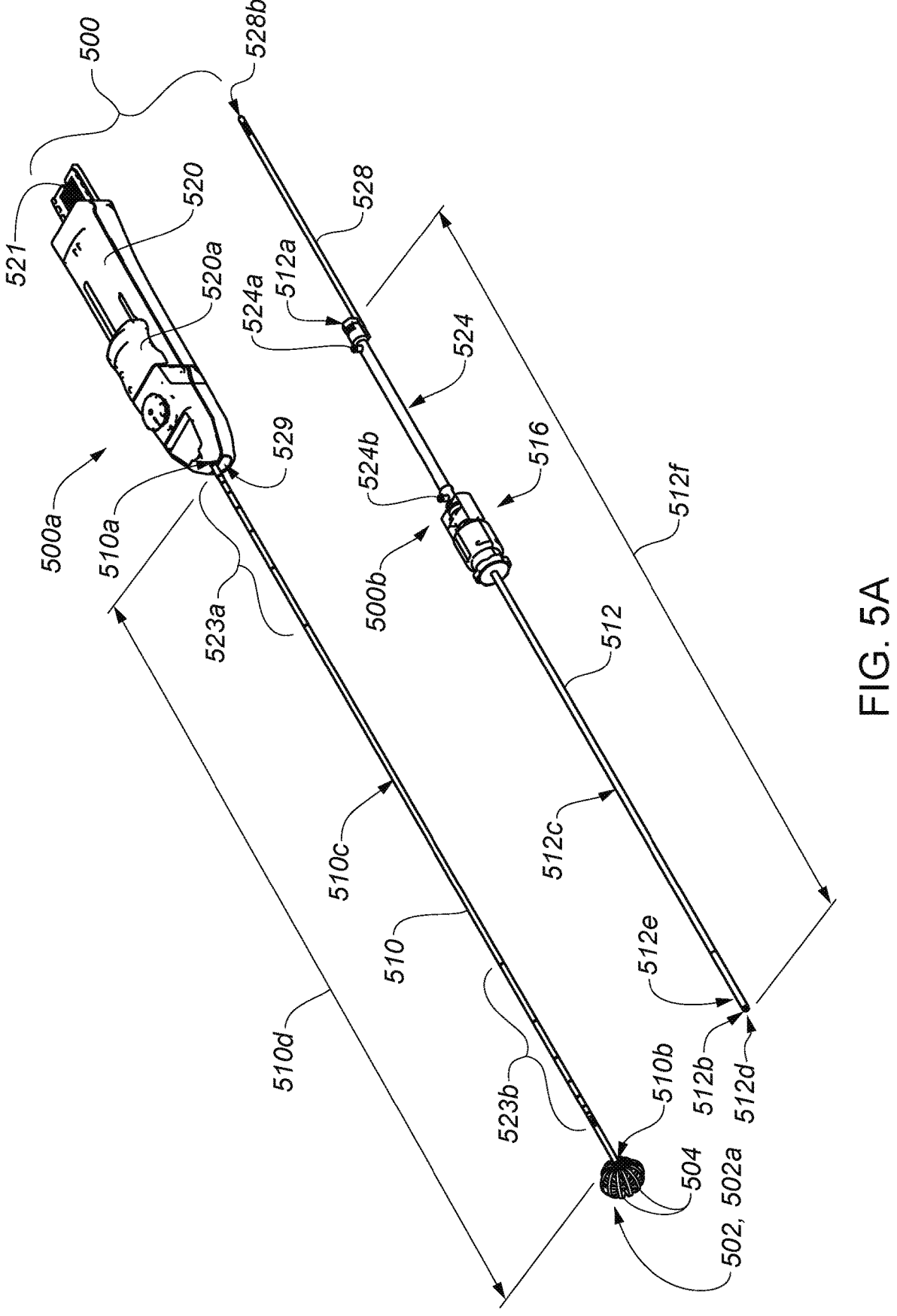
FIG. 5A is a perspective representation of a catheter system, according to some example embodiments.
Figure 5B:
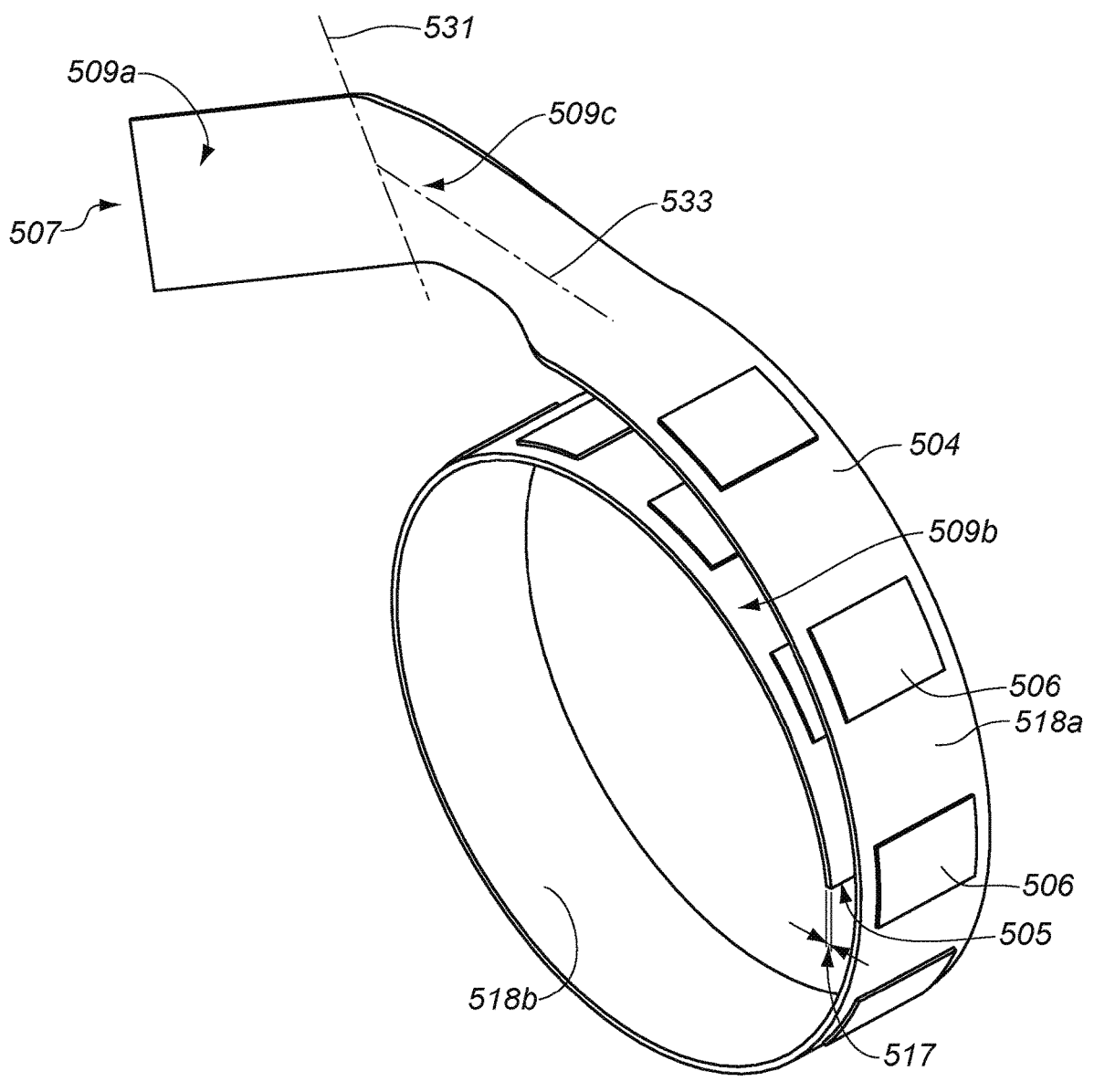
FIG. 5B is a perspective view of an elongate member of a structure provided by a manipulable portion of the catheter system of FIG. 5A, according to some example embodiments.
Figure 5C:
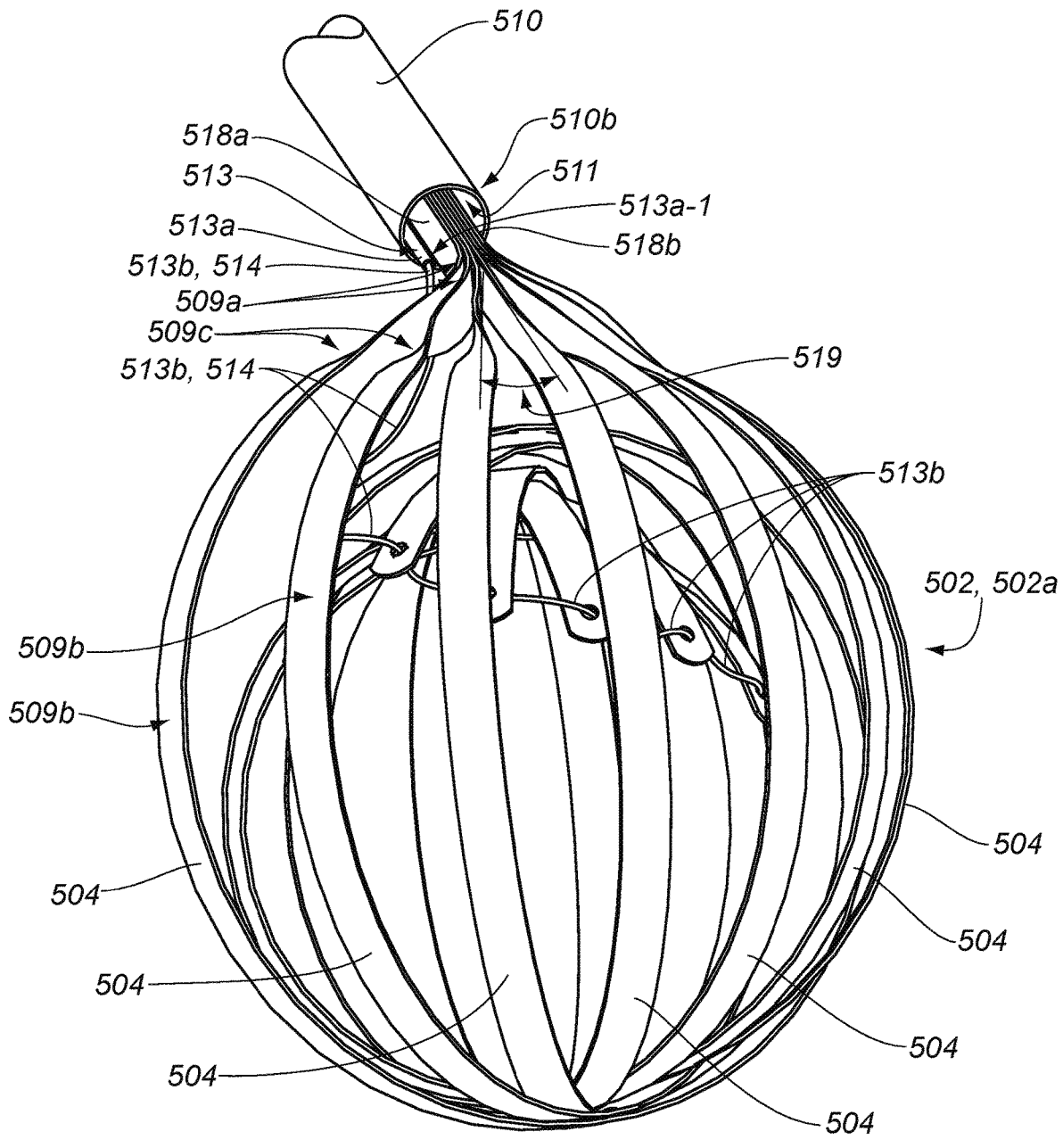
FIG. 5C is a perspective view of an end effector or manipulable portion of the catheter system of FIG. 5A, the manipulable portion in an initial or predisposed configuration, according to some example embodiments.
Figure 5D:
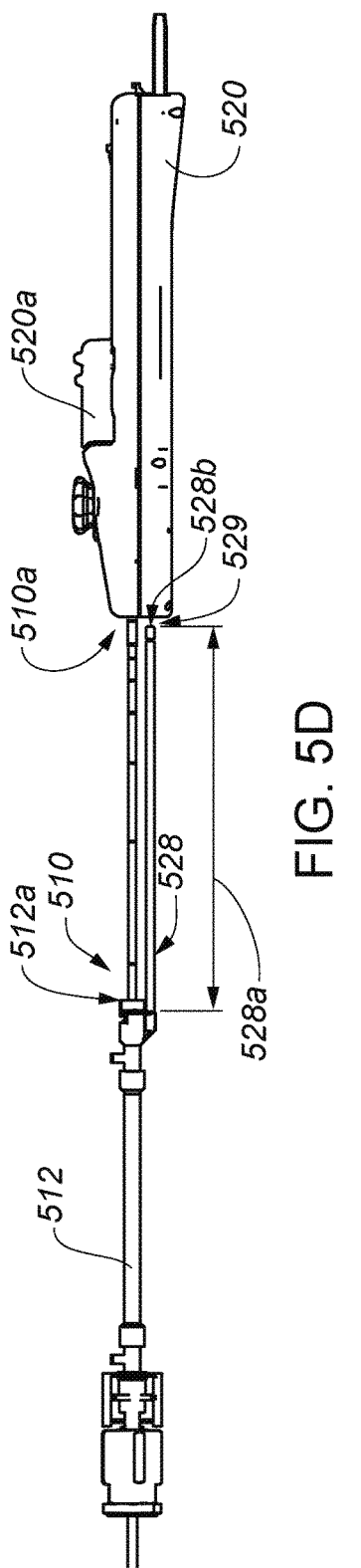
FIGS. 5D, 5E, and 5F are various side elevation views of a positioning of a shaft into a catheter sheath at three successive points in time, each of the shaft and the catheter sheath provided by the catheter system of FIG. 5A, according to some example embodiments.
Figure 5E:
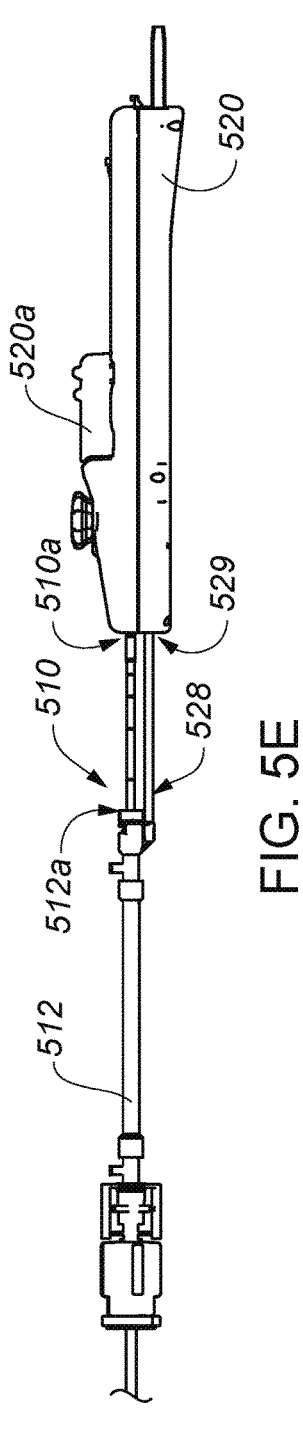
Figure 5F:
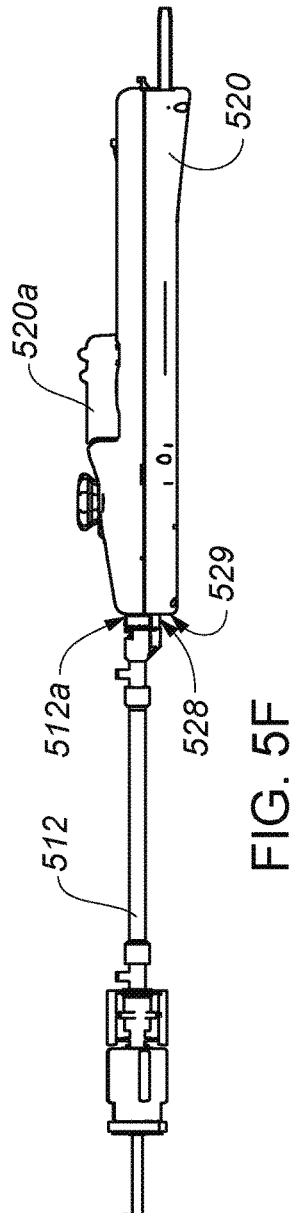
Figure 5G:
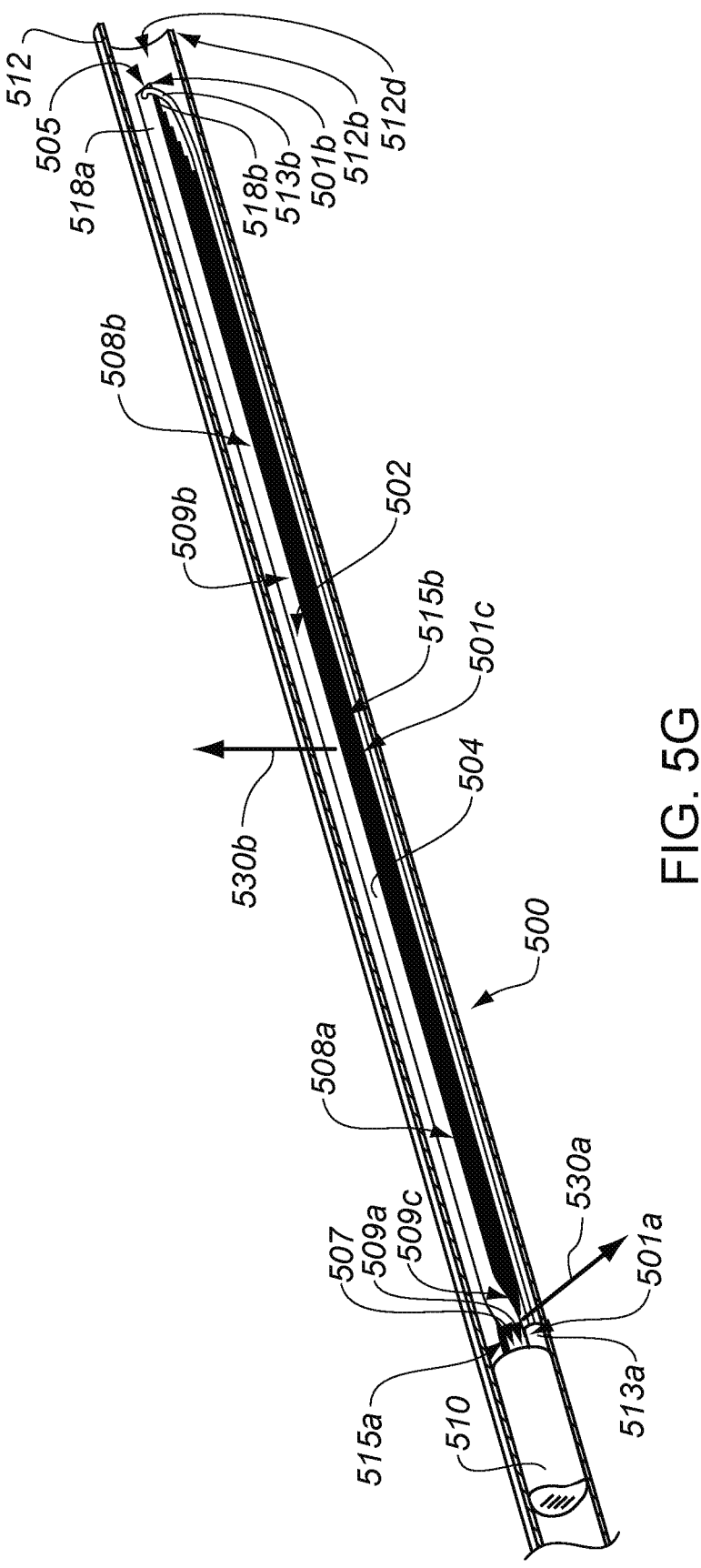
FIG. 5G is a perspective view of an end effector or manipulable portion of the catheter system of FIG. 5A, the manipulable portion in a delivery configuration, according to some example embodiments.
Figures 5H, 5I, 5J:
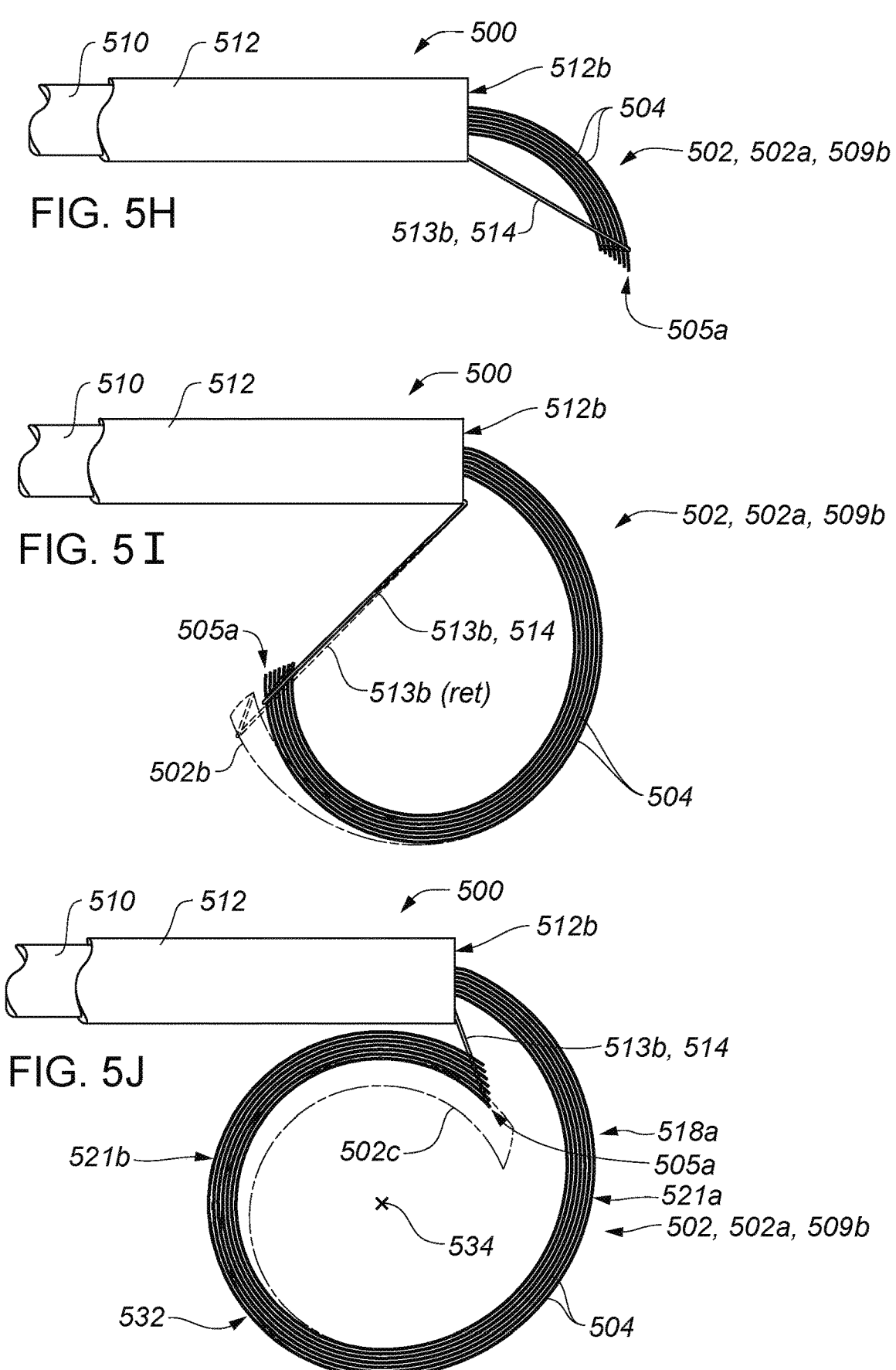
FIGS. 5H, 5I, and 5J are various side elevation views of various respective parts of an end effector or manipulable portion positioned at three successive points in time as a part of the manipulable portion is advanced outwardly from the confines of a lumen of a catheter sheath, according to some example embodiments, each of the manipulable portion and the catheter sheath provided by the catheter system of FIG. 5A, according to some example embodiments.
Figure 5K:
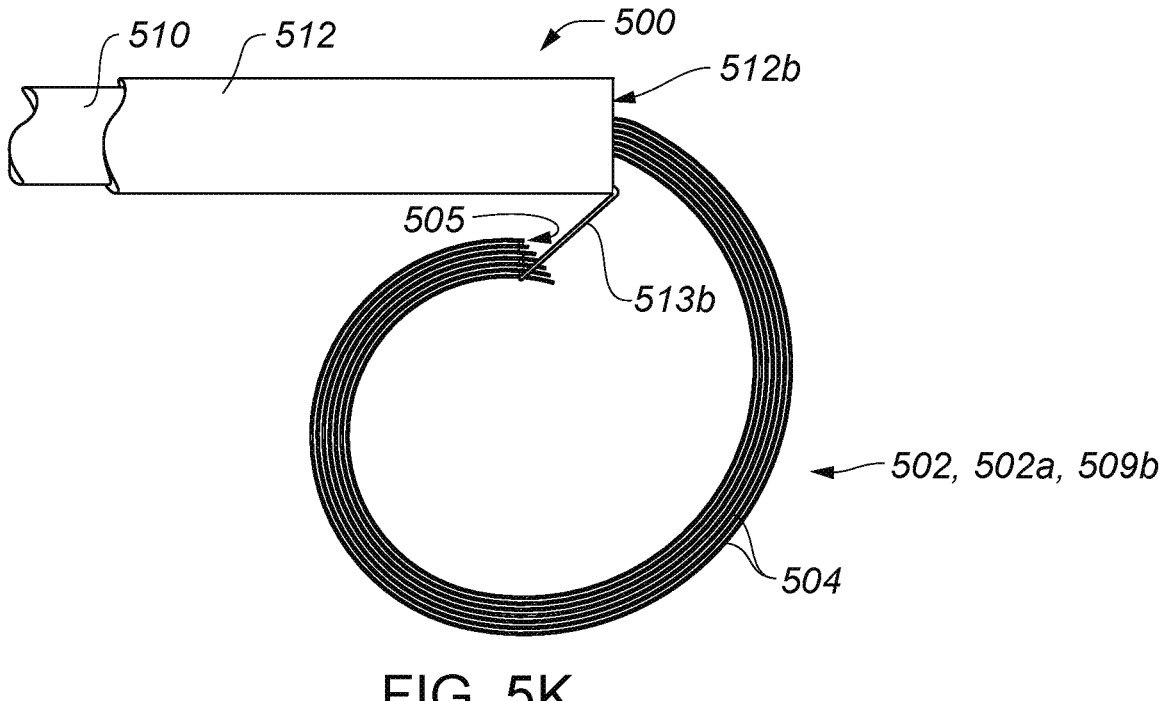
FIG. 5K is a side elevation view of a retraction of an end effector or manipulable portion to a particular location relative to a catheter sheath, each of the manipulable portion and the catheter sheath provided by the catheter system of FIG. 5A, according to some example embodiments.
Figures 1, 5L:
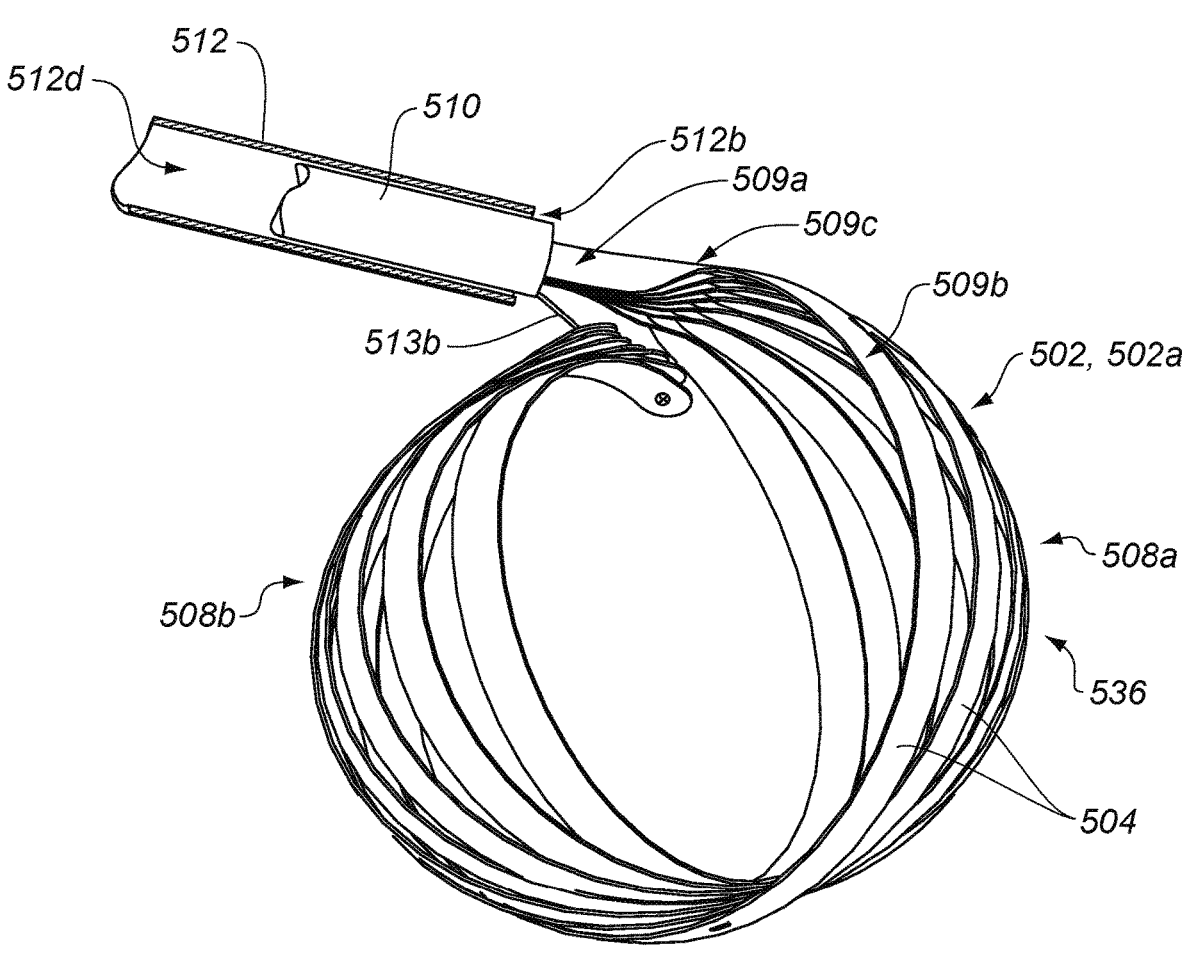
Figures 2, 5L:
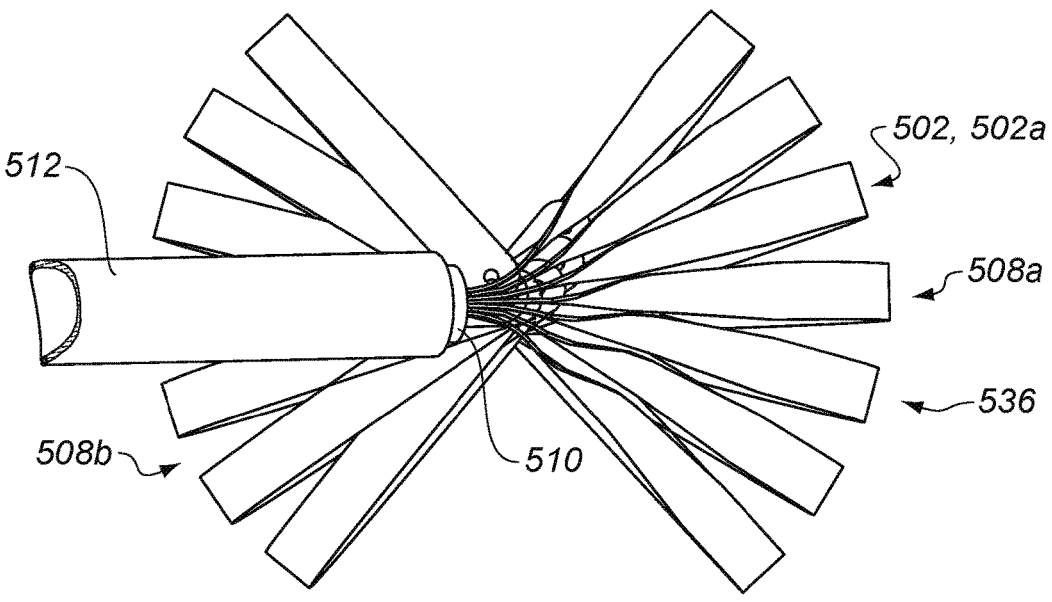
Figures 1, 2, 5M:
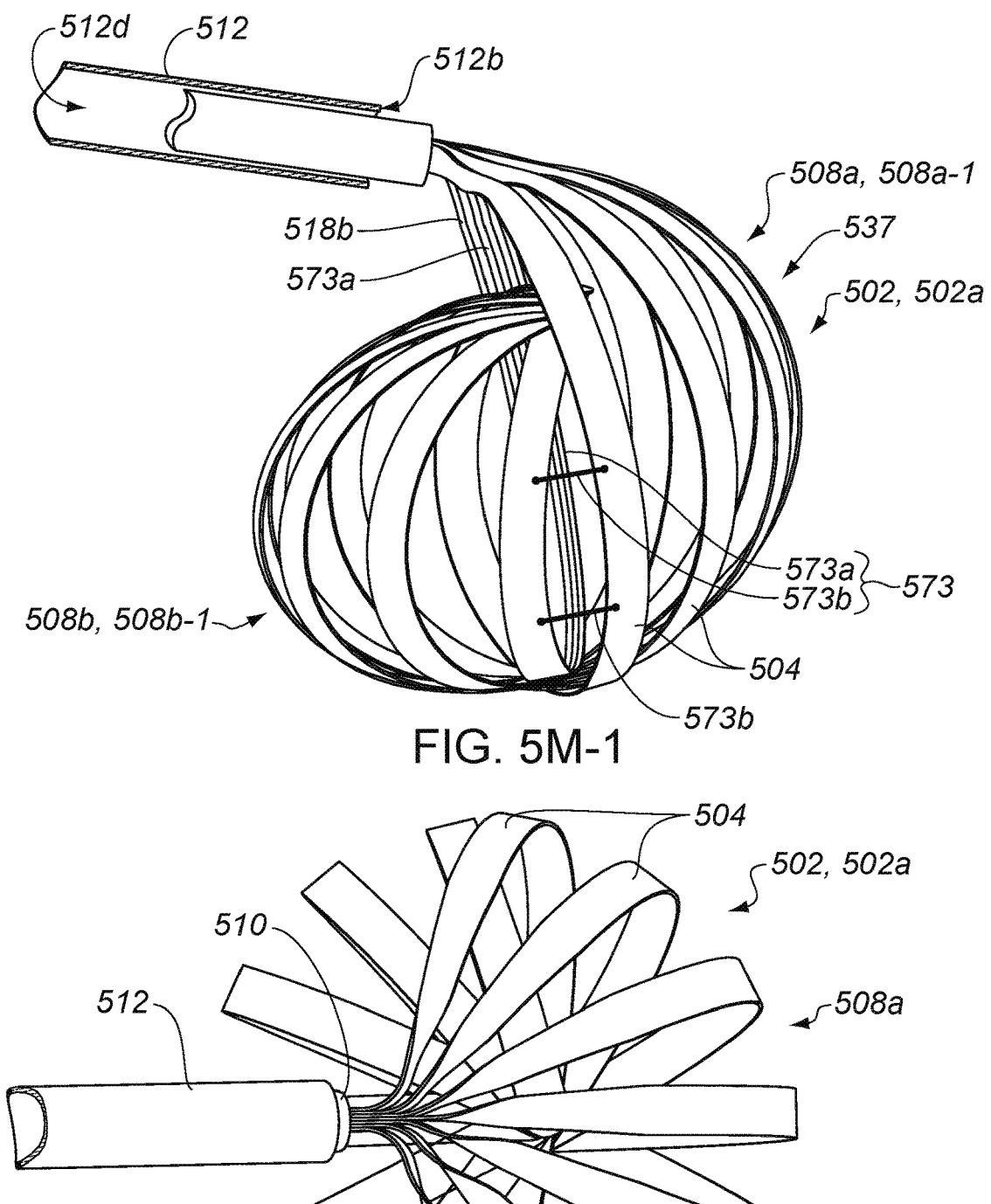
Figures 5N, 5O:
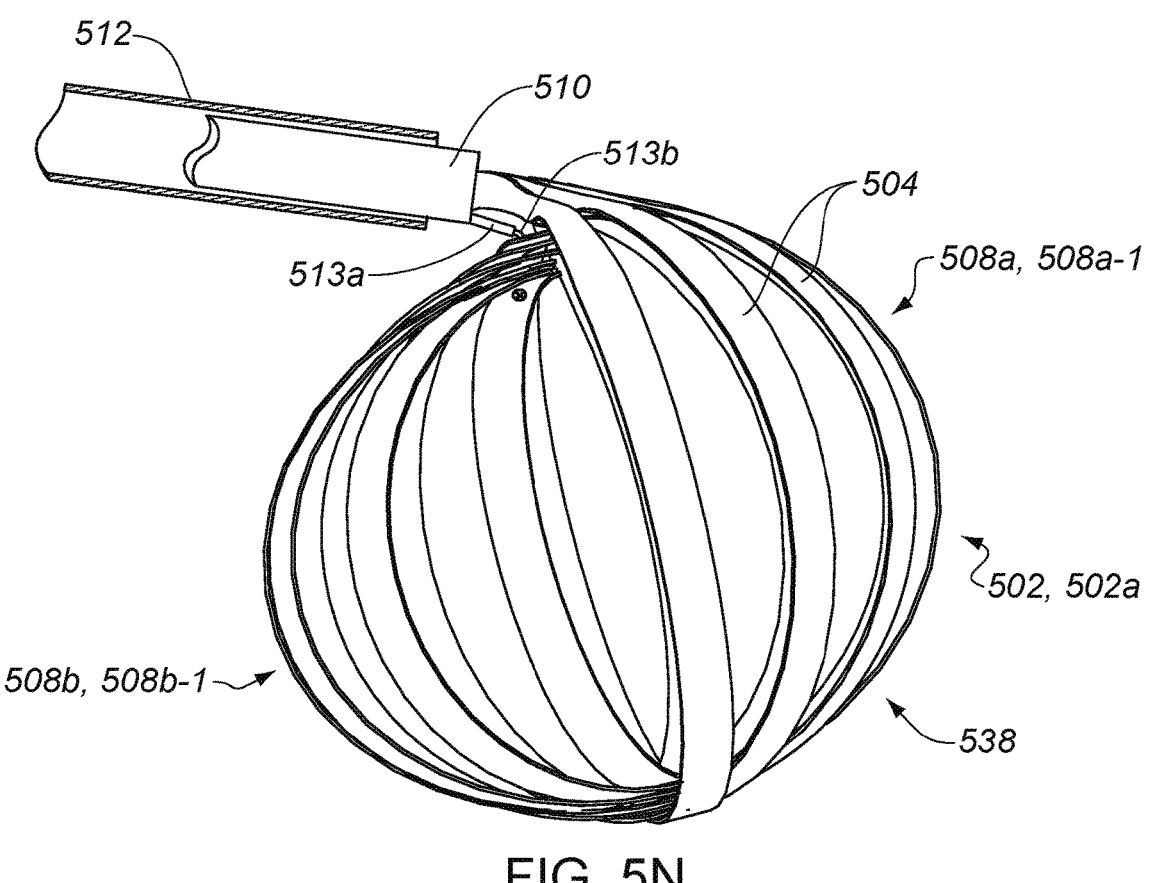
FIG. 5N is a perspective view of an end effector or manipulable portion of the catheter system of FIG. 5A configured in an expanded configuration known as enlarged expanded configuration, according to some example embodiments.
FIG. 5O is a perspective view of an end effector or manipulable portion of the catheter system of FIG. 5A configured in an expanded configuration known as a flattened expanded configuration, according to some example embodiments.
Figure 5P:
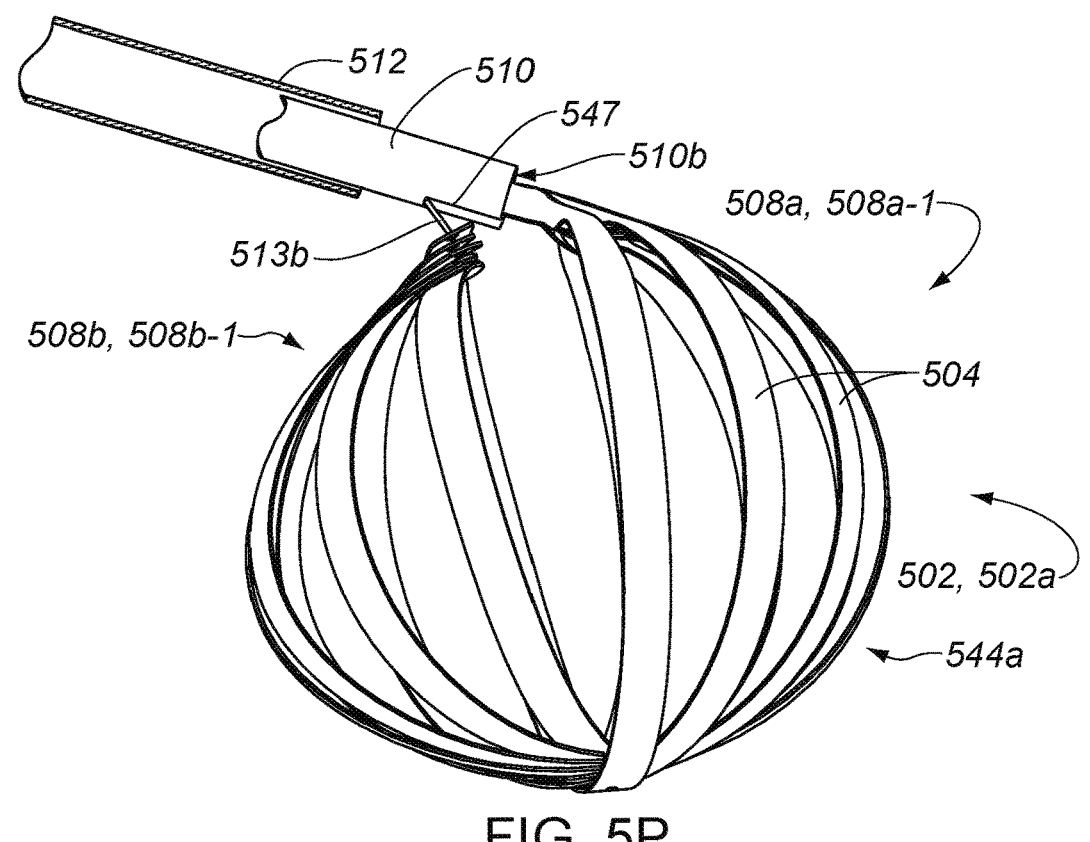
FIG. 5P is a perspective view of an end effector or manipulable portion of the catheter system of FIG. 5A configured in an expanded configuration known as an open clam shell configuration, according to some example embodiments.
Figure 5Q:
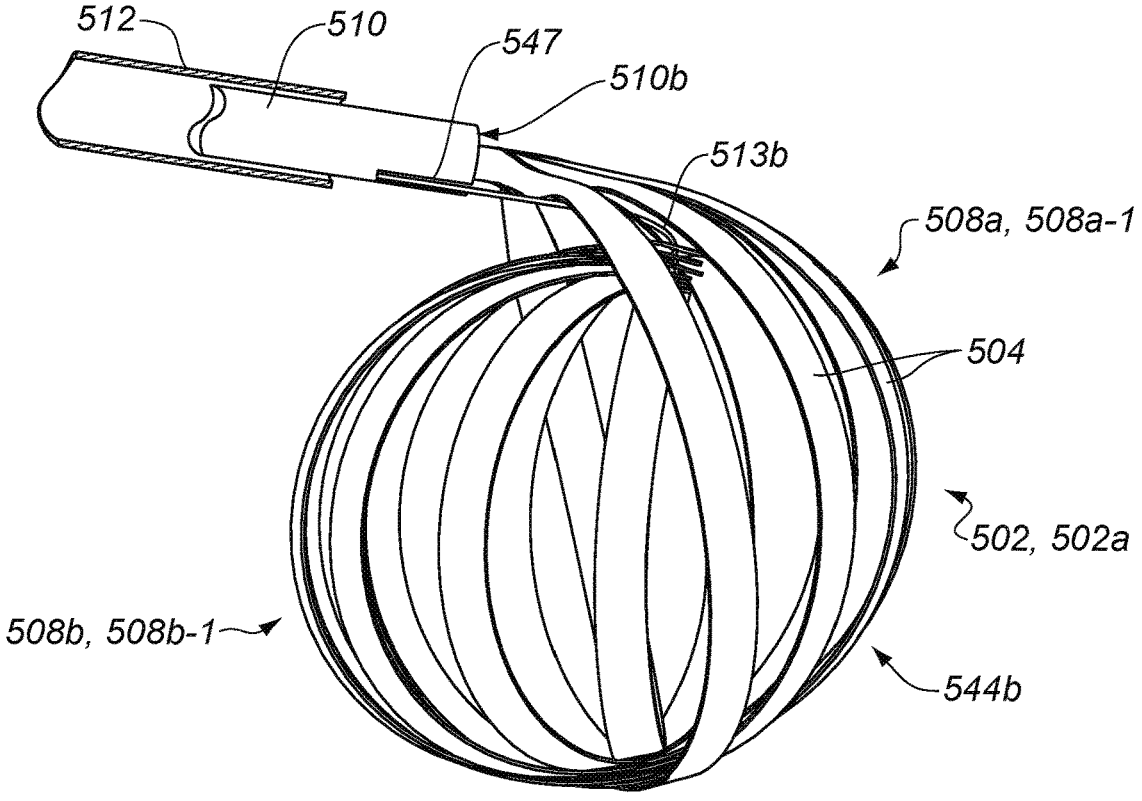
FIG. 5Q is a perspective view of an end effector or manipulable portion of the catheter system of FIG. 5A configured in an expanded configuration known as a closed clam shell configuration, according to some example embodiments.
Figures 1, 5R:
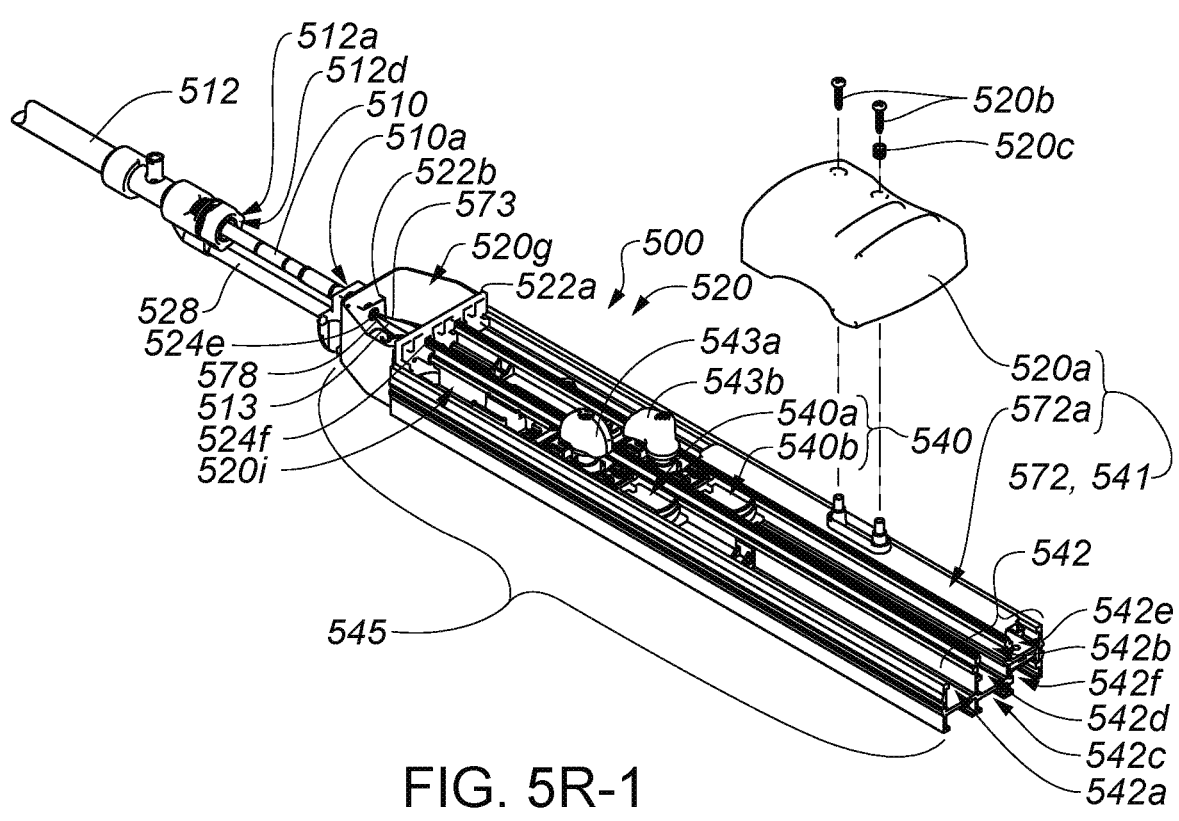
Figures 2, 5R:
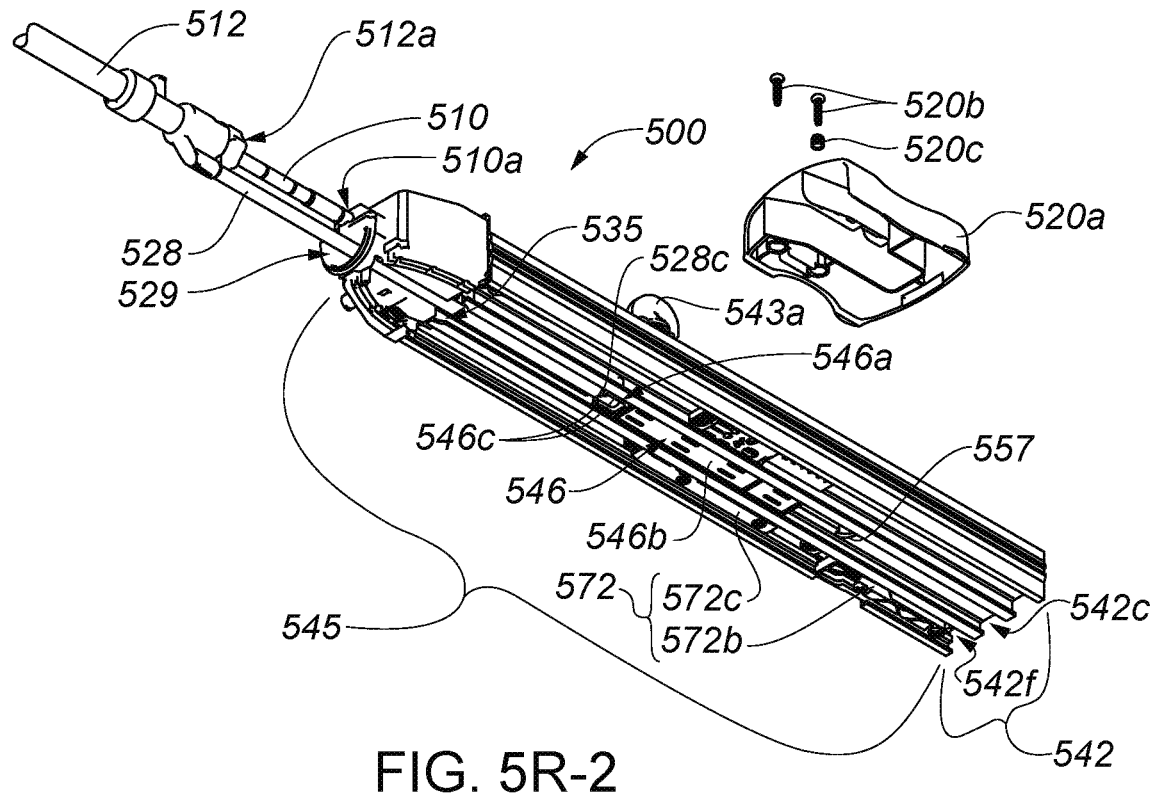
Figures 3, 5R:
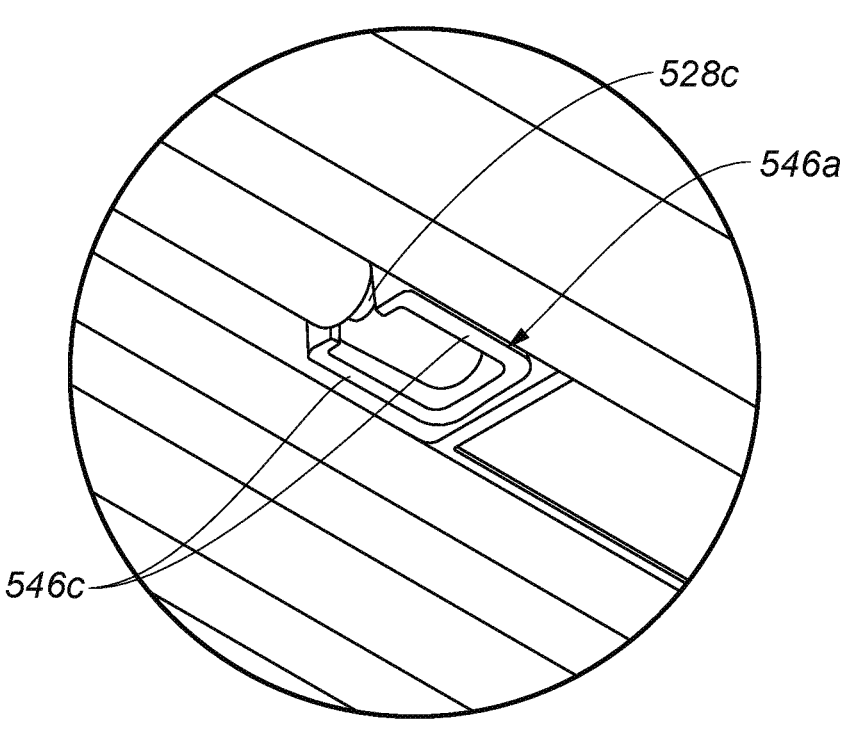
Figures 4, 5R:
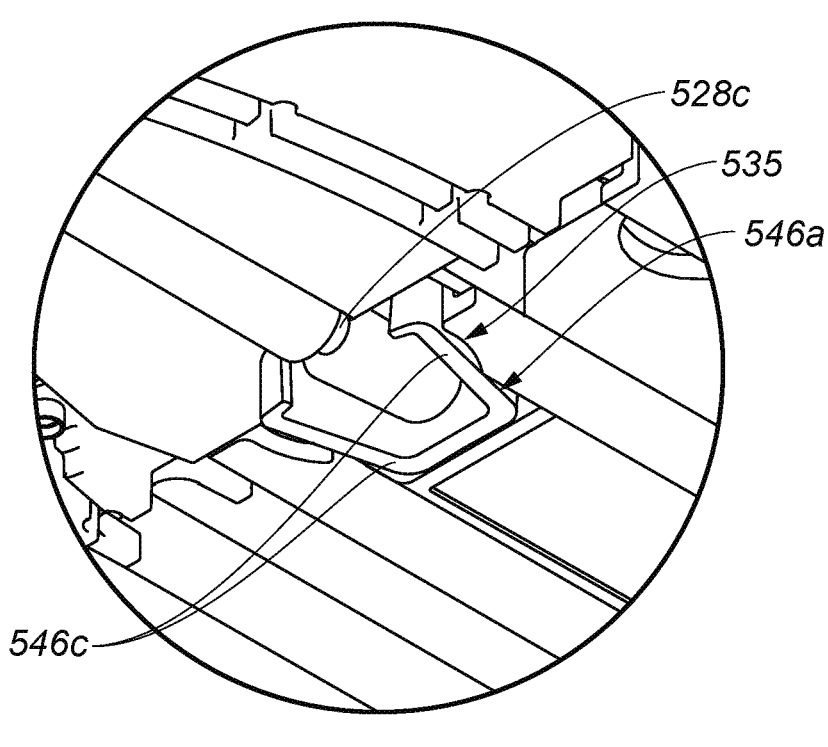

Each of FIGS. 5R-3 and 5R-4 represents a detailed view of a respective one of an engagement and disengagement between various parts of the catheter system of FIG. 5A, according to some example embodiments.

FIGS. 5S-1, 5S-2, 5S-3, 5S-4, 5S-5, and 5S-6 are top plan views of a number of actuators affiliated with a handle portion of the catheter system of FIG. 5A, various ones of the actuators positioned in respective activation positions, according to some example embodiments.

Figures 4, 5S:
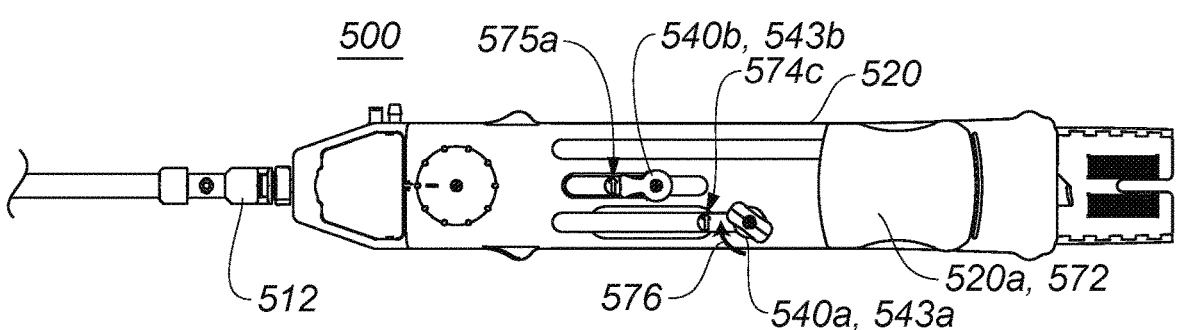
Figures 5, 5S:
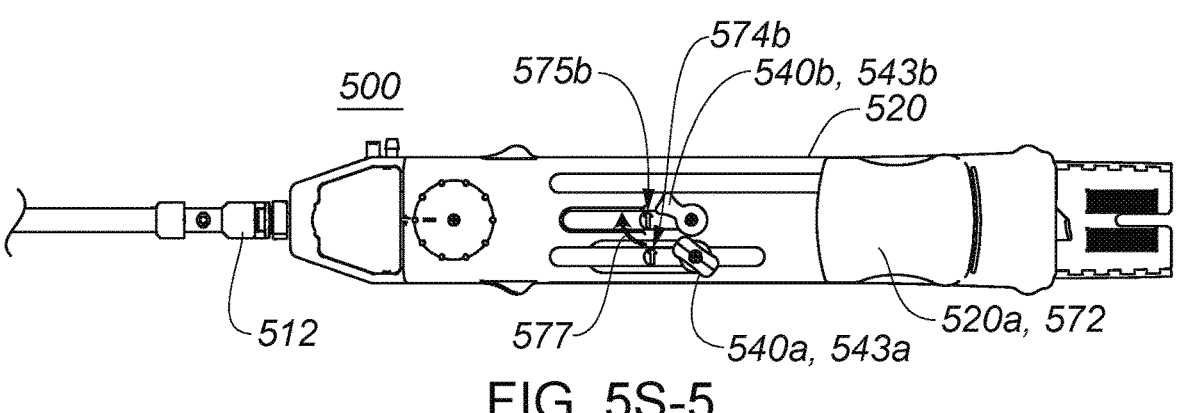
Figures 5, 5S, 6:
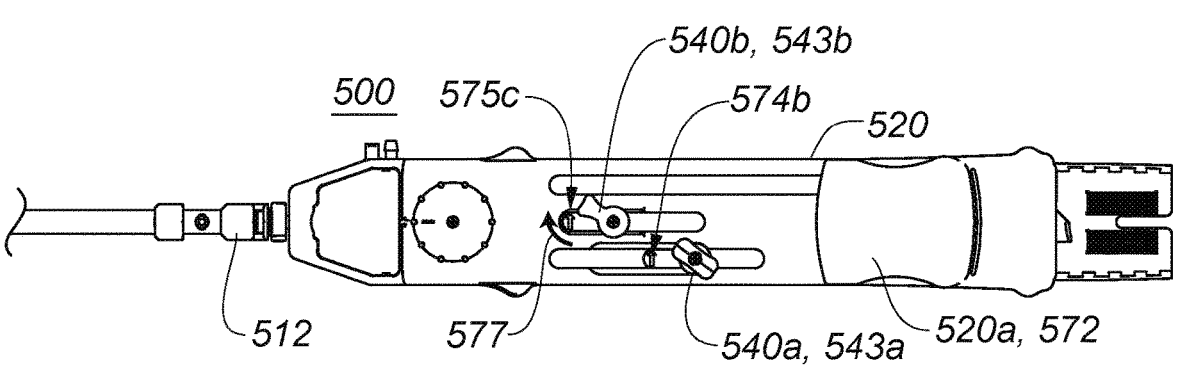
Figure 5T:
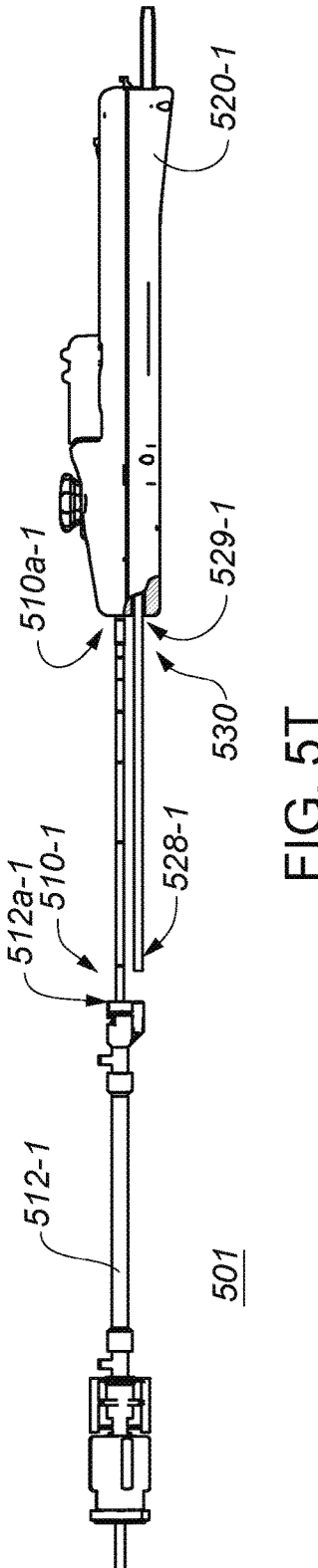
Figure 5U:
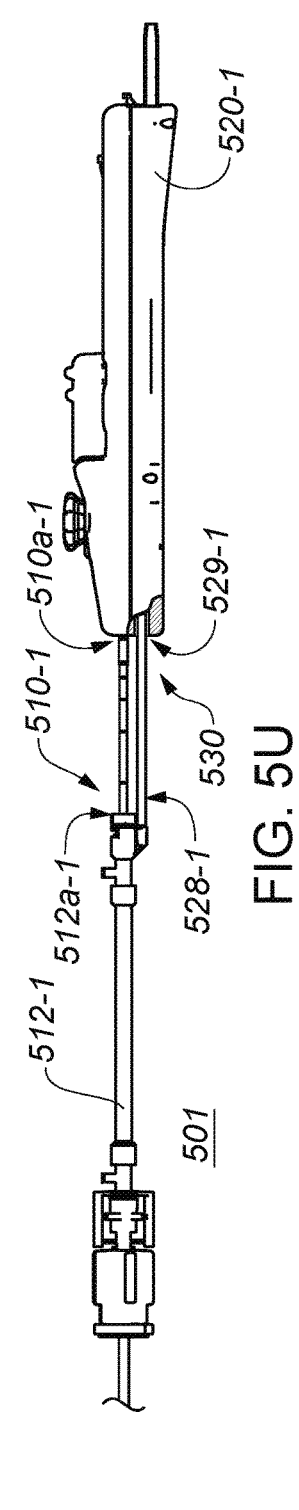
Figure 5V:
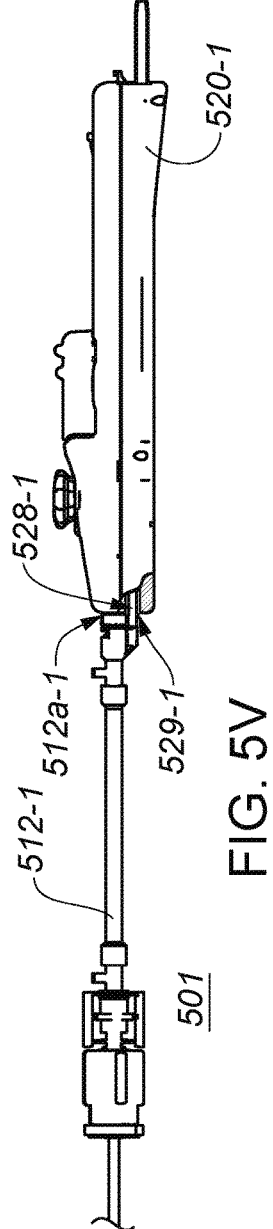

FIGS. 5T, 5U, and 5V are various side elevation views of a positioning of a shaft into a catheter sheath at three successive points in time, according to some example embodiments.

FIGS. 5W-1, 5W-2, 5W-3, and 5W-4 each respectively shows plan and elevation views of at least a portion of a catheter system, according to some embodiments.

Figures 1, 5W:
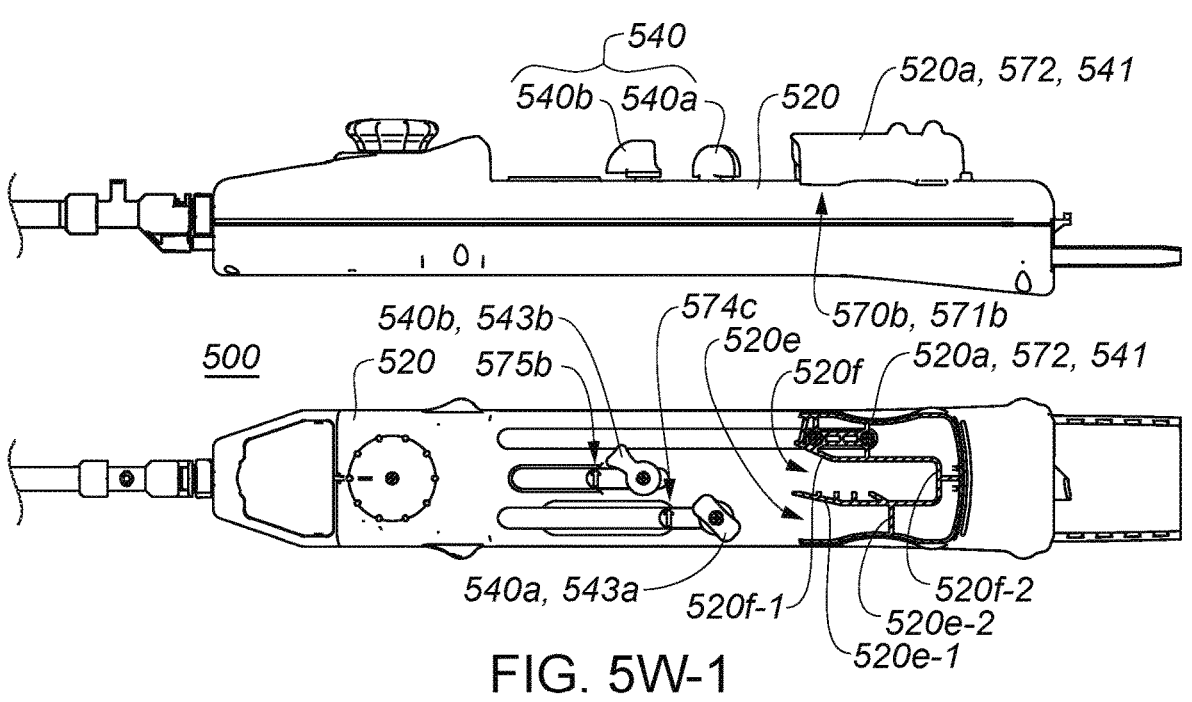
Figures 2, 5W:
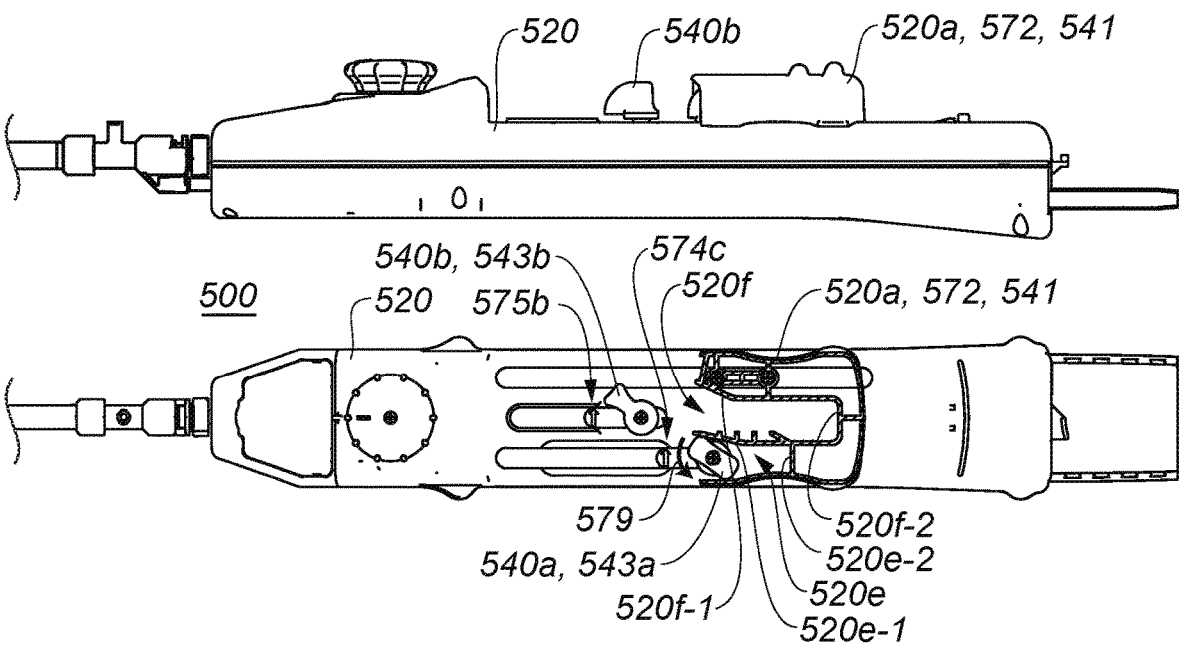
Figures 3, 5W:
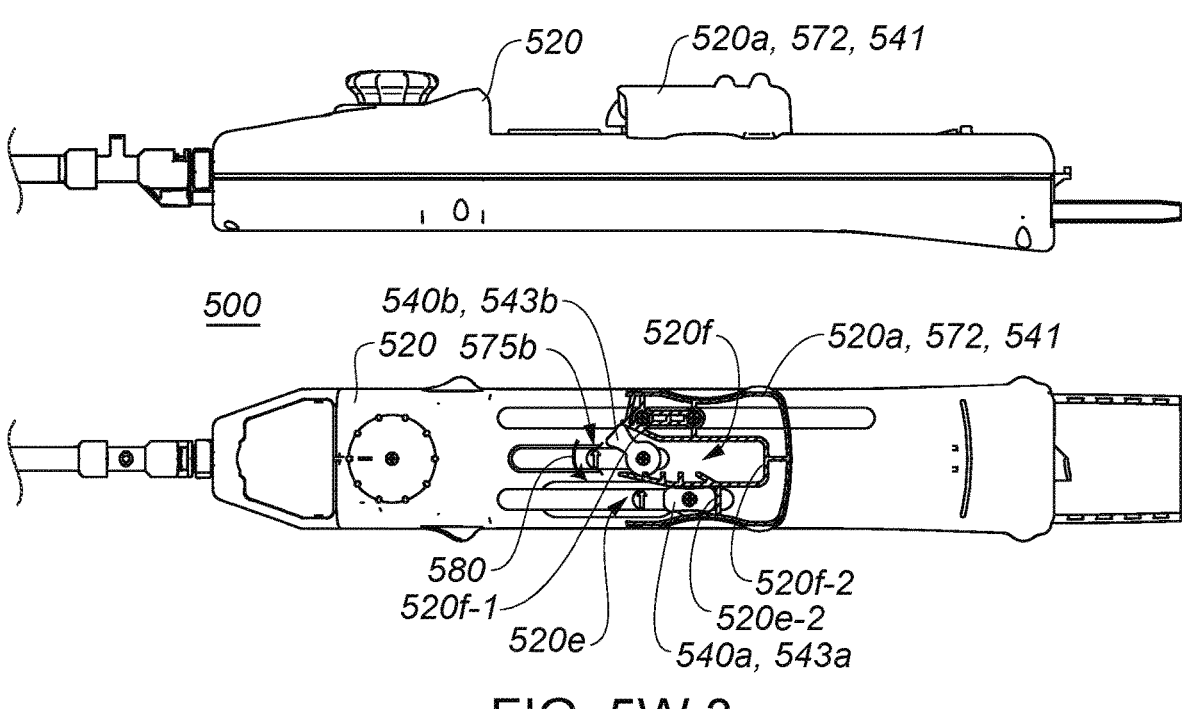
Figures 4, 5W:
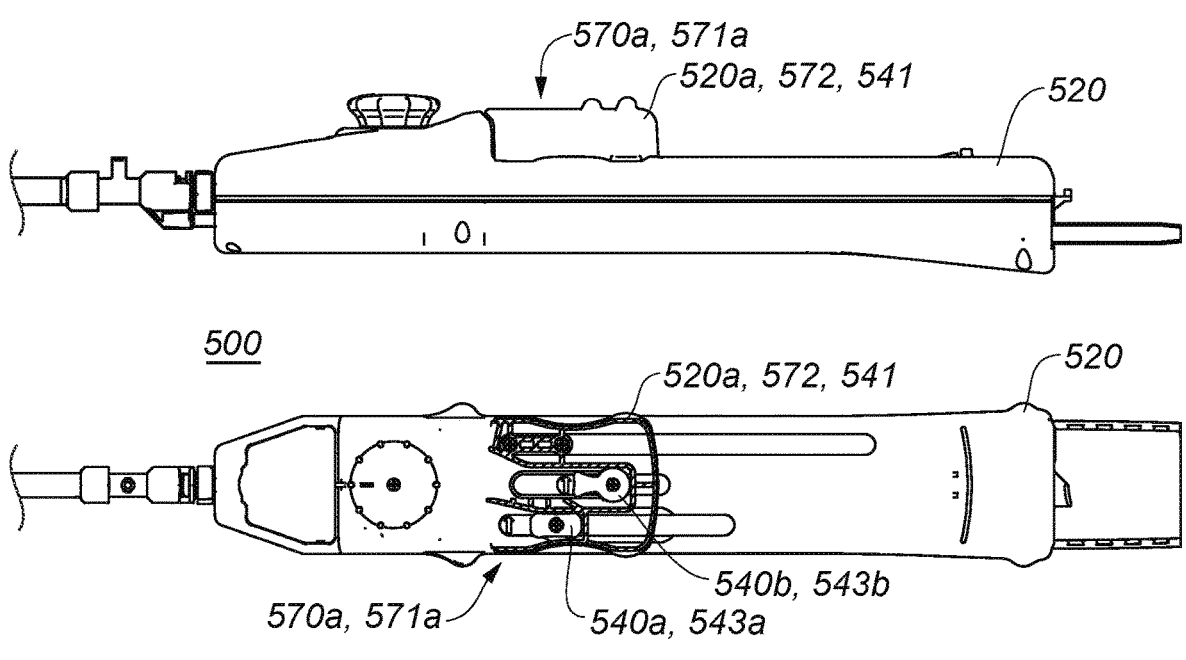
Figure 5X:
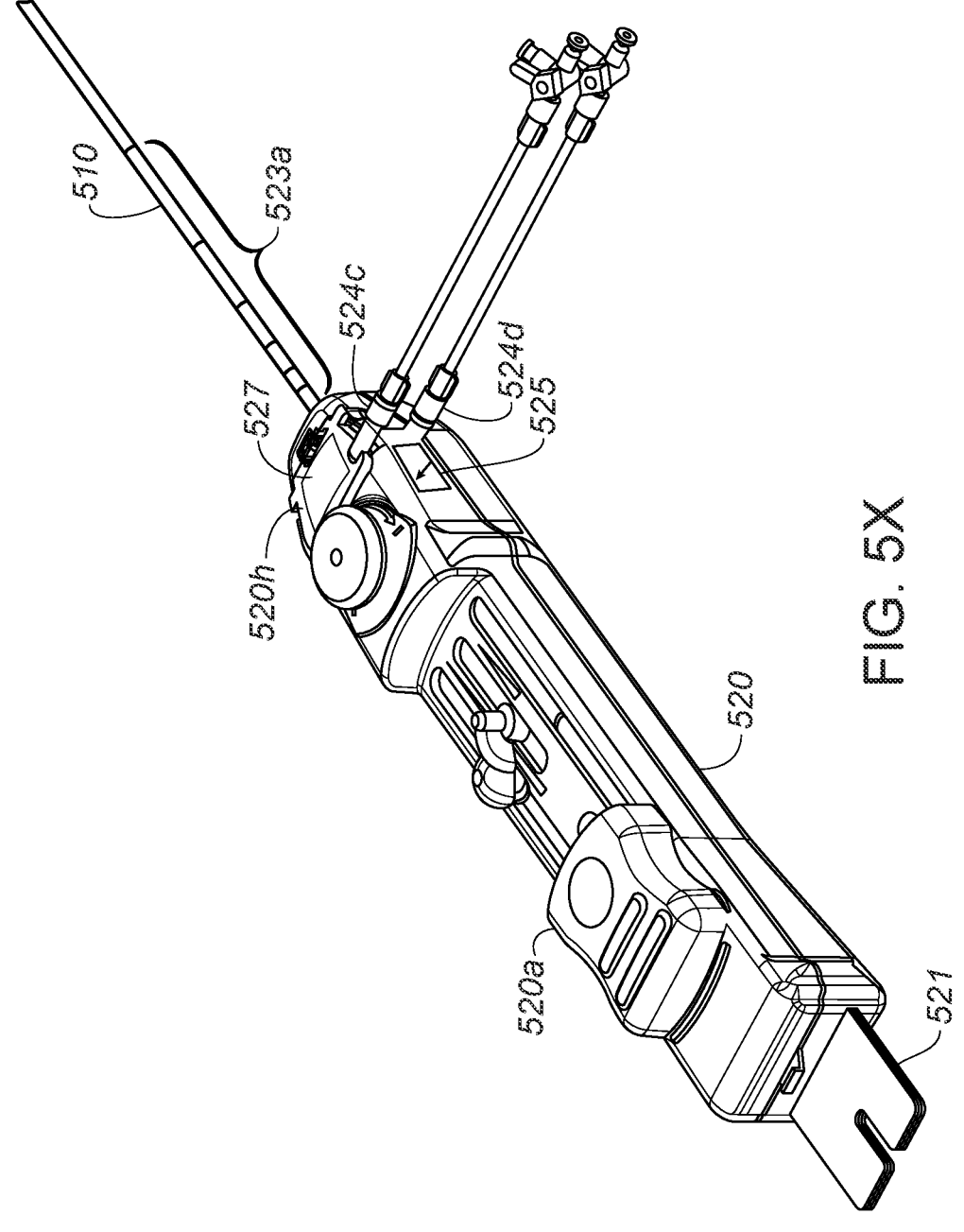
Figure 5Y:
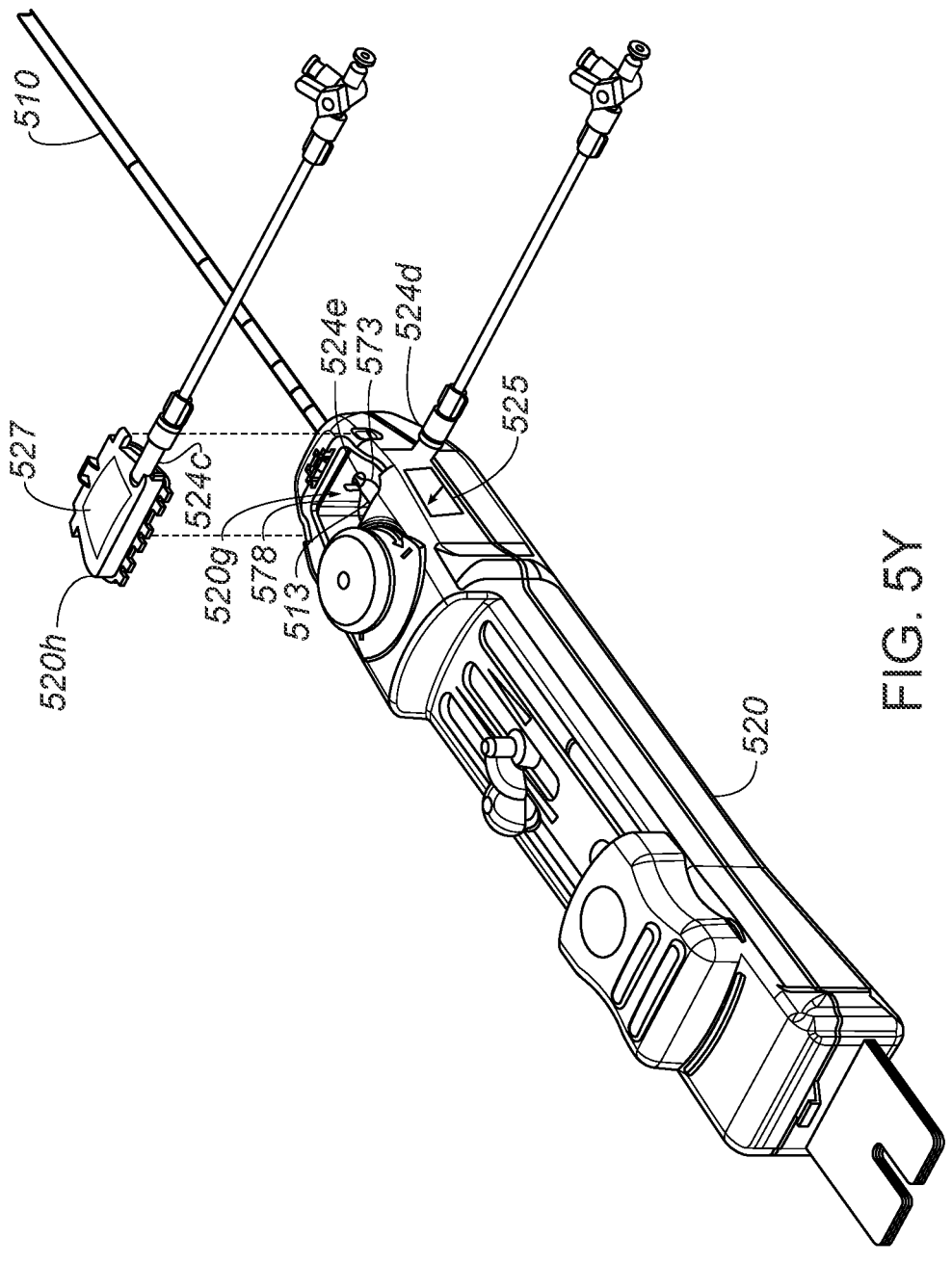
Figure 5Z:
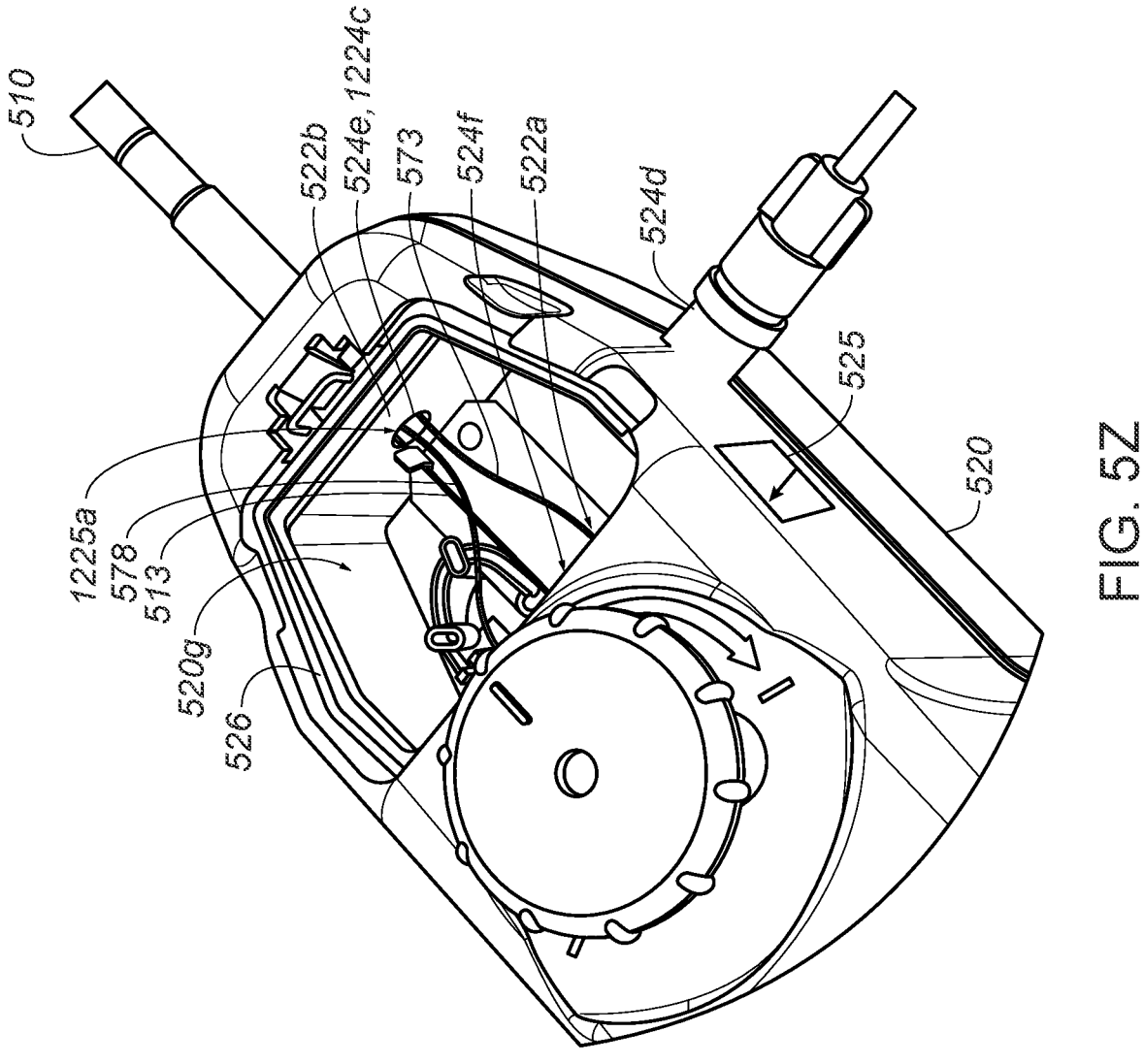
Figure 6:
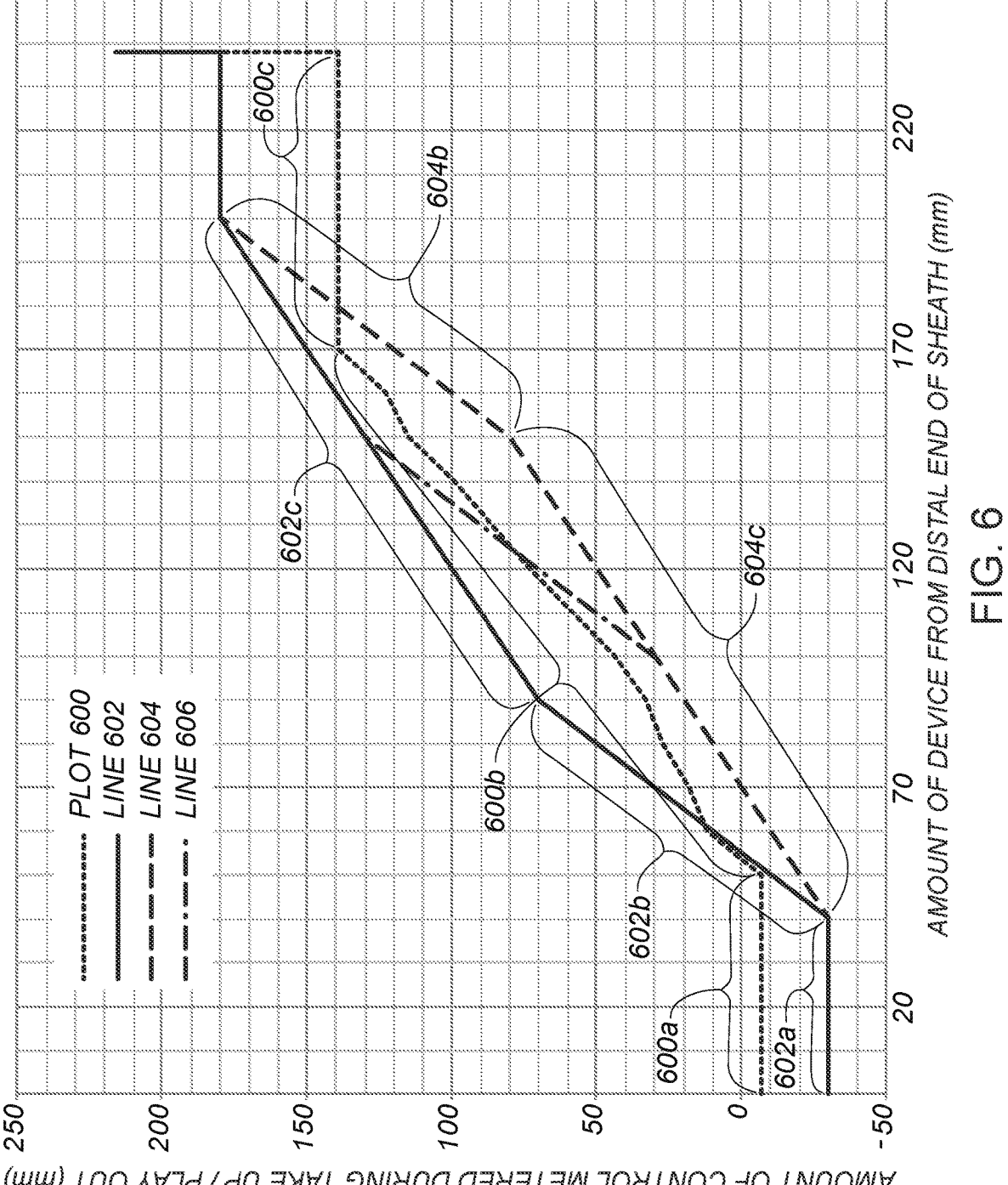

FIGS. 5X, 5Y, and 5Z are perspective schematic views of at least a portion of a catheter system, according to some example embodiments.

FIG. 6 is a graph that includes various lines representative of a metering of a control element during a take-up thereof and a play-out thereof, according to some example embodiments.

Figure 7A:
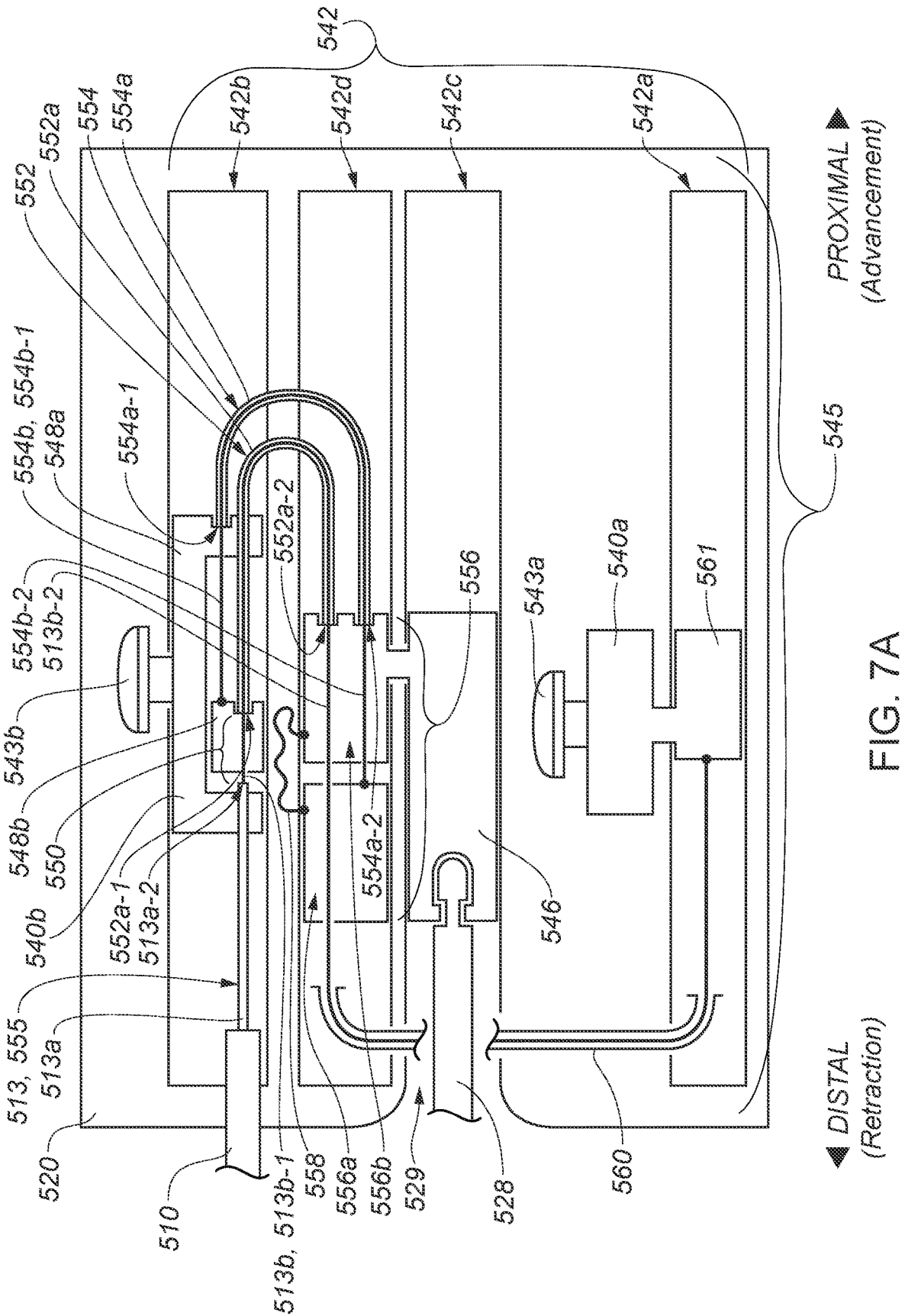
Figure 7B:
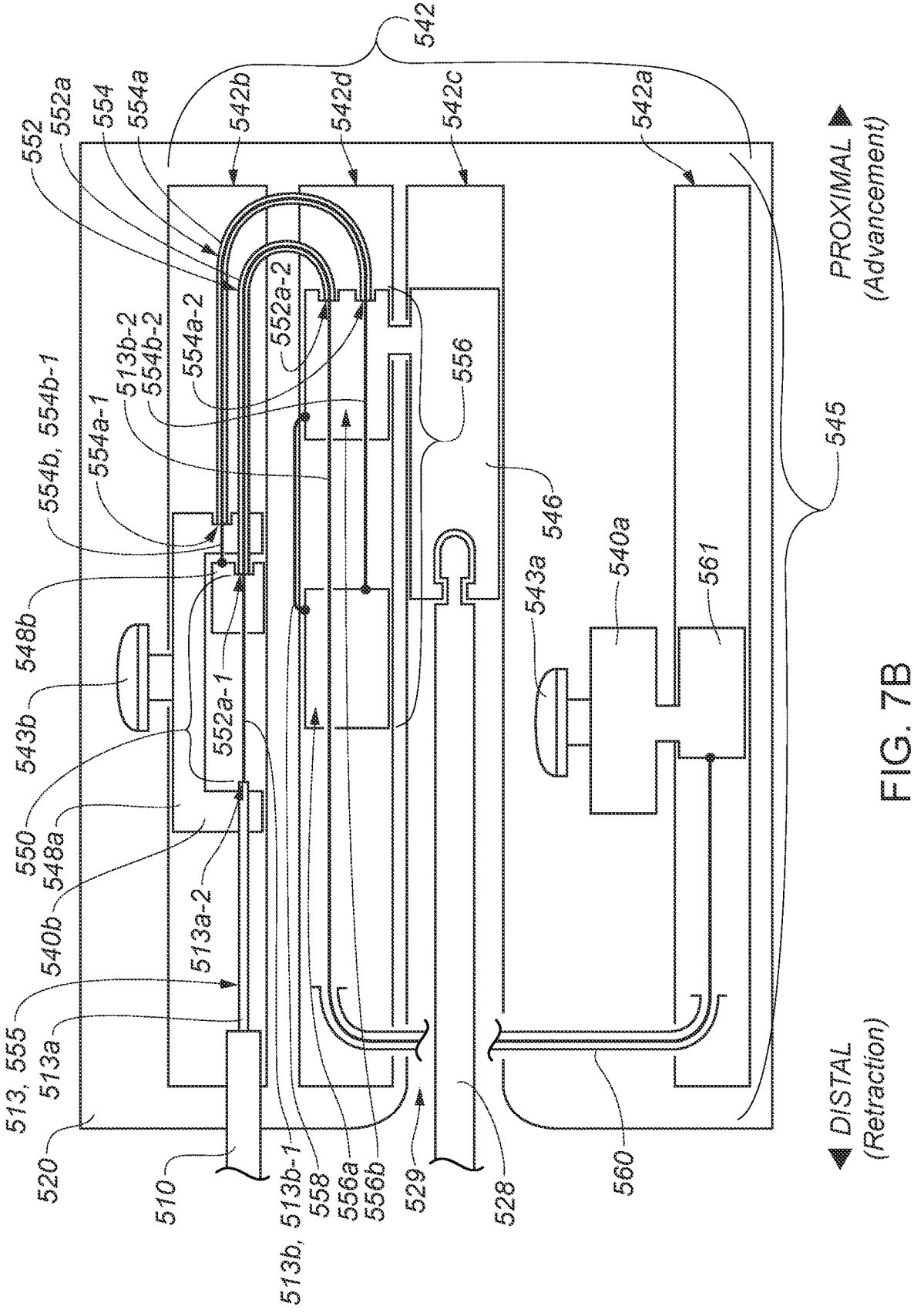

FIGS. 7A and 7B are schematic representations of at least one actuator at two successive points in time as employed in some example embodiments.

Figure 8A:
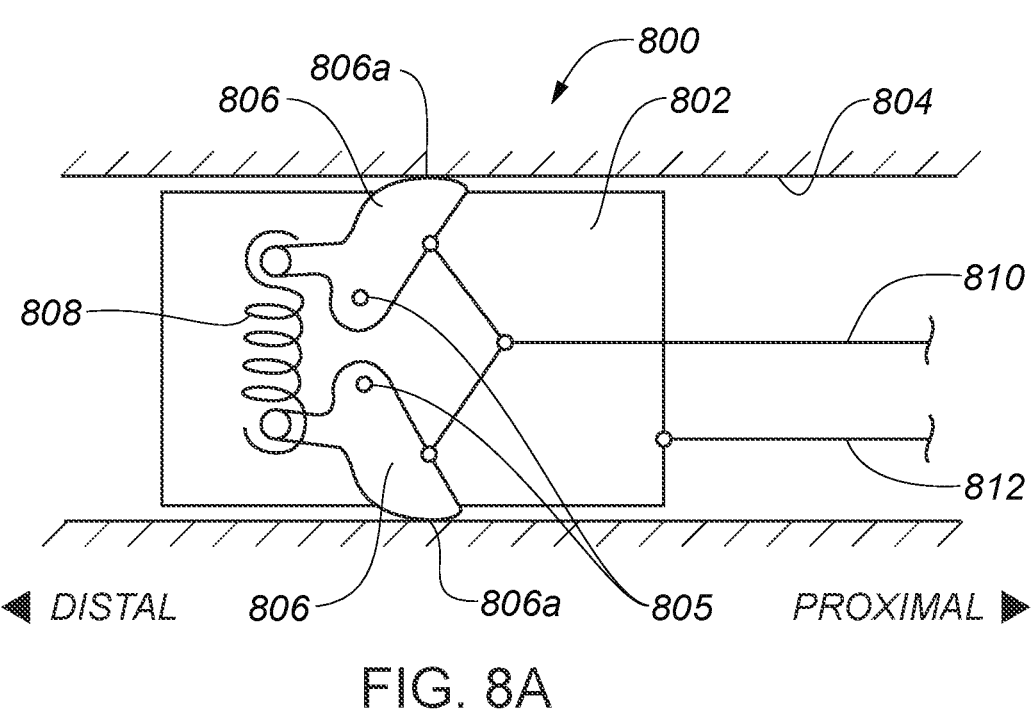
Figure 8B:
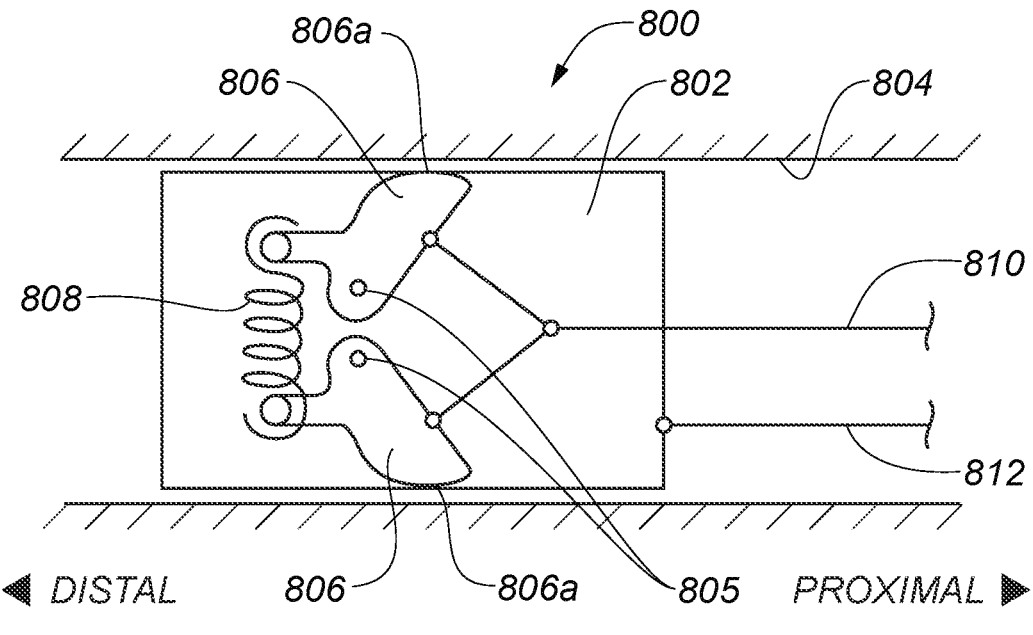

FIGS. 8A and 8B are schematic views of a locking device at two successive points in time as employed in some example embodiments.

Figure 9A:
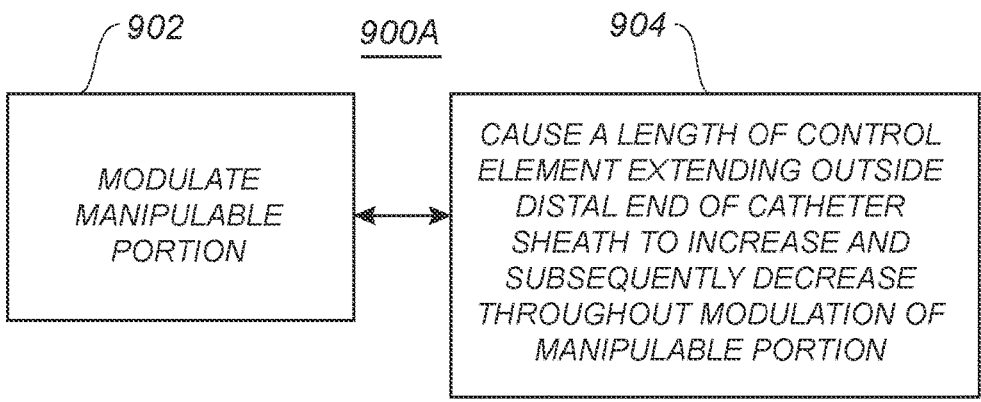

FIG. 9A is a flow chart representing a method for controlling a catheter system, according to some example embodiments.

Figure 9B:
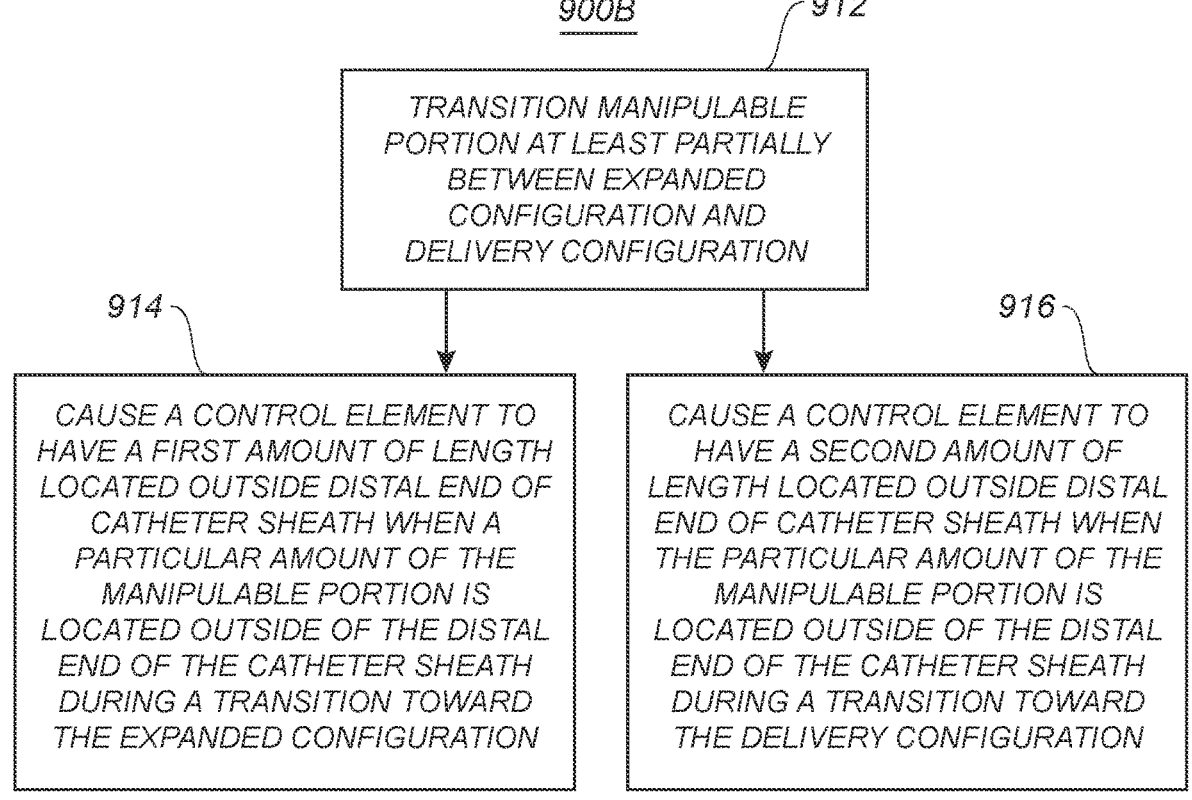

FIG. 9B is a flow chart representing a method for controlling a catheter system, according to some example embodiments.

FIG. 9C is an exploded view of one of the blocks in the flow chart of FIG. 9B, according to some example embodiments.

FIG. 9D is a flow chart representing a method for controlling a catheter system, according to some example embodiments.

FIG. 9E is a flow chart representing a method for controlling a catheter system, according to some example embodiments.

FIGS. 10A, 10B, 10C, and 10D illustrate a slider locking device, according to some example embodiments.

FIG. 11 is a flow chart representing a method of operating a medical device system, according to some example embodiments.

Figure 12A:
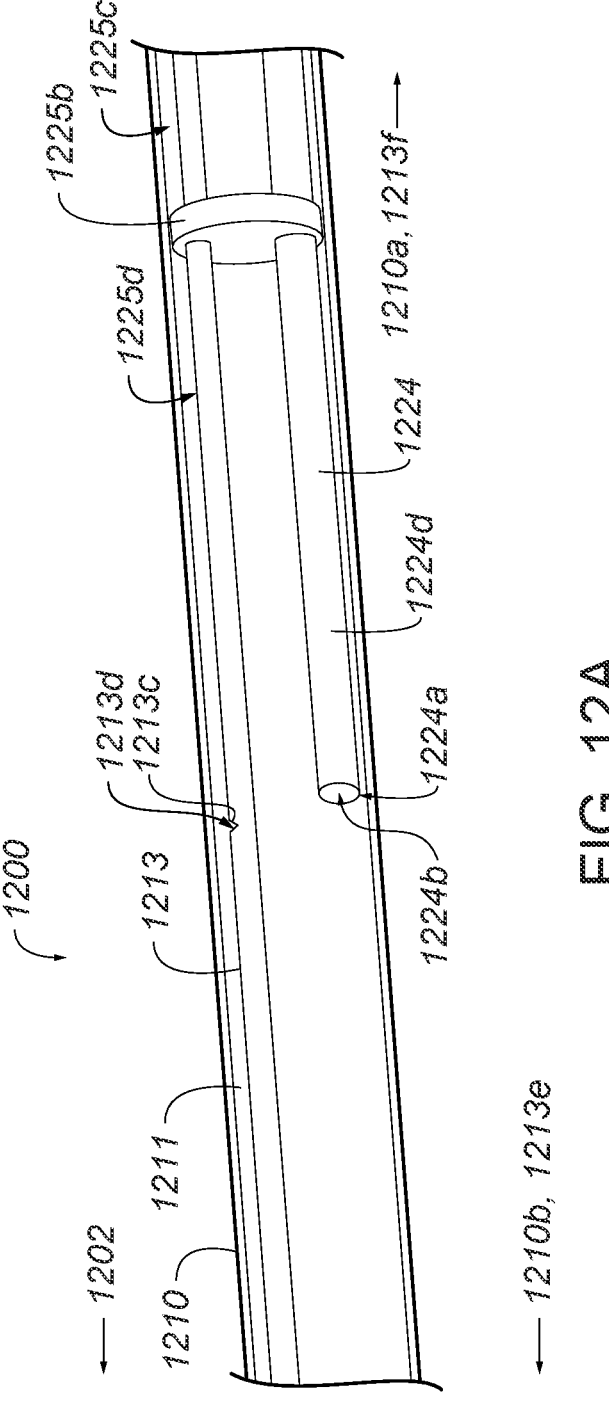

FIG. 12A is a perspective side view of at least a portion of a catheter system, according to some example embodiments.

Figure 12B:
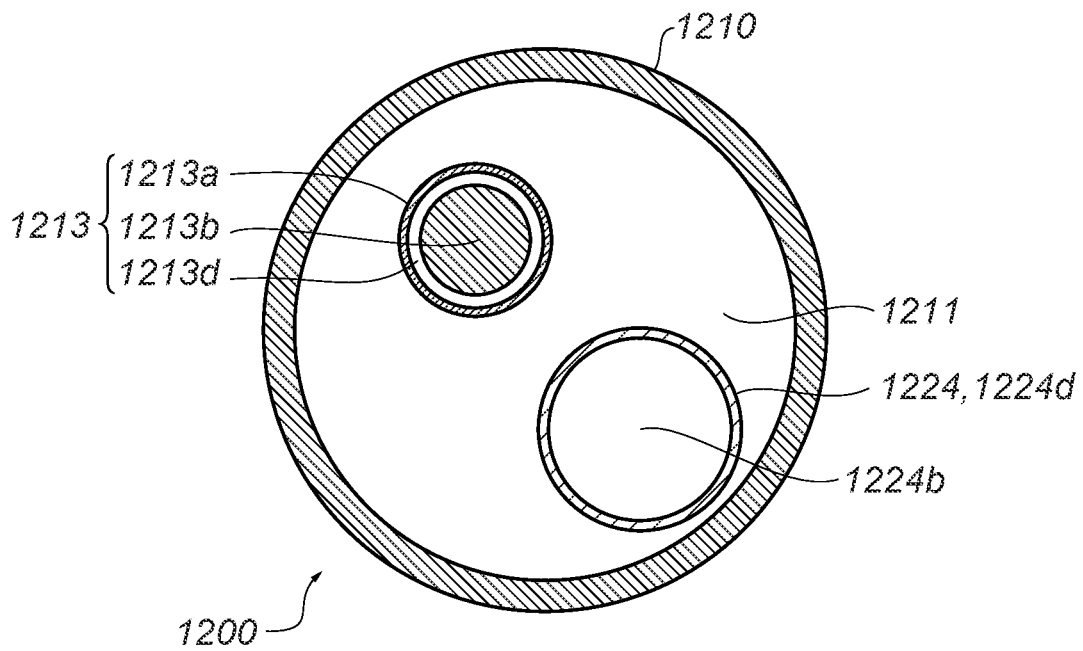

FIG. 12B is a schematic cross-sectional view of at least a portion of a catheter system, according to some example embodiments.

DETAILED DESCRIPTION

According to some embodiments of the present invention, a medical device system includes a catheter sheath and an elongated catheter shaft sized for delivery through a lumen of the catheter sheath. The catheter shaft may be operatively coupled to an end effector at or adjacent a distal end of the catheter shaft. In some embodiments, the end effector may be considered a manipulable portion configured to be deliverable percutaneously or intravascularly to a bodily cavity and deployed within the bodily cavity to operate on a tissue wall of the bodily cavity. In some embodiments, the end effector is selectively moveable between a delivery configuration in which the end effector is sized to be percutaneously or intravascularly deliverable to a bodily cavity or bodily organ and an expanded or deployed configuration in which the end effector is sized too large to be percutaneously or intravascularly deliverable to a bodily cavity or bodily organ. In some embodiments, the end effector may be delivered through a natural bodily opening. According to some embodiments, the catheter shaft includes a lumen and one or more control elements. The one or more control elements may be coupled to the end effector and may reside within the lumen of the catheter shaft. According to some embodiments, physical access is provided to a portion of each of the one or more control elements. In some embodiments, the physical access is provided within an enclosure coupled to or adjacent a proximal end of the catheter shaft. According to some embodiments, severing or otherwise disabling of at least one of the one or more control elements via the physical access causes or allows for a retreat (e.g., by a release in tension) in the end effector from its deployed configuration toward its percutaneous-delivery configuration. Such retreat from the deployed configuration toward the delivery configuration facilitates safe and simplified removal of the end effector from the bodily cavity. Accordingly, for example, if a situation arises where the end effector is unable to be removed from the bodily organ by intended or designed operation of the one or more control elements, the end effector may still be removed from the bodily organ by severing or otherwise disabling of one or more of the control elements, thereby improving the medical device system's overall safety profile.

According to some embodiments, at least one particular control element of the one or more control elements includes a sleeve, which provides a lumen, and includes a flexible control cable within the lumen of the sleeve. Such lumen may be referred to as a control cable lumen, because it includes the control cable within it. Unless explicitly noted or required by context, the phrase "control cable lumen" is not intended to refer to a lumen within the control cable, because the control cable likely does not have its own interior lumen in some embodiments. Instead, unless explicitly noted or required by context, the phrase "control cable lumen" refers to the lumen within the sleeve of the control element in which the flexible control cable resides. In any event, according to some embodiments, the sleeve of the control element is provided with a liquid intake port located closer to a distal end of such sleeve than a proximal end of such sleeve. With such a liquid intake port, flushing liquid that is added into an interior of the catheter shaft may enter the lumen of the sleeve of the control element toward the distal end of the sleeve via the liquid intake port. As the liquid enters the liquid intake port, it may spread both distally and proximally within the lumen of the sleeve of the control element. If proximally-directed liquid is not needed, the liquid may be blocked in such direction, e.g., by a bulkhead. Because the liquid intake port is located distally, liquid can be provided to the distal portion of the control element quickly, so that the medical device system can be inserted into a body (i.e., of a patient) promptly, while the proximal portion of the control element continues to receive liquid, if such proximally-directed liquid is needed, e.g., for the purposes of flushing fluid (e.g., air). Accordingly, the medical device system according to some embodiments may be operably used more quickly as compared to an arrangement that provides liquid through a lumen of a control element from the proximal end of the control element to the distal end of the control element.

These and other benefits of various embodiments will be described below with reference to the figures.

In the descriptions herein, certain specific details are set forth in order to provide a thorough understanding of various embodiments of the invention. However, one skilled in the art will understand that the invention may be practiced at a more general level without these details. In other instances, well-known structures have not been shown or described in detail to avoid unnecessarily obscuring descriptions of various embodiments of the invention.

Any reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, any appearance of the phrase "in one embodiment" or "in an embodiment" or "in an example embodiment" or "in this illustrated embodiment" or "in this particular embodiment" or the like in this specification is not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects. In addition, unless otherwise explicitly noted or required by context, the word "subset" is intended to mean a set having the same or fewer elements of those present in the subset's parent or superset.

Further, the phrase "at least" is used herein at times to emphasize the possibility that other elements may exist besides those explicitly listed. However, unless otherwise explicitly noted (such as by the use of the term "only") or required by context, non-usage herein of the phrase "at least" includes the possibility that other elements exist besides those explicitly listed. For example, the phrase, 'based at least upon A' includes A, as well as the possibility of one or more other additional elements besides A. In the same manner, for example, the phrase, 'based upon A' includes A as well as the possibility of one or more other additional elements besides A. However, for example, the phrase, 'based only upon A' includes only A.

Various terms and phrases may be used herein to describe lumen-providing members, such as sleeve, shaft, sheath, conduit, tubular member, and elongate member in various contexts. It should be noted that, unless otherwise explicitly noted or required by context, such phrases are interchangeable in various embodiments. For example, where a sleeve is described as providing a lumen in some embodiments, such sleeve or at least a portion thereof may be a shaft, a sheath, a conduit, a tubular member, an elongate member or other lumen-providing member in other or the same embodiments. A lumen may be defined as an interior of a lumen of a lumen-providing member.

The word "ablation" as used in this disclosure should be understood to include any disruption to certain properties of tissue. Most commonly, the disruption is to the electrical conductivity of tissue and may be achieved by heating, which may be generated with resistive or radio-frequency (RF) techniques for example. Other properties of tissue, such as mechanical or chemical, and other means of disruption, such as optical, are included when the term "ablation" is used. In some embodiments, ablation includes electroporation. In some embodiments, ablative power levels for RF ablation may be within the range of 3 W to 5 W (as compared, e.g., to a non-tissue-ablative power level range of 50 mW to 60 mW that may be used for typical impedance determinations). In some embodiments, ratios of employed ablative power levels to employed non-tissue-ablative power levels (e.g., used for typical impedance determinations) may be: at least equal or greater than 50:1 in various embodiments; at least greater than 60:1 in some embodiments; at least greater than 80:1 in other various embodiments; and at least greater than 100:1 in yet other embodiments. In some embodiments, systems are configured to perform ablation of non-fluidic tissue while avoiding the delivery of excessive energy to fluidic tissue, because energy that is sufficient to ablate non-fluidic tissue may also impact fluidic tissue in some circumstances. For example, energy that is sufficient to ablate non-fluidic tissue, in some circumstances, may cause blood (an example of fluidic tissue)

to coagulate. In these and other embodiments where ablative energy transferred to fluidic tissue is not desired, it should be understood that any statement or reference to the 'ablation of tissue' or the like in these contexts is intended to refer to ablation of non-fluidic tissue, as opposed to ablation of fluidic tissue. Techniques, according to some embodiments disclosed herein, facilitate the detection of conditions where energy that is intended to ablate non-fluidic tissue might unintentionally be delivered to blood or another object.

The word "fluid" as used in this disclosure should be understood to include any fluid that can be contained within a bodily cavity or can flow into or out of, or both into and out of a bodily cavity via one or more bodily openings positioned in fluid communication with the bodily cavity. In some embodiments, the word "fluid" may include fluid that is not inherent to the bodily cavity, such as saline or other fluid that might be artificially introduced into the bodily cavity or recirculated along path that flows at least in part within the bodily cavity. In the case of cardiac applications, fluid such as blood will flow into and out of various intra-cardiac cavities (e.g., a left atrium or right atrium). In addition, the word "fluid" is intended to include liquid and gas, while the word "liquid" is intended to exclude gas.

The words "bodily opening" as used in this disclosure should be understood to include, for example, a naturally occurring bodily opening or channel or lumen; a bodily opening or channel or lumen or perforation formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath or catheter introducer) may be present in various embodiments. These elements may provide a passageway through a bodily opening for various devices employed in various embodiments.

The words "bodily cavity" as used in this disclosure should be understood to mean a cavity in a body. The bodily cavity may be a cavity provided in a bodily organ (e.g., an intra-cardiac cavity or chamber of a heart). The bodily cavity may be provided by a bodily vessel.

The word "tissue" is often used in this disclosure, and tissue may include non-fluidic tissue and fluidic tissue. Non-fluidic tissue generally (or predominantly) has solid-like properties, such as tissue that forms a surface of a body or a surface within a bodily cavity, a surface of an anatomical feature or a surface of a feature associated with a bodily opening positioned in fluid communication with the bodily cavity. Non-fluidic tissue may include part or all of a tissue wall or membrane that defines a surface of the bodily cavity. In this regard, the tissue may form an interior surface of the cavity that at least partially surrounds a fluid within the cavity. In the case of cardiac applications, non-fluidic tissue may include tissue used to form an interior surface of an intra-cardiac cavity such as a left atrium or right atrium. Fluidic tissue, on the other hand, generally (or predominantly) has fluid-like properties (as compared to solid-like properties). An example of fluidic tissue is blood. In this regard, it should be noted that fluidic tissue may have some solid-like component(s) (e.g., fluidic tissue may include solid-like components), and non-fluidic tissue may have some fluid-like component(s) (e.g., non-fluidic tissue may include fluidic tissue within it). Unless otherwise explicitly noted or required by context, the word "tissue" should include non-fluidic tissue and fluidic tissue. However, some contexts where the word "tissue" would not include fluidic tissue are when tissue ablation is discussed, and ablation of fluidic tissue could be undesired, as discussed below. In various embodiments, non-fluidic tissue does not include excised tissue.

The term "transducer" as used in this disclosure should be interpreted broadly as any device capable at least of distinguishing between fluid and non-fluidic tissue, sensing temperature, creating heat, ablating tissue and measuring electrical activity of a tissue surface, stimulating tissue or any combination thereof. A transducer may convert input energy of one form into output energy of another form. Without limitation, a transducer may include an electrode, and references to a "transducer" herein may be replaced with "electrode" according to some embodiments. Without limitation, a transducer may include an electrode or a sensing device, or both an electrode and a sensing device. An electrode, in some embodiments, may be configured at least as a sensing device. Because a transducer may include an electrode according to various embodiments, any reference herein to a transducer may also imply a reference to an electrode, or vice versa. A transducer may be constructed from several parts, which may be discrete components or may be integrally formed.

The term "activation" and related terms, at least when used in the context of activating a particular function of one or more transducers or electrodes, such as those disclosed herein, should be interpreted broadly as making active the particular function, for example. Particular functions may include, but are not limited to, tissue ablation, sensing electrophysiological activity, sensing temperature and sensing electrical characteristics (e.g., tissue impedance). For example, in some embodiments, activation of a tissue ablation function of a particular transducer is initiated by causing energy sufficient for tissue ablation from an energy source device system to be delivered to the particular transducer. In some embodiments, activation of a tissue ablation function of a particular electrode is initiated by causing energy from an energy source device system to be delivered to the particular electrode, the energy sufficient for tissue ablation. In some embodiments, activation of a tissue ablation function of a particular electrode is initiated by causing energy sufficient for tissue ablation to be transmitted by the particular electrode. Alternatively, in some embodiments, the activation may be deemed to be initiated when the particular transducer or particular electrode causes tissue that is to be ablated to reach or acquire a temperature sufficient for ablation of the tissue, which may be due to the energy provided by the energy source device system or due to the energy transmitted by the particular transducer or electrode. In some embodiments, the activation may last for a duration concluding when the ablation function is no longer active, such as when energy sufficient for the tissue ablation is no longer provided to, or transmitted by, the particular transducer or particular electrode. Alternatively, in some embodiments, the activation period may be deemed to be concluded when the tissue that is being ablated has a temperature below that sufficient for ablation of the tissue, which may be due to a reduction or cessation of the energy provided by the energy source device system or transmitted by the particular transducer or electrode. In some contexts, however, the word "activation" may merely refer to the initiation of the activating of a particular function, as opposed to referring to both the initiation of the activating of the particular function and the subsequent duration in which the particular function is active. In these contexts, the phrase or a phrase similar to "activation initiation" may be used. For example, in some embodiments activation initiation may cause initiation of a transmission of energy (e.g., energy sufficient for tissue ablation) from a particular transducer or electrode.

The term "program" in this disclosure should be interpreted as a set of instructions or modules that may be executed by one or more components in a system, such as a controller system or data processing device system, in order to cause the system to perform one or more operations. The set of instructions or modules may be stored by any kind of memory device, such as those described subsequently with respect to the memory device system 130, 330, or both, shown at least in FIGS. 1, 3A, and 3B. In addition, this disclosure may describe or similarly describe that the instructions or modules of a program are configured to cause the performance of an action.

The phrase "configured to" in this context is intended to include at least (a) instructions or modules that are presently in a form executable by one or more data processing devices to cause performance of the action (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the action (e.g., in the case where the instructions or modules are encrypted in a non-executable manner, but through performance of a decryption process, would be translated into a form ready for execution). The word "module" may be defined as a set of instructions. In some instances, this disclosure describes that the instructions or modules of a program perform a function. Such descriptions should be deemed to be equivalent to describing that the instructions or modules are configured to cause the performance of the function.

Further, it is understood that information or data may be operated upon, manipulated, or converted into different forms as it moves through various devices or workflows. In this regard, unless otherwise explicitly noted or required by context, it is intended that any reference herein to information or data includes modifications to that information or data. For example, "data X" may be encrypted for transmission, and a reference to "data X" is intended to include both its encrypted and unencrypted forms. For another example, "image information Y" may undergo a noise filtering process, and a reference to "image information Y" is intended to include both the pre-processed form and the noise-filtered form. In other words, both the pre-processed form and the noise-filtered form are considered to be "image information Y". In order to stress this point, the phrase "or a derivative thereof" or the like may be used herein. Continuing the preceding example, the phrase "image information Y or a derivative thereof" refers to both the pre-processed form and the noise-filtered form of "image information Y", with the noise-filtered form potentially being considered a derivative of "image information Y". However, non-usage of the phrase "or a derivative thereof" or the like nonetheless includes derivatives or modifications of information or data just as usage of such a phrase does, as such a phrase, when used, is merely used for emphasis.

Each of the phrases "derived from", "derivation of", "derivation thereof" and the like is intended to mean to come from at least some part of a source, be created from at least some part of a source, or be developed as a result of a process in which at least some part of a source forms an input. For example, a data set derived from some particular portion of data may include at least some part of the particular portion of data, or may be created from at least part of the particular portion of data, or may be developed in response to a data manipulation process in which at least part of the particular portion of data forms an input. In some embodiments, a data set may be derived from a subset of the particular portion of data. In some embodiments, the particular portion of data is analyzed to identify a particular subset of the particular portion of data, and a data set is derived from the subset. In various ones of these embodiments, the subset may include some, but not all, of the particular portion of data. In some embodiments, changes in least one part of a particular portion of data may result in changes in a data set derived at least in part from the particular portion of data.

In this regard, each of the phrases "derived from", "derivation of", "derivation thereof", and the like may be used herein merely to emphasize the possibility that such data or information may be modified or subject to one or more operations. For example, if a device generates first data for display, the process of converting the generated first data into a format capable of being displayed may alter the first data. This altered form of the first data may be considered a derivative or derivation of the first data. For instance, the first data may be a one-dimensional array of numbers, but the display of the first data may be a color-coded bar chart representing the numbers in the array. For another example, if the above-mentioned first data is transmitted over a network, the process of converting the first data into a format acceptable for network transmission or understanding by a receiving device may alter the first data. As before, this altered form of the first data may be considered a derivative or derivation of the first data. For yet another example, generated first data may undergo a mathematical operation, a scaling, or a combining with other data to generate other data that may be considered derived from the first data. In this regard, it can be seen that data is commonly changing in form or being combined with other data throughout its movement through one or more data processing device systems, and any reference to information or data herein is intended to include these and like changes, regardless of whether or not the phrase "derived from" or "derivation of" or "derivation thereof" or the like is used in reference to the information or data. As indicated above, usage of the phrase "derived from" or "derivation of" or "derivation thereof" or the like merely emphasizes the possibility of such changes. Accordingly, the addition of or deletion of the phrase "derived from" or "derivation of" or "derivation thereof" or the like should have no impact on the interpretation of the respective data or information. For example, the above-discussed color-coded bar chart may be considered a derivative of the respective first data or may be considered the respective first data itself.

The word "device", the word "system", and the phrase "device system" are intended to be interchangeable and each is intended to include one or more physical devices or sub-devices (e.g., pieces of equipment) that interact to perform one or more functions, regardless of whether such devices or sub-devices are located within a same housing or different housings. In this regard, for example, the phrase "electrode-based device" may equivalently be referred to as an "electrode-based device system", or vice versa. Similarly, the phrase "medical system" may equivalently be referred to as a "medical device system", or vice versa.

In some contexts, the term "adjacent" may be used to refer to objects that do not have another substantially similar object between them. For example, object A and object B could be considered adjacent if they contact each other (and, thus, it could be considered that no other object is between them), or if they do not contact each other but no other object that is substantially similar to object A, object B, or both objects A and B, depending on context, is between them. In some contexts, the term "adjacent" additionally refers to at least a sufficient proximity between the objects defined as adjacent to allow the objects to interact in a designated way. For example, if object A performs an action on an adjacent object B, objects A and B would have at least a sufficient proximity to allow object A to perform the action on object B. In this regard, some actions may require contact between the associated objects, such that if object A performs such an action on an adjacent object B, objects A and B would be in contact.

Further, the phrase "in response to" may be used in this disclosure. For example, this phrase might be used in the following context, where an event A occurs in response to the occurrence of an event B. In this regard, such phrase includes, for example, that at least the occurrence of the event B causes or triggers the event A.

In some contexts, the term "proximity" is used in this disclosure to refer to a degree of closeness between various objects. For example, a proximity between an object A and an object B could be considered to mean a degree of closeness of (a) object A to object B, (b) object B to object A, or both (a) and (b). Such degree of closeness may include contact in some embodiments.

The phrase "physically coupled" is intended to include, for example, a coupling between two objects that involves a physical contacting of the two objects. The phrase "fixedly coupled" is intended to include, for example, a secure coupling between two objects that may, in some instances, not involve a mechanism configured to release the coupling of the two objects. The phrase "operatively coupled" is intended to include, for example, a coupling between two objects that transmits force, energy, information, or other influence at least from one of the two objects to the other of the two objects. An operative coupling does not exclude the possibility of a physical or fixed coupling. In this regard, in some embodiments, reference to an operative coupling includes a physical coupling, and in other embodiments, reference to an operative coupling includes a fixed coupling. Mere usage of the word "coupled" without preceding it with the adjective "physically", the adjective "fixedly", the adverb "operatively", or the like, should be interpreted to include any type of coupling, unless otherwise explicitly stated or required by context. In addition, when a coupling is described merely as "coupled" without a preceding type-identifier, such as "physically", "fixedly", "operatively", or the like, various embodiments of the present invention implement each of these different types of couplings, unless one or more of such other types are explicitly excluded or required by context to be excluded. In some embodiments, reference to an operative coupling (e.g., operatively coupled) should be treated as reference to a coupling (e.g., coupled), without a preceding type-identifier.

Figure 1:
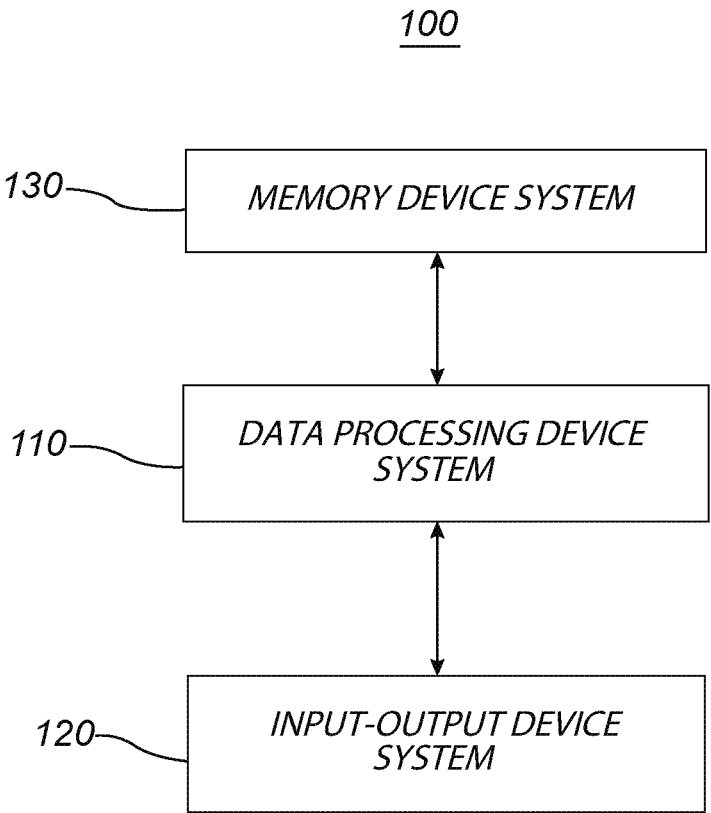
FIG. 1 is a schematic representation of a system, according to some example embodiments, the system including a data processing device system, an input-output device system, and a processor-accessible memory device system.

FIG. 1 schematically illustrates a system 100, according to some embodiments. The system 100 may be included as part of a medical device system or catheter device system according to various embodiments described herein. The system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement methods by controlling, driving, or otherwise interacting with various structural components described herein, including, but not limited to, one or more of the various structural components illustrated in at least FIGS. 2-5, 7, 8, 10, and 12. Each of the phrases "data processing device", "data processor", "processor", and "computer" is intended to include any data processing device, such as a central processing unit ("CPU"), a desktop computer, a laptop computer, a mainframe computer, a tablet computer, a personal digital assistant, a cellular phone, and any other device for processing data, managing data, or handling data, whether implemented with electrical, magnetic, optical, biological components, or otherwise.

The memory device system 130 includes one or more processor-accessible memory devices configured to store information, including the information needed to execute the methods, including, in some embodiments, some or all of one or more of the methods of FIG. 9, implemented by the data processing device system 110. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single housing or data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include or be a processor-accessible (or computer-readable) data storage medium. In some embodiments, each of the phrases "processor-accessible memory" and "processor-accessible memory device" is intended to include or be a non-transitory processor-accessible (or computer-readable) data storage medium. In some embodiments, the memory device system 130 may be considered to include or be a non-transitory processor-accessible (or computer-readable) data storage medium system. And, in some embodiments, the memory device system 130 may be considered to include or be a non-transitory processor-accessible (or computer-readable) data storage medium system.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing device system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 can be implemented by a single application-specific integrated circuit (ASIC) in some embodiments.

The input-output device system 120 may include a mouse, a keyboard, a touch screen, a computer, a processor-accessible memory device, some or all of a medical device system or catheter device system (e.g., at least systems 200, 300, 400, 500, 1200 described below), or any device or combination of devices from which a desired selection, desired information, instructions, or any other data is input to the data processing device system 110. The input-output device system 120 may include a user-activatable control system that is responsive to a user action. The input-output device system 120 may include any suitable interface for receiving a selection, information, instructions, or any other data from other devices or systems described in various ones of the embodiments. In this regard, the input-output device system 120 may include various ones or portions of other systems or devices described in various embodiments.

The input-output device system 120 also may include an image generating device system, a display device system, a processor-accessible memory device, some or all of a medical device system or catheter device system (e.g., at least systems 200, 300, 500, 1200 described below), or any device or combination of devices to which information, instructions, or any other data is output by the data processing device system 110. In this regard, if the input-output device system 120 includes a processor-accessible memory device, such memory device may or may not form part or all of the memory device system 130. The input-output device system 120 may include any suitable interface for outputting information, instructions, or any other data to other devices or systems described in various ones of the embodiments. In this regard, the input-output device system 120 may include various other devices or systems described in various embodiments.

Various embodiments of catheter systems are described herein. It should be noted that any catheter system described herein may also be referred to as a medical system. Some of the described devices of such systems are medical devices that are percutaneously or intravascularly deployed. Some of the described devices are deployed through a bodily opening that is accessible without puncturing, cutting or otherwise perforating bodily tissue to create an access to the bodily opening. Some of the described devices employ transducer-based devices or device systems. Some of the described devices are moveable between a delivery or unexpanded configuration in which a portion of the device is sized, shaped, or both for passage through a bodily opening leading to a bodily cavity, and an expanded or deployed configuration in which the portion of the device has a size, shape, or both too large for passage through the bodily opening leading to the bodily cavity. An example of an expanded or deployed configuration is when the portion of the catheter system is in its intended-deployed-operational state inside the bodily cavity. Another example of the expanded or deployed configuration is when the portion of the catheter system is being changed from the delivery configuration to the intended-deployed-operational state to a point where the portion of the device now has a size, shape, or both too large for passage through the bodily opening leading to the bodily cavity.

In some example embodiments, the catheter system includes transducers that sense characteristics (e.g., convective cooling, permittivity, force) that distinguish between fluid, such as a fluidic tissue (e.g., blood), and tissue forming an interior surface of the bodily cavity. Such sensed characteristics can allow a medical device system to map the cavity, for example using positions of openings or ports into and out of the cavity to determine a position or orientation (i.e., pose), or both of the portion of the device in the bodily cavity. In some example embodiments, the described devices are capable of ablating tissue in a desired pattern within the bodily cavity. In some example embodiments, the devices are capable of sensing characteristics (e.g., electrophysiological activity) indicative of whether an ablation has been successful. In some example embodiments, the devices are capable of providing stimulation (e.g., electrical stimulation) to tissue within the bodily cavity. Electrical stimulation may include pacing.

In some embodiments, one or more lumens of the catheter system (e.g., at least system 500 or 1200 described below) may provide a flow of fluid. For example, ablation catheters employing cryogenic ablation techniques provide a flow of cryogenic fluid through a lumen in a catheter shaft to an end effector. In some cases, a fluid is delivered through a lumen provided in a catheter shaft to cause an enlargement in an expandable structure (for example, a balloon in a balloon catheter). In some example embodiments, one or more lumens of the catheter system (e.g., at least FIG. 3A, 3B, 4, or system 500 or 1200 described below) may be flushed to remove fluids, such as gases (e.g., air), from various portions of the catheter system.

In this regard, in some example embodiments, a fluid-providing portion (e.g., including fluid-providing portion 1224, according to some embodiments, described below with respect to at least FIG. 12A) of the catheter system is configured to provide fluid, for example, to flush various lumens of the catheter system. In some embodiments, the fluid-providing portion of the catheter system may include one or more of the lumens (e.g., fluid-providing portion lumen 1224b or catheter shaft lumen 1211, possibly among others, according to some embodiments, described below with respect to at least FIG. 12A) of the catheter system. In some embodiments, the fluid-providing portion may include one or more ports (e.g., ports 1224a, 1224c, according to some embodiments, described below with respect to at least FIGS. 5Z and 12A) to provide fluid inlet or outlet. In some embodiments, at least one of the one or more ports of the fluid-providing portion may be located at a distal end of the respective lumen or at least closer to a distal end of a respective lumen than a proximal end of the respective lumen. In some embodiments, at least one of the ports is located at or adjacent the proximal end of the respective lumen. In some embodiments, the fluid-providing portion of the catheter system includes an elongate fluid-providing member (e.g., an elongate portion of fluid-providing portion 1224, catheter shaft lumen 1211, or control cable sleeve 1213a, according to some embodiments). The elongate fluid-providing member may include a proximal end and a distal end. The elongate fluid-providing member may include a lumen extending between the proximal end and the distal end. In some embodiments, a control cable (e.g., control cable 1213b, according to some embodiments, described below with respect to at least FIG. 12A) may be located within the lumen of the elongate fluid-providing member. In some example embodiments, the catheter system includes a control element (e.g., control element 1213, according to some embodiments, described below with respect to at least FIG. 12A). In some embodiments, the control element includes an elongate member (e.g., a sleeve 1213a) including a lumen (e.g., lumen 1213d, according to some embodiments, described below with respect to at least FIG. 12A) and a control cable (e.g., control cable 1213b) received within the lumen of the elongate member. In some embodiments, the elongate fluid-providing member and at least part of the elongate member of the control element are the same. However, in some embodiments, the elongate fluid-providing member is separate from the control element. In some embodiments where the elongate fluid-providing member and the elongate control element are the same, a port of the fluid-providing portion is implemented as a liquid intake port (e.g., liquid intake port 1213c, according to some embodiments, described below with respect to at least FIG. 12A), such as provided by a notch, channel, hole, or other opening that interrupts the elongate member of the control element. The liquid intake port may be configured to provide ingress of fluid to flush the lumen of the elongate member of the control element. In some embodiments, the control cable may be present in the lumen of the elongate member when fluid is received in the lumen of the elongate member to flush the lumen of the elongate member. The fluid-providing portion, the control element, or both may be placed in a same or different lumens of the catheter system. In some embodiments the liquid intake port (e.g., liquid intake port 1213c) is located in the catheter shaft (e.g., 1210) closer to a distal end of the sleeve (e.g., 1213a) that provides the flushed lumen (e.g., 1213d) than to a proximal end of such sleeve.

Although some of the embodiments disclosed herein are described in the context of flushing of fluid, such as air, from one or more lumens, the same or similar embodiments may be executed to provide cryogenic fluid for cryogenic ablation or for providing fluid to expand or inflate an expandable structure, such as a balloon catheter by way of non-limiting examples.

Figure 2:
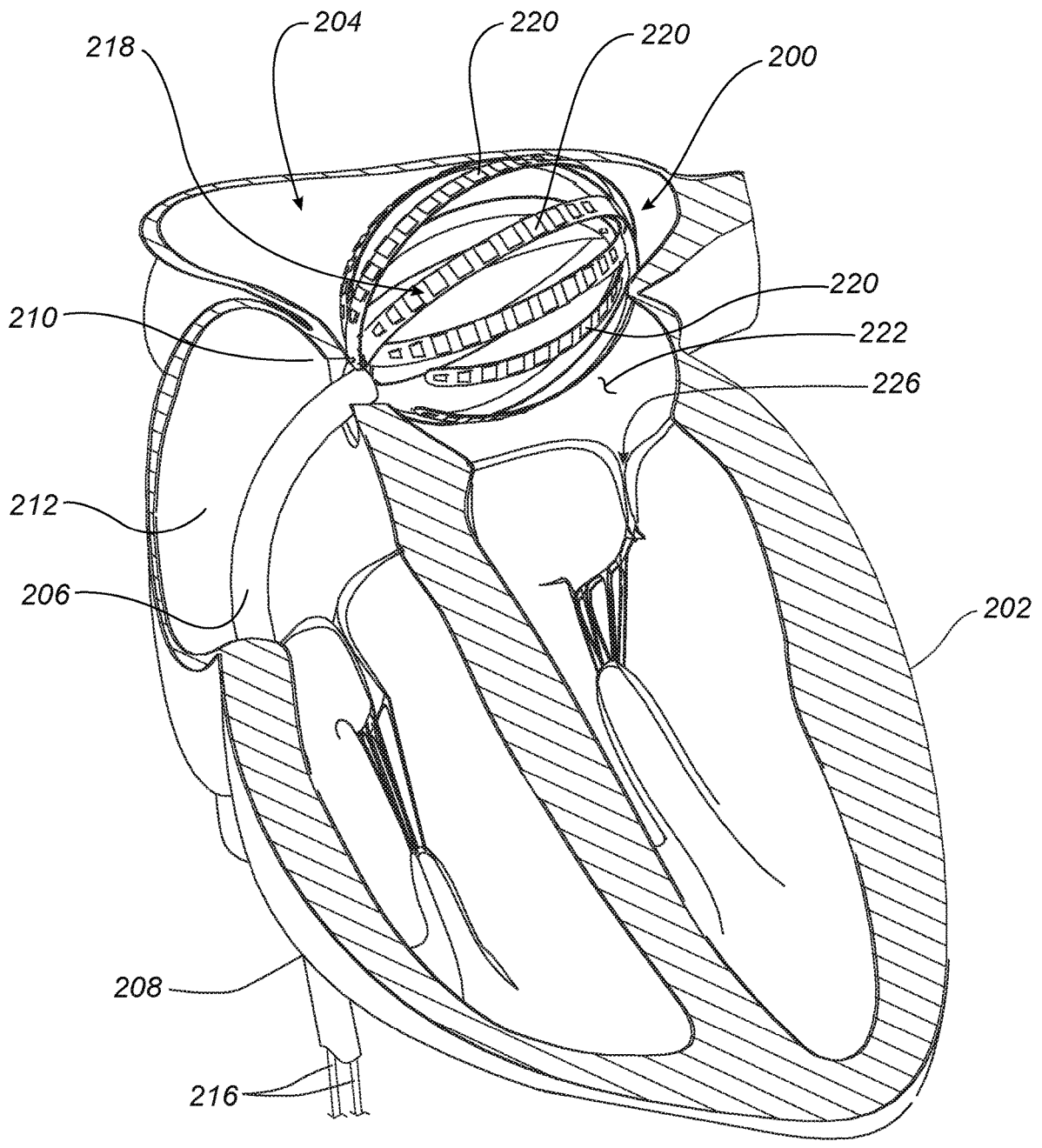
FIG. 2 is a cutaway diagram of a heart showing a transducer-based device percutaneously placed in a left atrium of the heart, according to some example embodiments.

FIG. 2 shows a portion of a catheter system, according to some embodiments, such portion including a transducer-based device 200, which may be at least part of a medical device useful in investigating or treating a bodily organ, for example a heart 202, according to some example embodiments. The transducer-based device 200 may also be referred to as a manipulable portion or end effector, due to its ability to have its size, shape, or both size and shape altered, according to some embodiments described below. Transducer-based device 200 can be percutaneously or intra-vascularly inserted into a portion of the heart 202, such as an intra-cardiac cavity like left atrium 204.

In the example of FIG. 2, the illustrated portion of the catheter system also includes a catheter 206, which may be inserted via the inferior vena cava 208 and may penetrate through a bodily opening in transatrial septum 210 from right atrium 212. In other embodiments, other paths may be taken.

Catheter 206 includes an elongated flexible rod or shaft member appropriately sized to be delivered percutaneously or intravascularly. Various portions of catheter 206 may be steerable. Catheter 206 may include one or more lumens. The lumen(s) may carry one or more communications or power paths, or both. For example, the lumens(s) may carry one or more electrical conductors 216 (two shown in this embodiment). Electrical conductors 216 provide electrical connections to transducer-based device 200 that are accessible externally from a body (i.e., of a patient) in which the transducer-based device 200 is inserted. In some embodiments, the elongated flexible rod or shaft member includes an elongated fluid-providing member. The elongated fluid-providing member may be located within a lumen of the elongated flexible rod or shaft member.

In various embodiments, transducer-based device, or manipulable portion, 200 includes a frame or structure 218, which assumes an unexpanded configuration for delivery to left atrium 204. Structure 218 is expanded (i.e., shown in a deployed or expanded configuration in FIG. 2) upon delivery to left atrium 204 to position a plurality of transducers 220 (three called out in FIG. 2) proximate the interior surface formed by tissue 222 of left atrium 204. In this regard, it can be stated that one or more of the transducers 220 are moveable with one or more parts of the transducer-based device, or manipulable portion, 200. In some embodiments, at least some of the transducers 220 are used to sense a physical characteristic of a fluid (i.e., blood) or tissue 222, or both, that may be used to determine a position or orientation (i.e., pose), or both, of a portion of transducer-based device 200 within, or with respect to left atrium 204. For example, transducers 220 may be used to determine a location of pulmonary vein ostia (not shown) or a mitral valve 226, or both. In some embodiments, at least some of the transducers 220 may be used to selectively ablate portions of the tissue 222. For example, some of the transducers 220 may be used to ablate a pattern or path around various ones of the bodily openings, ports or pulmonary vein ostia, for instance to reduce or eliminate the occurrence of atrial fibrillation.

Figure 3A:
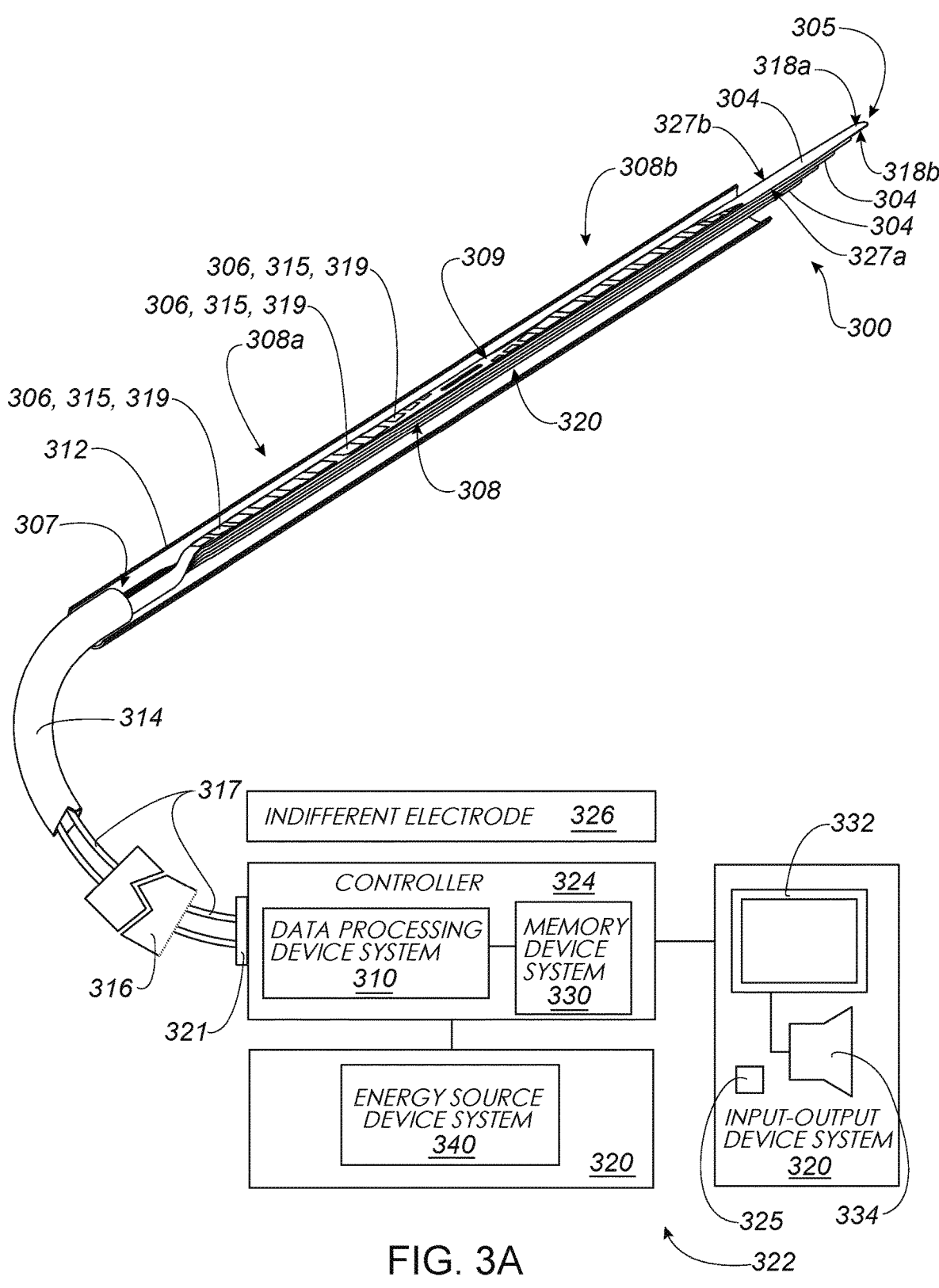
FIG. 3A is a partially schematic representation of a catheter system, according to some example embodiments, the system, which may also be referred to as a medical system, including a data processing device system, an input-output device system, a processor-accessible memory device system, and a manipulable portion shown in a delivery or unexpanded configuration.
Figure 3B:
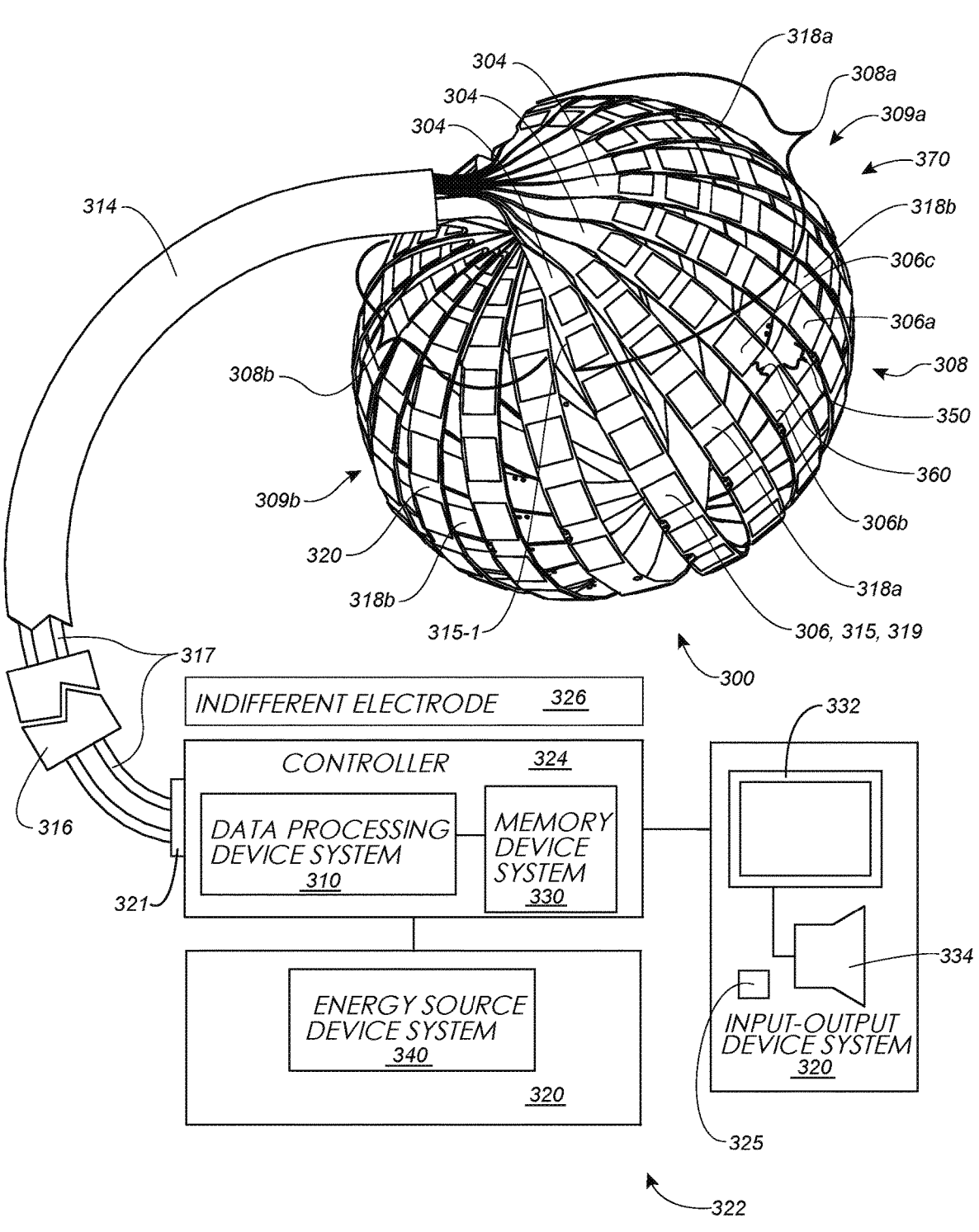
FIG. 3B is the catheter system of FIG. 3A with the manipulable portion shown in a deployed or expanded configuration, according to some example embodiments.

FIGS. 3A and 3B show a catheter system (i.e., a portion thereof shown schematically) that includes a transducer-based device 300 according to one illustrated embodiment. The transducer-based device 300 may correspond to the transducer-based device 200 and, in this regard, may also be referred to as a manipulable portion, due to its ability to have its size, shape, or both size and shape altered, according to some embodiments described below. The transducer-based device 300 may also be referred to as an end effector. Transducer-based device 300 may include a plurality of elongate members 304 (three called out in each of FIGS. 3A and 3B) and a plurality of transducers 306 (three called out in FIG. 3A, and three called out in FIG. 3B as 306*a*, 306*b* and 306*c*). As will become apparent, the plurality of transducers 306 is positionable within a bodily cavity. For example, in some embodiments, the transducers 306 are able to be positioned in a bodily cavity by movement into, within, or into and within the bodily cavity, with or without a change in a particular configuration of the plurality of transducers 306. In some embodiments, the plurality of transducers 306 are arrangeable to form a two- or three-dimensional distribution, grid or array of the transducers capable of mapping, ablating, or stimulating an inside surface of a bodily cavity or lumen without requiring mechanical scanning. As shown, for example, in FIG. 3A, the plurality of transducers 306 are arranged in a distribution receivable in a bodily cavity, as the transducer-based device 300 and its plurality of transducers 306 are located within the catheter sheath 312. Stated differently, in FIG. 3A, for example, the plurality of transducers 306 are arranged in a distribution suitable for delivery to a bodily cavity. (It should also be noted, however, that the expanded or deployed configuration (e.g., FIGS. 2, 3B) may also be considered to have the transducers 306 arranged in a distribution receivable in a bodily cavity, as the transducer-based device 300 and its transducers 306 may be returned to the delivery configuration of FIG. 3A, for example.) In some embodiments, each of the transducers 306 includes an electrode 315 (one called out in FIG. 3B) including an energy transmission surface 319 (one called out in FIG. 3B) suitable for transmitting energy in various directions. In some embodiments, tissue-ablating energy is transmitted toward or away from an electrode 315. In some embodiments, tissue-based electrophysiological energy is transmitted toward an electrode 315.

The elongate members 304 form part of a manipulable portion or end effector, and in various embodiments, are arranged in a frame or structure 308 that is selectively moveable between an unexpanded or delivery configuration (i.e., as shown in at least FIG. 3A) and an expanded or deployed configuration (i.e., as shown in at least FIG. 3B) that may be used to position elongate members 304 against a tissue surface within the bodily cavity or position the elongate members 304 in the vicinity of or in contact with the tissue surface. In this regard, it may also be stated that the transducer-based device, or manipulable portion, 300 is selectively moveable between an unexpanded or delivery configuration (i.e., as shown in at least FIG. 3A) and an expanded or deployed configuration (i.e., as shown in at least FIG. 3B). In some embodiments, the transducer-based device, or manipulable portion, 300, (e.g., the structure 308 thereof) has a size, shape, or both a size and a shape in the unexpanded or delivery configuration suitable for percutaneous delivery through a bodily opening (for example, via catheter sheath 312, not shown in FIG. 3B) to the bodily cavity. In some embodiments, structure 308 has a size, shape, or both a size and a shape in the expanded or deployed configuration too large for percutaneous delivery through a bodily opening (i.e., via catheter sheath 312) to the bodily cavity. The elongate members 304 may form part of a flexible circuit structure (i.e., also known as a flexible printed circuit board (PCB) circuit). The elongate members 304 can include a plurality of different material layers, and each of the elongate members 304 can include a plurality of different material layers. The structure 308 can include a shape memory material, for instance Nitinol. The structure 308 can include a metallic material, for instance stainless steel, or non-metallic material, for instance polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (i.e., pose) or both of structure 308 in the bodily cavity, or the requirements for successful ablation of a desired pattern. The number of elongate members depicted in FIG. 3B is non-limiting.

FIG. 4 is a schematic side elevation view of at least a portion of a transducer-based device 400 that includes a flexible circuit structure 401 that is employed to provide a plurality of transducers 406 (two called out) according to an example embodiment. In some embodiments, the flexible circuit structure 401 may form part of a structure (e.g., structure 308) that is selectively moveable between a delivery configuration sized for percutaneous delivery and an expanded or deployed configuration sized too large for percutaneous delivery. In some embodiments, the flexible circuit structure 401 may be located on, or form at least part of, of a structural component (e.g., elongate member 304) of a transducer-based device system.

The flexible circuit structure 401 can be formed by various techniques including flexible printed circuit techniques. In some embodiments, the flexible circuit structure 401 includes various layers including flexible layers 403a, 403b and 403c (i.e., collectively flexible layers 403). In some embodiments, each of flexible layers 403 includes an electrical insulator material (e.g., polyimide). One or more of the flexible layers 403 can include a different material than another of the flexible layers 403. In some embodiments, the flexible circuit structure 401 includes various electrically conductive layers 404a, 404b and 404c (collectively electrically conductive layers 404) that are interleaved with the flexible layers 403. In some embodiments, each of the electrically conductive layers 404 is patterned to form various electrically conductive elements. For example, electrically conductive layer 404a is patterned to form a respective electrode 415 of each of the transducers 406. Electrodes 415 have respective electrode edges 415-1 that form a periphery of an electrically conductive surface associated with the respective electrode 415. FIG. 3B shows another example of electrode edges 315-1 and illustrates that the electrode edges can define electrically-conductive-surface-peripheries of various shapes.

Returning to FIG. 4, electrically conductive layer 404b is patterned, in some embodiments, to form respective temperature sensors 408 for each of the transducers 406 as well as various leads 410a arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404c is patterned to provide portions of various leads 410b arranged to provide an electrical communication path to electrodes 415. In some embodiments, leads 410b are arranged to pass though vias in flexible layers 403a and 403b to connect with electrodes 415. Although FIG. 4 shows flexible layer 403c as being a bottom-most layer, some embodiments may include one or more additional layers underneath flexible layer 403c, such as one or more structural layers, such as a steel or composite layer. These one or more structural layers, in some embodiments, are part of the flexible circuit structure 401 and can be part of, e.g., elongate member 304. In addition, although FIG. 4 shows only three flexible layers 403a-403c and only three electrically conductive layers 404a-404c, it should be noted that other numbers of flexible layers, other numbers of electrically conductive layers, or both, can be included.

In some embodiments, electrodes 415 are employed to selectively deliver RF energy to various tissue structures within a bodily cavity (e.g., an intra-cardiac cavity). The energy delivered to the tissue structures may be sufficient for ablating portions of the tissue structures. The energy delivered to the tissue may be delivered to cause monopolar tissue ablation, bipolar tissue ablation or blended monopolar-bipolar tissue ablation by way of non-limiting example.

Energy that is sufficient for tissue ablation may be dependent upon factors including tissue characteristics, transducer location, size, shape, relationship with respect to another transducer or a bodily cavity, material or lack thereof between transducers, et cetera.

In some embodiments, each electrode 415 is employed to sense an electrical potential in the tissue proximate the electrode 415. In some embodiments, each electrode 415 is employed in the generation of an intra-cardiac electrogram. In some embodiments, each resistive member 409 is positioned adjacent a respective one of the electrodes 415. In some embodiments, each of the resistive members 409 is positioned in a stacked or layered array with a respective one of the electrodes 415 to form at least part of a respective one of the transducers 406. In some embodiments, the resistive members 409 are connected in series to allow electrical current to pass through all of the resistive members 409. In some embodiments, leads 410a are arranged to allow for a sampling of electrical voltage in between each resistive member 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow). In some embodiments in which the transducer-based device is deployed in a bodily cavity (e.g., when the transducer-based device 300 is part of a catheter system and may be arranged to be percutaneously or intravascularly delivered to a bodily cavity via a catheter), it may be desirable to perform various mapping procedures in the bodily cavity. For example, when the bodily cavity is an intra-cardiac cavity, a desired mapping procedure can include mapping electrophysiological activity in the intra-cardiac cavity. Other desired mapping procedures can include mapping of various anatomical features within a bodily cavity. An example of the mapping performed by devices according to various embodiments may include locating the position of the ports of various bodily openings positioned in fluid communication with a bodily cavity. For example, in some embodiments, it may be desired to determine the locations of various ones of the pulmonary veins or the mitral valve that each interrupts an interior surface of an intra-cardiac cavity such as a left atrium.

Referring to FIGS. 3A, 3B, transducer-based device or manipulable portion 300 may communicate with, receive power from, or be controlled by a control system 322. In some embodiments, elongate members 304 can form a portion of an elongated cable 316 of control leads 317, for example, by stacking multiple layers, and terminating at a connector 321 or other interface with control system 322. The control leads 317 may correspond to the electrical conductors 216 in FIG. 2 in some embodiments. The control system 322 may include a controller 324 that may include a data processing device system 310 (e.g., data processing device system 110 from FIG. 1) and a memory device system 330 (e.g., memory device system 130 from FIG. 1) that stores data and instructions that are executable by the data processing device system 310 to process information received from transducer-based device 300 or to control operation of transducer-based device 300, for example activating various selected transducers 306 to ablate tissue. Controller 324 may include one or more controllers.

In some embodiments, the controller 324 may be configured to control deployment, expansion, retraction, or other manipulations of the shape, positioning, or both shape and positioning of the transducer-based device (e.g., manipulable portion) 300 at least by driving (e.g., by an electric or other motor) movement of various actuators or other catheter system components described below, with respect to, e.g., FIGS. 5 and 7.

In this regard, in some embodiments, some of which are described later in this disclosure, the controller 324 is at least part of a control system, which may include one or more actuators, configured to advance at least part of the transducer-based device (e.g., 200, 300, 400, or 502), at least a portion of which may be considered a manipulable portion, out of the catheter sheath 312, retract at least part of the transducer-based device back into the catheter sheath 312, expand, contract, or otherwise change at least part of the shape of the transducer-based device.

Control system 322 may include an input-output device system 320 (e.g., an example of 120 from FIG. 1) communicatively connected to the data processing device system 310 (i.e., via controller 324 in some embodiments). Input-output device system 320 may include a user-activatable control that is responsive to a user action. Input-output device system 320 may include one or more user interfaces or input/output (I/O) devices, for example one or more display device systems 332, speaker device systems 334, keyboards, mice, joysticks, track pads, touch screens or other transducers to transfer information to, from, or both to and from a user, for example a care provider such as a health care provider or technician. For example, output from a mapping process may be displayed on a display device system 332.

Control system 322 may also include an energy source device system 340 including one or more energy source devices connected to transducers 306. In this regard, although FIG. 3A shows a communicative connection between the energy source device system 340 and the controller 324 (and its data processing device system 310), the energy source device system 340 may also be connected to the transducers 306 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through catheter body 314, elongated cable 316 or catheter sheath 312) that does not pass through the controller 324. In this regard, the energy source device system 340 may provide results of its delivering energy to, receiving energy from, or both delivering energy to and receiving energy from one or more of the transducers 306 to the controller 324 (and its data processing device system 310) via the communicative connection between the energy source device system 340 and the controller 324.

In any event, the number of energy source devices in the energy source device system 340 may be fewer than the number of transducers in some embodiments. The energy source device system 340 may, for example, be connected to various selected transducers 306 to selectively provide energy in the form of electrical current or power (e.g., RF energy), light or low temperature fluid to the various selected transducers 306 to cause ablation of tissue. The energy source device system 340 may, for example, selectively provide energy in the form of electrical current to various selected transducers 306 and measure a temperature characteristic, an electrical characteristic, or both at a respective location at least proximate each of the various transducers 306. The energy source device system 340 may include as its energy source devices various electrical current sources or electrical power sources. In some embodiments, an indifferent electrode 326 is provided to receive at least a portion of the energy transmitted by at least some of the transducers 306. Consequently, although not shown in FIG. 3A, the indifferent electrode 326 may be communicatively connected to the energy source device system 340 via one or more communication lines in some embodiments. In addition, although shown separately in FIG. 3A, indifferent electrode 326 may be considered part of the energy source device system 340 in some embodiments. In some embodiments, the indifferent electrode 326 is provided outside the body or at least the bodily cavity in which the transducer-based device (e.g., 200, 300, or 400) or catheter system 500 is, at least in part, located.

In some embodiments, the energy source device system 340 may include one or more driving motors configured to drive movement, in response to instructions from the controller 324, of various actuators or other catheter system components described, below, with respect to, e.g., FIGS. 5 and 7 to control deployment, expansion, retraction, or other manipulations of the shape, positioning, or both shape and positioning of the transducer-based device (e.g., manipulable portion) 300.

It is understood that input-output device system 320 may include other systems. In some embodiments, input-output device system 320 may optionally include energy source device system 340, transducer-based device 300 or both energy source device system 340 and transducer-based device 300 by way of non-limiting example.

Structure 308 of transducer-based device 300 can be delivered and retrieved through a catheter member, for example, a catheter sheath 312. In some embodiments, the structure 308 provides expansion and contraction capabilities for a portion of a medical device (e.g., an arrangement, distribution or array of transducers 306). The transducers 306 can form part of, be positioned or located on, mounted or otherwise carried on the structure and the structure may be configurable to be appropriately sized to slide within a lumen of catheter sheath 312 in order to be deployed percutaneously or intravascularly. FIG. 3A shows one embodiment of such a structure. In some embodiments, each of the elongate members 304 includes a respective distal end 305 (only one called out), a respective proximal end 307 (only one called out) and an intermediate portion 309 (only one called out) positioned between the proximal end 307 and the distal end 305. The respective intermediate portion 309 of each elongate member 304 includes a first or front surface 318a that is positionable to face an interior tissue surface within a bodily cavity and a second or back surface 318b opposite across a thickness of the intermediate portion 309 from the front surface 318a. In various embodiments, the intermediate portion 309 of each of the elongate members 304 includes a respective pair of side edges of the front surface 318a, the back surface 318b, or both the front surface 318a and the back surface 318b, the side edges of each pair of side edges opposite to one another, the side edges of each pair of side edges extending between the proximal end 307 and the distal end 305 of the respective elongate member 304. In some embodiments, each pair of side edges includes a first side edge 327a (only one called out in FIG. 3A) and a second side edge 327b (only one called out in FIG. 3A). In some embodiments, each of the elongate members 304, including each respective intermediate portion 309, is arranged front surface 318a-toward-back surface 318b in a stacked array during an unexpanded or delivery configuration (e.g., FIG. 3A, 5G). In many cases, a stacked array allows the structure 308 to have a suitable size for percutaneous or intravascular delivery. A stacked array can allow structure 308 to have a spatially efficient size for delivery through a lumen of catheter sheath 312. In some embodiments, the elongate members 304 are arranged to be introduced into a bodily cavity distal end 305 first. For clarity, not all of the elongate members 304 of structure 308 are shown in FIG. 3A. A flexible catheter body or shaft 314 is used to deliver structure 308 through catheter sheath 312. In some embodiments, each elongate member includes a twisted portion proximate proximal end 307 (e.g., also FIG. 5B, discussed below).

In some embodiments, each of the elongate members 304 is arranged in a fanned arrangement 370 in FIG. 3B. In some embodiments, the fanned arrangement 370 is formed during the expanded or deployed configuration in which the transducer-based device (e.g., manipulable portion) 300 or structure 308 thereof is manipulated to have a size, shape, or both size and shape too large for percutaneous or intravascular delivery, for example a size, shape, or both size and shape too large for percutaneous or intravascular delivery toward a bodily cavity, or a size, shape, or both size and shape too large for percutaneous or intravascular delivery away from a bodily cavity. In some embodiments, the fanned arrangement 370 is formed during the expanded or deployed configuration in which the transducer-based device (e.g., manipulable portion) 300 or structure 308 thereof is manipulated to have a size, shape, or both size and shape too large for delivery through a lumen of catheter sheath 312, for example, a size, shape, or both size and shape too large for delivery through a lumen of catheter sheath 312 toward a bodily cavity, or a size, shape, or both size and shape too large for delivery through a lumen of catheter sheath 312 away from a bodily cavity.

In some embodiments, the transducer-based device (e.g., manipulable portion) 300 or structure 308 thereof includes a proximal portion 308a including a first domed shape 309a and a distal portion 308b including a second domed shape 309b when the transducer-based device (e.g., manipulable portion) 300 or structure 308 thereof is in the expanded or deployed configuration. In some embodiments, the proximal and the distal portions 308a, 308b include respective portions of elongate members 304. In some embodiments, the transducer-based device (e.g., manipulable portion) 300 or structure 308 thereof is arranged to be delivered or advanced distal portion 308b first into a bodily cavity when the transducer-based device (e.g., manipulable portion) 300 or structure 308 thereof is in the unexpanded or delivery configuration as shown in FIG. 3A. In some embodiments, the proximal and the distal portions 308a, 308b are arranged in a clam shell configuration in the expanded or deployed configuration shown in FIG. 3B. In various example embodiments, each of the front surfaces 318a (two called out in FIG. 3B) of the intermediate portions 309 of the plurality of elongate members 304 face outwardly from the structure 308 when the structure 308 is in the deployed configuration. In various example embodiments, each of the front surfaces 318a of the intermediate portions 309 of the plurality of elongate members 304 are positioned adjacent an interior tissue surface of a bodily cavity in which the structure 308 (i.e., in the deployed configuration) is located. In various example embodiments, each of the back surfaces 318b (two called out in FIG. 3B) of the intermediate portions 309 of the plurality of elongate members 304 face an inward direction when the structure 308 is in the deployed configuration.

The transducers 306 can be arranged in various distributions or arrangements in various embodiments. In some embodiments, various ones of the transducers 306 are spaced apart from one another in a spaced apart distribution in the delivery configuration shown in FIG. 3A. In some embodiments, various ones of the transducers 306 are arranged in a spaced apart distribution in the deployed configuration shown in FIG. 3B. In some embodiments, various pairs of transducers 306 are spaced apart with respect to one another. In some embodiments, various regions of space are located between various pairs of the transducers 306. For example, in FIG. 3B the transducer-based device 300 includes at least a first transducer 306a, a second transducer 306b and a third transducer 306c (all collectively referred to as transducers 306). In some embodiments each of the first, the second, and the third transducers 306a, 306b and 306c are adjacent transducers in the spaced apart distribution. In some embodiments, the first and the second transducers 306a, 306b are located on different elongate members 304 while the second and the third transducers 306b, 306c are located on a same elongate member 304. In some embodiments, a first region of space 350 is between the first and the second transducers 306a, 306b. In some embodiments, the first region of space 350 is not associated with any physical portion of structure 308. In some embodiments, a second region of space 360 associated with a physical portion of device 300 (i.e., a portion of an elongate member 304) is between the second and the third transducers 306b, 306c. In some embodiments, each of the first and the second regions of space 350, 360 does not include a transducer of transducer-based device 300. In some embodiments, each of the first and the second regions of space 350, 360 does not include any transducer. It is noted that other embodiments need not employ a group of elongate members 304 as employed in the illustrated embodiment. For example, other embodiments may employ a structure including one or more surfaces, at least a portion of the one or more surfaces defining one or more openings in the structure. In these embodiments, a region of space not associated with any physical portion of the structure may extend over at least part of an opening of the one or more openings. In other example embodiments, other structures may be employed to support or carry transducers of a transducer-based device such as a transducer-based catheter device. For example, an elongated catheter member may be used to distribute the transducers in a linear or curvilinear array. Basket catheters or balloon catheters may be used to distribute the transducers in a two-dimensional or three-dimensional array.

In some embodiments, a manipulable portion, or end effector such as, but not limited to, a transducer-based device (e.g., 200 or 300) is manipulated to transition between a delivery configuration (e.g., FIG. 3A) and an expanded or deployed configuration (e.g., FIG. 3B) manually (e.g., by a user's manual operation) or at least in part by way of motor-based driving (e.g., from the energy source device system 340) of one or more actuators or other catheter system components described, below, with respect to, e.g., FIGS. 5 and 7. Motor-based driving may augment or otherwise be in response to manual actions, may be responsive to automated control of a data processing device system (e.g., 110 in FIG. 1 or 310 in FIGS. 3A and 3B), or may use a hybrid manual-automated approach.

In this regard, each of the individual figures of FIG. 5, FIG. 7, and FIG. 12 shows some or all of a catheter system 500, which includes a manipulable portion or end effector 502 (which may also refer to manipulable portion or end effector 1202), according to various embodiments. In this regard, it should be noted that any of the catheter systems described herein may also be referred to as a medical system and, consequently, that catheter system 500 may be referred to as a medical system 500. In some embodiments, the manipulable portion 502 corresponds to the transducer-based device 200 or 300, although the manipulable portion 502 need not be a transducer-based device and may be some other form of catheter-based manipulable portion (e.g., a stent or other implant).

According to some embodiments, the catheter system 500 includes several different types of motions to control the deployment, retraction, positioning, size, and shape of the manipulable portion or end effector 502. These different types of motions may include coiling, uncoiling, fanning, un-fanning, bifurcated doming, flattening, clam shelling, or a combination of some or all of these motions. In some embodiments, these motions facilitate accommodation of different bodily cavity sizes (e.g., different atrium sizes), as well as proper positioning of the manipulable-portion within the bodily cavity (e.g., atrium) and contact with one or more tissue walls of the bodily cavity.

With respect to these types of motions, for example, deployment of the manipulable portion 502 may involve a coiling of the manipulable portion 502 by way of a built-in predisposition of the manipulable portion 502 to autono-mously coil when released from the confines of a catheter sheath 512 or some other confining member, by way of a control element 513 (e.g., a cable 513b), or by way of both autonomous coiling and a control element. See, e.g., the sequence of FIGS. 5H, 5I, and 5J, discussed in detail below. In some embodiments, the control element (e.g., cable 513b) is physically or at least operatively coupled to the manipu-lable portion 502 (e.g., at least proximate a distal end 505a thereof) to transmit force to the manipulable portion or end effector 502 and to selectively enable a particular function of the manipulable portion 502, such as controlling a position-ing of at least part of the manipulable portion 502 during coiling or uncoiling. Uncoiling of the manipulable portion 502 during retraction is described in more detail below, with respect to at least the sequence of Figures of 5J, 5I, and 5H. Such uncoiling may occur by way of a control element 513 (e.g., a cable 513b), by way of a containment force applied by the catheter sheath 512 or some other confining member as the manipulable portion 502 is retracted into the catheter sheath 512 or other confining member, or by way of both a control element and a containment force of a confining member into which the manipulable portion 502 is retracted.

In some embodiments, the coiling/uncoiling motion dur-ing deployment/retraction of the manipulable portion 502 is caused and controlled, at least in part, by activation or movement of a second particular actuator 540b and an internal receiving mechanism 546 with respect to a first particular actuator 540a, which may act as an anchor in some configurations. In some embodiments, the coiling/uncoiling motion during deployment/retraction involves a metering of a portion of the control element 513 (e.g., a cable 513b) with different rates under the control of a master slider 556a, a sleeve slider 556b, and the second particular actuator 540b, which are described in more detail, below, with respect to at least FIGS. 7A and 7B.

In some embodiments, once the manipulable portion 502 is extended outside of the distal end 512b of the catheter sheath 512, as shown, for example, at least in FIGS. 5L-1 and 5L-2, the manipulable portion 502 may be fanned, or additionally fanned, as shown in FIGS. 5M-1 and 5M-2 by action of a sliding actuator 572, of which a cover 520a of housing 520 is a part, and a control element 573, which are described in more detail, below, with respect to at least FIGS. 5S-1 and 5S-2. In this regard, according to some embodiments, the control element 573 is physically or at least operatively coupled to the manipulable portion or end effector 502 (e.g., at least proximate a distal end 505a thereof) to transmit force to the manipulable portion 502 and to selectively enable a particular function of the manipulable portion 502, such as controlling a position of the manipu-lable portion 502 during fanning or un-fanning. Un-fanning of the manipulable portion 502 to return the manipulable portion 502 back into a retraction-ready shape may also be controlled by the sliding actuator 572, as described in more detail, below.

In some embodiments, at least when the manipulable portion 502 is fanned, different portions 508a, 508b (e.g., hemispheres in some embodiments) of the manipulable portion 502 may be controlled to have different domed shapes. This type of motion may be referred to as bifurcated doming and is described in more detail, below, with respect to FIGS. 5M-1 and 5M-2, for example. This type of motion may be controlled by positioning of cover 520a, described in more detail, below, with respect to FIGS. 5S-1 and 5S-2, for example. The position of cover 520a in this regard controls at least a positioning of control element 573 to further control the positioning of the manipulable portion 502, according to some embodiments. FIGS. 5N-5Q, dis-cussed below, also illustrate different domed shapes to which the manipulable portion 502 may be controlled to have, e.g., at least by way of a control element 578 or 513, according to some embodiments. In this regard, according to some embodiments, the control element 578 is physically or at least operatively coupled to the manipulable portion or end effector 502 (e.g., at least proximate a distal end 505a thereof) to transmit force to the manipulable portion 502 and to selectively enable a particular function of the manipulable portion 502, such as controlling a position of the manipu-lable portion 502 in various domed states.

In some embodiments, at least when the manipulable portion 502 is fanned, the manipulable portion 502 may be flattened, as described in more detail, below, with respect to FIGS. 5N and 5O. In some embodiments, this flattening motion may be caused and controlled by activation or action of the first particular actuator 540a and control element 578, which are described in more detail, below, with respect to FIGS. 5S, 7A, and 7B.

In some embodiments, at least when the manipulable portion 502 is fanned, the manipulable portion 502 may be subjected to clam shelling as described in more detail, below, with respect to FIGS. 5P and 5Q. In some embodi-ments, this clam shelling may be caused and controlled by activation or action of the second particular actuator 540b and control element 513, which are described in more detail, below, with respect to FIGS. 5S, 7A, and 7B.

In order to remove the manipulable portion or end effector 502 from the bodily cavity, the manipulable portion is retracted from a deployed configuration (e.g., at least FIG. 3B, 5M-1, 5M-2, 5N, 5O, 5P, or 5Q) to a delivery configu-ration (e.g., at least FIG. 3A or 5G), for example, by operation of one or more control elements (e.g., 513, 573, 578, or a combination thereof). However, in the event of a failure scenario where the manipulable portion 502 is unable to be retracted, such as by a failure of an operation of a control element or a mechanism or actuator coupled thereto, or by the manipulable portion or end effector 502 being caught on tissue, for example, the medical device system 500 is configured to provide physical access to the one or more control elements in some embodiments for severing of one or more of the control elements. For example, as described in more detail below at least with respect to FIG. 5X, an enclosure lid 520h of housing (or enclosure) 520 may be provided. When this enclosure lid 520h is opened, physical access is provided to an interior cavity 520g (called out in at least FIG. 5Y) of the housing or enclosure 520, as well as portions of the one or more control elements (e.g., at least control element 513 in FIG. 5Y, 5R-1) therein via an access port. The access port may be an opening provided by the lid 520h when the lid 520h is opened. When the lid 520h is in the open state, an operator or user of the medical device system 500 may sever, cut, or otherwise disable at least a portion or region of at least one of the one or more the control elements within the interior cavity 520g of the enclosure 520, for example, by passing at least a portion of a tool through the access port made accessible by the opening of the enclosure lid 520h. The tool may be a cutter, such as surgical scissors. In various embodiments, a sterile cutter is preferred. In some embodiments, the cutter is distinct or separate from the catheter. In some embodiments, the cutter forms an integral part or assembly of the catheter. In some embodiments, this severing or otherwise disabling may release forces acting on the manipulable portion 502 that keep it in an undesired state, and thereby allow the manipulable portion 502 to be released from the undesired state and to be withdrawn into a catheter shaft 510 and removed from the bodily cavity. In some embodiments, the act of withdrawing the manipulable portion 502 into the catheter shaft 510 in this reduced-force state allows the walls of the catheter shaft 510 to reduce any remaining fanning or expansion of the elongate members 504 by funneling the elongate members 504 into a delivery configuration as the manipulable portion 502 is withdrawn into the catheter shaft 510. Accordingly, a safe procedure for removing the manipulable portion 502 from the bodily cavity even in a failure state is provided.

Stated differently, at least some embodiments of the present invention are beneficial at least in a medical device system that includes a manipulable portion, which is primarily controlled by one or more actuators coupled to one or more control elements that are coupled to the manipulable portion. In such systems, where the one or more control elements are able to place the manipulable portion or end effector into a higher energy state (e.g., a higher potential energy state) by actuation of at least one of the one or more actuators, at least some embodiments of the present invention are beneficial at least by providing a secondary control capability (as opposed to the primary control via the one or more actuators) to transition the manipulable portion into a potentially safer lower energy state (e.g., a lower potential energy state) at least by providing a simple mechanism to physically access and sever, otherwise disable, or allow physical manual manipulation of the one or more control elements.

Now, each of the figures of FIG. 5 (collectively referred to as "FIGS. 5") will be described. FIG. 5 illustrate various views of various aspects of medical systems or catheter systems, according to various embodiments. In this regard, the systems of FIG. 5 (as well as the other remaining figures) may be particular implementations of the systems of FIGS. 2 and 3, according to some embodiments. Accordingly, descriptions herein regarding the systems of FIGS. 2 and 3 apply to the systems of FIG. 5 (as well as the other remaining figures), according to some embodiments.

As shown in FIG. 5A, catheter system 500 includes various devices including a catheter shaft member 500a (also referred to as shaft member 500a) and, in some embodiments, a catheter sheath member 500b (also referred to as sheath member 500b). Shaft member 500a includes a catheter shaft 510 (e.g., the same or similar to catheter body 314) that includes a proximal end 510a, a distal end 510b, and an intermediate or elongated portion (also referred to as an elongate member) 510c extending between the proximal end 510a and the distal end 510b (e.g., extending along a path that connects proximal end 510a and distal end 510b). In some embodiments associated with various ones of FIG. 5, the manipulable portion or end effector 502 is located at least proximate the distal end 510b. The manipulable portion or end effector 502 may be connected or coupled to an enclosure, such as housing 520, via shaft 510 extending between the manipulable portion or end effector 502 and the enclosure 520. In some embodiments, the shaft 510 is physically or operatively coupled to the housing 520.

Catheter sheath member 500b includes a catheter sheath 512 (e.g., the same or similar to sheath 312) that includes proximal end 512a, a distal end 512b and a body portion 512c between the proximal end 512a and the distal end 512b. In various embodiments, catheter sheath 512 includes one or more lumens, each of at least some of the one or more lumens extending between proximal end 512a and distal end 512b (e.g., extending along a path that connects proximal end 512a and distal end 512b). In various embodiments associated with various ones of FIG. 5, catheter sheath 512 includes a first lumen 512d extending between (or connecting, in some embodiments) proximal end 512a and distal end 512b. Catheter sheath member 500b is provided in various embodiments to provide a passageway for at least a portion of shaft member 500a (e.g., a part of shaft 510) to be delivered therethrough to a location within a body during a medical procedure. In some embodiments, catheter sheath member 500b is deployed percutaneously or intravascularly into a body. In this regard, it may be stated that at least part of the shaft 510 is sized for percutaneous delivery to the bodily cavity. In various embodiments, at least a portion of catheter sheath member 500b (e.g., at least a portion of the catheter sheath 512) is delivered distal end 512b first through a naturally occurring bodily opening toward a bodily cavity. For instance, the catheter sheath 512 may be receivable in, insertable into, or positionable in a bodily opening. In some of these various embodiments, the bodily opening is accessed by a natural orifice or port provided by the body. In some of these embodiments, the bodily opening is accessed by a perforation made in bodily tissue. In various embodiments, a portion or part of shaft member 500a (e.g., at least part of the shaft 510) is received in, receivable in, or sized for delivery through the first lumen 512d of the catheter sheath 512 to a bodily cavity or to deliver the manipulable portion 502 through the first lumen 512d of the catheter sheath 512 to a bodily cavity (e.g., a bodily vessel, chamber or cavity within a bodily organ). In this regard, in some embodiments, at least the distal end 510b of the shaft 510 is sized for delivery through a bodily opening leading to a bodily cavity located in a body. It is understood that, although each of shaft 510 and catheter sheath 512 is depicted in FIG. 5A in an essentially straight configuration, each of shaft 510 (or at least part of the shaft 510 receivable in the lumen 512d of the catheter sheath 512) and catheter sheath 512 may be flexible or bendable or may include one or more flexible or bendable portions that that allow bending or deflection or the assumption of a bent or curved (e.g., arcuate) form, e.g., during or for delivery to a bodily cavity. In various embodiments, shaft member 500a is arranged with respect to catheter sheath member 500b such that the distal end 510b of shaft 510 is configured, arranged, or sized to be delivered through the first lumen 512d of the catheter sheath 512 prior to at least the elongated portion 510c of the shaft 510, when the distal end 510b of shaft 510 is delivered toward or to the bodily cavity. In various embodiments, shaft member 500a is arranged with respect to catheter sheath member 500*b* such that the distal end 510*b* of shaft 510 is configured, arranged, or sized to be delivered through the first lumen 512*d* of the catheter sheath 512 in a direction extending from the proximal end 512*a* of catheter sheath 512 toward the distal end 512*b* of catheter sheath 512 when the distal end 510*b* of shaft 510 is delivered toward or to the bodily cavity.

In various embodiments, the manipulable portion 502 includes a proximal end 501*a* (e.g., in the vicinity of elongate member proximal ends 507 in FIG. 5G), a distal end 501*b* (e.g., in the vicinity of elongate member distal ends 505 in FIG. 5G), and an elongated part 501*c* (e.g., FIG. 5G) extending between the proximal end 501*a* and the distal end 501*b* of the manipulable portion 502. In some embodiments, the manipulable portion is delivered and advanced outwardly, e.g., distal end 501*b* first with respect to or as compared to other parts of the manipulable portion 502, through the first lumen 512*d* of the catheter sheath 512 toward or to the bodily cavity as the shaft 510 is advanced accordingly through first lumen 512*d*. It is noted that each of shaft 510 and catheter sheath 512 has a respective elongated portion that can have longitudinal or axial components. For example, the shaft 510 has a longitudinal length 510*d* extending between the respective proximal end 510*a* and distal end 510*b*, according to some embodiments. Similarly, the sheath 512 has a longitudinal length 512*f* extending between the respective proximal end 512*a* and distal end 512*b*, according to some embodiments. As used in this disclosure, words such as "longitudinal" or "axial" are not limited to various members having generally straight forms but can include members that have bent or arcuate forms or forms that have been bent from a generally straight form into a generally non-straight form.

In various embodiments, manipulable portion 502 is selectively configurable or moveable, e.g., based at least upon user (e.g., a health care provider, technician, or other user) input (e.g., by way of actuators 540*a*, 540*b*, or 546 described with respect to FIG. 7, below, by way of actuator 572 described with respect to FIG. 5S, below, or by relative movement of the shaft 510 and catheter sheath 512) or other sensory input (e.g., from sensors in the input-output device system 120 of FIG. 1), into various configurations. For example, in some embodiments, the manipulable portion 502 may form at least part of a steerable portion of shaft member 500*a*. Catheter devices employing steerable portions may be used to better negotiate tortuous paths sometimes encountered during delivery to a bodily cavity. Catheter devices employing steerable portions may be employed to better achieve a desired positioning of various devices (e.g., implants or transducer systems). In some embodiments, the manipulable portion 502 may be selectively detachable from the shaft member 500*a*. For example, the manipulable portion 502 may, in some embodiments, form part of an implant (e.g., a stent). In some of these embodiments, an implant provided at least in part by the manipulable portion 502 may be selectively configurable or moveable (e.g., by way of a modulator or other actuator or control element described in this disclosure) between a delivery configuration (e.g., at least FIG. 3A) in which the implant is appropriately sized for delivery through the first lumen 512*d* toward or to a particular location in the bodily opening or bodily cavity and a deployed or expanded configuration (e.g., at least FIG. 3B) in which the implant is sized too large for delivery through the first lumen 512*d* toward or to the particular location in the bodily opening or bodily cavity. In some of these embodiments, the implant may be positioned in the deployed configuration when implanted or otherwise brought into engagement with tissue (e.g., a stent that is selective expanded to grip or to otherwise be secured within a bodily vessel).

In some embodiments associated with various ones of FIG. 5, manipulable portion 502 forms a part of a transducer-based device (e.g., 200, 300) with various sets of one or more transducers located on, or forming part of the manipulable portion 502. For example, in some embodiments, manipulable portion 502 includes a structure 502*a* (e.g., the same or similar to structure or frame 308) and various transducers 506 (not shown for clarity in FIG. 5A, but may be the same or similar to transducers 220, 306, 406) that are located on or carried by a surface of the manipulable portion 502 or the structure 502*a* thereof. In a manner that is the same or similar to other embodiments described above in this disclosure, manipulable portion 502 or structure 502*a* is selectively configurable or moveable (e.g., by way of a modulation or other actuator described in this disclosure) between a delivery configuration (e.g., at least FIG. 3A) in which at least the structure 502*a* is appropriately sized, shaped, or both sized and shaped for delivery through the first lumen 512*d* of the catheter sheath 512 at least toward or to a bodily cavity located in a body and an expanded or deployed configuration (e.g., at least FIG. 3B) in which at least the structure 502*a* is sized, shaped, or both sized and shaped too large for delivery through the first lumen 512*d* of the catheter sheath 512 at least toward or to the bodily cavity. In various embodiments, the manipulable portion 502 or structure 502*a* thereof is physically coupled to the shaft 510 at a location at least proximate the distal end 510*b* of the shaft 510. In this regard, the manipulable portion 502 or structure 502*a* thereof may include a plurality of elongate members 504 (two called out in FIG. 5A) that are physically coupled to shaft 510, which is employed to transport the elongate members 504 through first lumen 512*d* when the structure 502*a* is in a delivery configuration. The number of elongate members 504 shown in various ones of FIG. 5 is non-limiting. An enlarged view of the manipulable portion 502 illustrated in FIG. 5A is shown in FIG. 5C, which is described in more detail below.

FIG. 5B is an isometric view of a representative one of the elongate members 504 in an initial or predisposed configuration as employed in some embodiments. Various dimensions of the representative one of the elongate member 504 have been exaggerated for clarity in FIG. 5B. Each of the elongate members 504 includes a respective first or distal end 505 and a respective second or proximal end 507. Each intermediate portion includes a respective length between the respective proximal and distal ends 507, 505 of the elongate member 504. Each elongate member 504 includes a respective length between the respective proximal and distal ends 507, 505 of the elongate member 504. In various embodiments, two or more of the elongate members 504 may have substantially equal lengths or substantially unequal lengths. In various example embodiments, a respective portion of each of the elongate members 504 has a length that is at least approximately equal to or greater than a circumference of a portion of an interior tissue surface of a bodily cavity into which the elongate member 504 is to be positioned at least proximate to when the manipulable portion 502 is in an expanded or deployed configuration. The circumference of the portion of the interior tissue surface may have a measured or anticipated value. In a manner that is the same or similar to other described embodiments, a set of transducer elements 506 (two called out) are distributed along a surface (e.g., surface 518*a*) of each of various ones of the elongate members 504. In some example embodiments, each elongate member 504 includes at least a portion of a flexible circuit structure (e.g., the same or similar to that employed by embodiments of FIG. 4) that at least provides an electrically communicative path to various ones of the transducer elements 506.

In various embodiments, each of the elongate members 504 includes a plurality of various portions including first portion 509*a*, second portion 509*b*, and third portion 509*c* (collectively portions 509) arranged between the respective proximal and distal ends 507, 505 of the elongate member 504. The second portion 509*b*, which may be considered an intermediate portion of the respective elongate member 504, may be positioned between the first (e.g., distal) end 505 and the second (e.g., proximal) end 507 of the respective elongate member 504. In some embodiments, each intermediate portion 509*b* includes a set of two opposing major faces or surfaces 518 denominated as a front surface 518*a* and a back surface 518*b* in FIG. 5B. The two opposing surfaces 518 may be separated from one another by a thickness 517 of the elongate member 504, such that the back surface 518*b* is opposite across the thickness 517 from the front surface 518*a*. In some embodiments, each of one or more of portions 509 may be considered an intermediate portion of the respective elongate member 504. In FIG. 5B, the third portion 509*c*, positioned between the first and the second portions 509*a*, 509*b*, and first portion 509*a* is located along the elongate member 504 relatively closer to proximal end 507 than to distal end 505, and the second portion 509*b* is located along the elongate member 504 relatively closer to distal end 505 than to proximal end 507. In various embodiments, the various portions 509 are combined in a unitary structure. In various embodiments, a number of the respective portions 509 of various ones of the elongate members 504 include various distortions or deformations. As used in reference to this context, the words "distortion" or "deformation" are used interchangeably herein to mean modification in shape away from an elongated strip-like form that, prior to any distortion or deformation, was predominately a body with a relatively small thickness as compared to a length or width, although major faces of the body may not necessarily have smooth planar surfaces. For example, the respective second portion 509*b* of the representative elongate member 504 shown in FIG. 5B has a coiled profile (e.g., a profile that curves or curls back on itself). In this particular embodiment, the respective second portion 509*b* includes a volute shaped profile in the initial or predisposed configuration. Also for example, the respective third portion 509*c* of the representative elongate member 504 shown in FIG. 5B includes a twisted profile about a respective twist axis 533 extending across at least part of the third portion 509*c* of the elongate member 504, the twist in the third portion 509*c* arranged to rotationally offset (e.g., angularly rotated or twisted out of plane about an axis that may extend generally along a length of the elongate member prior to any distortion of deformation thereof) the respective second portion 509*b* of the elongate member 504 from the respective first portion 509*a* of the elongate member 504 along a portion of the length of the elongate member 504. In this example embodiment of FIG. 5B, the respective first portion 509*a* of the representative elongate member 504 includes a bent profile about a respective bending axis 531. It is understood that the number of elongate members 504 employed by the various embodiments of manipulable portion 502 associated with various ones of FIG. 5 is non-limiting.

In FIGS. 5A, 5B, and 5C, each of the elongate members 504 is arranged in an arrangement having an initial or predisposed configuration in which each elongate member 504 is provided essentially in its distorted form. In various embodiments, the initial or predisposed configuration is associated with an initial, low, or lowest (potential) energy state. In various embodiments, each elongate member 504 is a resilient member and further distortion of various portions 509 of the elongate member 504 can increase spring or potential energy of the elongate member 504 and thereby bring it into a higher energy state. The (a) bent profiles of the respective first portions 509*a*, (b) the twisted profiles of the respective third portion 509*c*, or both (a) and (b) of various ones of the elongate members 504 in the initial or predisposed configuration may be arranged to fan or partially fan at least the respective second portions 509*b* of various ones of elongate members 504 into a fanned array as shown, for example, in FIG. 5C. It is noted, however, that various fanning angles 519 (only one called out in FIG. 5C) may be achieved between a respective pair of the first and the second portions 509*a*, 509*b* by positional adjustments of the twist axis 533, according to some embodiments.

In some embodiments, various ones of the elongate members 504 are physically or operatively coupled with at least one other elongate member 504 by at least one coupler. In FIG. 5C, at least one coupler is arranged to couple at least the respective first portions 509*a* of the elongate members 504 together in the initial configuration. Various couplers may be employed in these embodiments. For example, in embodiments where each of various ones of the elongate members 504 includes a flexible printed structure including a relatively large number of electrically conductive traces, a coupler that couples at least the side edges of the first portions 509*a* may be well suited to avoid imposing undesired space constraints on the placement of the electrically conductive traces. In various example embodiments, additional couplers may also be employed to couple various other portions (e.g., portions 509) of various ones of the elongate members 504 together. In this regard, as shown in FIG. 5C, a control cable 513*b* passes through openings at distal end portions of the elongate members 504 to operatively couple such distal end portions of elongate members 504 in some embodiments. A coupling system like that illustrated by control cable 513*b* in FIG. 5C may be used to couple other portions (e.g., various portions 509) of elongate members 504 in some embodiments.

In some example embodiments, a control system including one or more control elements, such as control element 513 (including control cable 513*b* in at least FIG. 5C), control element 573 (e.g., at least FIG. 5M-1), control element 578 (e.g., at least FIG. 5O), control element 1213 (e.g., at least FIG. 12A) or a combination of some or all of such control elements, controls the transition of the manipulable portion 502 from a delivery configuration (e.g., at least FIG. 3A) to or toward a fully expanded configuration (e.g., at least FIG. 3B). In some embodiments, the manipulable portion 502 is predisposed to transition from the delivery configuration to a partially or fully expanded configuration. In some embodiments, the delivery configuration may include a stacked array of elongate members 504 (e.g., FIG. 3A or 5G) configured to be deliverable via the catheter system 500. In some embodiments, the stacked array of elongate members 504 is in an uncoiled state for delivery. In some embodiments, this uncoiled state corresponds to a higher energy configuration for the manipulable portion 502 as compared to a coiled state (e.g., at least FIG. 5B or 5J) outside the catheter sheath 512 (or 312). In some embodiments the manipulable portion 502 transitions to such a lower energy coiled state as it advances through the distal end 510*b* of the catheter sheath 512 within the intra-bodily cavity (e.g., at least FIGS. 5H, 5I, and 5J). In some embodiments, the manipulable portion 502 proceeds to an even lower energy state, which may correspond to a partially fanned configuration (e.g., FIGS. 5L-1 and 5L-2). This partially fanned configuration is the lowest energy state, in some embodiments. According to some embodiments, one or more control cables (513b, 573b, 578b, or a combination of some or all thereof) operate on the elongate members 504 to transition the manipulable portion 502 from the partially fanned configuration to an expanded fanned configuration (e.g., FIG. 3B). In some embodiments, as discussed in more detail below, severing one or more control cables, such as the control cable 513b, releases tension in the control cable 513b, thereby transitioning the manipulable portion of 502 from the expanded fanned configuration (e.g., FIG. 3B) toward or to the partially fanned configuration (e.g., FIGS. 5L-1 and 5L-2). In some embodiments, the manipulable portion 502 can be removed from the bodily cavity via catheter shaft 510 when in the partially fanned configuration (e.g., FIGS. 5L-1 and 5L-2) with one or more of the control cables severed, as the distal end of the catheter shaft 510 funnels the elongate members 504 toward the coiled configuration (e.g., at least FIG. 5B or 5J) and then an uncoiled delivery configuration (e.g., FIG. 3A or 5G).

Referring back to FIG. 5A, in various embodiments, the intermediate or elongated portion 510c of the shaft 510 has a length 510d extending between the proximal end 510a and the distal end 510b of shaft 510. The length 510d may be sized to position the proximal end 510a at a location outside of a body when the distal end 510b (or the manipulable portion 502) is located in a bodily cavity within the body. In various embodiments associated with FIG. 5, a housing 520 of the shaft member 500a is physically or operatively coupled to shaft 510 at a location at least proximate the proximal end 510a of the shaft 510, the proximal end 512a of the catheter sheath 512, or both (e.g., at a location outside a body when the manipulable portion 502 is positioned at a desired location within a bodily cavity located in the body).

One or more control systems (e.g., one or more components of control system 322, control system 545, or both control system 322 and control system 545 described in this disclosure) may be provided by housing (also referred to as enclosure) 520 (e.g., in, on, or both in and on housing 520). In this regard, the housing 520 may be referred to as a control system housing. Such housing 520 may be located at least proximate the proximal end 510a of the shaft 510.

Various actuator sets described in this disclosure may be provided by housing 520 (e.g., in, on, or both in and on housing 520). For example, in some embodiments, at least (a) some of the shaft 510 (e.g., at least part of the proximal end 510a of the shaft 510), (b) some of the control element 513, (c) some of one or more of the actuators described herein with respect to at least FIGS. 5R, 5S, 5W, 7, 8, and 10, (a) and (b), (a) and (c), (b) and (c), or (a), (b), and (c) may be enclosed within the housing 520. The various actuator sets may, by way of non-limiting example, be part or all of such control system(s) and be configured to control or modulate, in response to user or other input, a size, shape, or both size and shape of various configurations of manipulable portion 502 (e.g., delivery and expanded or deployed configurations). In some embodiments, the various actuator sets control or modulate the manipulable portion 502 by way of at least control element 513 (or control element 573, 578, or 1213). One or more of the various actuator sets may be referred to as an actuator system, such that, for example, the actuator system is located, at least in part, in the housing 520. An actuator system may, by way of non-limiting example, be operatively coupled to the manipulable portion 502 and configured to move or transition, in response to or under the control of user or other input, manipulable portion 502 between various configurations (e.g., delivery and expanded or deployed configurations). The actuator system may, by way of non-limiting example, be configured to control, in response to or under the control of user or other input (e.g., from a control system such as controller 324 or data processing device system 110), various control elements employed by catheter system 500. For example, at least some of these control elements may be controlled, e.g., by user or otherwise (e.g., from a control system such as controller 324 or data processing device system 110) to selectively provide (a) a desired amount of force outputted by an actuator in the actuator system, (b) a desired duration of a force outputted by an actuator in the actuator system, or both (a) and (b) to manipulable portion 502.

Control elements may include, by non-limiting example, control or push-pull rods, control lines, control cables, Bowden cables, other force transmission components configured or arranged to selectively deliver force or energy outputted by an actuator to a particular device or structure (e.g., manipulable portion 502). In some embodiments, a control element forms part of a bending system that operates on the manipulable portion 502 to bend at least some of the manipulable portion 502. For example, the control element may be employed to transmit a bending force to the manipulable portion 502 to bend at least a part thereof.

In some embodiments, an actuator system includes at least a portion of one or more of the various actuators described herein (e.g., with respect to at least any one of the figures in at least FIGS. 5R, 5S, 5W, 7, 8, and 10). In this regard, in embodiments where the actuator system is controlled by a control system (e.g., from a control system such as controller 324 or data processing device system 110), such control system is operatively coupled to the actuator system, for example, to control motion or other activation of at least a portion of the one or more of the actuators in the actuator system.

In various embodiments, housing 520 includes a cover 520a that is moveable along a surface of housing 520 to provide access to an interior portion of housing 520. In some of these various embodiments, cover 520a is moveable to provide access (e.g., user access) to various actuators associated with housing 520. In various embodiments, housing 520 may be directly handled by a user during a medical procedure in which catheter system 500 is employed. As shown in FIG. 5A, housing 520 may include at least part of an electrical coupling 521 which may in some embodiments allow for data, power, or both data and power communication with various transducers (e.g., transducers 506). Electrical coupling 521 may allow for electrical communication with (a) a controller (e.g., controller 324 or data processing device system 110) or (b) an energy source device system (e.g., energy source device system 340) or both (a) and (b).

As best shown in FIG. 5C, shaft 510 can include, in various embodiments, one or more lumens extending between the proximal end 510a (not shown in this figure) and the distal end 510b of shaft 510, the one or more lumens including at least a second lumen 511 (to be distinguished from the first lumen 512d of the catheter sheath 512). In various embodiments at least one control element is provided in the second lumen 511. For example, an elongated control element 513 is provided in second lumen 511 in FIG. 5C. In embodiments where the shaft 510 is within the first lumen 512d of the catheter sheath 512, the control element 513 within the second lumen 511 of the shaft 510 may also be considered to be within the first lumen 512*d* of the catheter sheath 512, because the shaft 510 is within the catheter sheath 512 in these embodiments. It is understood that additional or alternate control elements may be received in the second lumen 511 in other embodiments.

In various embodiments, control element 513 is physically coupled to the manipulable portion (also referred to as end effector) 502 to transmit force to the manipulable portion and includes multiple components or portions. For example, in FIG. 5C, control element 513 includes a sleeve 513*a* and a control cable 513*b* located, at least in part, in a lumen of the sleeve 513*a*. In some embodiments, the sleeve 513*a* includes an elongate portion within the elongate portion 510*c* of the catheter shaft 510. The control cable 513*b* may be physically coupled to the manipulable portion 502 to transmit force to the manipulable portion. Each of the cable 513*b* and the sleeve 513*a* may be located, at least in part, in the lumen 511 of the shaft 510. In some embodiments, sleeve 513*a* and cable 513*b* (and any sleeve and cable of a Bowden cable described herein) are moveable independently or separately with respect to one another to allow (a) the sleeve 513*a* to move independently or separately from the cable 513*b* to cause the sleeve 513*a* to slide over the cable 513*b* (e.g., during a first manipulation of the manipulable portion 502 to change a size, shape, or both thereof), and to allow (b) the cable 513*b* to move independently or separately from the sleeve 513*a* to cause the cable 513*b* to slide through the lumen of the sleeve 513*a* (e.g., during a second manipulation of the manipulable portion to change a size, a shape, or both thereof). This can occur, for example, when the at least a portion of the cable 513*b* received in the lumen of the sleeve 513*a* is translated in a direction that the lumen of the sleeve 513*a* extends along. In some embodiments, a portion of cable 513*b* and a portion of sleeve 513*a* are each translated concurrently (for example, in a direction that a portion of the lumen of the sleeve 513*a* extends along). In some embodiments, cable 513*b* is provided by a flexible control line (e.g., a flexible control line having a polymeric, metallic, or composite composition). In this regard, the control element 513 may be considered a flexible control element in some embodiments. In some embodiments, sleeve 513*a* is also flexible and can be bent (i.e., elastically or plastically) to have an arcuate form. In various embodiments, sleeve 513*a* comprises sufficient axial stiffness to withstand a particular compressive force, for example created by a tensioning of cable 513*b*. In various embodiments, sleeve 513*a* has a polymeric, metallic or composite composition. For example, the present inventors have employed thin-walled stainless steel tubing in some embodiments.

In some embodiments, sleeve 513*a* and cable 513*b* form part of a Bowden cable. A Bowden cable is a generally flexible cable used to transmit force by the movement of an inner cable relative to a hollow outer cable housing (also sometimes referred to as a sleeve or sheath). The housing may be generally of composite construction, for example a tightly helically wound metallic wire sometimes lined with a friction reducing polymer. Typically, a first part of the cable extends outwardly from a first end of the sleeved housing, and a second part of the cable extends outwardly from a second end of the sleeved housing. The translational movement of the inner cable is most often used to transmit a pulling force, although push/pull cables are also employed. The cable housing provides the Bowden cable with compressive strength to resist buckling during a tensioning of the inner cable. The cable housing maintains a fixed separation with respect to the length of the inner cable so that displacing the inner cable relative to one end of the cable housing results in an equal displacement at the other end, regardless of the cable's path in-between. In FIG. 5C, a portion 514 of cable 513*b* (i.e., also called part 514 in some embodiments) of elongated control element 513 extends or is located outwardly from an end 513*a*-1 of sleeve 513*a* and is physically coupled to the manipulable portion 502 at least by being physically coupled to one or more of the elongate members 504. In this regard, cable 513*b* (an example of a control element or an elongated control element) includes a distal end positionable outside of the distal end 512*b* of the catheter sheath 512 when a particular amount of the manipulable portion 502 is located outside of the distal end 512*b* of the catheter sheath 512. In embodiments such as those illustrated by FIG. 5C, cable 513*b* extends through a respective opening provided near the distal end 505 (not called out in FIG. 5C) of each of a majority of the elongate members 504 and terminates near the distal end 505 of another of the elongate members 504. In some embodiments, this arrangement couples distal end portions of the elongate members 504 and allows the distal ends 505 of the elongate members 504 to be drawn together in a purse string-like manner. In various embodiments, both the sleeve 513*a* and the cable 513*b* extend through the second lumen 511 to housing or enclosure 520 (enclosure 520 is shown in at least FIG. 5V (with reference 520-1), 5X, 5Y, 5Z). In various embodiments, (e.g., as described later in this disclosure) each of the sleeve 513*a* and the cable 513*b* extends through the second lumen 511 to a respective actuator provided by housing 520, which, in some embodiments, couples at least one of the respective actuators to the manipulable portion 502. In some embodiments, each of these respective actuators is operable to move a respective one of the sleeve 513*a* and the cable 513*b* independently or separately of the other of the sleeve 513*a* and the cable 513*b*. In some embodiments, each of these respective actuators is operable to move a respective one of the sleeve 513*a* and the cable 513*b* independently or separately of the other of the sleeve 513*a* and the cable 513*b* to cause translational movement of a portion of the cable 513*b* through a portion of the sleeve 513*a* or to cause translational movement of a portion of the sleeve 513*a* over a portion of the cable 513*b*. In FIG. 5C, cable 513*b* may be in a slackened configuration or a configuration having limited tension imposed on the cable 513*b* when the manipulable portion 502 is in the initial configuration.

In various embodiments, the body portion 512*c* of catheter sheath 512 has a length 512*f* (e.g., FIG. 5A) extending between the proximal end 512*a* and the distal end 512*b* and sized and dimensioned to position manipulable portion 502 at a desired location outwardly from the distal end 512*b*, when the shaft 510 has delivered the manipulable portion 502 through the first lumen 512*d* (i.e., along a path extending from the proximal end 512*a* toward the distal end 512*b* of catheter sheath 512), such that the proximal end 510*a* of the shaft 510 is positioned at a desired location with respect to the proximal end 512*a* of the catheter sheath 512. Positioning indicia set 523*a* may be provided on a visible surface of the elongated portion 510*c* of shaft 510 proximate the proximal end 510*a*, to provide a user with a visual indication of a distance between a location on the shaft 510 (e.g., proximal end 510*a*) and a location on the sheath 512 (e.g., the proximal end 512*a*) as the two locations are advanced with respect to one another to reduce a distance therebetween (for example, during an advancement of manipulable portion 502 toward a bodily cavity as the manipulable portion 502 is moved through first lumen 512*d*). Positioning indicia set 523*b* may be provided on a visible surface of the elongated portion 510*c* of shaft 510 proximate the distal end 510*b*, to provide a user a visual indication of a distance between a location on the shaft 510 (e.g., the distal end 510*b*) and a location on the sheath 512 (e.g., the proximal end 512*a*) as the two locations are advanced with respect to one another to increase a distance therebetween (for example during a retraction of manipulable portion 502 away from a bodily cavity as the manipulable portion 502 is moved through first lumen 512*d*).

The positioning indicia sets 523*a* and 523*b* can visually indicate a magnitude of their respective shaft 510-to-catheter sheath 512 spacing in various ways. For example, in some embodiments associated with FIG. 5A, the spacing between successive pairs of indicia in each one of the respective sets 523*a*, 523*b* is reduced (i.e., as compared to the pair of indicia immediately preceding the successive pair) to indicate a reduction in the magnitude of the respective shaft 510-to-catheter sheath 512 distance. The positioning indicia sets 523*a*, 523*b* can be employed by a user to determine an approach of an end-of-travel condition between the shaft 510 and the catheter sheath 512.

In some embodiments, catheter sheath 512 includes a steerable portion 512*e*. In FIG. 5A, steerable portion 512*e* is located at least proximate to distal end 512*b* but may be located at other locations in other embodiments. The steerable portion can be caused to bend or deflect in a desired manner by user or other (e.g., data processing device system) operation of a catheter sheath actuator 516. Steering of the steerable portion 512*e* may be motivated by various reasons including assisting delivery of the catheter sheath 512 through a bodily opening extending along a tortuous path to the bodily cavity. Various suitable catheter sheath steering mechanisms are known in the art and are not elaborated in further detail in this disclosure.

In some embodiments, catheter system 500 includes a fluid-providing portion 524 that includes various ports 524*a*, 524*b* configured to provide an inlet or outlet, or both an inlet and outlet for a fluid (e.g., saline) to be introduced to reduce occurrences of gas (e.g., air) that may be present or sometimes entrapped (for example within first lumen 512*d* of the catheter sheath 512). In some embodiments, the fluid-providing portion 524 includes an elongate fluid-providing member. In some embodiments, fluid-providing portion 524 is detachable from catheter sheath 512.

In some embodiments, the fluid-providing portion 524 includes mechanisms configured to additionally or alternatively expeditiously provide treatment liquid, or expeditiously provide flushing liquid to reduce occurrences of various fluids (e.g., gases such as air) that may be present or sometimes trapped within the catheter shaft 510 and one or more lumens within the catheter shaft 510. In this regard, the fluid-providing portion 524 may include one or more ports, such as at least ports 524*c*, 524*d*, fluidly coupled to an interior cavity 520*g* of enclosure or housing 520, as shown at least in part in at least FIGS. 5X, 5Y, and 5Z. The interior cavity 520*g* may be defined by the enclosure lid 520*h* and a portion of the enclosure 520, such as a set of surrounding or encompassing walls of the enclosure 520. In various embodiments, the enclosure lid 520*h* is completely removable from the enclosure 520 to expose interior cavity 520*g*. In various embodiments, the enclosure lid 520*h* is hingedly coupled to enclosure 520 and is opened when swung or pivoted away from the enclosure 520 to expose interior cavity 520*g*. In some embodiments, the enclosure lid 520*h* is smaller than the enclosure 520. In some embodiments, the catheter shaft 510 is physically, and in some embodiments, fixedly coupled to the enclosure 520 rather than to the enclosure lid 520*h*. In some embodiments, the port 524*c*

(e.g., a first port) may be located on the enclosure lid 520*h* of the enclosure 520. In some embodiments, the port 524*d* (e.g., a second port) may be located on the enclosure 520, e.g., in a fixed wall of the enclosure 520 distinct from the lid 520*h*. In some embodiments, the catheter system 500 may include a seal 526 (FIG. 5Z) arranged between the enclosure lid 520*h* and a portion of the enclosure 520. It is noted that enclosure lid 520*h* is not shown in FIG. 5Z (i.e., the enclosure lid has been removed). The seal 526 may be configured to restrict or prevent the flow of fluid (e.g., air or a liquid such as saline) from the interior cavity 520*g* through the enclosure lid 520*h* (or through an interface between the enclosure lid 520*h* and the enclosure 520) or vice versa when the lid 520*h* is in a closed position. In this regard, when the lid 520*h* is closed, interior cavity 520*g* may be hermetically sealed due at least to the seal 526. The seal 526 may be formed of an elastomeric material, and may be formed of a different material than that of the enclosure lid 520*h*, the enclosure 520, or both the enclosure lid 520*h* and the enclosure 520. In some embodiments, a portion of the seal 526 may be provided on a) the enclosure 520, b) the enclosure lid 520*h*, or both a) and b). In some embodiments, each of the one or more ports 524*c*, 524*d* is arranged to allow liquid flow therebetween and egress of liquid out from or ingress of liquid into the interior cavity 520*g* of the enclosure 520.

In some embodiments, port 524*d* is an inlet port configured to allow for ingress of liquid (e.g., saline) into the interior cavity 520*g* of the enclosure 520, and in some embodiments, port 524*c* is an outlet port configured to allow for flow of fluid, including fluid (e.g., air) other than the liquid out of the interior cavity 520*g*. In some embodiments, liquid, such as saline, may be introduced into the interior cavity 520*g* by way of inlet port 524*d* and flow into the interior cavity 520*g* and proceed into the catheter shaft 510 via a port 524*e* (at least FIGS. 5Y and 5Z) to facilitate the providing of liquid, e.g., for treatment or flushing of fluid (e.g., air) from various parts of the catheter shaft 510. Details of this liquid-provision are provided in more detail below. As liquid (e.g., saline) continues to fill the interior cavity 520*g*, fluid (e.g., air) that was originally present in the interior cavity 520*g* may be flushed, at least in part, out of the interior cavity 520*g* via outlet port 524*c*, according to some embodiments. In this regard, in some embodiments, while liquid from the inlet port 524*d* is directed into the interior cavity 520*g*, fluid other than the liquid is expelled from the outlet port 524*c*.

In some embodiments, a window 527 (shown in FIGS. 5X and 5Y) may be formed of a transparent or translucent material and may be positioned as part of the enclosure lid 520*h* to provide visual access to the interior cavity 520*g* at least when the enclosure lid 520*h* is closed. The visual access may allow an operator or user of the medical device system 500 to view at least a portion of one or more control elements (e.g., 513, 573, or 578) therein or to determine a level of the liquid in the interior cavity 520*g* of the enclosure 520. In this regard, at least some of one or more or all of the surrounding walls of the interior cavity 520*g* besides the window 527 may be opaque to restrict visual access into some or all of the interior cavity 520*g* at least when the enclosure lid 520*h* is closed. Such an opaque part or parts of the enclosure 520 may restrict visual access to at least a portion of one or more control elements (e.g., 513, 573, or 578) in the interior cavity 520*g* or to determine a level of the liquid in the interior cavity 520*g* of the enclosure 520. In this regard, the opaque part(s) combined with the window 527 may be employed to focus a user's view to a particular portion of the interior cavity 520*g*. For example, the user's view may be focused or directed to a particular portion of the interior cavity 520*g* to ascertain when the cavity has been filled with a liquid to a predetermined level or to a particular portion of the interior cavity 520*g* housing a particular control element. In some embodiments, the enclosure lid 520*h* may include a transparent or translucent material. In some embodiments, the enclosure lid 520*h* may be entirely formed of a transparent or translucent material.

Including a port 524*d* on the enclosure lid 520*h* rather than on the enclosure 520 (e.g., along with port 524*c*) may be beneficial for various reasons. For example, by positioning port 524*d* on the enclosure lid 520*h*, the port 524*d* is positioned higher than if it were to be positioned on the enclosure itself. Such a configuration reduces the amount of air that can be entrapped during the flushing of the air from the interior cavity 520*g* since the air is pushed upward during the flushing (i.e., the flushing fluid being typically denser than the air) and is allowed to escape at a higher location in the structure (i.e., port 524*d* being positioned on lid 520*h*) that encloses the interior cavity. Both the enclosure and the lid may be plastic parts made by various molding techniques (e.g., injection molding). In addition, the enclosure 520, as a manufactured part, is typically more complicated than the enclosure lid 520*h*. By providing the port 524*d* on the enclosure lid 520*h* rather than on the enclosure 520 itself may reduce the complexity of the enclosure 520 as a manufacturing part, thereby reducing manufacturing costs.

With reference again to FIG. 5A, in various embodiments, an extension or projection 528 extends from a location proximate a first one of the proximal end 512*a* of catheter sheath 512 and the proximal end 510*a* of shaft 510. In some embodiments, projection 528 extends beyond the first one of the proximal end 512*a* of catheter sheath 512 and the proximal end 510*a* of shaft 510 at least when a part of the shaft 510 is received in first lumen 512*d*. In some embodiments, projection 528 extends outwardly from the first one of the proximal end 512*a* of catheter sheath 512 and the proximal end 510*a* of shaft 510 toward one of the proximal end 512*a* of catheter sheath 512 and the proximal end 510*a* of shaft 510 other than the first one, at least when part of the shaft 510 is received in first lumen 512*d*. In some embodiments, a receiver 529 located, at least in part, in the housing 520, and sized to matingly receive at least a portion of the projection 528, is provided at a location proximate a second one of the proximal end 512*a* of catheter sheath 512 and the proximal end 510*a* of shaft 510. In some of these various embodiments, the projection 528 and the receiver 529 are configured to matingly engage at least when a first amount of part of the shaft 510 is received in the first lumen 512*d* of the catheter sheath 512, but to not matingly engage at least when a second amount of the part of the shaft is received in the lumen of the catheter sheath, the second amount being a non-zero amount in some embodiments. For example, projection 528 may form part of a male component while receiver 529 forms part of a female component sized to mate with the male component. In some embodiments, the projection 528 and the receiver 529 are configured or arranged to additionally matingly engage the catheter member (e.g., catheter sheath) 512 to the shaft 510 at least when part of the shaft 510 is matingly received in the first lumen 512*d* of the sheath 512. In various embodiments, the projection 528 includes a length (e.g., a longitudinal length) that extends from a location at least proximate the first one of the proximal end 512*a* of the catheter sheath 512 and the proximal end 510*a* of the shaft 510 to an end 528*b* of the projection 528, the end 528*b* of the projection 528 configured to be received first in the receiver 529, as compared to other parts of the projection 528 when the projection 528 is inserted into receiver 529. In various embodiments, projection 528 has a length 528*a* (called out in FIG. 5D) that is different than the longitudinal length 510*d* of the shaft 510. In this regard, in some embodiments, the longitudinal length 510*d* of the shaft 510 is greater than the longitudinal length 528*a* of the projection 528.

It is noted that in some embodiments, the first one of the proximal end 512*a* of catheter sheath 512 and the proximal end 510*a* of shaft 510 is a same one as the second one of the proximal end 512*a* of catheter sheath 512 and the proximal end 510*a* of shaft 510 (for example, when projection 528 and receiver 529 are integrated into or form part of a plunger assembly located on one of the shaft 510 (or shaft member 500*a*) and the catheter sheath 512 (or catheter sheath member 500*b*). FIGS. 5T, 5U, and 5V are various side elevation views of a catheter system 501 comprising a shaft 510-1 physically coupled to a housing 520-1 (which may be housing or enclosure 520 in some embodiments), the shaft 510-1 (which may be the shaft 510 in some embodiments) sized and dimensioned for insertion into a lumen of a catheter sheath 512-1 (which may be the sheath 512 in some embodiments) according to some embodiments. In particular, FIGS. 5T, 5U, and 5V show a positioning of shaft 510-1 into the lumen of catheter sheath 512-1 at three successive points in time (from FIG. 5T to FIG. 5V, or vice versa). Catheter system 501 (which may be the system 500 in some embodiments) includes a plunger assembly 530 that includes a projection 528-1 received in a receiver 529-1, each of the projection 528-1 and receiver 529-1 provided at least in part in housing 520-1 (i.e., shown partially sectioned) at a location proximate a proximal end 510*a*-1 of the shaft 510-1. In FIG. 5T, shaft 510-1 has been inserted into the lumen of catheter sheath 512-1 by an amount insufficient to cause an end of projection 528-1 to engage with the catheter sheath 512-1 (e.g., at a location proximate a proximal end 512*a*-1 of the catheter sheath 512). As the amount of the shaft 510-1 inserted into the lumen of catheter sheath 512 increases, the distance between the proximal end 512*a*-1 of catheter sheath 512-1 and the proximal end 510*a*-1 of the shaft 510-1 decreases and causes engagement between the projection 528-1 and the catheter sheath 512-1 to occur. As the amount of the shaft 510-1 inserted into the lumen of catheter sheath 512 increases, the distance between the proximal end of catheter sheath 512-1 and the proximal end 510*a*-1 of the shaft 510-1 decreases and causes increasing amounts of projection 528-1 to be received in receiver 529-1 as shown in FIGS. 5U and 5V. In some embodiments, a biasing device such as a spring provides a restoring force sufficient to move projection 528-1 to its extended configuration as the distance between the proximal end of catheter sheath 512-1 and the proximal end 510*a*-1 of the shaft 510-1 increases.

In other embodiments, the first one of the proximal end 512*a* of catheter sheath 512 and the proximal end 510*a* of shaft 510 (i.e., the "first one" being the end proximate the location from which the extension or projection 528 extends) is different than the second one of the proximal end 512*a* of catheter sheath 512 and the proximal end 510*a* of shaft 510 (i.e., the "second one" being the end proximate the location at which the receiver 529 is provided). For example, in some embodiments associated with FIG. 5A, the projection 528 is located at least proximate the proximal end 512*a* of catheter sheath 512, the projection 528 sized and dimensioned to be matingly received in at least a receiver 529 provided, in some embodiments, at a location at least proximate the proximal end 510*a* of shaft 510 (e.g., in the housing 520 in FIG. 5A) at least when a part of shaft 510 is received in first lumen 512d. In some of the embodiments associated with FIG. 5A, a longitudinal axis of the first lumen 512d (e.g., when catheter sheath 512 assumes a straightened form) is not coaxial with a longitudinal axis of first projection 528. In some of the embodiments associated with FIG. 5A, a longitudinal axis of the first lumen 512d (e.g., when catheter sheath 512 assumes a straightened form) is not coaxial with a longitudinal axis along which projection 528 is moveable within receiver 529. In some of the embodiments associated with FIG. 5A, the manipulable portion 502 is arranged to not be inserted into the receiver 529 when the manipulable portion 502 is delivered though first lumen 512d of the catheter sheath 512, e.g., to a bodily cavity. In some embodiments, the receiver 529 and first lumen 512d may be coaxially arranged when the manipulable portion 502 is delivered outwardly from the distal end 512b of catheter sheath 512. In some embodiments, the projection 528 is coupled to, or forms part of, shaft member 500a. In some embodiments, the receiver 529 is coupled to, or forms part of, sheath member 500b. In some embodiments, the projection 528 is distinct from shaft member 500a.

FIGS. 5D, 5E, and 5F are various side elevation views of a positioning of shaft 510 into the first lumen 512d (not called out in these figures) of catheter sheath 512 at three successive points in time (from FIG. 5D to FIG. 5F, or vice versa). At least one portion of the catheter system 500 (e.g., manipulable portion 502, not shown in FIGS. 5D, 5E and 5F) is selectively reconfigured according to various embodiments during at least some of these points in time. It is understood that in each of FIGS. 5D, 5E and 5F, the distal end 510b (not shown in FIGS. 5D-5F) of shaft 510 has been introduced into the first lumen 512d (not shown in FIGS. 5D-5F) of catheter sheath 512 and is advanced from the proximal end 512a of the catheter sheath 512 toward the distal end 512b (not shown in FIGS. 5D-5F) of catheter sheath 512. As best shown in FIG. 5A, in some embodiments, shaft 510 includes a longitudinal length 510d extending between the proximal and distal ends 510a, 510b of shaft 510, the longitudinal length 510d of the shaft being different (e.g., greater in FIG. 5A) than the longitudinal length 528a of projection 528.

In some embodiments associated with various ones of FIG. 5, a first particular amount of the longitudinal length 528a of the first projection 528 is located in receiver 529 when a second particular amount of the longitudinal length 510d of shaft 510 is located inside first lumen 512d of the catheter sheath 512, the first particular amount of the longitudinal length 528a of the first projection 528 being less than the second particular amount of the longitudinal length 510d of shaft 510. In various embodiments, the projection 528 and receiver 529 are configured to matingly engage at least when a first amount of part of the shaft 510 is received in the first lumen 512d (e.g., as shown respectively by each of FIGS. 5E and 5F), and the projection 528 and receiver 529 are configured not to matingly engage at least when a second amount of the part of the shaft 510 is received in the first lumen 512d (e.g., as shown in FIG. 5D). In some of these various embodiments, the first amount is different (e.g., greater) than the second amount, and in some embodiments, the first amount and the second amount are each an amount of the longitudinal length 510d of the shaft 510.

In some embodiments, projection 528 and receiver 529 are configured to matingly engage when shaft 510 is not received in first lumen 512d. This circumstance can occur in some embodiments, when projection 528 and receiver 529 form part of a plunger assembly (e.g., plunger assembly 530) provided on one of shaft 510 and catheter sheath 512. This circumstance can occur in some embodiments that are the same or similar to that shown in FIG. 5A where a particular positioning and orientation between shaft 510 and catheter sheath 512 allow for a mating between projection 528 and receiver 529 without the shaft 510 being received in first lumen 512d.

In FIG. 5D, projection 528 extending from the proximal end 512a of catheter sheath 512 has not been received in the first receiver 529 provided in the housing 520, while various amounts of the projection 528 have been received in receiver 529 in FIGS. 5E and 5F, the amounts varying (e.g., increasing) with the advancement of shaft 510 through first lumen 512d. In the configuration evolution from FIG. 5D, to FIG. 5E, and to FIG. 5F, manipulable portion 502 (not shown in FIGS. 5D, 5E and 5F) is advanced through the first lumen 512d from the proximal end 512a of the catheter sheath 512 toward the distal end 512b of catheter sheath 512. A control system or actuator system (e.g., one or more components of control system 322 or system 545, possibly including one or more of the components of at least FIG. 5R, 5S, 5W, 7, 8, or 10) may respond to or be controlled by varying amounts of the length 528a of the projection 528 being within the receiver 529 and alter aspects of the manipulable portion 502 in response to or under the control of these varying amounts. For example, the control system or actuator system physically or operatively coupled to the manipulable portion 502 may respond to or be controlled by varying amounts of the length 528a of projection of 528 being within receiver 529 by varying force transmitted to the manipulable portion 502 in accordance with the varying amounts of the length 528a of projection of 528 being within receiver 529, e.g., while the distal end of the manipulable portion 502 advances outwardly from the distal end 512b of the catheter sheath 512 along an arcuate or coiled path (for instance, FIGS. 5H, 5I, 5J).

As shown in FIG. 5G, the respective first portions 509a (only one called out) of the elongate members 504 (only one called out) are arranged with respect to one another front surface 518a-toward-back surface 518b in a first direction represented by arrow 530a in a first stacked array 515a (see, e.g., proximal end 307 in FIG. 3A for a closer look at such a first stacked array) sized and shaped to be delivered through first lumen 512d of catheter sheath 512 when a portion of the catheter system 500 (e.g., manipulable portion 502) is in a delivery configuration also known as a first or unexpanded configuration in some embodiments. In various embodiments, manipulable portion 502 is in the delivery configuration as it is delivered through the first lumen 512d as described above, for example, in regards to FIGS. 5D, 5E, and 5F. As shown in FIG. 5G, the respective second (intermediate) portions 509b (only one called out) of the elongate members 504 are arranged with respect to one another front surface 518a-toward-back surface 518b in a second direction as represented by arrow 530b in a second stacked array 515b sized to be delivered through the first lumen 512d when the portion of the catheter system 500 is in the delivery configuration. In various embodiments, the first direction (i.e., arrow 530a) and the second direction (i.e., arrow 530b) are non-parallel directions at least when the arrayed elongate members 504 assume a straightened form.

In various embodiments, the elongate members 504 of the manipulable portion 502 are arranged within catheter sheath 512 such that each elongate member 504 is to be advanced distal end 505 first into a bodily cavity. In various embodiments, the elongate members 504 are arranged within catheter sheath 512 such that each elongate member 504 is to be advanced out distal end 505 first from the distal end 512b of catheter sheath 512. In some embodiments, manipulable portion 502 includes a first or proximal portion 508a and a second or distal portion 508b, each of these portions comprising a respective part of each of at least some of the elongate members 504. In some embodiments, the proximal and the distal portions 508a, 508b include respective portions of elongate members 504. In some embodiments, the manipulable portion 502 is arranged to be delivered second or distal portion 508b first through the lumen 512d of the catheter sheath 512 into a bodily cavity when the manipulable portion 502 is delivered in the unexpanded or delivery configuration as shown, e.g., in FIG. 5G.

Notably, as used herein, the term "stacked" does not necessarily require the elongate members 504 rest directly or even indirectly upon one another, but rather refers to an ordered arrangement which may include spaces or gaps between immediately adjacent or most immediate neighboring pairs of elongate members 504. It is also noted that while illustrated in FIG. 5G as a plurality of substantially parallel stacked plates or strips, the elongate members 504 need not be perfectly rigid, so there may be some flex, sag, or curvature even when the catheter sheath 512 is essentially straight. It is further noted that in use, the catheter sheath 512 may curve or even twist to follow a bodily lumen. The elongate members 504 may adopt or conform to such curvatures or twists as the elongate members 504 are advanced through catheter sheath 512. In either of these situations, the elongate members 504 generally maintain the relative positions to one another as a stacked arrangement.

In various embodiments, the respective first, second, and third portions 509a, 509b and 509c (only one of each called out in FIG. 5G) of various ones of the elongate members 504 have been stressed into a higher energy state illustrated in FIG. 5G, as compared to a lower energy state shown, e.g., in FIGS. 5A, 5B, and 5C. In various embodiments, the respective second portions 509b of various ones of the elongate members 504 in the initial or predisposed configuration (e.g., as shown in FIGS. 5A, 5B, and 5C) have been stressed into a higher energy state suitable for unbending or uncoiling them sufficiently enough to allow the elongate members 504 to be delivered through catheter sheath 512 in the delivery configuration as shown in FIG. 5G. In various embodiments, at least one of the respective first portions 509a and the third portions 509c of each of various ones of the elongate members 504 has been stressed into a higher energy state by un-fanning at least the second portions 509b of the elongate members 504 sufficiently to allow the elongate members 504 to be introduced into, and delivered though catheter sheath 512. In some of these embodiments, potential energy is imparted to the various elongate members 504 in the delivery configuration by the higher energy state, the potential energy sufficient to return the arrangement of elongate members 504 generally back toward a lower energy state when released from the confines of catheter sheath 512. In some embodiments, the lower energy state includes a partial fanning of at least the second portions 509b of the elongate members 504.

In some example embodiments, the arrangement of elongate members 504 is stressed into a higher energy state by retracting the arrangement of elongate members 504 into at least a portion of catheter sheath 512 prior to inserting catheter sheath 512 into a body. For example, in various embodiments the arrangement of elongate members 504 is stressed into a higher energy state by retracting the arrangement of elongate members 504 at least into the fluid-providing portion 524 of catheter sheath 512. In some of these various embodiments, the fluid-providing portion 524 is detached from the remainder of the catheter sheath 512 when the arrangement of elongate members 504 is retracted into the fluid-providing portion 524 with the fluid-providing portion 524 subsequently attached or reattached to the remainder of the catheter sheath 512 after the retraction. This technique may advantageously allow for a more efficient operation as the arrangement of elongate members 504 need not be retracted through the entirety of the catheter sheath 512.

In some embodiments, the arrangement of elongate members 504 is stressed into a higher energy state by uncoiling the elongate members 504 and inserting the arrangement of elongate members 504 into catheter sheath 512. In some embodiments, the arrangement of elongate members 504 is reconfigured from the initial or predisposed configuration shown in FIGS. 5A, 5B, 5C, which is typically provided or calibrated at the time of manufacturing, to the delivery configuration shown in FIG. 5G at a point of use. In some embodiments, the arrangement of elongate members 504 is reconfigured from the initial or predisposed configuration shown in FIGS. 5A, 5C to the delivery configuration shown in FIG. 5G at a place of manufacture, assembly, or distribution. In various embodiments, various devices including various guides or manipulators may be employed to reconfigure the arrangement of elongate members 504 from the initial or predisposed configuration shown in FIGS. 5A, 5C to the delivery configuration shown in FIG. 5G. In some of these various embodiments, these devices form part of catheter system 500 (e.g., fluid-providing portion 524). In some embodiments, the devices are extraneous to catheter system 500. The higher energy states may be controlled to not cause damage to portions of catheter system 500 during delivery through catheter sheath 512. In FIG. 5G, cable 513b is extended along the elongate members 504 in the delivery configuration. In various embodiments, cable 513b is delivered through first lumen 512d when the elongate members 504 are advanced in a delivery configuration toward a bodily cavity. In various embodiments, cable 513b is drawn through first lumen 512d by the manipulable portion 502 as the manipulable portion 502 is advanced in a delivery configuration toward a bodily cavity.

FIGS. 5H, 5I, and 5J are various side elevation views of various respective parts of manipulable portion 502 positioned at three successive points in time as each respective part of the manipulable portion 502 or structure 502a thereof is advanced outwardly from the confines of the first lumen 512d (not called out in these figures) of catheter sheath 512 (i.e., from the distal end 512b). These figures illustrate coiling and uncoiling of the manipulable portion 502 during deployment and retraction, respectively, of the manipulable portion.

FIG. 5J shows a portion of the catheter system 500 including the plurality of elongate members 504 (two called out) positioned in an expanded configuration also referred to as a second or bent configuration. In Figured 5J, the manipulable portion 502 (or at least an elongated part thereof) has a volute or coiled shape, e.g., after a control system or actuator system (e.g., as described herein) that is operatively or physically coupled to the manipulable portion 502 varies a size, shape, or both size and shape of at least part of the manipulable portion extending outside of the distal end 512b of the catheter sheath 512 to, at least in part, cause the distal end of the manipulable portion to move along a first trajectory. In FIG. 5J, the respective second portions 509b (only one called out) of various ones of the elongate members 504 have cleared the confines of first lumen 512d (not called out) while other portions of the elongate members 504 remain within the confines of first lumen 512d. In various embodiments, each of at least the respective second portions 509b of each elongate member 504 is curved about a respective bending axis 534 (i.e., one represented by symbol "X") into an arcuate stacked array 532. Each bending axis 534 extends in a direction having a directional component transversely oriented to the respective longitudinal length of the respective elongate members 504. In various embodiments, each of the respective second portions 509b of various ones of the elongate members 504 in the arcuate stacked array 532 is coiled about a respective bending axis 534 into a coiled stacked array. In various embodiments, each respective second portion 509b is bent to have a scroll or volute shaped profile. In various embodiments, each second portion 509b is arranged to have a curvature that varies at least once along the respective length of the elongate member 504. In some embodiments, when positioned in the second or bent configuration, a first portion 521a of the front surface 518a (only one called out) of the respective second portion 509b of each elongate member 504 is positioned diametrically opposite to a second portion 521b of the front surface 518a in the volute shaped structure 502a. When positioned in the second or bent configuration, the coiled arrangement of elongate members 504 is sized, shaped, or both sized and shaped too large for delivery through the first lumen 512d, at least in a direction toward the bodily cavity. In this regard, it can be said that when the coiled arrangement of elongate members 504 is in the second or bent configuration (e.g., FIG. 5J), the manipulable portion 502 comprises a coiled form in an expanded configuration.

In various embodiments, the respective second portions 509b of various ones of the elongate members 504 are pre-formed to autonomously bend when the second portions 509b are advanced outwardly from the confines of first lumen 512d. As the respective second portions 509b are advanced from the confines of first lumen 512d, they are urged or biased to seek their low energy state (e.g., their initial coiled configuration). In various embodiments, the respective distal ends 505 of various ones of the elongate members 504 (only one called out in each of FIGS. 5H, 5I, and 5J) move along a trajectory that follows a coiled path (e.g., a path that curves back on itself) during the advancement of various parts of manipulable portion 502 outwardly from the confines of first lumen 512d. In various embodiments, the coiled path makes at least one full turn. In some embodiments, at least part of the coiled path may extend along a volute path. In some embodiments, manipulable portion 502 or structure 502a thereof has a distal end (i.e., the same or different than a distal end 505 of an elongate member 504) configured to be delivered first, with respect to other parts of the manipulable portion 502 through the first lumen 512d or outwardly from the distal end 512b of catheter sheath 512.

In various embodiments, the respective second portions 509b of various ones of the elongate members 504 are pre-formed to autonomously coil as they are advanced into a bodily cavity in a manner that may advantageously reduce physical interactions between at least the distal end 505 of the elongate members 504 and an interior tissue surface within the bodily cavity (not shown in FIG. 5 but may be exemplified by left atrium 204 of FIG. 2) into which they are deployed. In various embodiments, the elongate members 504 are arranged to continuously bend or curl to move at least the respective distal ends 505 of the elongate members away from an interior tissue surface within a bodily cavity into which they are advanced. A reduction of contact and other physical interaction of the elongate members 504 with an interior tissue surface within a bodily cavity during the advancement may reduce occurrences of, or the severity of, damage inflicted to various tissue structures (i.e., especially damage caused by the distal end 505 of an elongate member 504 which may catch on various tissue structures during the advancement). In some embodiments, the arcuate stacked array 532 is arranged to have a predetermined size that will allow the arcuate stacked array 532 to be positioned within a bodily cavity with at most relatively minor amounts of contact with an interior tissue surface within the bodily cavity.

FIGS. 5H, 5I, and 5J show various interactions between a portion of control element 513 (e.g., cable 513b) and the manipulable portion 502 (e.g., structure 502a) as various respective parts of the manipulable portion 502 or structure 502a thereof are advanced outwardly from the confines of first lumen 512d. For example, FIGS. 5H, 5I, and 5J show various interactions between the part or portion 514 (FIG. 5C) of cable 513b located outside the distal end 512b of catheter sheath 512 and the manipulable portion 502 (e.g., structure 502a) as various respective parts of the manipulable portion 502 or structure 502a thereof are advanced outwardly from the confines of first lumen 512d. In some embodiments, a control system or actuator system (e.g., as described herein) responds to or is controlled by relative movement between shaft 510 and catheter sheath 512, and may control one or more actuators to cause these interactions. In some embodiments, a control system (e.g., from a control system such as controller 324 or data processing device system 110) is operatively coupled to an actuator system and is operable to control activation of one or more actuators of the actuator system in response to the relative movement between shaft 510 and catheter sheath 512. For example, in some embodiments, at least a portion of at least one actuator or modulation actuator (e.g., actuator 546, some other actuator or actuator set, or a portion of at least one of these actuators) physically or operatively coupled to a control element (e.g., 513) is moveable in each of a first direction and a second direction different than the first direction. In some embodiments, movement of at least the portion of the actuator (e.g., modulation actuator) in the first direction may accompany an increase in an amount of manipulable portion 502 extending outwardly from the distal end 512b of catheter sheath 512 (e.g., as shown by the sequence of FIGS. 5H, 5I, and 5J), e.g., as the shaft 510 is moved distally through the catheter sheath 512. In some embodiments, movement of at least the portion of the actuator (e.g., modulation actuator) in the second direction may accompany a decrease in an amount of manipulable portion 502 extending outwardly from the distal end 512b of catheter sheath 512 (e.g., as shown by the sequence of FIGS. 5J, 5I, and 5H), e.g., as the shaft 510 is moved proximally through the catheter sheath 512.

In various embodiments, it may be important to prevent tension levels in various control elements (e.g., cable 513b) from reducing below certain threshold levels during the outward advancement of the various respective parts of the manipulable portion 502 or structure 502a thereof from the confines of first lumen 512d. For example, reduction of tension in the cable 513b to a level where slack develops in the cable member 513b as parts of the manipulable portion 502 or structure 502a are advanced outwardly from the confines of the first lumen 512d of catheter sheath 512 may lead to various undesired conditions. In some cases, if sufficient slack in cable 513b results, portions of cable 513b may become wrapped, or otherwise entangled with the manipulable portion 502 and interfere with, or restrict a current or subsequent manipulation or deployment of the manipulable portion 502 (e.g., a subsequent manipulation or deployment as shown in FIGS. 5L-1, 5L-2, 5M-1, 5M-2, 5N, 5O, 5P, and 5Q). Maintaining a desired tension on cable 513b can be complicated when the elongate members 504 are advanced outwardly from the confines of first lumen 512d along a path that requires both an advancement of portions of the cable 513b from the first lumen 512d and a subsequent retraction of portions of the cable 513b into the first lumen 512d during the movement along the path. For example, the coiled path that a distal end of the manipulable portion 502 follows as the manipulable portion 502 is advanced outwardly from the confines of first lumen 512d of the catheter sheath 512 (e.g., as shown in FIGS. 5H, 5I and 5J) may require an advancement of various portions of the cable 513b from the first lumen 512d and a subsequent retraction of various portions of the cable 513b into the first lumen 512d when some desired level of tension is required in cable 513b (e.g., a level of tension sufficient to reduce occurrences of slackness in the cable 513b). In various embodiments, modulation of a size, a shape, or both, of the manipulable portion 502 or structure 502a thereof occurs at least in a state where at least a part of the manipulable portion 502 or structure 502a thereof and a part of the control element 513 (e.g., cable 513b) extends outside the distal end 512b of the catheter sheath 512. In some of these embodiments, a length of the part of the control element 513 is required to increase and then subsequently decrease during or throughout the modulation of the manipulable portion 502 or structure 502a. In some of these various embodiments, the manipulable portion 502 or structure 502a is sized or shaped during or throughout the modulation to have a size or shape sufficient to limit or restrict movement of at least the part of the manipulable portion 502 or structure 502a through the first lumen 512d.

FIG. 6 is a graph that includes a data set (i.e., represented by plot 600) measured by some of the present inventors using a device that is the same or similar in construction to the manipulable portion 502 shown in FIG. 5. The device includes a structure comprised of a stacked array of resilient elongate members approximately 240 millimeters in length and pre-shaped to autonomously coil as the elongate members are advanced outwardly from the confines of a catheter lumen along which the device has been advanced (e.g., in a manner the same or similar to embodiments previously described with respect to FIGS. 5H, 5I, and 5J). Plot 600 represents a required movement of a control line physically coupled to the distal ends of the device elongate members (i.e., the same or similar to cable 513b) as the elongate members are positioned at different locations outwardly from the distal end of the catheter sheath as the elongate members autonomously bend to follow a coiled path upon advancement from the confines of the catheter sheath. The horizontal axis of the FIG. 6 graph is associated with an amount that a distal end of the structure (e.g., a distal end of at least one of the elongate members, such as distal end 505) travels along a path that extends outwardly from a distal end of the catheter sheath while the vertical axis is associated with an amount of the control line that is metered during the movement along the path in accordance with various embodiments.

As used in this disclosure, the word "meter" means to supply or provide in a measured or regulated amount. In this regard, the metering of a control line (e.g., control cable 513b or other elongated control element or portion thereof) can occur in different directions. For example in some embodiments, the control line can be caused (e.g., by one or more of the actuators 540a, 540b, 546 in FIG. 7) to be metered or to move along a path with a controlled or regulated rate in a first direction (e.g., an action associated with "take-up" of the control line) suitable to reduce or decrease an amount of at least a portion of the control line (e.g., control cable 513b) located outside a distal end (e.g., distal end 512b) of the catheter sheath (e.g., catheter sheath 512) during one of (a) a transition toward or to an expanded configuration of a manipulable portion (e.g., manipulable portion 502) and (b) a transition toward or to a delivery configuration of the manipulable portion (e.g., manipulable portion 502). In some embodiments, the control line can be caused (e.g., by one or more of the actuators 540a, 540b, 546 in FIG. 7) to be metered or to move along a path with a controlled or regulated rate in a second direction (e.g., an action associated with "play-out" of the control line) suitable to increase an amount of at least a portion of the control line (e.g., control cable 513b) located outside a distal end (e.g., distal end 512b) of the catheter sheath (e.g., catheter sheath 512) during the other of (a) and (b), or which can result in a relatively larger portion of the control line being available for extension outwardly from a distal end of the sheath.

In various embodiments, metering during play-out can reduce tension in the control line, sometimes to the point of imparting slackness in the control line. In some of these various embodiments, metering during play-out may allow increased amounts of the control line to be pulled outwardly from the distal end of the catheter sheath (for example by a release of stored potential energy in manipulable portion 502). In some embodiments, metering during take-up can increase tension in the control line. It is noted that, in some circumstances, slack in the control line can exist during some part of a take-up procedure. For example, slack in cable 513b may arise if the metering rate during take-up is insufficient to take up a portion of the cable 513b that extends outwardly from the distal end 512b of sheath 512 with a rate appropriate for the advancement of manipulable portion 502 from the distal end 512b of sheath 512 along a coiled trajectory as shown in FIGS. 5H, 5I and 5J. In various embodiments, the control line is metered with a rate that is dependent on a rate in which the distal end of the structure (e.g., structure 502a) advances outwardly from the distal end of the catheter sheath or advances inwardly into the distal end of the catheter sheath.

A portion 600a of plot 600 shows that the control line is advanced outwardly from the distal end of the catheter sheath up to about a point where the stacked elongate members have been initially advanced outwardly from the distal end of the catheter sheath by approximately 50 mm along the path (e.g., in a manner that is the same or similar to that shown in FIG. 5H). In various embodiments, the control line is not actively metered and the control line may be advanced outwardly from the catheter sheath as the stacked array of elongate members pulls the control line outwardly during this initial advancement. Any slack in the control line may be taken up at least in part during this initial advancement. Further advancement along the path (i.e., from 50 mm up to about 170 mm) of the stacked elongate members outwardly from the distal end of the catheter sheath requires, in these embodiments, that the control line be taken-up to cause a portion of the control line to be retracted back into the distal end of the catheter sheath. In particular, portion 600b of plot 600 is associated with an amount of the control line, in these embodiments, to be taken up without imparting particular force on the advanced portion of the elongate members extending outwardly from the distal end of the catheter sheath, the particular force sufficient to noticeably move the advanced portion of the elongate members away from their low potential energy state. It is noted that force transmitted to the elongate members by the control line can cause bending of the elongate members that in turn can impart potential or spring energy to the elongate members. It is understood that if an amount of control line taken-up between the 50 mm and 170 mm points on the horizontal axis is less than that required by plot 600 (i.e., below portion 600*b*), then slack in the control line may exist, which may in turn, lead to various undesired results.

In portion 600*c* of plot 600, the control line is controlled in accordance with a further movement of the coiled structure outwardly from the distal end of the catheter sheath according to various embodiments (for example as shown in FIGS. 5C, 5L-1, 5L-2). It is understood that different plots will result for other devices having different dimensions or different configurations, and the plot 600 is only presented by way of non-limiting example.

Ideally, in some embodiments, the take-up of the control line of the device described above in conjunction with FIG. 6 should occur above the "minimal" take-up amount specified by the portion 600*b* of plot 600 to increase the likelihood that the control line does not slacken during the advancement of the device outwardly from the confines of the catheter sheath.

FIG. 6 includes a line 602 associated with a particular control line metering action employed according to some embodiments. Portion 602*a* of line 602 is associated with a condition in which the control line is not taken up as the stacked elongate members are initially advanced outwardly from the distal end of the catheter sheath about 40 mm along a deployment path. During an additional or subsequent advancement of the stacked elongate members outwardly from the distal end of the catheter sheath along the deployment path, the control line is taken up or metered with a first rate (i.e., associated with the portion 602*b* of line 602) to cause a portion of the control line to be retracted inwardly into the distal end of the catheter sheath during a first part of the take-up. In FIG. 6, this first part of the control line take-up occurs when the stacked elongate members have been advanced between 40 mm and 90 mm along the deployment path outwardly from the distal end of the catheter sheath. During further advancement of the stacked arrangement of the elongate members outwardly from the distal end of the catheter sheath, the control line is taken up or metered with a second rate (i.e., associated with the portion 602*c* of line 602) during a second part of the take-up. In FIG. 6, this second part of the control line take-up occurs when the stacked elongate members have been advanced between 90 mm and 200 mm along the deployment path outwardly from the distal end of the catheter sheath. In various embodiments, the first metering rate is different than the second metering rate. For example, in FIG. 6, the first metering rate is twice the second metering rate as indicated by the difference in the slopes of line portions 602*b* and 602*c*. In this regard, in some embodiments, the first metering rate may be referred to as a "2× rate", and the second metering rate may be referred to as a "1× rate". Different rates may be employed in other embodiments. In various embodiments, metering of the control line, with the first rate, the second rate or each of the first and second rates occurs along a particular direction that is relative to, or respective with, a reference frame that is provided by a portion of the catheter device (e.g., the catheter shaft to which the manipulable portion is coupled) that is moveable with respect to the catheter sheath. In various embodiments, metering of the control line, with the first rate, the second rate or each of the first and second rates, may lead to different respective rates of movement of the control line with respect to a reference point on the catheter sheath (e.g., a distal end of the catheter sheath).

A large portion of the control line take-up represented by portion 602*b* of line 602 is above the "minimum" threshold provided by the portion 600*b* of plot 600 and occurrences of slack in the control line are reduced when the control line is metered in accordance with line 602. The different metering rates represented by portions 602*b*, 602*c* of plot 600 may be motivated by different reasons. For example, with reference to FIG. 5I, a first (e.g., a relatively higher) take-up rate similar to the first rate represented by the slope of portion 602*b* in FIG. 6 may be employed to ensure proper retraction of control cable 513*b* since the manipulable portion 502 is being further advanced along a portion of its trajectory outwardly from the distal end 512*b* of the catheter sheath 512 (i.e., as compared between FIGS. 5H and 5I) along a path that coils or curls back on itself and may thus benefit from a relatively rapid take-up of the cable 513*b*. It is noted that in various embodiments associated with FIG. 5, the manipulable portion 502 autonomously coils as the manipulable portion 502 is advanced outwardly from the confines of the first lumen 512*d*. As previously described above in this disclosure, the autonomous coiling may be motivated by different reasons including reducing occurrences of undesired contact between a distal end 505*a* (e.g., provided by at least one of the distal ends 505 in some embodiments) of the manipulable portion 502 and a tissue surface defining a bodily cavity into which the manipulable portion 502 is advanced. The first take-up rate can be defined or predetermined to cause the take-up of the cable 513*b* to be sufficient to additionally bend the manipulable portion 502 or structure 502*a* thereof to cause portions thereof to assume a smaller radius of curvature than they would normally have from their autonomously formed shapes. This situation can in turn result in an advancement trajectory of the distal end of the manipulable portion 502 outwardly from the distal end 512*b* of the catheter sheath 512 that has a "tighter" curvature than an un-modified respective trajectory that the distal end of the manipulable portion 502 undergoes solely on the basis of its autonomous coiling during the advancement. In some embodiments, this situation can in turn result in a coiled advancement trajectory of the distal end of the manipulable portion 502 outwardly from the distal end 512*b* of the catheter sheath 512 that is "tighter" or more closely wound than an un-modified respective trajectory that the distal end of the manipulable portion 502 undergoes solely on the basis of its autonomous bending during the advancement. A tighter, more compact or more closely wound advancement path may, in some cases, further reduce occurrences of undesired contact between the distal end of the manipulable portion 502 and the tissue surface during the advancement of the distal end of the manipulable portion 502 into the bodily cavity. It is noted that this additional bending of the structure 502*a* during the take-up of the cable 513*b* with the first rate imparts additional potential or spring energy in the structure. However, unlike various embodiments described in co-assigned International Patent Application No. PCT/US2012/022061 in which similar structures are bent into an arcuate or coiled configuration from a low energy configuration in which the similar structures are generally straight in form, lower amounts of potential energy are imparted onto structure 502*a* by the take-up of cable 513*b* since structure 502*a* is being bent from a pre-formed coiled shape having a low energy state. Nonetheless, additional deflection imparted on manipulable portion 502 by cable 513b may be limited to reduce the amount of spring-back that would occur in manipulable portion 502 should a failure in cable 513b occur. A phantom line 502b is representative of a portion of manipulable portion 502 in its initial or predisposed configuration (i.e., a low energy state) in FIG. 5I.

In various embodiments, further advancement of the manipulable portion 502 outwardly from the confines of first lumen 512d further advances the distal end of manipulable portion 502 along the coiled path and coils manipulable portion 502 from a state shown in a FIG. 5I to a state as shown in FIG. 5J. In these embodiments, a second (e.g., a relatively lower) take-up rate similar to the second rate represented by the slope of portion 602c in FIG. 6 may be employed to take up control cable 513b since the manipulable portion 502 is being further advanced along a portion of its trajectory back generally toward the distal end 512b of the catheter sheath 512 along a portion of the coiled path where a relatively slower take-up of the cable 513b may be required. The slower second take-up rate may be motivated for various reasons including providing a better match for the profile of plot 600. In some embodiments, the distal portions of the elongate members 504 in the structure 502a may be pre-formed with a tight curvature in their initial or predisposed configuration to promote a rapid transition away from a tissue surface of the bodily cavity as the structure is advanced outwardly from the distal end 512b of the catheter sheath 512. Although these relatively tightly coiled distal portions of the elongate members 504 may enhance advancement of the manipulable portion 502 into the bodily cavity, they may hinder or restrict other required functions of the manipulable portion 502. For example, fanning of the various curved portions of the coiled elongate members 504 as described later in this disclosure may be required, and various factors such as the widths of the curved portions the elongate members 504 as well as the amount of curvature along the coiled form may restrict or hinder the required fanning.

In some embodiments associated with FIG. 5J, the second take-up rate can be defined or predetermined to cause the take-up of the cable 513b to be sufficient to additionally bend the manipulable portion 502 to cause portions thereof to assume a larger radius of curvature than they would normally have from their autonomously formed shapes. The larger radius of curvature is contrasted with a phantom line 502c, which is representative of a part of manipulable portion 502 in its initial or predisposed configuration (i.e., a low energy state). It is noted that the take-up of cable 513b associated with FIG. 5J has imparted larger dimensions to manipulable portion 502 or structure 502a thereof as compared with the initial or predisposed configuration of manipulable portion 502 or structure 502a thereof. In some embodiments, this may advantageously simplify or reduce complexity for additional actions to manipulate manipulable portion 502 to cause manipulable portion 502 or structure 502a thereof to better conform (e.g., to further expand to conform) with a tissue surface of a bodily cavity into which the manipulable portion 502 has been deployed. It is noted that a failure of at least cable 513b in FIG. 5J would cause manipulable portion 502 to contract inwardly onto itself from any release of stored potential energy caused by such a failure. This can, in some embodiments, reduce occurrences of tissue damage that may be possibly associated with a failure of cable 513b. In the sequence depicted by FIG. 5H, 5I and 5J, an end or terminus of cable 513b (an example of at least part of a control element) advances along a coiled path as the manipulable portion 502 is advanced outwardly from the distal end 512b of the catheter sheath 512.

FIG. 5L-1 shows an expanded configuration in which the manipulable portion 502 has been advanced outwardly from the confines of the first lumen 512d sufficiently to allow potential energy from at least the respective first portions 509a of the elongate members to be released and cause the first portions 509a to be urged or biased to assume a lower energy state (i.e., the same or similar to their initial or predisposed configuration shown in FIG. 5A). This situation in turn causes at least the respective second portions 509b of various ones of the elongate members 504 to autonomously fan, at least in part, with respect to one another into an expanded configuration also known as a first fanned configuration 536. In some example embodiments, as the respective third portions 509c are advanced from the confines of catheter sheath 512, stored potential energy is released and the respective third portions 509c are urged or biased into a lower energy state to cause at least the respective second portions 509b of various ones of the elongate members 504 to autonomously fan, at least in part, with respect to one another into the first fanned configuration 536. In some example embodiments, as both the respective third portions 509c and the respective first portions 509a of various ones of the elongate members 504 are advanced from the confines of catheter sheath 512, stored potential energy is released and the respective first and third portions 509a, 509c are urged or biased into respective lower energy states to cause at least the respective second portions 509b of various ones of the elongate members 504 to autonomously fan at least in part, with respect to one another into the first fanned configuration 536. In various embodiments, the manipulable portion 502 is sized too large for delivery through the first lumen 512d at least in a direction toward the distal end portion 512b of the catheter sheath 512 when the manipulable portion 502 is positioned in the first fanned configuration 536. A crossing location between various elongate members 504 in the first fanned configuration 536 is positioned between the proximal and distal portions 508a and 508b of manipulable portion 502 in FIG. 5L-1.

In various embodiments, additional fanning mechanisms or actuators (for example, as described later in this disclosure, such as with respect to FIG. 5S) may be employed to assist in the fanning of, or to promote an additional fanning of various ones of the elongate members 504 as the elongate members 504 are moved into various additional expanded configurations. Additional manipulations of manipulable portion 502 (for example, as described later in this disclosure) may be employed to further modify the expanded configuration shown in FIG. 5L-1. In various embodiments, various manipulations of manipulable portion 502 may be employed to transition the expanded configuration of the manipulable portion 502 between various particular states.

A discussion will now be made on the interplay between the metering of cable 513b and a retraction of manipulable portion 502 into the confines of first lumen 512d that occurs in some embodiments. In the state of FIG. 5J, if effort was made to retract manipulable portion 502 back into the confines of the first lumen 512d (for example by a relative movement between shaft 510 and catheter sheath 512), the tensioned cable 513b would likely impede or resist these efforts. In some cases, cable 513b would be subjected to significant forces in response to these attempts to urge the manipulable portion 502 into the first lumen 512d. In some cases, these forces may be sufficient to raise concerns about damage to or failure of the cable 513b or manipulable portion 502. In some embodiments, as discussed in more detail, below, one or more control elements, which may include the control element 513, may be severed to permit retraction of manipulable portion or end effector 502 back into the confines of the first lumen 512*d* in the event that an intended operation on the manipulable portion is unable to be performed.

In some embodiments, the cable 513*b* is controlled to develop reduced tension in various portions of the cable 513*b* to a level or levels sufficient to reduce resistance (e.g., tension) that would impede the retraction of manipulable portion 502 into the first lumen 512*d*. For example, in some embodiments, cable 513*b* is so controlled by clutching or decoupling a take-up mechanism coupled to the cable 513*b* to "free-wheel" so as to allow the cable 513*b* to be freely pulled outwardly from the distal end 512*b* of the catheter sheath 512 to allow various portions of manipulable portion 502 to be retracted into the first lumen 512*d* with reduced levels of resistance. In some embodiments, cable 513*b* is played out with a metered rate to allow a portion of the cable 513*b* to be moved outwardly from the distal end 512*b* of the catheter sheath 512 in a regulated manner during the retraction of the manipulable portion 502 into the first lumen 512*d*. In some embodiments, cable 513*b* is metered to regulate reduced tension levels (e.g., slack) formed in the cable 513*b*. In FIG. 6, line 604 represents a particular control line metering action employed according to some embodiments. Portion 604*b* of line 604 is associated with a condition in which the control line (e.g., control line previously described in conjunction with FIG. 6) is played-out or metered with a third rate (e.g., represented by the slope of portion 604*b* of line 604) to cause a portion of the control line to have a reduced tension level (e.g., slackened). A slackened portion of the control line in some embodiments is sufficient to allow a portion of the array of elongate members protruding outwardly from the catheter sheath to autonomously bend toward (e.g., inwardly to) a lower energy position (for example, an inward location the same or similar to that represented by phantom line 502*c* in FIG. 5J) as the arrayed elongate members undergo retraction back into the catheter sheath. In FIG. 6, this part of the control line play-out occurs when the stacked elongate members have been retracted from a point approximately 200 mm along the coiled retraction path (i.e., as measured outwardly from the distal end of the catheter sheath) to a point approximately 180 mm along the coiled retraction path. At the point approximately 180 mm along the horizontal axis in FIG. 6, portion 604*b* of line 604 crosses plot 600 indicating that the arrayed structure is in a low energy state (for example as represented by a retraction of manipulable portion 502 to a particular location shown in FIG. 5K). In various embodiments, further play-out of the control line in accordance with the remaining part of portion 604*b* of line 604 and the subsequent portion 604*c* of line 604 essentially maintains a portion of the arrayed structure protruding outside the catheter sheath in a low energy state as the arrayed structure is retracted back into the lumen of the catheter sheath. For example, phantom line 502*b* in FIG. 5I may be used to envision a position of manipulable portion 502 in a low energy state during the further play-out of the cable 513*b* that occurs during the retraction of the manipulable portion 502 back into first lumen 512*d*. It is understood that portions of the structure (e.g., structure 502*a*) entering the catheter sheath are brought into a higher energy state due to the shape restrictions imposed by the lumen of the catheter sheath.

During further retraction of the stacked arrangement of the elongate members into the distal end of the catheter sheath, the control line is played out or metered with a fourth rate (i.e., as represented by the slope of portion 604*c* of line 604) during a second part of the play-out to cause a portion of the control line to have a reduced tension level (e.g., slackened level). A slackened portion of cable 513*b* in some embodiments is sufficient to allow a portion of the arrangement of elongate members protruding outwardly from the catheter sheath to autonomously continue to bend toward (e.g., outwardly to) a lower energy configuration or generally maintain the lower energy configuration as the arrangement of elongate members continues to undergo retraction into the catheter sheath. In FIG. 6, this second part of the control line play-out occurs when the arrangement of elongate members has been retracted from a point of 150 mm along the retraction path to a point about 40 mm along the retraction path (i.e., again as measured outwardly from the distal end of the catheter sheath). In various embodiments, the third metering rate (e.g., as represented by the slope of portion 604*b* of line 604) is different than the fourth metering rate (e.g., as represented by the slope of portion 604*c* of line 604). For example, in FIG. 6, the third metering rate associated with the slope of portion 604*b* of line 604 is twice the fourth metering rate associated with the slope of portion 604*c* of line 604. In some embodiments, the third metering rate associated with the slope of portion 604*b* of line 604 is generally equal to the first metering rate associated with the slope of portion 602*b* of line 602. In some embodiments, the fourth metering rate associated with the slope of portion 604*c* of line 604 is generally equal to the second metering rate associated with the slope of portion 602*c* of line 602. In this regard, in some embodiments, the third metering rate may be referred to as a "2× rate", like the first metering rate, and the fourth metering rate may be referred to as a "1× rate" like the second metering rate. Different rates may be employed in other embodiments. It is noted in various embodiments associated with FIG. 6 that a large part of line 604 remains below the data of plot 600 indicating that slack in the control line is present during or throughout the metering of the control line in conjunction with line 604.

In various embodiments, advancement of various parts of manipulable portion 502 outwardly from the confines of first lumen 512*d* (i.e., outwardly from the distal end 512*b* of catheter sheath 512) accompanies a first relative movement between the shaft 510 and catheter sheath 512 that results in a reduction or decrease in a distance between the proximal end 510*a* of the shaft 510 and the proximal end 512*a* of the catheter sheath 512 (e.g., as shown by the sequence depicted in FIGS. 5D, 5E and 5F), and also results in an increase in an amount of at least a part of the manipulable portion 502 extending outside the distal end of the catheter sheath 512. In this regard, in some embodiments, the distal end of the manipulable portion 502 is located outside of the distal end 512*b* of the catheter sheath 512 at a first location when a particular spatial relationship exists between the shaft 510 and the catheter sheath 512 during the first relative movement. See, e.g., the non-phantom lined first location of the distal end of the manipulable portion 502 in FIG. 5I. A reduction in a distance between the proximal end 510*a* of shaft 510 and the proximal end 512*a* of catheter sheath 512 may correspond to a reduction in a distance between a location on shaft 510 and a location on catheter sheath 512 during the first relative movement. In various embodiments, this reduction in distance may be accomplished by (a) a forward advancement of shaft 510 (e.g., away from housing 520 in FIG. 5A), (b) a rearward retraction of catheter sheath 512 (e.g., toward housing 520), or both (a) and (b).

In various embodiments, retraction of various parts of manipulable portion 502 inwardly into the confines of first lumen 512d (i.e., inwardly into the distal end 512b of catheter sheath 512) accompanies a second relative movement between the shaft 510 and catheter sheath 512 that results in an increase in a distance between the proximal end 510a of the shaft 510 and the proximal end 512a of the catheter sheath 512 (i.e., for example, as may occur in a sequence reverse to the sequence depicted in FIGS. 5D, 5E and 5F), and also results in a decrease in an amount of at least a part of the manipulable portion 502 extending outside the distal end of the catheter sheath 512. In this regard, in some embodiments, the distal end of the manipulable portion 502 is located outside of the distal end 512b of the catheter sheath 512 at a second location (different than, e.g., the non-phantom lined first location of the distal end of the manipulable portion 502 in FIG. 5I) when the same particular spatial relationship exists (as compared to advancement of various parts of manipulable portion 502 outwardly from the confines of first lumen 512d, discussed above) between the shaft 510 and the catheter sheath 512 during the second relative movement, the particular spatial relationship being a spatial relationship between a third location on the shaft 510 and a fourth location on the catheter sheath 512. See, e.g., the phantom lined second location of the distal end of the manipulable portion 502 in FIG. 5I. An increase in a distance between the proximal end 510a of shaft 510 and the proximal end 512a of catheter sheath 512 may correspond to an increase in a distance between a (third) location on shaft 510 and a (fourth) location on catheter sheath 512 during the second relative movement. In various embodiments, this may be accomplished by (a) a rearward retraction of shaft 510 (e.g., in a direction toward the housing 520 in FIG. 5A), (b) a forward advancement of catheter sheath 512 (e.g., in a direction away from the housing 520), or both (a) and (b).

In some embodiments, a control system or actuator system (e.g., as described herein) that is operatively or physically coupled to the manipulable portion 502 varies a size, a shape, or both, of the manipulable portion 502. In some embodiments, the control system or actuator system may respond to or be controlled by the first relative movement by causing at least one actuator to vary a size, a shape, or both, of at least part of the manipulable portion 502 extending outside (or located outside) the distal end 512b of catheter sheath 512 to, at least in part, cause the distal end of the manipulable portion 502 to move along a first trajectory during the first relative movement (for example as described above with respect to line 602 in FIG. 6). As discussed above, the first relative movement may be a relative movement between the catheter sheath 512 and a part of the shaft 510 when a distance between a location on the part of the shaft 510 and a location on the catheter sheath 512 decreases (e.g., as shown by the sequence depicted in FIGS. 5D, 5E and 5F)

The control system or actuator system may additionally respond to or be controlled by the second relative movement by varying a size, a shape, or both of at least the part of the manipulable portion 502 extending outside (or located outside) the distal end 512b of catheter sheath 512 to, at least in part, cause the distal end of the manipulable portion 502 to move along a second trajectory during the second relative movement (for example as described above with respect to line 604 in FIG. 6). In some of these embodiments, the first trajectory and the second trajectory are different trajectories. As discussed above, the second relative movement may be a relative movement between the catheter sheath 512 and a part of the shaft 510 when a distance between a location on the part of the shaft 510 and a location on the catheter sheath 512 increases (e.g., as may occur in a sequence reverse to the sequence depicted in FIGS. 5D, 5E and 5F). As used in this disclosure, the word trajectory means a path described by an object moving in space (e.g., a gaseous or fluidic space) under the influence of various forces. It is understood that the word trajectory refers to the path of movement and not the particular direction of travel along the path of movement. That is, travel along a particular trajectory from either direction is considered to be travel along the same trajectory in either case.

With respect to FIGS. 5H, 5I and 5J, a distal end 505a of the manipulable portion 502 moves along a first trajectory under the influence of a control element (e.g., the metered cable 513b), according to some embodiments. The control element (e.g., metered cable 513b), in some embodiments, is operatively or physically coupled to a control system or actuator system to, at least in part, cause the distal end of the manipulable portion to move along the first trajectory. In this regard, in some embodiments, the first trajectory is a modified trajectory following a respective path along which the distal end of the manipulable portion 502 moves during the first relative movement as compared to a respective trajectory along which the distal end of the manipulable portion 502 would move during the first relative movement absent the control element (e.g., the metered cable 513b). For example, in some embodiments, the first trajectory is modified from a trajectory that the distal end 505a of the manipulable portion 502 would follow solely from the autonomous coiling of the manipulable portion during the advancement of the manipulable portion 502 outwardly from the distal end 512b of the catheter sheath 512.

In some embodiments, (a) the distal end of the manipulable portion 502 follows a coiled path during the first relative movement, (b) the distal end of the manipulable portion 502 follows a coiled path during the second relative movement, or both (a) and (b). In some embodiments, the control system or actuator system responds to or is controlled by, the first relative movement by varying a radius of curvature of a surface of at least part of the manipulable portion 502 extending outside the distal end 512b of catheter sheath 512 to decrease during the first relative movement (for example, as shown in FIG. 5I) and then subsequently increase (for example as shown in FIG. 5J) during the first relative movement.

In various embodiments, the manipulable portion 502 is selectively moveable between a delivery configuration in which the manipulable portion 502 is sized, shaped, or both sized and shaped to be delivered through the first lumen 512d of catheter sheath 512 and an expanded configuration in which the manipulable portion 502 is sized, shaped or both sized and shaped too large for delivery through the first lumen 512d. In some of these various embodiments, an actuator system (e.g., one or more of the components of at least FIG. 5R, 5S, 5W, 7, 8, or 10) is physically or operatively coupled to at least a control element (e.g., cable 513b), and may be controlled by a control system (e.g., one or more components of at least control system 322 or control system 545) to transition the manipulable portion 502, at least in part, toward or to the expanded configuration as the manipulable portion is advanced out of the distal end 512b of the catheter sheath 512, and to transition, at least in part, the manipulable portion 502 toward or to the delivery configuration as the manipulable portion is retracted into the distal end 512b of the catheter sheath 512. In some embodiments, the control system or actuator system is operatively or physically coupled to the control element (e.g., cable 513b)

to cause, when a particular amount of the manipulable portion 502 is located outside of the distal end 512b of the catheter sheath 512 during the transition toward or to the expanded configuration, at least a portion of the control element (e.g., cable 513b) to have a first amount of length located outside the distal end 512b of the catheter sheath 512 (for example, cable 513b in FIG. 5I is shown with a first amount of length during the outward advancement of manipulable portion 502).

The control system or actuator system may be operatively or physically coupled to the control element (e.g., cable 513b) to cause, when the same particular amount of the manipulable portion 502 is located outside of the distal end 512b of the catheter sheath 512 during the transition toward or to the delivery configuration, at least the portion of control element (e.g., cable 513b) to have a second amount of length located outside of the distal end 512b of the catheter sheath 512, the second amount of length being different than the first amount of length. For example, although FIG. 5I is associated with the outward advancement of manipulable portion 502 from catheter sheath 512, phantom line 502b can be envisioned to reflect a same particular amount (e.g., a length or other dimension) of the manipulable portion 502 extending outwardly from the distal end 512b of catheter sheath 512 to the distal end of the manipulable portion 502 during a retraction of the manipulable portion 502 as compared to advancement thereof. Cable 513b is represented as cable 513b(ret) (i.e., shown in broken lines) for the case of retraction. When the same particular amount of the manipulable portion 502 is located outside the distal end 512b of catheter sheath 512 during the retraction of manipulable portion 502 as compared with the advancement of manipulable portion 502, the amount of length of cable 513b, 513b(ret) located outside of the distal end 512b of catheter sheath 512 is greater during the retraction of manipulable portion 502 than during the advancement of manipulable portion 502 (e.g., length of cable 513b(ret) outside the distal end 512b is greater than length of cable 513b outside the distal end 512b).

In some embodiments, the particular amount of the manipulable portion located outside the distal end 512b of the catheter sheath 512 is a particular size of the manipulable portion between the distal end 512b of the catheter sheath 512 and the distal end of the manipulable portion 502. In some embodiments, the particular amount of the manipulable portion located outside the distal end 512b of the catheter sheath 512 is a particular length of the manipulable portion 502 extending from the distal end 512b of the catheter sheath 512 to the distal end of the manipulable portion 502. In some embodiments, the particular amount of the manipulable portion located outside the distal end 512b of the catheter sheath 512 is a particular length of the manipulable portion 502 extending along a surface of the manipulable portion 502 from the distal end 512b of the catheter sheath 512 to the distal end of the manipulable portion 502.

In some embodiments, the control system or actuator system is physically or operatively coupled to the control element (e.g., cable 513b) to cause, when a particular relative positioning (e.g., a relative longitudinal positioning) exists between the catheter sheath 512 and the shaft 510 received in the first lumen 512d of the catheter sheath 512 during the transition toward or to the expanded configuration, at least part of the control element to have a first amount of length located outside of the distal end 512b of the catheter sheath 512. The control system or actuator system may be physically or operatively coupled to the control element (e.g., cable 513b) to cause, when the same particular relative positioning exists between the catheter sheath 512 and the shaft 510 received in the first lumen 512d during the transition toward or to the delivery configuration, at least part of the control element (e.g., cable 513b) to have a second amount of length located outside of the distal end 512b of the catheter sheath 512, the second amount of length being different than the first amount of length. In some embodiments, the control system or actuator system is physically or operatively coupled to the control element (e.g., cable 513b) to cause, when the particular relative positioning (e.g., a relative longitudinal positioning) exists between the catheter sheath 512 and the shaft 510 received in the first lumen 512d of the catheter sheath 512 during the transition toward or to the expanded configuration, the control element (e.g., cable 513b) to have a third amount of length located outside of end 513a-1 (i.e., shown in FIG. 5C) of sleeve 513a. In addition, the control system or actuator system may be physically or operatively coupled to the control element (e.g., cable 513b) to cause, when the same particular relative positioning exists between the catheter sheath 512 and the shaft 510 received in the first lumen 512d during the transition toward or to the delivery configuration, the control element to have a fourth amount of length located outside of the end 513a-1 of sleeve 513a, the fourth amount of length being different than the third amount of length. In some embodiments, cable 513b and sleeve 513a form part of a Bowden cable (e.g., third Bowden cable 555, called out in FIG. 7).

An actuator system (e.g., part or all of system 545, in some embodiments), which may be controlled at least in part by a control system (e.g., one or more components of control system 322, control system 545, or both control system 322 and control system 545 described in this disclosure), may employ one or more various actuators to manipulate or control various portions of a control element (e.g., control element 513) in accordance with various embodiments. For example, in some embodiments the use of projection 528 and receiver 529 may be employed to control a portion of control element 513. For instance, existence of a particular state (e.g., location, amount of tension, or both) of the control of control element 513 may be based, at least in part, on a particular amount of the length 528a received in receiver 529. It is noted that, in some embodiments, a particular aspect of the control of control element 513 based on a particular positioning between catheter sheath 512 and shaft 510 in the first lumen 512d of catheter sheath 512 may be analogous to a particular aspect of the control of control element 513 that is based, at least in part, on a particular amount of the length 528a of projection 528 received in receiver 529.

In some embodiments, the use of projection 528 and receiver 529 may be employed to meter cable 513b in a manner that is the same or similar to that described with respect to FIG. 6. In some embodiments, an actuator system (e.g., one or more of the components of at least FIG. 7 or others, in some embodiments) and one or more actuators thereof is or operatively or physically coupled to the manipulable portion 502 (e.g., via each of at least one of a plurality of Bowden cables, for example, first Bowden cable 552 (an example of at least part of a control element) or cable 513b thereof) to transmit force to the manipulable portion. This operative coupling between the actuator system and the manipulable portion 502 may be configured to meter, e.g., control cable 513b to vary an amount of the cable 513b that extends outwardly (or is located outwardly) from the distal end 512b of catheter sheath 512 when part of shaft 510 is received in the first lumen 512*d* of catheter sheath 512 and, e.g., during a change in a size, a shape, or both, of the manipulable portion 502. In some embodiments, the actuator system may be configured to respond to, or be controlled by, varying amounts of the length 528*a* of projection 528 being within the receiver 529 by varying a rate in which the cable 513*b* is metered. In some embodiments, the actuator system responds to or is controlled by a rate of change in an amount of the length 528*a* of the projection 528 being within the receiver 529 by varying a rate in which the cable 513*b* is metered.

Turning now to FIGS. 5R-1 and 5R-2, respective top and bottom perspective views are illustrated of a part of catheter system 500 with various external portions of housing 520 removed for viewing of various internal mechanisms and actuators contained, at least in part, in housing (also referred to as an enclosure) 520.

In FIG. 5R-1, it can be seen that various control elements, such as control elements 513, 573, and 578, pass through an interior cavity 520*g* of the housing 520, according to some embodiments. In some embodiments, the portion(s) of at least one of the control elements that passes through the interior cavity 520*g* includes a bent or arcuate shaped (e.g., an 'S' shape). Control elements that have such a shape may be at least control elements 573 and 578. In some embodiments, the portion(s) of at least one of the control elements that passes through the interior cavity 520*g* has slack in it. In some embodiments, the portion(s) of at least one of the control elements that passes through the interior cavity 520*g* is taut. A control element that is taut in this manner may be the control element 513. These control elements may couple various actuators in the housing 520 to the manipulable portion 502, for example, as described in this disclosure. In this regard, in some embodiments, the control elements (e.g., at least 513, 573, or 578), and, in some embodiments, the flexible sleeves or tubular members (e.g., at least 513*a*, 573*a*, 578*a*) and flexible control cables (e.g., at least 513*b*, 573*b*, or 578*b*), which are disposed in the flexible sleeves or tubular members, of such control elements, may span at least a portion of an interior of the catheter shaft 510 (e.g., within a lumen of the catheter shaft 510 spanning elongate member 510*c*) between the manipulable portion or end effector 502 and a portion of the enclosure or housing 520. It is noted that catheter shaft 510 is required to bend especially when it is delivered percutaneously along a tortuous path through a bodily opening. When at least one of the control elements extends through a portion of catheter shaft 510 and are secured at opposing ends thereof (for example secured to the manipulable portion or end effector 502 and a particular actuator), the at least one control element may act as a tendon-like member with the catheter shaft 510 that restricts or impedes the ability of the catheter shaft 510 to bend. In some embodiments, providing slack in at least part of the at least one control element at least during a time when the catheter shaft is bending or is intended to bend may be employed to reduce a tendon-like nature of the at least one control element and facilitate or enhance the bending or intended bending of the catheter shaft 510. In some embodiments, a portion of the at least one control element may have a bent or arcuate shape (e.g., an S-shape) that permits lateral movement of the portion of the at least one control element during a bending of the catheter shaft 510. That is, bending of the catheter shaft 510 can apply axial forces on the at least one control element which may be relieved at least in part by the arcuate or bent shaped portion as it shifts laterally and transitions to a less arcuate or bent form in response to the axial forces. In some embodiments in which the control element is a Bowden cable, at least part of which includes a bent or arcuate shape, tension levels in the cable portion of the Bowden cable may not significantly change during bending of the catheter shaft 510.

It is noted that, elements other than the control elements may also act as tendon-like structures that can hinder, impede, or restrict bending of the catheter shaft. For example, various communication or power cables coupled to various transducers located on the manipulable portion or end effector 502 may act as tendon-like members. In some embodiments, a power or communication cable is provided by a flexible circuit structure that may act as a tendon-like member when the catheter shaft 510 is bent. In some of these embodiments, providing slack in these members or elements at least during an intended bending of the catheter shaft 510 may be employed to reduce forces that may impede the intended bending. In some of these embodiments, providing an arcuate or bent form (e.g., an S-shape) in a portion of each of these members or elements at least during an intended bending of the catheter shaft 510 may be employed to reduce forces that may impede the intended bending.

In this regard, although FIG. 5R-1, as well as FIGS. 5Y and 5Z, show only control elements 573, 578 as having such an arcuate or bent form in the interior cavity 520*g* for purposes of clarity, additional control elements or other elements, such as power or communication cables or fluid-providing members, may also be provided and have the same or similar configuration. In addition, although FIG. 5R-1, as well as FIGS. 5Y and 5Z, show only control elements 513 as having a taut form in the interior cavity 520*g* for purposes of clarity, additional control elements or other elements, such as power or communication cables or fluid-providing members, may also be provided and have the same or similar configuration. Also, it should be noted that although FIG. 5R-1, as well as FIGS. 5Y, 5Z, 12A, and 12B illustrate only a few control or other elements (e.g., one instance each of control elements 513, 573, 578 in FIGS. 5R-1, 5Y, and 5Z, and e.g., only control element 1213 and fluid-providing portion 1224 in FIGS. 12A and 12B) for clarity, additional control elements or other elements, such as power or communication cables or fluid-providing members, may also be provided.

In some embodiments, each of the control elements 513, 573, 578 includes a respective cable 513*b*, 573*b*, 578*b*. In some embodiments, each of the control elements 513, 573, 578 includes a respective cable 513*b*, 573*b*, 578*b*, and a respective elongate member. Each respective elongate member may be provided by at least an elongate portion of a respective sleeve 513*a*, 573*a*, 578*a*. In some embodiments, each respective elongate member includes a first end, a second end, and an elongated portion extending between the first end and the second end. The first end and second end may correspond to a distal end (e.g., toward or at the manipulable portion or end effector 502) and a proximal end (e.g., toward or at the housing or enclosure 520), respectively, or vice versa, according to some embodiments. In some embodiments, the first end of the elongate member is arranged to be delivered ahead of the second end of the elongate member during percutaneous delivery of at least a portion of the catheter shaft 510. In some embodiments, the respective elongate member includes or provides a lumen (e.g., a lumen of the respective sleeve 513*a*, 573*a*, 578*a*, such lumen may be referred to as a control cable lumen) configured to receive the respective control cable 513*b*, 573*b*, 578*b* therein. As described in more detail below, such an elongate member may include an inlet (e.g., liquid intake port 1213*c* in FIG. 12A) at a location spaced from each of the first end and the second end and configured to receive a flow of liquid and provide such liquid through a portion of the control cable lumen while a portion of the control cable is located in the portion of the control cable lumen, the flow of liquid flowing through the portion of the control cable lumen toward the first end, the second end, or both, according to various embodiments.

In some embodiments, each of the respective control cable lumen of the respective elongate member (e.g., sleeve 513a, 573a, 578a) and each of the respective control cable 513b, 573b, 578b spans at least a portion of the interior of the catheter shaft 510 between the end effector 502 and a portion of the enclosure 520. In some embodiments, the portion of the enclosure 520 is the portion proximate to the proximal end of the catheter shaft 510. In some embodiments, the respective control element 513, 573, 578 is physically or at least operatively coupled to the end effector 502 to selectively enable a particular end effector function of the end effector 502 in response to a relative positioning between a portion of the respective control cable 513b, 573b, 578b and a portion of the respective control cable lumen (e.g., the respective lumen of the respective sleeve 513a, 573a, 578a) in which the portion of the respective control cable 513b, 573b, 578b is located. The particular end effector function may be a function of retracting, deploying, or otherwise manipulating a size or shape of the end effector (e.g., 502, 1202), for example, into various ones of the positions shown in one or more of FIGS. 5G-5Q, 3A, 3B.

In various embodiments, each respective sleeve 513a, 573a, 578a (which may be or provide a respective elongate member of the respective control element 513, 573, 578) is sealed (e.g., by sealant or other physical seals such as grommets, o-rings) or fixedly coupled (e.g., by adhesive) to at least one wall of the enclosure 520 surrounding interior cavity 520g at each of at least one of at least two spaced-apart openings or locations (e.g., 524e, 524f in FIGS. 5R-1 and 5Z) on or in the enclosure 520. For example, each respective sleeve (or elongate member) 513a, 573a, 578a may be hermetically sealed (e.g., by sealant) or fixedly coupled to a rear or proximal wall 522a (FIGS. 5R-1 and 5Z) of the interior cavity 520g at port 524f, the proximal wall 522a located between interior cavity 520g and an interior cavity 520i of the enclosure 520. The interior cavity 520i is located more toward the interior (e.g., proximally) than the interior cavity 520g according to some embodiments. The seal of proximal port 524f prevents or at least restricts an egress of fluid from the interior cavity 520g of the enclosure 520 into the interior cavity 520i at the opening of port 524f. As discussed in more detail below with respect to FIGS. 12A and 12B, a fluid-providing portion 1224 may be provided to allow the flow of fluid from the interior cavity 520g through the front or distal wall 522b into a lumen of the shaft 510.

In some embodiments, each of at least some of the respective sleeves 573a, 578a terminates at least proximate the proximal port 524f, while the respective cables 573b, 578b therein proceed beyond the respective sleeve termination locations in the port 524f and extend into the interior cavity 520i to couple to respective actuators. In some embodiments, at least one of the respective sleeves e.g., 513a extend into the interior cavity 520i toward or to a respective actuator (e.g., as shown in FIGS. 7A and 7B).

In this regard, in some embodiments, each respective sleeve 513a, 573a, 578a within the interior cavity 520g does not include any inlets that permit ingress of fluid from the interior cavity 520g of the enclosure 520 into the lumen of the respective sleeve 513a, 573a, 578a according to some embodiments. Stated differently, when the interior cavity

520g is filled with liquid, such as saline, each particular part of each respective sleeve (or elongate member in some embodiments) 513a, 573a, 578a that is submerged in the liquid in the interior cavity 520g does not include or lacks any inlets that permit or allow ingress of the liquid from the interior cavity 520g of the enclosure 520 into the lumen of the respective sleeve 513a, 573a, 578a, in some embodiments. Accordingly, as described in more detail below, liquid that is located within a lumen of a sleeve, such as sleeve 513a, 573a, or 578a can proceed proximally through such lumen through a portion of the respective control element (e.g., 513, 573, or 578) in the interior cavity 520g and then empty into the interior cavity 520i at a location where the sleeve terminates in the proximal port 524f. In flushing applications, this may be used to separate flushing liquid that has returned after traveling along a particular flushing path from new or fresh flushing liquid that is introduced at the beginning of the flushing path. By always introducing fresh or new flushing liquid and segregating the previously employed flushing liquid, improved sterility and reduced introduction of particulate matter into the body may result.

In some embodiments, each respective sleeve 513a, 573a, 578a (which may provide a respective elongate member of the respective control element 513, 573, 578) and each respective control cable 513b, 573b, 578b extends outwardly from the interior cavity 520g of the enclosure 520 through each of at least two spaced-apart openings or locations (e.g., 524e, 524f) provided in at least one wall of the enclosure 520 (e.g. FIGS. 5R-1 and 5Z). In some embodiments, the enclosure 520 includes an inlet port 524d for providing flushing or wetting liquid to the interior cavity 520g of the enclosure 520. In some embodiments, the enclosure 520 includes an outlet port 524c for expelling the liquid or for expelling a fluid (such as air) other than the liquid, as the liquid provided into the interior cavity 520g (e.g., via inlet port 524d) increases in volume in the interior cavity 520g. In some embodiments, the enclosure 520 itself includes the source of the liquid.

In some embodiments, the interior cavity 520g of the enclosure 520 is accessed by opening the enclosure lid 520h. In some embodiments, opening the enclosure lid 520h provides access to the interior cavity 520g of the enclosure 520 via an access port made accessible by the opening of the enclosure lid 520h. In some embodiments, the access port is configured to receive at least a portion of at least one tool, such as a cutter (e.g., a sterile surgical scissors), which may be used to cut, sever or otherwise disable one or more of the control elements therein, such as control elements 513, 573, and 578.

In some embodiments, at least a portion of one or more of the control elements 513, 573, 578 (or one or more elongate members (e.g., sleeves), cables, or both thereof) may be severed, cut, or otherwise disabled within a region of the respective control element within the interior cavity 520g of the enclosure 520 to inhibit or prevent a particular end effector function of the end effector 502. The particular end effector function may be the deployment, retraction, positioning, size-adjustment, or shape-adjustment of the end effector 502 described at least with respect to FIGS. 5G-5Q, 3A, 3B. In some embodiments, the particular end effector function is a coiling/uncoiling motion, a fanning/unfanning motion, a flattening motion, a clam shelling motion, or a combination of some or all of these motions described at least with respect to FIGS. 5G-5Q, 3A, 3B. In this regard, one or more of the control elements 513, 573, 578 may be severed, cut or otherwise disabled to inhibit or prevent a motion to control the deployment, retraction, positioning, size, shape, or a combination thereof, of the manipulable portion 502. In some embodiments, the manipulable portion 502 may be predisposed to transition to a lower energy configuration (e.g., a lower potential energy configuration), such as toward or to a partially expanded or fully unexpanded configuration from a more fully-expanded configuration, in response to the severing, cutting, or otherwise disabling of the one or more of the control elements 513, 573, 578. In some embodiments, the manipulable portion 502 may be predisposed to transition to a lower energy configuration, such as toward or to a partially fanned or fully unfanned configuration from a more fully-fanned configuration, in response to the severing, cutting or otherwise disabling of the one or more of the control elements 513, 573, 578. In some embodiments, one or more of the control elements 513, 573, 578 may be subject to tension to control the movement of the manipulable portion 502, and severing one or more of the control elements 513, 573, 578 may decrease or release the tension in the control element 513, 573, 578 (or control cables therein). In some embodiments, retracting the manipulable portion or end effector 502 through the catheter sheath 512 may cause the manipulable portion or end effector 502 to move from a fanned or partially fanned configuration to the delivery configuration. In some cases, an actuator may fail (e.g., jam or otherwise become incapacitated) and become incapable of manipulating various one or more of the control elements 513, 573, 578 to execute a desired functioning of the manipulable portion or end effector 502. In some cases, the manipulable portion or end effector 502 itself may encounter a failure mode (e.g., tangled control lines, various jammed elements or an undesired interaction with a particular anatomical feature) that prevents it from performing a desired manipulable-portion function. In either circumstance, if the particular mode hinders removal of at least part of the catheter from the body (e.g., a failure mode that does not readily allow the manipulable portion or end effector 502 to move into the delivery configuration from a particular expanded configuration), the severing, cutting or otherwise disabling of the one or more of the control elements 513, 573, 578 may allow forces maintaining the manipulable portion or end effector 502 in the particular expanded configuration or forces preventing the manipulable portion 502 from assuming the delivery configuration to be released or otherwise diminished and advantageously allow the removal of the manipulable portion or end effector 502 from the bodily cavity.

In some embodiments, in a state where the interior cavity 520g is filled with a wetting liquid, (e.g., a flushing liquid such as saline, a coolant, a hydraulic expansion liquid, etc.), a portion of each respective control element 513, 573, 578 may be submerged in or wetted by such liquid within the interior cavity 520g of the enclosure 520. In this regard, such submerging or wetting may occur at least before or during an operation of one or more of the control elements to execute or perform a particular end effector function of the end effector 502. Further in this regard, liquid may be directed from the inlet port 524d into the interior cavity 520g of the enclosure 520 at least before or during an initiating operation of the control element to execute or perform the particular end effector function. Still further in this regard, the above-discussed severing, cutting, or otherwise disabling of at least a portion of a control element (or elongate member (e.g., sleeve), control cable, or both thereof) within a region of the respective control element within the interior cavity 520g of the enclosure 520 may occur while at least the portion or the region of the respective control element (or elongate member (e.g., sleeve), control cable, or both thereof) is submerged in or wetted by the liquid in the interior cavity 520g of the enclosure 520. In this regard, while a control element's sleeve (e.g., 513a, 573a, or 578a) is submerged in a liquid in the interior cavity 520g, it may be considered that the control element's cable (e.g., 513b, 573b, or 578b) also is submerged in the liquid in the interior cavity 520g even though cable is shielded from the liquid in the interior cavity 520g by the sleeve and the cable, consequently, is not contacting the liquid in the interior cavity 520g, according to some embodiments.

In some embodiments, one or more indicators, such as instructions in a digital operating manual stored in memory device system 130 and displayed or otherwise presented (e.g., audibly) via a display device of input-output device system 120, may provide instructions for severing, cutting or otherwise disabling at least a respective portion of each of one or more of the control elements 513, 573, 578. In some embodiments, the one or more indicators may provide instructions for wetting one or more of the control elements 513, 573, 578 with liquid (e.g., saline) prior to severing, cutting or otherwise disabling at least a respective portion of each of one or more of the control elements 513, 573, 578.

In some example embodiments, the one or more indicators may include a gauge or meter 525 (e.g., FIG. 5Z), which may provide an indication of an amount of tension associated with one or more of the control elements 513, 573, 578. In some embodiments, the one or more indicators may provide instructions to sever, cut or otherwise disable at least a respective portion of each of one or more of the control elements 513, 573, 578 in response to a tension value associated with one or more of the control elements 513, 573, 578 exceeding a predetermined threshold or, in some cases, being less than a predetermined threshold. Exceeding the predetermined threshold may indicate a failure condition of the manipulable portion 502 or an associated actuator when, for example, the manipulable portion 502 is stuck in an expanded configuration, when an actuator is stuck in a position that causes a control element to retain tension when it should not, when an actuator is struck in a position that causes a control element to continue to apply force to the manipulable portion or end effector 502 when it should not, or when the manipulable portion 502 is caught on bodily tissue. Being under a predetermined threshold may indicate a failure condition of the manipulable portion 502 or an associated actuator, when, for example, an actuator is unable to provide tension in a control element when it should be able to, or when the manipulable portion 502 fails to transition to a state when tension in a control element is released by an actuator, even though such release of tension should transition the manipulable portion 502 into such state.

In some embodiments, the one or more indicators may provide instructions to severe, cut or otherwise disable (e.g., decouple the control element from a respective actuator) at least a respective portion of each of one or more of the control elements 513, 573, 578 in response to an indication (e.g., a signal provided by input-output device system 120, or a visual or audible cue provided as feedback to a user) indicating a failure in the ability of one or more actuators to manipulate at least one particular one of the control elements 513, 573, 578. For example, the indication may indicate a failure in the ability to move a portion of at least one particular one of the control elements 513, 573, 578 (e.g., a failure to play out or otherwise supply a control cable or control line of the at least one particular one of the control elements 513, 573, 578 from the enclosure 520, or a failure to take up a control cable or control line of the at least one particular one of the control elements 513, 573, 578 into the enclosure 520). In some embodiments, the one or more indicators may provide instruction of a particular location or locations to sever, cut or otherwise disable at least a respective portion of each of one or more of the control element 513, 573, 578. By way of non-limiting example, one or more indicators indicating on or more locations for the severing, cutting or otherwise disablement may be provided on a portion of enclosure 520 (e.g., on a surface defining at least part of interior cavity 520g).

With reference again to each of FIGS. 5R-1 and 5R-2, at least part of projection 528 is shown received in receiver 529, while a portion of shaft 510 is received in first lumen 512d (not called out in FIG. 5R-2). For clarity, various portions of catheter system 500 (e.g., manipulable portion 502) are not shown in FIGS. 5R-1 and 5R-2. As best seen in FIG. 5R-1, a first actuator set 540, which may comprise some or all of an actuator system, includes a first particular actuator 540a and a second particular actuator 540b, the operation of each of which is described later in this disclosure. In this regard, the first actuator set 540 is located at least proximate the proximal end 510a of the shaft 510, according to some embodiments. As best seen in FIG. 5R-1, cable 513b (e.g., a portion of control element 513) extends along a particular path toward or to the second particular actuator 540b. In some embodiments, each actuator in the first actuator set 540 is operatively coupled to the manipulable portion by at least one respective flexible control element (e.g., at least the control cable 513b) arranged to selectively transmit force provided by the respective actuator in at least the first actuator set 540 to the manipulable portion 502.

Each of the actuators in the first actuator set 540 may be independently, separately, or selectively moveable from the other actuators in the first actuator set 540 from a respective first activation position toward or to a respective second activation position to vary a size, shape, or both a size and a shape of a deployed or expanded configuration of the manipulable portion 502 into a particular state. Each of the actuators in the first actuator set 540 may include various passive and active components suitable for causing force to be transmitted to manipulable portion 502 to change a size or shape thereof according to various embodiments. Different types of actuators may be employed in various embodiments. By way of non-limiting example, various ones of the first actuator set 540 can include a rotary actuator, a portion of which is rotatable from a first activation position toward or to a second activation position to cause a size, shape, or both a size and a shape of manipulable portion or structure 502a thereof to be varied.

In some embodiments, a third particular actuator 572 (described in detail later in this disclosure) is employed. In some embodiments, actuator 572 may be independently, separately, or selectively moveable from the other actuators (e.g., actuators in the first actuator set 540) from a respective first activation position toward or to a respective second activation position to vary a size, shape, or both a size and a shape of a deployed or expanded configuration of the manipulable portion 502 into a particular state. In some embodiments, actuator 572 is a particular actuator in a second actuator set 541, in which actuator 572 is moveable between two activation positions to cause one or more actuators (or sometimes two or more actuators in some embodiments) in the first actuator set 540 that are positioned in their respective second activation positions to move away from their respective activation positions as described later in this disclosure. The second actuator set 541 may comprise some or all of an actuator system. In some embodiments, the second actuator set 541 is located at least proximate the proximal end 510a of the shaft 510.

In FIGS. 5R-1 and 5R-2, each of actuators 540a, 540b, and 572 is a linear actuator, a portion of each translatable from a respective first activation position toward or to a respective second activation position to cause a size, shape, or both a size and a shape of manipulable portion 502 or structure 502a thereof to be varied. In FIGS. 5R-1 and 5R-2, each of actuators 540a, 540b, 572 is a linear actuator, a portion of each translatable from a respective first activation position toward or to a respective second activation position (for example, as described later in this disclosure) to cause a size, shape, or both a size and a shape of an expanded configuration of the manipulable portion 502 or structure 502a thereof to be varied into a particular state. In FIGS. 5R-1 and 5R-2, a portion of each of actuators 540a and 540b is guided by a respective one of guides 542a, 542b of guide system 542. In FIG. 5R-1, a portion of actuator 572 is guided by a guide 542e. In various embodiments, guide system 542 is configured to capture various portions (e.g., slider portions) of each of actuators 540a, 540b and 572 while allowing the portions of each of actuators 540a, 540b, and 572 to slide along a respective one of guides 542a, 542b, 542e. In some embodiments, guide system 542 is provided at least in part by an extrusion (e.g., an aluminum extrusion) while various portions of each of actuators 540a, 540b, and 572 can include a combination of metallic and non-metallic components. In various embodiments, each of various ones of the guides of guide system 542 includes a guide channel. In various embodiments, each of various ones of the guides of guide system 542 includes a guide rail.

In various embodiments illustrated in FIGS. 5R-1 and 5R-2, each of various ones of the guides (e.g., guides 542a, 542b) includes a channel-like member configured to at least partially enclose respective ones of at least some of the actuators in the first and second actuator sets 540, 541. In various embodiments, each of actuators 540a and 540b includes a respective one of handles 543a and 543b, each of the handles 543a, 543b manipulable by a user (e.g., a health care provider or technician) to move the respective one of actuators 540a, 540b at least toward or away from its respective second activation position. In various embodiments, each of the handles 543a, 543b is engageable to move the respective one of actuators 540a, 540b toward or away from (a) its respective first activation position, (b) its respective second activation position, or both (a) and (b). In various embodiments, each of one or more of actuators 540a, 540b is selectively lockable to maintain one or more desired positions (e.g., the second activation position) along respective ones of the guides 542a, 542b. For example, in some embodiments, each or one or more of handles 543a, 543b is rotatable (for example, in a clockwise direction) to lock a respective one of actuators 540a, 540b so as to maintain a desired positioning along a respective one of guides 542a, 542b. In some embodiments, each of one or more of handles 543a, 543b is rotatable (for example, in a counter-clockwise direction) to unlock a respective one of actuators 540a, 540b so as to allow the respective one of actuators 540a, 540b to move away from a particular positioning along a respective one of guides 542a, 542b. The locking of a particular actuator of the first set actuators 540 may be accomplished by various mechanisms that can cause the particular actuator to grip or otherwise become secured to a guide 542.

Figures 10A, 10B, 10C, 10D:
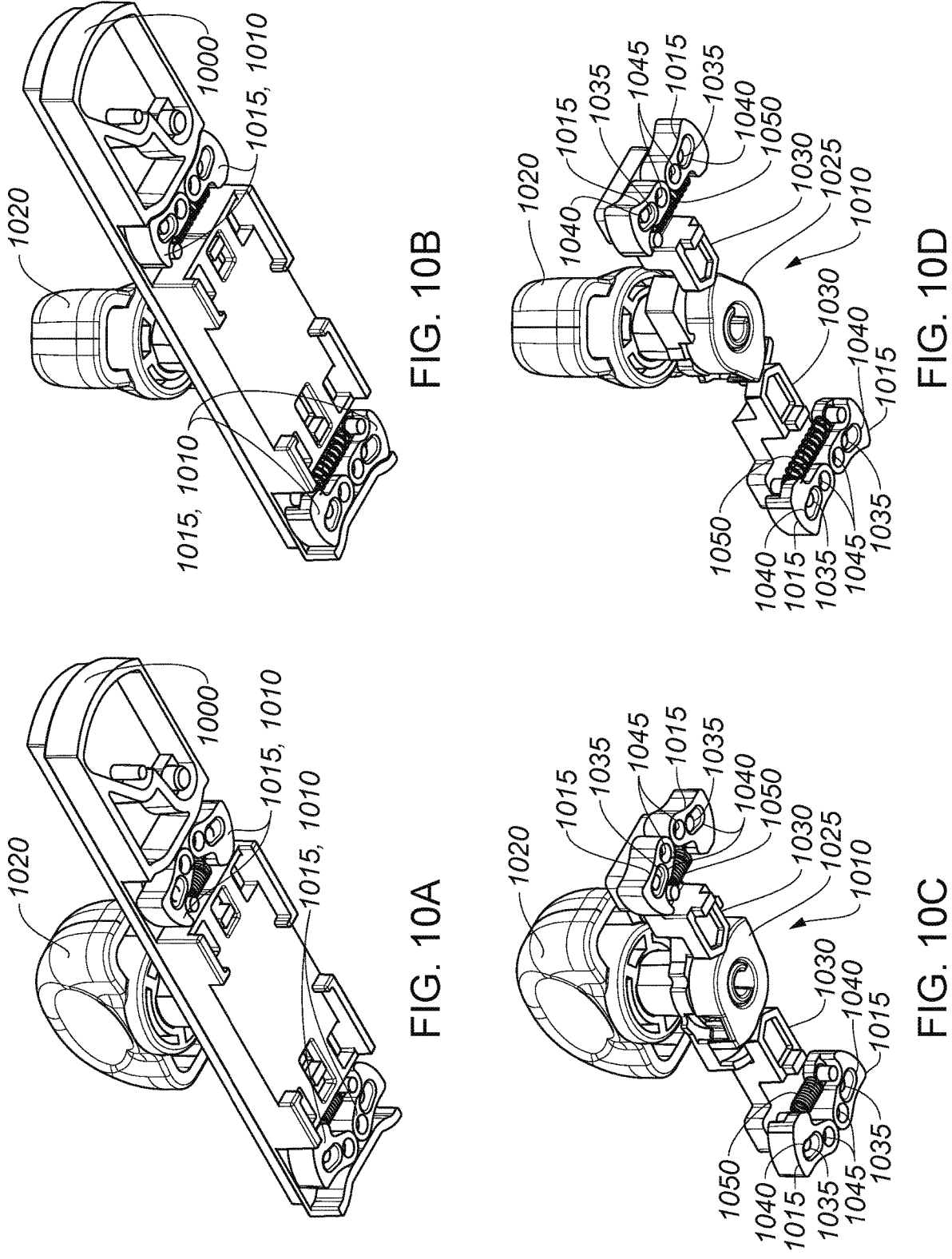

In some embodiments, various ones of handles 543*a*, 543*b* may be physically or operatively coupled to one or more cams that can be selectively brought into and out of frictional engagement with a guide of the guide system 542. For example, FIGS. 10A and 10B show respective perspective views of a locking device 1010 employed by a slider 1000 which may function in a similar or same manner to one or both of actuators 540*a*, 540*b* according to some embodiments. In this regard, in some embodiments, each respective actuator in the first actuator set 540 may include a respective locking device like that shown in FIG. 10).

In some embodiments, the locking device 1010 is selectively moveable between or operable in an unlocked configuration (e.g., FIGS. 10A and 10C) and a locked configuration (e.g., FIGS. 10B and 10D). In embodiments where the locking device 1010 is part of an actuator (e.g., each of one or more actuators in the first set of actuators 540), the unlocked configuration permits or allows the actuator to move (e.g., at least in a direction toward or away from a respective activation position). In embodiments where the locking device 1010 is part of an actuator (e.g., each of one or more actuators in the first set of actuators 540), the locked configuration restricts or prevents the actuator from moving (e.g., at least in the direction toward or away from a respective activation position).

In FIG. 10A, locking device 1010 is in an unlocked configuration which allows slider 1000 to move with respect to a guide element (not shown for clarity but similar to, or the same as one or both of guides 542*a*, 542*b* in some embodiments), while in FIG. 10B, locking device 1010 is in a locked configuration which restricts slider 1000 from moving with respect to the guide element. Detailed perspective views of locking device 1010 are provided in FIG. 10C (i.e., unlocked configuration) and FIG. 10D (i.e., locked configuration). Various parts of slider 1000 are not shown in FIGS. 10C and 10D to better show parts of locking device 1010 not visible in FIGS. 10A and 10B. In some embodiments, locking device 1010 employs a plurality of locking cams 1015 (i.e., four in this illustrated embodiment) that may be selectively moved between the unlocked configuration and the locked configuration. In some embodiments, the locking cams 1015 are moved between the unlocked and the locked configuration by rotation of handle 1020 (which may correspond to handle 543*a*, 543*b*, or each of 543*a* and 543*b* in some embodiments). For example, in some embodiments, handle 1020 is physically coupled to a drive cam 1025 of locking device 1010 in a manner suitable for rotating the drive cam 1025 in each of a clockwise or counter clockwise direction. In some embodiments, drive cam 1025 is engageable with one or more (two in this illustrated embodiment) cam followers 1030. Each of the cam followers 1030 may include a drive pin 1035 received in a respective channel 1040 provided in each of the locking cams 1015. Rotation of handle 1020 in a manner that rotates drive cam 1025 such that it forces the cam followers 1030 relatively further apart from one another causes the locking device 1010 to move from the unlocked configuration (e.g., FIG. 10A, 10C) toward or to the locked configuration (e.g., FIGS. 10B, 10D) by causing the drive pins 1035 to rotate the locking cams 1015 (i.e., about pivots 1045) outwardly into frictional engagement with the guide element (not shown for clarity but similar to, or the same as one or both of guides 542*a*, 542*b* in some embodiments). Rotation of the drive cam 1025 in an opposite direction may be employed to restore the locking device 1010 back to its unlocked configuration. In some embodiments, biasing members 1050 employ a biasing action that biases the locking device 1010 toward or to the unlocked configuration. Other locking/unlocking mechanisms may be employed in other embodiments.

Returning to FIGS. 5R-1 and 5R-2, actuator 572 includes cover 520*a* in various embodiments. For example, in FIGS. 5R-1 and 5R-2 cover 520*a* is operatively coupled to a first fanning slider 572*a* that makes up at least part of actuator 572 and which is guided by guide system 542. In this illustrated embodiment, the cover 520*a* is physically coupled to first fanning slider 572*a* via fasteners 520*b* and biasing member 520*c*. Biasing member 520*c* may include a compression spring in some embodiments. In some embodiments, cover 520*a* forms a handle of actuator 572. Other operations or functions associated with cover 520*a* are described later in this disclosure. The interaction of cover 520*a* with respect to actuator 572 is shown in exploded view in each of FIGS. 5R-1 and 5R-2 for clarity of illustration.

In various embodiments, catheter system 500 includes a control system 545 (which also may be referred to as an actuator system in some embodiments) comprising a set of devices or a device system that manages, controls, directs, or regulates the behavior of other device(s) or sub-system(s) that make up system 500. For example, control system 545 can, in some embodiments, control or include a transition actuator (e.g., actuator 540*a*, 540*b*, 546, 572, some other actuator or actuator set, or a portion of at least one of these actuators) physically or operatively coupled to the manipulable portion 502 to transition or modulate manipulable portion 502 or structure 502*a* thereof at least partially between various states or configurations (e.g., between a delivery configuration and an expanded or deployed configuration, or vice versa). In some embodiments, control system 545 is configured to control or include a modulation actuator (e.g., an actuator in FIG. 7, some other actuator or actuator set, or a portion of at least one of these actuators) physically or operatively coupled to the manipulable portion 502 (e.g., via at least the elongated control element 513) to modulate at least a size, a shape, or both a size and a shape of manipulable portion 502, for example, at least in a state where at least a part of the manipulable portion 502 and a part of the control element 513 extend outside the distal end of the catheter sheath 512 (e.g., FIG. 5C). In some embodiments, control system 545 can control or include a control element manipulation actuator (e.g., an actuator in FIG. 5S or 7, some other actuator or actuator set, or a portion of at least one of these actuators) to manipulate various control elements (e.g., control element 513) in system 500. In some embodiments, various ones of the transition, modulation, and control element manipulation actuators may be the same or separate devices or may be combined into a single device or system. For example, one of the actuators in FIG. 5S or 7 may be deemed a transition actuator, another one of these actuators may be deemed a modulation actuator, and yet another one of these actuators may be deemed a control element manipulation actuator. Or, in some embodiments, some or all of the transition actuator, modulation actuator, and control element manipulation actuator may be the same actuator. The points made in this discussion also apply to other actuators described herein. In various embodiments, various actuators (e.g., modulation, transition, and control element manipulation actuators) controlled by control system 545 may form part of control system 545 or may be distinct from control system 545. In some embodiments, the control system 545 may include one or more components of system 100 or control system 322, such as controller 324, that control one or more of the actuators described in this paragraph or otherwise herein.

Control system (which may also be referred to as an actuator system) 545 may trigger, be triggered, or cause an operation of a series of mechanical actuators in the correct sequence to perform a task associated with catheter system 500. Control system 545 may, in some embodiments, include a feedback system responsive to various inputs (e.g., user actions, machine action, or a combination of both) to initiate a particular function or transition between particular functions of system 500. In some embodiments, control system 545 is provided at least in part by at least one data processor, for example, as provided by one or more components of system 100 or control system 322, such as controller 324, and as such may be responsive to or controlled by various transducer data, machine data, or data input by a user. In various embodiments, control system 545 includes or takes the form of a mechanical system that includes a receiving mechanism configured to receive input force or input movement and a conversion mechanism that converts the input force or input movement to achieve a particular application of output force or output movement. In some of these various embodiments, the mechanical system may include various sensors, force limiters, or movement limiters that compare the output to a desired value and then directs the input or the conversion of the input. In some embodiments, control system 545 is entirely provided by a mechanical system. In some embodiments, input force or input movement is provided manually. Manual application of force or movement may be preferred for some medical device systems to avoid undesired outcomes that may accompany a misapplication of power-based (e.g., electrical, hydraulic or pneumatic) force or movement. Some example operations associated with control system 545 are schematically represented, according to some embodiments, in FIGS. 7A and 7B, which are described in more detail later in this disclosure.

In various embodiments, control system (which also may be referred to as an actuator system in some embodiments) 545 is responsive to or is controlled by relative movement between shaft 510 and catheter sheath 512 (e.g., at least when a portion of shaft 510 is received in the first lumen 512d of catheter sheath 512) to (a) modulate or control a particular configuration or state of manipulable portion 502 (e.g., by varying a force applied to the manipulable portion 502), (b) control a transition between various particular configurations or states of manipulable portion 502, (c) manipulate a control element (e.g., control element 513) or some particular combination of some or all of (a), (b), and (c). In some embodiments, control system 545 is responsive to or controlled by varying amounts of the length 528a of projection 528 being received within receiver 529 to (a) modulate or control a particular configuration or state of manipulable portion 502 (e.g., by varying a force applied to the manipulable portion 502), (b) control a transition between various particular configurations or states of manipulable portion 502, (c) manipulate a control element (e.g., control element 513), or some particular combination of some or all of (a), (b), and (c). In this regard, in some embodiments, the control system 545 responds to or is controlled by movement of the internal receiving mechanism 546 within the receiver 529 caused by a change in an amount of the length of the projection 528 within the receiver 529 by varying the force transmitted to the manipulable portion 502. In some embodiments, the control system 545 responds to or is controlled by a rate of change in an amount of the length of the projection 528 within the receiver 529 by varying a rate at which a control cable (e.g., cable 513b) is metered, e.g., as described with respect to FIG. 6 in this disclosure.

In some embodiments, at least a portion of at least one actuator (e.g., 546, described later in this disclosure, which may include a modulation actuator) is moveable in each of a first direction and a second direction different than the first direction. In some embodiments, the control system 545 may be configured to cause at least the portion of the actuator (e.g., modulation actuator) to move in the first direction to cause or accompany an increase in an amount of manipulable portion 502 extending outwardly from the distal end 512b of catheter sheath 512 and may be configured to cause at least the portion of the actuator (e.g., modulation actuator) to move in the second direction to cause or accompany a decrease in an amount of manipulable portion 502 extending outwardly from the distal end 512b of catheter sheath 512. In other words, at least the actuator (e.g., modulation actuator) may be operable to cause or accompany an increase or decrease in the amount of manipulable portion 502 extending outwardly from the distal end 512b of catheter sheath 512, depending upon when at least a portion of the actuator moves in the first direction or second direction, respectively.

In some embodiments associated with FIGS. 5R-1 and 5R-2, the receiver 529 includes an internal receiving mechanism 546 (which may be an example of an actuator or a particular actuator) configured to engage with a part of projection 528 received in receiver 529. In some embodiments, the internal receiving mechanism 546 is sized to matingly receive at least a portion of the projection 528. As best seen in FIG. 5R-2, the internal receiving mechanism 546 includes a coupler portion 546a (also referred to as coupler 546a) and a slider portion 546b (also referred to as receiver slider 546b) physically coupled to the coupler 546a. Receiver slider 546b is configured to move along guide 542c of guide system 542. In various embodiments, coupler 546a captively or otherwise physically couples the internal receiving mechanism 546 to at least the portion of the projection 528 matingly received in the internal receiving mechanism 546. The captive coupling allows at least the coupler 546a of internal receiving mechanism 546 to move along guide 542c during each of a first relative movement between projection 528 and receiver 529 that increases the amount of length 528a of projection 528 within receiver 529, and a second relative movement between projection 528 and receiver 529 that decreases the amount of length 528a of projection 528 within receiver 529. In various embodiments, coupler 546a includes a set of gripper arms 546c configured to engage or otherwise physically couple with a recess 528c of first projection 528 as best shown in FIG. 5R-3 which is a detailed view of part of FIG. 5R-2. In some of these various embodiments, the gripper arms 546c are biased to move apart (for example by means of a flexure) to disengage from recess 528c when the coupler 546a is positioned at a particular location along guide 542c (e.g., at location 535) where the gripper arms 546c are not constrained by a channel associated with guide system 542. This arrangement advantageously allows at least a portion of the projection 528 to self-couple (e.g., physically couple) to the coupler 546a (and internal receiving mechanism 546) when a first relative positioning between projection 528 and receiver 529 positions the gripper arms 546c within a confining structure of guide 542c, the positioning of the gripper arms 546c in the confining structure causing the gripper arms 546c to move together in a pinching or gripping manner that securely couples the gripper arms 546c to projection 528. Additionally, this arrangement advantageously allows at least a portion of the projection 528 to self-decouple (e.g., physically de-couple) from coupler 546a (and internal receiving mechanism 546) when a second relative positioning (different than the first relative positioning) between projection 528 and receiver 529 positions the gripper arms 546c at a location (e.g., location 535) where the gripper arms 546c are not confined but are allowed to move or flex apart to release the projection 528 from the gripper arms 546c, thereby allowing the shaft 510 and catheter sheath 512 to be pulled apart and become fully separated, if desired.

FIGS. 7A and 7B schematically show an operation of at least one actuator of a control system (which may also be referred to as an actuator system in some embodiments) 545 associated with housing 520 at two successive points in time. In various embodiments, operation of various actuators and control elements associated with FIGS. 7A and 7B may be employed during a change in a size, a shape, or both a size and a shape of manipulable portion 502 (not shown in FIGS. 7A and 7B). In various embodiments, operation of various actuators and control elements associated with FIGS. 7A and 7B may be employed to cause, at least in part, a change in a size, a shape, or both a size and a shape of manipulable portion 502 (for example as depicted in the sequence shown in FIGS. 5H, 5I and 5J). In FIGS. 7A and 7B, schematic representations are employed for ease of discussion. Additionally, for the ease of discussion, the movement proximally or distally of various elements in FIG. 7A, 7B as discussed herein is made in accordance with the "◄ DISTAL" and "PROXIMAL►" indicators provided at the bottom of each of the FIGS. 7A and 7B. In this regard, in some embodiments, each of the control system 545 and at least one actuator or modulation actuator (e.g., 540a, 540b, 546, 572, some other actuator or actuator set, or a portion of at least one of these actuators) thereof are located, at least in part, at respective locations at least proximate the proximal end of the shaft 510.

In some embodiments, the coiling/uncoiling motion during deployment/retraction of the manipulable portion 502 (e.g., FIGS. 5H, 5I, and 5J) is caused and controlled, at least in part, by activation or movement of a second particular actuator 540b and an internal receiving mechanism 546 with respect to a first particular actuator 540a, which may act as an anchor in some configurations. In some embodiments, the coiling/uncoiling motion during deployment/retraction involves a metering of a portion of the control element 513 (e.g., a cable 513b) with different rates under the control of a master slider 556a, a sleeve slider 556b, and the second particular actuator 540b. In some embodiments, movement of the first particular actuator 540a causes or controls flattening of the manipulable portion 502 (e.g., FIGS. 5N and 5O). In some embodiments, clam shelling of the manipulable portion (e.g., FIGS. 5P and 5Q) may be caused and controlled by activation or action of the second particular actuator 540b.

With this context in mind, a portion of control element 513 may be operatively coupled to second particular actuator 540b to at least in part control coiling/uncoiling of the manipulable portion 502 during deployment/retraction. In some embodiments, the second particular actuator 540b includes various portions including a first slider portion 548a (also referred to in some embodiments as sleeve slider 548a) configured to slide along guide 542b, and a second slider portion 548b (also referred to in some embodiments as slave slider 548b) configured to slide within or with respect to, sleeve slider 548a. In some of these various embodiments, a portion of sleeve 513a proximate a proximal end

513a-2 of sleeve 513a (i.e., an end of sleeve 513a located relatively closer to the proximal end 510a of shaft 510 than the distal end 510b of shaft 510) is physically coupled (or, in some embodiments, fixedly coupled) to sleeve slider 548a. In this regard, axial or longitudinal movement of sleeve slider 548a along guide 542b can also cause longitudinal or axial movement of a portion of sleeve 513a in second lumen 511 within shaft 510. A particular location of sleeve slider 548a along guide 542b can be maintained by operating handle 543b to operate an associated lock as described herein.

As shown in FIGS. 7A and 7B, a first part 513b-1 of cable 513b extends outwardly from a first end 552a-1 of sleeve 552a at least across a region of space 550, the region of space 550 extending between first end 552a-1 and end 513a-2 of sleeve 513a. Cable 513b further extends through a lumen of a sleeve 552a and is physically or operatively coupled to first particular actuator 540a. In particular, a second part 513b-2 of cable 513b extends outwardly from a second end 552a-2 of sleeve 552a along a path that extends to first particular actuator 540a. In FIGS. 7A and 7B, sleeve 552a is physically coupled (or, in some embodiments, fixedly coupled) to slave slider 548b to accompany or move in tandem with slave slider 548b. In some embodiments, sleeve 552a and cable 513b form part of a Bowden cable (e.g., first Bowden cable 552). In various embodiments, the first part 513b-1 of cable 513b includes at least the portion 514 of cable 513b (not shown in FIGS. 7A and 7B, but shown at least in FIGS. 5H, 5I and 5J). In some embodiments, the part 513b-1 of cable 513b is physically coupled to manipulable portion 502 to, at least in part change the size, shape, or both, of the manipulable portion 502. A size of the region of space 550 varies when the slave slider 548b moves relative to the sleeve slider 548a. When the slave slider 548b is distally positioned as shown in FIG. 7A, the region of space 550 has a relatively smaller size than when the slave slider 548b is proximally positioned (e.g., as shown in FIG. 7B). The varying size of region of space 550 will result in different distances between the end 513a-2 of the sleeve 513a and first end 552a-1 of sleeve 552a in various embodiments. It is noted that various levels of tension on the cable 513b can lead to shortening of a distance between the end 513a-2 of the sleeve 513a and first end 552a-1 of sleeve 552a. In some embodiments, tension on the cable 513b may urge the slave slider 548b to move distally.

In various embodiments, a first part 554b-1 of a second cable 554 extends outwardly from the first end 554a-1 of a second sleeve 554a. In some embodiments, the second cable 554b is located at least in part of a lumen of second sleeve 554a, and second cable 554b and second sleeve 554a form part of a Bowden cable (e.g., second Bowden cable 554). In various embodiments, the first part 554b-1 of second cable 554b is physically coupled (or, in some embodiments, fixedly coupled) to the slave slider 548b. In some of these various embodiments, second cable 554b is operable to allow for a movement of the slave slider 548b in at least one of the proximal and distal directions. In some embodiments associated with FIGS. 7A and 7B, second sleeve 554a is physically coupled (or, in some embodiments, fixedly coupled) to sleeve slider 548a. It is noted in various embodiments that when the sleeve slider 548a is moved along guide 542b, sleeve 513a, slave slider 548b, and at least the respective first ends 552a-1, 554a-1 of sleeve 552a and second sleeve 554a also move with sleeve slider 548a. It is also noted in some embodiments that little or no relative movement between the sleeve 513a and the cable 513b occurs due to an adjustment in a positioning of the sleeve slider 548a, for example, as described later in this disclosure.

In various embodiments, the first part 554b-1 of cable 554b of the second Bowden cable 554 is physically or operatively coupled to the first Bowden cable 552 to cause at least the first end 552a-1 of the respective sleeve 552a of the first Bowden cable 552 to translate in response to, or during, at least part of a varying, caused by at least one actuator (e.g., 540b, 546, some other actuator or actuator set, or a portion of at least one of these actuators), of the amount of length of the first part 554b-1 of the cable 554b of the second Bowden cable 554 that extends outwardly from the first end 554a-1 of the respective sleeve 554a of the second Bowden cable 554. In some embodiments, the control (or actuator) system 545 or an actuator or other portion thereof is responsive to or controlled by variances in a relative positioning between the shaft 510 and the catheter sheath 512 (i.e., when part of the shaft 510 is received in the lumen 512d of the catheter sheath 512) to vary the length of at least part of cable 554b of the second Bowden cable 554 that extends from the first end 554a-1 of the sleeve 554a of the second Bowden cable. In this regard, in some embodiments, a control system (e.g., one or more components of system 100 or control system 322, such as controller 324) may be operatively coupled to an actuator system and operable to control activation of one or more actuators of the actuator system to vary the amount of length of a first part of the respective cable of each of the at least some of a plurality of Bowden cables that extends outwardly from the first end of the respective sleeve thereof during a change in a size, a shape, or both a size and a shape of the manipulable portion 502.

In some embodiments, the lumen of the sleeve 552a of the first Bowden cable 552 extends longitudinally in a particular direction from the first end 552a-1 of the sleeve 552a of the first Bowden cable 552, and the first part 554b-1 of cable 554b of the second Bowden cable 554 is physically or operatively coupled to the first Bowden cable 552 to cause at least the first end 552a-1 of the respective sleeve 552a of the first Bowden cable 552 to translate in a direction having a component parallel to this particular (longitudinal) direction (of the first Bowden cable 552) in response to, or at least during part of, the varying, caused by at least one actuator, of the amount of length of the first part 554b-1 of the cable 554b that extends outwardly from the first end 554a-1 of the respective sleeve 554a of the second Bowden cable 554. In some embodiments, at least one actuator (e.g., 556a, 556b, some other actuator or actuator set, or a portion of at least one of these actuators) is physically or operatively coupled to the first Bowden cable 552 to cause the length of the first part 513b-1 of cable 513b that extends from the first end 552a-1 of the respective sleeve 552a of the first Bowden cable 552 to vary during at least part of the varying of the amount of length of the first part 554b-1 of the cable 554b of the second Bowden cable 554 that extends outwardly from the first end 554a-1 of the respective sleeve 554a of the second Bowden cable 554 caused by at least one actuator (e.g., 540b, 546, some other actuator or actuator set, or a portion of at least one of these actuators) in housing 520.

In FIGS. 7A and 7B, various portions of the receiver 529 (e.g., internal receiving mechanism 546) can be moved (e.g., pushed) proximally or moved (e.g., pulled) distally by the projection 528. For example, in some embodiments, internal receiving mechanism 546 is moved proximally by projection 528 when a first relative movement between catheter sheath 512 and a part of the shaft 510 received in the first lumen 512d causes a distance between a location on the part of the shaft 510 and a location on the catheter sheath 512 to decrease (for example, as the shaft 510 and sheath 512 are drawn together as shown in a sequence depicted consecutively by FIGS. 5D, 5E, and 5F). In some embodiments, internal receiving mechanism 546 is moved distally by projection 528 when a second relative movement between catheter sheath 512 and a part of the shaft 510 received in the first lumen 512d causes a distance between a location on the part of the shaft 510 and a location on the catheter sheath 512 to increase (for example, as the shaft 510 and sheath 512 are drawn apart as shown in a sequence depicted consecutively by FIGS. 5F, 5E, and 5D).

As shown in FIGS. 7A and 7B, internal receiving mechanism 546 may include a physically coupled slider mechanism 556 (which may be an example of an actuator or a particular actuator), portions of which are configured to move along guide 542d (also called out in FIG. 5R-1). In FIG. 5R-2, an aperture 557 in guide system 542 allows for a physical coupling between internal receiving mechanism 546 and slider mechanism 556. In some embodiments, internal receiving mechanism 546 is fixedly coupled to slider mechanism 556. In some embodiments, internal receiving mechanism 546 is releasably coupled to slider mechanism 556. In some embodiments, internal receiving mechanism 546 is configured to selectively couple to, or decouple from, slider mechanism 556 at one or more particular locations along a path of travel along guide 542c. For example, various mechanisms activatable at different locations along guide 542c can be employed to selectively couple or decouple internal receiving mechanism 556 respectively to or from slider mechanism 556 at the different positions or at other positions having a defined relationship to the different positions. In some embodiments, slider mechanism 556 includes various moveable portions including a first portion 556a (also referred to as master slider 556a in some embodiments) and a second portion 556b (also referred to as second sleeve slider 556b in some embodiments).

As shown in FIGS. 7A and 7B, the two sleeves 552a and 554a may be physically coupled (or, in some embodiments, fixedly coupled) to the second sleeve slider 556b. In various embodiments, second sleeve slider 556b is physically coupled to master slider 556a with a mechanism, such as with a tether 558, that delays a movement of master slider 556a until second sleeve slider 556b has been moved by a predetermined or defined amount or has moved to a predetermined or defined position.

In some embodiments associated with FIGS. 7A and 7B, the second sleeve slider 556b (an example of a second moveable portion) is physically coupled to master slider 556a (an example of a first moveable portion) by the tether 558. In various embodiments, second sleeve slider 556b can be moved proximally or distally by the projection 528 when the projection 528 repositions internal receiving mechanism 546 as described above in this disclosure.

In FIGS. 7A and 7B, master slider 556a is located distally of second sleeve slider 556b. In various embodiments, master slider 556a and second sleeve slider 556b are located on or guided by a same guide of guide system 542 (e.g., guide 542d). In various embodiments, master slider 556a is physically coupled to slave slider 548b by second cable 554b. In particular, a second part 554b-2 of cable 554b of second Bowden cable 554 extending outwardly from a second end 554a-2 of second sleeve 554a is physically coupled to master slider 556a (which is an example of a first moveable portion of a particular actuator (e.g., slider mechanism 556, internal receiving mechanism 546, some other actuator or actuator set, or a portion of at least one of these actuators)). In some embodiments, a portion of the sleeve 554*a* of the second Bowden cable 554 located at least proximate to the second end 554*a*-2 of the sleeve 554*a* of the second Bowden cable 554 is physically coupled to the second sleeve slider 556*b* (an example of a second moveable portion of a particular actuator (e.g., slider mechanism 556, internal receiving mechanism 546, some other actuator or actuator set, or a portion of at least one of these actuators)). In various embodiments associated with FIGS. 7A and 7B, each of the respective ends (represented by dots in FIGS. 7A and 7B) of second cable 554*b* and each of the respective ends 554*a*-1 and 554*a*-2 of second sleeve 554*a* are located at respective locations in housing 520. In various embodiments associated with FIGS. 7A and 7B, each of the respective ends of cable 554*b* and each of the respective ends 554*a*-1 and 554*a*-2 of second sleeve 554*a* are located at respective locations outside a body when the manipulable portion 502 is located at a desired location within a bodily cavity in the body.

In various embodiments, master slider 556*a* (which is an example of a first moveable portion of a particular actuator (e.g., slider mechanism 556, internal receiving mechanism 546, some other actuator or actuator set, or a portion of at least one of these actuators)) includes a locking device (not shown in FIGS. 5 and 7, but an example is illustrated in FIGS. 8A and 8B, which is described in more detail in this disclosure below) configured to restrict movement of master slider 556*a* (e.g., along guide 542*d*) when various forces suitable for translating master slider 556*a* along guide 542*d* are not applied to master slider 556*a*. In some embodiments, this restricting of movement occurs during a varying of the length of the first part 554*b*-1 of the cable 554*b* of the second Bowden cable 554 that extends outwardly from the first end 554*a*-1 of the sleeve 554*a* of the second Bowden cable 554. In some embodiments, the locking device (e.g., FIGS. 8A and 8B) is configured to allow movement of the master slider 556*a* (an example of a first moveable portion) of the internal receiving mechanism 546 (an example of a particular actuator) after completion of a varying of a length of a part of cable 554*b* of the second Bowden cable 554 that extends outwardly from the first end 554*a*-1 of the sleeve 554*a* of the second Bowden cable 554.

In various embodiments, the locking device remains normally locked or fixedly coupled to a structure (e.g., guide 542*d*) when various forces suitable for translating master slider 556*a* along guide 542*d* are not applied to master slider 556*a*. In various embodiments, master slider 556*a* remains normally locked or secured to guide 542*d* but is configured to move more freely when moved in one, but not both of the proximal and distal directions. For example, in various embodiments associated with FIGS. 7A and 7B, master slider 556*a* is configured to move more freely when master slider 556*a* is urged to move distally than when the master slider 556*a* is urged to move proximally. In various embodiments, when master slider 556*a* is subjected to an applied force that is directed distally, master slider 556*a* will move relatively freely in the distal direction. When the applied force is removed, master slider 556*a* will once again secure itself to the guide 542*d*. In various embodiments, associated with FIGS. 7A and 7B, when a force (i.e., not applied by tether 558) is applied to master slider 556*a* in a proximal direction, master slider 556*a* remains relatively fixed or secured to guide 542*d*. That is, in these embodiments, while there is slack (or a tension level magnitude lower than a defined threshold) on the tether 558, the master slider 556*a* is restricted from being moved proximally (for example, under the influence of tension exerted by second cable 554*b*). However, when there is a suitable tension (i.e., a tension level or magnitude at least equal to the defined threshold) on the tether 558, the master slider 556*a* unlocks from the guide 542*d* and can be moved proximally in these embodiments. In other words, the locking device (e.g., FIGS. 8A and 8B) is configured to allow movement of the master slider 556*a* (an example of a first moveable portion) of the internal receiving mechanism 546 (an example of a particular actuator) after the sleeve slider 556*b* (an example of a second moveable portion) of the internal receiving mechanism 546 translates by a defined amount (e.g., a length of the tether 558). If a magnitude or level of tension on tether 558 subsequently falls below the defined threshold, the master slider 556*a* once again locks to guide 542*d*. It is noted that although selective locking of master slider 556*a* to guide 542*d* has been described in these embodiments, master slider 556*a* may be selectively locked to other structures (e.g., other guides of guide system 542) in other embodiments.

Various mechanisms may be employed to provide the locking device(s) described above with respect to master slider 556*a*. For example, a slider assembly 800 is schematically represented in FIGS. 8A and 8B. The slider assembly 800 includes a slider body 802 that is selectively moveable in a guide channel 804 (which, in some embodiments, may correspond to guide 542*d*). In some embodiments, the slider body 802 may correspond to the master slider 556*a* or be coupled to the master slider 556*a*. A set of locking cams 806 (i.e., two cams in this illustrated embodiment) is provided in slider body 802. Each of locking cams 806 may be pivotable about a respective pin 805. A biasing member 808 (e.g., shown as a tension spring in FIG. 8A. 8B) may be coupled to the locking cams 806 to urge each of the locking cams 806 to pivot about its respective pin 805 and cause a respective engagement surface 806*a* of each locking cam 806 to engage with guide channel 804 as shown in FIG. 8A.

In various embodiments, the engagement surfaces 806*a* are shaped to provide unidirectional self-locking characteristics. For example, in FIG. 8A, the engagement surfaces 806*a* are shaped to cause the locking cams 806 to pivot inwardly and thereby reduce their locking or holding capability when a particular force is applied to move the slider body 802 distally (i.e., in the direction indicated as "◄ DISTAL" in FIG. 8A). Conversely, the shape of each of the engagement surfaces 806*a* is configured to urge the locking cams 806 to pivot outwardly and thereby increase locking or holding capability when a particular force is applied to move the slider body 802 proximally (i.e., in the direction indicated as "PROXIMAL►" in FIG. 8A).

A tether 810 (which, in some embodiments, may correspond to the tether 558) may be coupled to the set of locking cams 806 to selectively cause the locking cams 806 to pivot inwardly and unlock when a particular tension having a suitable magnitude to overcome the biasing action of biasing member 808 is applied to tether 810. When the particular tension is applied to tether 810, the slider body 802 can be moved proximally (i.e., in the direction indicated as "PROXIMAL►" for example, under the influence of tension provided by a cable member 812 (which, in some embodiments, may correspond to the cable 554*b*) physically coupled to slider body 802 as shown in FIG. 8B.

Returning to FIGS. 7A and 7B, as projection 528 is inserted into the housing 520 and is received by receiver 529, projection 528 may engage internal receiving mechanism 546 to cause internal receiving mechanism 546 to move (e.g., proximally in various embodiments) during the insertion. This movement in turn causes second sleeve slider 556*b* to move (i.e., proximally in various embodiments). During the movement of second sleeve slider 556*b*, an increasing distance develops between the moving second sleeve slider 556*b* and the stationary master slider 556*a*. It is noted that in various embodiments, master slider 556*a* remains stationary at this time because master slider 556*a* is locked in position, e.g., due to the locking mechanisms of FIG. 8. In various embodiments, an amount of length of the second part 554*b*-2 of second cable 554*b* that extends from second end 554*a*-2 of second sleeve 554*a* to master slider 556*a* increases with the increasing distance between second sleeve slider 556*b* and the stationary master slider 556*a*. That is, increasing amounts of length of the second part 554*b*-2 of the second cable 554*b* coupled to master slider 556*a* are pulled out of sleeve 554*a* with the increasing distance between second sleeve slider 556*b* and the stationary master slider 556*a*. This in turn, causes a varying of a length (e.g., a decrease in a length) of the first part 554*b*-1 of the cable 554*b* of the second Bowden cable 554 that extends outwardly from the first end 554*a*-1 of the sleeve 554*a* of the second Bowden cable 554.

It is noted that, in some embodiments such as those illustrated by FIGS. 7A and 7B, the second sleeve slider 556*b* (an example of at least part of an actuator) is at least operatively coupled to the second Bowden cable 554 to translate the second end 554*a*-2 of sleeve 554*a* of the second Bowden cable 554, the second end 552*a*-2 of the sleeve 552*a* of the first Bowden cable 552, or each of the second end 554*a*-2 and the second end 552*a*-2 of the sleeve 552*a* during at least part of a varying of the length of the first part 554*b*-1 of the cable 554*b* of the second Bowden cable 554 that extends outwardly from the first end 554*a*-1 of the sleeve 554*a* of the second Bowden cable 554 (e.g., due to the increasing distance between second sleeve slider 556*b* and the stationary master slider 556*a*).

It is also noted in various embodiments associated with FIGS. 7A and 7B, that an amount of translation undergone by an end or terminus of the second part 554*b*-2 of the cable 554*b* of the second Bowden cable 554 at a particular time during a varying of the length of the first part 554*b*-1 of the cable 554*b* of the second Bowden cable 554 that extends outwardly from the first end 554*a*-1 of the sleeve 554*a* of the second Bowden cable 554 (e.g., due to an increase in distance between second sleeve slider 556*b* and the stationary master slider 556*a*) has a magnitude less than an amount of translation undergone by the second end 554*a*-2 of sleeve 554*a* of the second Bowden cable 554 at the particular time during the varying of the length of the first part 554*b*-1 of the cable 554*b* of the second Bowden cable 554 that extends outwardly from the first end 554*a*-1 of the sleeve 554*a* of the second Bowden cable 554 (e.g., due to the increase in distance between second sleeve slider 556*b* and the stationary master slider 556*a*).

It is also noted in various embodiments associated with FIGS. 7A and 7B, that an amount of translation undergone through the lumen of the sleeve 552*a* of the first Bowden cable 552 by a portion of the cable 513 of the first Bowden cable 552 at a particular time during a varying of the length of the first part 554*b*-1 of the cable 554*b* of the second Bowden cable 554 that extends outwardly from the first end 554*a*-1 of the sleeve 554*a* of the second Bowden cable 554 (e.g., due to an increase in distance between second sleeve slider 556*b* and the stationary master slider 556*a*) is at least substantially equal in magnitude to an amount of translation undergone through the lumen of the sleeve 554*a* of the second Bowden cable 554 by a portion of the cable 554*b* of the second Bowden cable 554 at the particular time during the varying of the length of the first part 554*b*-1 of the cable 554*b* of the second Bowden cable 554 that extends outwardly from the first end 554*a*-1 of the sleeve 554*a* of the second Bowden cable 554 (e.g., due to the increase in distance between second sleeve slider 556*b* and the stationary master slider 556*a*).

A third Bowden cable may be employed in some embodiments. For example, a third Bowden cable 555 other than at least the second Bowden cable 554 may be employed in various embodiments. For example, control element 513 may, in some embodiments, provide a third Bowden cable 555 made up of sleeve 513*a* and cable 513*b*. It is also noted in various embodiments associated with FIGS. 7A and 7B, (and described in greater detail later in this disclosure) that an amount of translation undergone through the lumen of the sleeve 513*a* of the third Bowden cable 555 by a portion of the cable 513*b* of the third Bowden cable 555 at a particular time during a varying of the length of the first part 554*b*-1 of the cable 554*b* of the second Bowden cable 554 that extends outwardly from the first end 554*a*-1 of the sleeve 554*a* of the second Bowden cable 554 (e.g., due to an increase in distance between second sleeve slider 556*b* and the stationary master slider 556*a*) is greater in magnitude than an amount of translation undergone through the lumen of the sleeve 554*a* of the second Bowden cable 554 by a portion of the cable 554*b* of the second Bowden cable 554 at the particular time during the varying of the length of the first part 554*b*-1 of the cable 554*b* of the second Bowden cable 554 that extends outwardly from the first end 554*a*-1 of the sleeve 554*a* of the second Bowden cable 554 (e.g., due to the increase in distance between second sleeve slider 556*b* and the stationary master slider 556*a*). In this illustrated embodiment, the first Bowden cable 552 and the third Bowden cable 555 provided by control element 513 have different respective sleeves but share a common or same cable (i.e., cable 513*b*). In other embodiments, a third Bowden cable may be distinct from control element 513.

In some embodiments, such as those illustrated by FIGS. 7A and 7B, the second sleeve slider 556*b* (an example of an actuator) is at least operatively coupled to the first Bowden cable 552 to cause a change (e.g., an increase or decrease) in an amount of the length (e.g., due to the relative movement between the second sleeve slider 556*b* and the stationary master slider 556*a*) of the first part 513*b*-1 of the cable 513 of the first Bowden cable 552 that extends outwardly from the first end 552*a*-1 of sleeve 552*a* during at least part of a varying (e.g., due to the relative movement between the second sleeve slider 556*b* and the stationary master slider 556*a*) of the length of the first part 554*b*-1 of the respective cable 554*b* of the second Bowden cable 554 that extends outwardly from the first end 554*a*-1 of sleeve 554*a*.

In some embodiments associated with FIGS. 7A and 7B, each of the second end 554*a*-2 of the second sleeve 554*a* and the second end 552*a*-2 of the sleeve 552*a* translates during at least part of the varying of the length of the first part 554*b*-1 of the respective cable 554*b* that extends outwardly from the first end 554*a*-1 of second sleeve 554*a*.

Since the second cable 554*b* is physically coupled to slave slider 548*b* (i.e., via the first part 554*b*-1 of cable 554*b*), the slave slider 548*b* is also moved (i.e., proximally in this illustrated embodiment) relative to sleeve slider 548*a* during the relative movement between second sleeve slider 556*b* and the stationary master slider 556*a*.

While the second sleeve slider 556*b* moves proximally, away from the stationary master slider 556*a* with a particular rate (e.g., under the pushing influence from the projection 528), the control element 513 is metered with a relatively faster rate (e.g., the 2× rate in some embodiments) discussed herein with respect to FIG. 6, according to some embodiments. Typically, in various embodiments, this movement of the second sleeve slider 556*b* away from the stationary master slider 556*a*, and its accompanying control element faster metering rate, occurs while the manipulable portion 502 is being advanced outwardly from the distal end 512*b* of the catheter sheath 512 due to a relative movement between the shaft 510 and the catheter sheath 512. In some embodiments, this faster metering rate is due to the occurrence of two concurrent movements. The first of the two concurrent movements is a movement of a portion of the first Bowden cable 552 (e.g., at least the first end 552*a*-1 of its sleeve 552*a* together with its cable 513*b*) proximally due to the proximal movement of the slave slider 548*b*. The second of the two concurrent movements is a relative movement between the cable 513*b* of the first Bowden cable 552 and the sleeve 552*a* of the first Bowden cable 552 due to a proximal movement of at least the second end 552*a*-2 of sleeve 552*a* (e.g., due to proximal movement of the second sleeve slider 556*b*). The combination of the first and second of the two concurrent movements causes the faster control cable metering rate (e.g., the 2× rate in some embodiments).

However, as the second sleeve slider 556*b* continues to translate proximally under the influence of the pushing from the projection 528, in some embodiments, the distance between the master slider 556*a* and the second sleeve slider 556*b* reaches a defined amount sufficient to remove slack in tether 558 (or 810) and allow tether 558 (or 810) to be sufficiently tensioned to cause the master slider 556*a* to unlock (e.g., by way of a locking/unlocking device of FIG. 8) and move along guide channel 542*d* (or 804). Upon unlocking, master slider 556*a* is moveable (i.e., proximally in this illustrated embodiment) by further movement of second sleeve slider 556*b* (i.e., proximally in this illustrated embodiment), and, since there is no more relative movement between the master slider 556*a* and the second sleeve slider 556*b* (i.e., the master slider 556*a* is in an unlocked state), the cable 554*b* of the second Bowden cable 554 no longer moves relative to its sleeve 554*a* (e.g., FIG. 7B). Consequently, the first of the above-discussed two concurrent movements no longer exists, thereby leaving only the movement of the cable 513*b* through sleeve 552*a* as the second sleeve slider 556*b* continues to move proximally while pulling the master slider 556*a* with it. Without the movement of the first end 552*a*-1 of the sleeve 552*a* of the first Bowden cable 552 in this tensioned-tether state, the control element metering rate drops to a relatively slower rate (e.g., the 1× rate in some embodiments) discussed herein with respect to FIG. 6, according to some embodiments. In various embodiments of FIGS. 7A and 7B, sleeve slider 548*a* remains stationary during the associated movements.

In some embodiments, the tensioned-tether state (e.g., FIG. 7B) causes the slave slider 548*b* to cease moving relative to the sleeve slider 548*a*. In some embodiments, tether 558 acts as a stop configured to restrict at least the slave slider 548*b* from being translated by more than a maximum amount. In some embodiments, tether 558 acts as a stop configured to restrict at least the first end 552*a*-1 of sleeve 552*a* from being translated by more than a predetermined or defined amount. In various embodiments, the control system (which also may be referred to as an actuator system in some embodiments) 545, in a particular state in which the first end 552*a*-1 of sleeve 552*a* of the first Bowden cable 552 has been translated by a predetermined amount, causes the first Bowden cable 552 to vary the length of the first part 513*b*-1 of cable 513*b* of the first Bowden cable 552 that extends outwardly from the first end 552*a*-1 of sleeve 552*a* of the first Bowden cable 552, and causes the second Bowden cable 554 to cease varying the length of the first part 554*b*-1 of the cable 554*b* of the second Bowden cable 554 during a varying of the length of the first part 513*b*-1 of cable 513*b* of the first Bowden cable 552 that extends outwardly from the first end 552*a*-1 of sleeve 552*a* of the first Bowden cable 552 after at least the first end 552*a*-1 of sleeve 552*a* of the first Bowden cable 552 has translated by the predetermined amount. The predetermined amount may be an amount of or related to a distance between the master slider 556*a* and second sleeve slider 556*b* in which tension in the tether 558 reaches a predetermined threshold. In addition, in some embodiments, in the particular state in which the first end 552*a*-1 of sleeve 552*a* of the first Bowden cable 552 has been translated by the predetermined amount, the control system (which also may be referred to as an actuator system in some embodiments) 545 causes at least the second end 554*a*-2 of the sleeve 554*a* of the second Bowden cable 554 to translate during the varying of the length of the first part 513*b*-1 of cable 513*b* of the first Bowden cable 552 that extends outwardly from the first end 552*a*-1 of sleeve 552*a* of the first Bowden cable 552 after at least the first end 552*a*-1 of sleeve 552*a* of the first Bowden cable 552 has translated by the predetermined amount.

In FIGS. 7 and 8 tethers 558, 810 may be provided by a flexible element (e.g., a flexible cable or line) according to various embodiments. In other embodiments other forms of tethers may be employed including by way of non-limiting example, telescoping members that can telescope between predetermined minimum and maximum extents. In other embodiments, other tethers may be provided by a pin-in-channel type coupling in which a pin is physically coupled to a first member and the channel is coupled to a second member, and relative movement between the first and second members is controlled by various stop features that limit movement of the channel.

In some embodiments, the particular state is a state in which the second end 554*a*-2 of sleeve 554*a* of the second Bowden cable 554 has been translated by a predetermined amount (e.g., with respect to the master slider 556*a*). In some embodiments, the particular state is a state in which the length of the first part 554*b*-1 of the respective cable 554*b* of the second Bowden cable 554 that extends outwardly from the first end 554*a*-1 of the respective sleeve 554*a* of the second Bowden cable 554 has been varied by a predetermined amount.

It is noted in various embodiments, when the relative movement of the projection 528 relative to the housing 520 changes direction, the movement of the second sleeve slider 556*b* also changes direction. For example, when the movement of the projection 528 is changed from moving proximally to moving distally, the second sleeve slider 556*b* is also changed to move distally, thereby reducing tension on the tether 558 (or 810) and causing master slider 556*a* to lock (e.g., by the locking mechanism of FIG. 8) and thereby restrict movement thereof along guide 542*d* (or 804) in the proximal direction. In this case, the relative movement between the second sleeve slider 556*b* and the now stationary master slider 556*a* can cause a reduction of an amount of length of the second part 554*b*-2 of the cable 554*b* as the distance between the second end 554*a*-2 of sleeve 554*a* and the master slider 556*a* reduces. The reduction in the amount of length of the second part 554*b*-2 of the cable 554*b* causes an increase in an amount of length of the first part 554*b*-1 of cable 554*b* (e.g., an increase in length thereof which reduces tension in the first part 554*b*-1 of cable 554*b*), which in turn allows the slave slider 548*b* to move distally under the influence of a reactive force provided by sleeve 552*a* due to tension in control cable 513*b*. In various embodiments, distal movement of a portion of cable 513*b* outwardly from housing 520 accompanies distal movement of the slave slider 548*b*. In various embodiments, play-out of a portion of cable 513*b* outwardly from housing 520 accompanies distal movement of the slave slider 548*b*.

In various embodiments, the distal movement of slave slider 548*b* continues until the second sleeve slider 556*b* and the master slider 556*a* come into contact. At that point, further distal movement of the second sleeve slider 556*b* pushes the master slider 556*a* distally. A lack of relative movement between the master slider 556*a* and the second sleeve slider 556*b* results in no movement of the slave slider 548*b* relative to sleeve slider 548*a*. In some embodiments, as the second sleeve slider 556*b* pushes the master slider 556*a* distally, a reduction in the amount of length of the second part 513*b*-2 of control cable 513*b* occurs, which in turn, allows for a distal movement of a portion of cable 513*b* outwardly from housing 520. In some embodiments, as the second sleeve slider 556*b* pushes the master slider 556*a* distally, a reduction in the amount of length of the second part 513*b*-2 of control cable 513*b* occurs, which in turn, allows for a play-out of a portion of cable 513*b* outwardly from housing 520.

Withdrawal of the projection 528 from the housing 520 accompanies a distal movement of the internal receiving mechanism 556, according to some embodiments. In this state, in some embodiments, the second sleeve slider 556*b* moves toward the master slider 556*a*, releasing tension in the tether 558 and causing both of the above-discussed two concurrent movements (albeit distally, not proximally), and a relatively faster control element metering rate (e.g., the 2× rate in some embodiments). When the distal movement of the second sleeve slider 556*b* causes second sleeve slider 556*b* to come into contact with the master slider 556*a*, master slider 556*a* is pushed distally. In this state, both the second sleeve slider 556*b* and the master slider 556*a* move together distally, so that little or no relative movement occurs between the cable 554*b* and sleeve 554*a* of the second Bowden cable 554, leaving only or primarily, the movement of cable 513*b* relative to sleeve 552*a*. Without the relative movement occurring between the cable 554*b* and sleeve 554*a* of the second Bowden cable 554, the control element metering rate drops to a relatively slower rate (e.g., the 1× rate in some embodiments) discussed herein with respect to FIG. 6, according to some embodiments. In various embodiments, sleeve slider 548*a* remains stationary during these movements.

It is noted in various embodiments that when the second sleeve slider 556*b* moves distally or proximally in a manner where a relative positioning between the second sleeve slider 556*b* and the master slider 556*a* is changing, the slave slider 548*b* is caused to move in the same direction of travel as the second sleeve slider 556*b*. When the second sleeve slider 556*b* moves distally or proximally in a manner where a relative positioning between the second sleeve slider 556*b* and the master slider 556*a* is not changing (e.g., when the master slider 556*a* moves along with the second sleeve slider 556*b*), the slave slider 548*b* does not move relative to sleeve slider 548*a*.

In various embodiments described above, the movement of the projection 528 relative to the housing 520 moves at least a portion of an actuator (e.g., internal receiving mechanism 546, some other actuator or actuator set, or a portion of at least one of these actuators) in a first direction (e.g., proximally along a linear path as defined in FIGS. 7A and 7B) and may be employed during manipulation or metering movement of at least a portion of cable 513*b* (an example of an elongated control element in some embodiments) in a manner that is the same or similar to that described with the take-up of the control line associated with line 602 in FIG. 6. When the relative movement of the projection 528 relative to the housing member 520 changes direction, the portion of the actuator (e.g., internal receiving mechanism 546, some other actuator or actuator set, or a portion of at least one of these actuators) moves in a second direction different than (e.g., opposite) the first direction (e.g., distally along a linear path as defined in FIGS. 7A and 7B) and may be employed during manipulation or metering movement of cable 513*b* in a manner that is the same or similar to that described with the play-out of the control line associated with line 604 in FIG. 6. In various embodiments, movement of the portion of the actuator in the first direction is associated with an amount of the length 528*a* of projection 528 within receiver 529 increasing in magnitude, while movement of the portion of the actuator in the second direction is associated with an amount of the length 528*a* of projection 528 within receiver 529 decreasing in magnitude. In some embodiments, movement of the portion of the actuator (e.g., internal receiving mechanism 546, some other actuator or actuator set, or a portion of at least one of these actuators) in the first direction is associated with a transition of the manipulable portion 502, at least in part, toward or to an expanded configuration, while movement of the portion of the actuator in the second direction is associated with a transition of the manipulable portion 502, at least in part, toward or to a delivery configuration.

In various embodiments, the actuator (e.g., internal receiving mechanism 546, some other actuator or actuator set, or a portion of at least one of these actuators) is operatively coupled to the cable 513*b* (an example of at least a portion of an elongated control element) to cause an increase and a subsequent decrease in an amount of the length of the cable 513*b* located outside of the distal end 512*b* of catheter sheath 512 when at least the portion of the actuator moves in the first direction (e.g., proximally as defined in FIGS. 7A and 7B), which may, in some embodiments, accompany or be required by an advancement of manipulable portion 502 outwardly from the distal end 512*b* of the catheter sheath 512, as shown by the sequence represented consecutively in FIGS. 5H, 5I and 5J. In this regard, in some embodiments, at least a portion of the actuator (e.g., internal receiving mechanism 546, some other actuator or actuator set, or a portion of at least one of these actuators) is moveable (and, in some embodiments, is selectively moveable, e.g., by way of the projection 528, or by relative movement between shaft 510 and catheter sheath 512) in each of one particular direction (e.g., the first direction) and a second direction different than the one particular direction (e.g., the first direction) to manipulate at least the portion of the cable 513*b* (an example of at least part of a control element). This movement of at least the portion of the actuator in each of the first direction and the second direction may be with respect to the housing 520.

In various embodiments, the actuator (e.g., internal receiving mechanism 546, some other actuator or actuator set, or a portion of at least one of these actuators) is operatively coupled (to the cable 513b (an example of at least part of an elongated control element) to cause an increase and a subsequent decrease in an amount of the length of the cable 513b located outside of the distal end 512b of catheter sheath 512 when at least the portion of the actuator moves in the second direction (e.g., distally as defined in FIGS. 7A and 7B), which may, in some embodiments, accompany or be required by a retraction of manipulable portion 502 into the distal end 512b of the catheter sheath 512, as shown by the sequence represented consecutively in FIGS. 5J, 5I and 5H.

In some embodiments, a modulation actuator (e.g., second particular actuator 540b, some other actuator or actuator set, or a portion of at least one of these actuators) may be physically or operatively coupled to the manipulable portion 502 to modulate at least a size, a shape, or both a size and a shape of the manipulable portion 502, e.g., at least in a state where at least a part of the manipulable portion 502 and a part of the cable 513b (an example of at least part of a control element) extends outside of the distal end 512b of the catheter sheath 512 (e.g., FIG. 5C). In some embodiments, the modulation actuator is operable to selectively move at least in part (e.g., by way of the projection 528, or relative movement between shaft 510 and catheter sheath 512) the manipulable portion 502 between a delivery configuration in which the manipulable portion 502 is sized, shaped, or both sized and shaped to be delivered through the first lumen 512d of the catheter sheath 512 and an expanded configuration in which the manipulable portion 502 is sized, shaped, or both sized and shaped too large for delivery through the first lumen 512d of the catheter sheath 512.

In some embodiments, the control system (e.g., an actuator system in some embodiments) 545, or one or more components of system 100 or control system 322, such as controller 324) may be physically or operatively coupled to or include the actuator (e.g., the internal receiving mechanism 546, some other actuator or actuator set, or a portion of at least one of these actuators), and may be configured to cause the actuator (e.g., the internal receiving mechanism 546, some other actuator or actuator set, or a portion of at least one of these actuators) to manipulate at least the portion of the cable 513b (e.g., at least part of a control element) to cause a length of the part of the cable 513b extending outside the distal end 512b of the catheter sheath 512 to increase and then subsequently decrease during or throughout a movement of at least the portion of the actuator in the one particular direction (e.g., in the first direction, proximal direction causing the advancement sequence of FIG. 5H, 5I, 5J or in the second, distal direction causing the retraction sequence of FIGS. 5J, 5I, 5H). The movement of at least a portion of the actuator (e.g., the internal receiving mechanism 546, some other actuator or actuator set, or a portion of at least one of these actuators) in the one particular direction may be associated with a relative movement between the shaft 510 and the catheter sheath 512, when part of the shaft 510 is located in the lumen 512d of the catheter sheath 512. In some of these embodiments, a part of the manipulable portion 502 extends outside the distal end 512b of the catheter sheath 512 and has a size, a shape, or both a size and a shape too large to fit in the lumen of the catheter sheath (for example, as shown in FIGS. 5I and 5J) during or throughout the movement of at least the portion of the actuator in the one particular direction. In some of these embodiments, cable 513b is located, at least in part, in the lumen 512d of catheter sheath 512 during the movement of at least the portion of the actuator in the one particular direction. In some of these embodiments, shaft 510 is located at least in part, in the lumen 512d of catheter sheath 512 during the movement of at least the portion of the actuator in the one particular direction. In some embodiments, such control system 545 may be configured to cause the modulation actuator to modulate the manipulable portion 502, such that a part of the manipulable portion 502 extending outside the distal end 512b of the catheter sheath 512 has a size, a shape, or both a size and a shape too large to fit in the lumen 512d of the catheter sheath 512 (for example, as shown in FIGS. 5I and 5J) during or throughout the movement of at least a portion of the actuator (e.g., the internal receiving mechanism 546, some other actuator or actuator set, or a portion of at least one of these actuators) in the one particular direction.

In some embodiments, the actuator and the modulation actuator are the same device, or the actuator includes the modulation actuator. For example, the actuator may be the internal receiving mechanism 546, and the modulation actuator may be the master slider 556a or the sleeve slider 556b of the internal receiving mechanism 546. In this regard, it should be noted that the present invention is not limited to any particular actuator configuration. For example, although the internal receiving mechanism 546 is identified in some examples above as an actuator, any other component of catheter system 500 that achieves a desired function or result may alternatively be considered an actuator. For instance, although the internal receiving mechanism 546 may be deemed an actuator configured to move along a linear path when moving in the first direction (e.g., proximal direction in FIG. 7) or in the second direction (e.g., distal direction in FIG. 7), a portion of cable 554b, sleeve 554a, or each of the cable 554b and sleeve 554a may be considered a portion of such actuator (e.g., internal receiving mechanism 546, some other actuator or actuator set, or a portion of at least one of these actuators) due to their operative coupling, such that the portion of cable 554b, sleeve 554a, or each of the cable 554b and sleeve 554a follows an arcuate or coiled path (e.g., FIGS. 7A and 7B) when the internal receiving mechanism 546 is moving in the first direction (e.g., proximal direction in FIG. 7) or in the second direction (e.g., distal direction in FIG. 7).

In various embodiments, the amount of cable 513b within the housing 520 will vary in accordance with the movement of projection 528 when received by receiver 529. It is further noted that the amount of the portion 514 of cable 513b extending outwardly from the distal end 512b of the catheter sheath 512 will vary inversely (e.g., linearly or non-linearly) with an increase or decrease in an amount of the cable 513 located within the housing 520. In various embodiments, when movement of the projection 528 causes the second sleeve slider 556b to move distally or proximally in a manner where a relative positioning between the second sleeve slider 556b and the master slider 556a is changing, take-up of cable 513b (e.g., occurring during insertion of projection 528 inwardly into receiver 529) or play-out (e.g., occurring during retraction of projection 528 outwardly from receiver 529) occurs at a 2:1 ratio with the movement of the projection 528. This occurs because the slave slider 548b moves concurrently with the movement of the second sleeve slider 556b relative to the stationary master slider 556a. When movement of the projection 528 causes the second sleeve slider 556b to move distally or proximally in a manner where a relative positioning between the second sleeve slider 556b and the master slider 556a is not changing, take-up of cable 513b (e.g., occurring during insertion of projection 528 inwardly into receiver 529) or play-out of cable 513b (e.g., occurring during retraction of projection 528 outwardly from receiver 529) occurs at a 1:1 ratio with the movement of the projection 528. This occurs because the slave slider 548b does not move relatively to sleeve slider 548a during this movement.

It is understood that in various embodiments, the actual rate that cable 513b is metered during take-up or play-out is dependent on the actual rate of relative movement between projection 528 and receiver 529. That is, in various embodiments a defined speed ratio between the metering rate of cable 513b and the rate of relative movement between projection 528 and receiver 529 controls the actual metering rate of control cable 513b. The speed ratio specifies an output speed associated with an output portion of a particular device as a function of an input speed associated with an input portion of the particular device. It is noted in FIGS. 7A and 7B, that although a portion of a control element manipulation actuator (e.g., internal receiving mechanism 546, some other actuator or actuator set, or a portion of at least one of these actuators) moves along an essentially linear path during the take-up or play-out of cable 513b, the invention is not so limited, and the portion of the actuator may move along an arcuate path during the take-up or play-out of cable 513b in other embodiments.

In some embodiments, control system 545 is physically or operatively coupled to at least one control element manipulation actuator (e.g., internal receiving mechanism 546, some other actuator or actuator set, or a portion of at least one of these actuators) to control at least the actuator to cause movement of at least a portion of an elongated control element (e.g., cable 513b), e.g., along a path extending toward the manipulable portion 502, by metering the portion of the elongated control element with (a) a first rate of movement in response to at least a portion of the control element manipulation actuator (e.g., internal receiving mechanism 546, some other actuator or actuator set, or a portion of at least one of these actuators) moving (e.g., with respect to the housing 520) with a particular rate of movement in a first direction (e.g., proximally as defined in FIGS. 7A and 7B), and (b) a second rate of movement in response to the at least a portion of the control element manipulation actuator (e.g., internal receiving mechanism 546, some other actuator or actuator set, or a portion of at least one of these actuators) moving (e.g., with respect to the housing 520) with the same particular rate of movement in a second direction different than the first direction (e.g., distally as defined in FIGS. 7A and 7B), such that a first ratio of the first rate of movement to the particular rate of movement is different than a second ratio of the second rate of movement to the particular rate of movement, e.g., when a portion of cable 513b (an example of an elongated control element in some embodiments) is positioned at a particular location.

In various embodiments, a modulation actuator is operable to selectively move manipulable portion 502 or structure 502a thereof between a delivery configuration in which manipulable portion 502 or structure 502a thereof is sized or shaped to be delivered through a bodily opening leading to a bodily cavity and an expanded configuration in which manipulable portion 502 or structure 502a thereof is sized or shaped too large for delivery through the bodily opening. In some of these various embodiments, such as those described above with respect to FIG. 6, control system 545 controls at least one control element manipulation actuator by switching a ratio of (a) a rate at which the portion of the elongated control element (e.g., cable 513b) is metered to (b) a rate of movement of at least the portion of the control element manipulation actuator (e.g., internal receiving mechanism 546, some other actuator or actuator set, or a portion of at least one of these actuators) between each ratio of a first set of two or more different predetermined ratios when the modulation actuator transitions the manipulable portion 502 from the delivery configuration to the expanded configuration. On the other hand, in some embodiments, the control system 545 controls the control element manipulation actuator to vary movement of the control element by switching the ratio of (a) to (b) between each ratio of a second set of two or more different predetermined ratios when the modulation actuator transitions the manipulable portion 502 from the expanded configuration to the delivery configuration. In some of these various embodiments, the first ratio is a member of the first set and the second ratio is member of the second set. In some embodiments, at least one of the predetermined ratios in the first set is the same as one of the predetermined ratios in the second set. In some embodiments, at least two of the predetermined ratios in the first set are the same as at least two of the predetermined ratios in the second set.

For example, in FIG. 6, the control line is metered with a first set of two different predetermined rates (i.e., line 602) during take-up of the control line and is metered with a second set of two different predetermined rates (i.e., line 604) during play-out of the control line. When a particular amount of the associated structure is located outside the distal end of the catheter sheath (e.g., a particular amount represented by 70 mm on the horizontal axis), the control line is metered with a first rate of the first set during control line take-up (i.e., portion 602b of line 602) that is different (e.g., twice the rate) than a second rate of the second set that the control line is metered with during control line play-out (i.e., portion 604c of line 604). When the metering rate of the control element is dependent on a given rate of movement of the portion of the control line manipulation actuator in each of the metering directions (for example, as described with respect to FIGS. 7A and 7B), each of the predetermined rates in each of the first and second sets can be expressed as a ratio of the predetermined rate to the rate of movement of the portion of the control line manipulation actuator when the portion of the control line manipulation actuator is moved in each of different directions with the same rate of movement.

Stated another way, in various embodiments, a modulation actuator is operable to selectively move manipulable portion 502 or structure 502a thereof between a delivery configuration in which manipulable portion 502 or structure 502a thereof is sized or shaped to be delivered through a bodily opening leading to a bodily cavity and an expanded configuration in which the manipulable portion 502 or structure 502a thereof is sized or shaped too large for delivery through the bodily opening. In some of these various embodiments, such as those described above with respect to FIG. 6, control system 545 controls at least one control element manipulation actuator by switching a ratio of (a) a rate at which the portion of the elongated control element (e.g., cable 513b) is metered to (b) a rate of movement of at least the portion of the control element manipulation actuator (e.g., internal receiving mechanism 546, some other actuator or actuator set, or a portion of at least one of these actuators) between each ratio of a first set of two or more different ratios when the modulation actuator transitions the manipulable portion 502 from the delivery configuration to the expanded configuration. In some embodiments, each ratio in the first set of two or more different ratios has a value corresponding to a respective one of a first set of two or more different predetermined values. On the other hand, in some embodiments, the control system 545 controls the control element manipulation actuator to vary movement of the control element by switching the ratio of (a) to (b) between each ratio of a second set of two or more different ratios when the modulation actuator transitions the manipulable portion 502 from the expanded configuration to the delivery configuration. In some embodiments, each ratio in the second set of two or more different ratios has a value corresponding to a respective one of a second set of two or more different predetermined values. In some embodiments, the first ratio is a member of the first set of two or more different ratios and the second ratio is member of the second set of two or more different ratios. In some embodiments, at least one of the predetermined ratios in the first set is the same as one of the predetermined ratios in the second set. In some embodiments, at least two of the predetermined ratios in the first set are the same as at least two of the predetermined ratios in the second set.

In some embodiments, the particular amount of the associated structure (e.g., the structure 502a of the manipulable portion 502) located outside the distal end 512b of the catheter sheath 512 is a particular size of the manipulable portion 502 or structure 502a thereof between the distal end 512b and the distal end of the manipulable portion 502. In some embodiments, the particular amount of the manipulable portion 502 or structure 502a thereof located outside the distal end 512b of the catheter sheath 512 is a particular length of the manipulable portion 502 or structure 502a thereof extending from the distal end 512b to the distal end of the manipulable portion 502 or structure 502a thereof. In some embodiments, the particular amount of the manipulable portion 502 or structure 502a thereof located outside the distal end 512b of the catheter sheath 512 is a particular length of the manipulable portion 502 or structure 502a thereof extending along a surface of the manipulable portion 502 or structure 502a thereof from the distal end 512b to the distal end of the manipulable portion 502 or structure 502a thereof. In some embodiments, the particular amount of the manipulable portion 502 or structure 502a thereof located outside the distal end 512b of the catheter sheath 512 is a surface area or volume of a part of the manipulable portion 502 or structure 502a thereof located outside the distal end 512b of the catheter sheath 512. In some embodiments, a particular amount of the manipulable portion 502 or structure 502a thereof extending outwardly from the distal end 512b of catheter sheath 512 corresponds to a particular amount of the length 528a of projection 528 being received in receiver 529 (for example as shown in FIGS. 7A and 7B). In some embodiments where the control line metering scheme depicted in FIG. 6 is employed, a control system (e.g., control system 545, or one or more components of system 100 or control system 322, such as controller 324) may be configured to control at least a control line manipulation actuator that is the same or similar to that represented in FIGS. 7A and 7B, when a particular amount of length 528a of projection 528 is received within receiver 529 during a transition of the manipulable portion 502 toward or to an expanded configuration, to cause cable 513b (an example of at least part of a control element or cable) to be metered with a first rate. On the other hand, in some embodiments, the control system may be configured to control at least the control line manipulation actuator, when the same particular amount of length 528a of projection 528 is received within receiver 529 during a transition of the manipulable portion 502 toward or to a delivery configuration, to cause control cable 513b to be metered with a second rate different than the first rate.

When the control line metering scheme depicted in FIG. 6 is employed by a control line manipulation actuator that is the same or similar to that represented in FIGS. 7A and 7B, each of portion 602b of line 602 and portion 604b of line 604 may be associated with a condition in which a relative positioning between the second sleeve slider 556b and the master slider 556a is changing, while each of portion 602c of line 602 and portion 604c of line 604 may be associated with a condition in which a relative positioning between the second sleeve slider 556b and the master slider 556a is not changing. Accordingly a control loop that is the same or similar to that created by portions 602b, 602c, 604b and 604c may be established by the control system 545 for the metering of cable 513b as the manipulable portion 502 is advanced outwardly from the distal end 512b of catheter sheath 512 into an expanded configuration that is the same or similar to that shown in FIG. 5J and then subsequently retracted back into the confines of first lumen 512d (e.g., into a delivery configuration). It is noted in some embodiments, that metering action of the control line manipulation actuator represented in FIGS. 7A and 7B may in some cases be interrupted at various points along the control loop prior to a completion of an advancement of the manipulable portion 502 into the expanded configuration or prior to a completion of a retraction of the manipulable portion 502 back into the confines of first lumen 512d. The interruption may be motivated, for example, by a user decision to reverse a movement of manipulable portion 502 to (a) retract the manipulable portion 502 rather than proceeding with the advancement of the manipulable portion 502 toward or to the expanded configuration, or (b) advance the manipulable portion rather than proceeding with the retraction of the manipulable portion 502 into the confines of the first lumen 512d. In either case, a change in a metering direction of cable 513b is typically required during the reversal of movement of manipulable portion 502 caused by the interruption.

A required change in the metering direction of cable 513b may be motivated for various reasons including occurrences of slack or undesired level of tension in the cable 513b as described above in this disclosure. In various embodiments, an employed control element metering system (e.g., such as that represented in FIGS. 7A and 7B) is configured to, when interrupted from metering a portion of a control element (e.g., cable 513b) in a first particular metering direction to metering the portion of the control element in a second particular metering direction different than the first particular metering direction, cause a defined or predetermined change in metering rate to accompany the change in metering direction. That is, when the portion of the control element is interrupted from being metered with a first rate in a first metering direction to being metered in a second metering direction different than the first metering direction, the control element metering system can cause the portion of the control element to be metered with a second rate in the second metering direction, the second rate being different than the first rate. This mode of operation can occur at various points along the control loop. For example in FIG. 6, the control line is being metered with a first rate in a first metering direction (e.g., a take-up direction) associated with a portion 602c of line 602. If the metering of the control line along portion 602c in the first metering direction is interrupted and metered in a second different metering direction (e.g., a play-out direction) before less than an intended amount of the device has been advanced outwardly from the distal end of the catheter sheath (for example, when only approximately 150 mm of the device has been advanced outwardly from the catheter sheath), the control line is not metered in the second metering direction with the first rate, but rather a second rate represented by line 606. In various embodiments, the second rate is the same as the metering rate associated with portion 604*b* of line 604. Advantageously, these various embodiments allow for the device to be manipulated in a particular desired manner that may be required by the change in the metering direction during the interrupted cycle.

In various embodiments associated with FIGS. 5 and 7, control system 545 is configured to cause movement of a portion of control element 513 (e.g., cable 513*b*) along a path extending toward manipulable portion 502. Control system 545 may be further configured to, when a portion of the control element 513 is located at a particular position along the path, (a) meter movement of the portion of the control element 513 at a first rate in a first direction along the path away from the particular position at least in response to occurrence of a first state that triggers a transition of the manipulable portion 502 toward or to the expanded configuration, and (b) meter movement of the portion of the control element 513 at a second rate in a second direction along the path away from the particular position at least in response to occurrence of a second state that triggers a transition of the manipulable portion 502 toward or to the delivery configuration. In some embodiments, the second direction along the path is different than the first direction along the path and the second rate is different than the first rate.

In some embodiments, control system 545 is configured, when a particular amount of the manipulable portion 502 is located outside the distal end 512*b* of the catheter sheath 512 during a transition of the manipulable portion 502 toward or to the expanded configuration, to control an actuator to cause (a) control element 513 to have a first amount of length located outside the distal end 512*b* of the catheter sheath 512, at least in response to occurrence of a first state that triggers a transition of the manipulable portion 502 toward or to the expanded configuration, and when the same particular amount of the manipulable portion 502 is located outside the distal end 512*b* of the catheter sheath 512 during a transition of the manipulable portion 502 toward or to the delivery configuration, to control the actuator to cause (b) control element 513 to have a second amount of length located outside the distal end 512*b* of the catheter sheath 512, at least in response to occurrence of a second state that triggers a transition of the manipulable portion 502 toward or to the delivery configuration. In various ones of these embodiments, the first amount of length is different than the second amount of length.

In some embodiments, control system 545 is configured, when a particular relative positioning exists between the catheter sheath 512 and the shaft 510 received in the first lumen 512*d* of the catheter sheath 512 during a transition of the manipulable portion 502 toward or to the expanded configuration, to control an actuator to cause (a) control element 513 to have a first amount of length located outside the distal end 512*b* of the catheter sheath 512, at least in response to occurrence of a first state that triggers a transition of the manipulable portion 502 toward or to the expanded configuration, and when the same particular relative positioning exists between the catheter sheath 512 and the shaft 510 received in the first lumen 512*d* of the catheter sheath 512 during a transition of the manipulable portion 502 toward or to the delivery configuration, to control the actuator to cause (b) control element 513 to have a second amount of length located outside the distal end 512*b* of the catheter sheath 512, at least in response to occurrence of a second state that triggers a transition of the manipulable portion 502 toward or to the delivery configuration. In various ones of these embodiments, the first amount of length is different than the second amount of length. The particular relative positioning may be a relative longitudinal positioning in some embodiments.

The first and the second states described above can take different forms in various embodiments. For example, the first state may be associated with a direction of relative moment between catheter sheath 512 and a portion of shaft 510 in first lumen 512*d* that decreases a distance between a location on catheter sheath 512 and a location on shaft 510 and the second state may be associated with a direction of relative moment between catheter sheath 512 and a portion of shaft 510 in first lumen 512*d* that increases a distance between a location on catheter sheath 512 and a location on shaft 510.

In some embodiments associated with FIGS. 7A and 7B, after leaving the confines of the sleeve 552*a*, the second part 513*b*-2 of cable 513*b* is subjected to a bend (e.g., a 180 degree bend) in a guide 560 before coupling to the forming slider 561 associated with first particular actuator 540*a*. In various embodiments, guide 560 is relatively rigid in form and does not flex like sleeves 552*a* and 554*a*. The use of guide 560 may be motivated by various reasons including imparting a serpentine path to the cable 513*b* to reduce an overall size of housing 520 or additionally or alternatively, guiding cable 513*b* to another guide in guide system 542 or additionally or alternatively, changing an activation direction of forming slider 561. Forming slider 561 may be configured to move along guide 542*a*. The operation of forming slider 561 is described later in this disclosure.

FIGS. 5S-1, 5S-2, 5S-3, 5S-4, 5S-5, and 5S-6 (collectively FIG. 5S) are top plan views of various actuator sets associated with catheter system 500, various ones of the actuators in the sets positioned in particular activation positions associated with different particular states of the expanded configuration of manipulable portion 502 according to various embodiments. In some embodiments, various ones of the actuator sets may include one or more actuators selectively moveable between at least two different activation positions. For example, an actuator may be selectively moveable from a respective first activation position into a second activation position to change a size, a shape, or both a size and a shape of an expanded configuration of manipulable portion 502 from one particular state to another particular state. In various embodiments, an actuator set (e.g., first actuator set 540) may include two or more actuators, each of the actuators in the actuator set independently or separately moveable from the other actuators in the actuator set from a respective first activation position into a respective second activation position to independently change a size, a shape, or both a size and a shape of an expanded configuration of manipulable portion 502 from one particular state into another particular state. It is noted in at least some of the embodiments of FIG. 5S that shaft 510 (not called out) is inserted into the first lumen 512*d* of catheter sheath 512 and that projection 528 (not called out) is received in receiver 529 (not called out in these figures).

In various embodiments, various components or devices associated with housing 520 have respective positionings depicted in FIG. 5S-1 that correspond to an expanded configuration of manipulable portion 502 having a state that is the same or similar to the first fanned configuration 536 exemplified in FIG. 5L-1. It is understood that other configurations or configuration states of manipulable portion 502 may correspond to the configuration of housing 520 in FIG. 5S-1 in other embodiments. Cover 520*a* is shown in a first position 570*a* in FIG. 5S-1. In various embodiments, first position 570a is also referred to as a closed position that may restrict user access to some other portion of housing 520 or some particular device or devices accommodated by housing 520. In various embodiments, user access to various actuators in an actuator set is restricted when cover 520a is in the first position 570a. For example, user access to a first actuator set (e.g., first actuator set 540) that includes first particular actuator 540a and second particular actuator 540b (or at least part of each of first particular actuator 540a and second particular actuator 540b) is restricted when cover 520a is in the first position 570a in some embodiments. In various embodiments, cover 520a is selectively moveable between first position 570a and a second position 570b (shown in FIG. 5S-2) located to allow or permit user access to first particular actuator 540a and second particular actuator 540b. In some embodiments, second position 570b is also referred to as an open position. In some embodiments, cover 520a forms part of an interlock whose operation prevents an operation of another device. For example, when the cover 520a is moved into the first position 570a from another position, access to, or operation of, first particular actuator 540a and second particular actuator 540b is prevented.

In various embodiments cover 520a forms part of, or is physically or operatively coupled to, an actuator that is selectively moveable between at least two different activation positions. In some embodiments, cover 520a forms part of, or is physically coupled to, an actuator that is selectively moveable between at least two activation positions to vary a size, a shape, or both a size and a shape of manipulable portion 502 or an expanded configuration of the manipulable portion 502. For example, in some embodiments, cover 520a forms a part of an actuator set comprising an actuator 572 configured to vary a size, shape, or both size and shape of an expanded configuration of manipulable portion 502 from the first fanned configuration 536 exemplified in FIGS. 5L-1, 5L-2 to a second fanned configuration 537 (also referred to as a bifurcated doming configuration) exemplified in FIGS. 5M-1, 5M-2 when a movement of cover 520a causes actuator 572 (e.g., at least first fanning slider 572a shown in FIG. 5R-1) to move from a first activation position (e.g., position 571a shown in FIG. 5S-1) into a second activation position (e.g., position 571b shown in FIG. 5S-2). In this regard, the actuator 572 (also referred to herein as a third particular actuator in some embodiments) is selectively moveable into a respective activation position (e.g., 571b) to fan at least some of the plurality of elongate members 504 with respect to one another to create a fanned arrangement radiating from a location between the proximal portion 508a and the distal portion 508b of the manipulable portion 502 when the manipulable portion 502 is in the expanded configuration. It is understood that although first position 570a and position 571a are shown as being the same position in FIG. 5S-1 and second position 570b and position 571b are shown as being the same position in FIG. 5S-2, (a) first position 570a and the first activation position may be different, (b) second position 570b and the second activation position may be different, or both (a) and (b) in other embodiments. In FIG. 5M-1, at least some of the elongate members 504 are additionally fanned by actuator 572 to reconfigure an expanded configuration of manipulable portion 502 from the first fanned configuration or state 536 to the second fanned configuration or state 537. In various embodiments, at least some of the elongate members 504 are additionally fanned (e.g., fanned in addition to the autonomous fanning described above in this disclosure) to more fully or more evenly increase a circumferential distribution of the elongate members 504. For example, FIGS. 5L-2 and 5M-2 respectively show top plan views of the expanded manipulable portion 502 in the first fanned configuration 536 and the second fanned configuration 537. As compared with FIG. 5L-2, various portions of the elongate members 504 are more fully or more completely circumferentially distributed in FIG. 5M-2.

A fuller or more complete circumferential distribution of the elongate members 504 may be motivated by various reasons. For example, such a distribution may be better suited for distributing an array of transducers (e.g., transducers 506) over a greater interior surface region of bodily cavity into which manipulable portion 502 is introduced. In various embodiments associated with FIG. 5M-1, the proximal portion 508a of manipulable portion 502 forms a first domed shape 508a-1, and the distal portion 508b of manipulable portion 502 forms a second domed shape 508b-1, when the manipulable portion is in a deployed configuration.

Different actuators may be implemented as actuator 572 in various embodiments. In some embodiments associated with FIG. 5M-1, actuator 572 may work in a same or similar fashion to the separator 2852 described in co-assigned International Application No.: PCT/US2012/022061, which is incorporated herein by reference. For example, actuator 572 may include a mechanism that converts an input movement (e.g., an input movement of cover 520a) into an output movement of various control elements 573 (shown in FIG. 5M-1) in a manner suitable for additionally fanning of the elongate members 504. In FIG. 5M-1, each control element 573 includes a control cable 573b received in a lumen of sleeve 573a (e.g., the same or similar to flexible lines 2853 and tubular members 2854 in co-assigned International Application No.: PCT/US2012/022061, which is incorporated herein by reference). In FIG. 5M-1 sleeves 573a are physically coupled (or, in some embodiments, fixedly coupled) to surface 518b of an elongate member 504 (e.g., an elongate member 504 positioned at the bottom of the stacked arrangement), each of the sleeves 573a sized to terminate at a respective location along a length of the elongate member 504. In various embodiments, each of at least some of the sleeves 573a is sized to terminate at different longitudinal locations along the length of elongate member 504. Each of the termination locations is a selected position where exiting portions of the respective cables 573b may be positioned at a desired location along the length of the elongate member 504. Each termination location may be chosen to advantageously allow the respective exiting cable 573b to apply force with sufficient mechanical advantage to move the expanded configuration of the manipulable portion 502 between the two fanned states. From each termination location, the respective exiting cable 573b is physically coupled to an adjacent elongate member 504. In FIG. 5M-1 two sets of exiting cables 573b couple the two portions 508a and 508b to additionally fan the elongate members (i.e., one set of the exiting cables 573b being on a far side of manipulable portion 502 depicted in FIG. 5M-1 and thereby not visible). In various embodiments, movement of the actuator 572 from the first activation position (e.g., position 571a) into the second activation position (e.g., position 571b) (for example, as a consequence of movement of cover 520a) increases tension levels in various cables 573b sufficiently to draw the associated coupled adjacent elongate members 504 toward each other to move the manipulable portion 502 from the first fanned configuration or state 536 into the second fanned configuration or state 537. For example, with reference to FIGS. 5R-1 and 5R-2, actuator 572 includes a first fanning slider 572a moveable along guide 542e and a pair of second fanning sliders 572b, 572c, each moveable along guide 542f. In various embodiments, various ones of the cables 573b (not shown in FIGS. 5R-1, 5R-2 for clarity) are physically coupled to respective ones of the second fanning sliders 572b, 572c. First fanning slider 572a is physically coupled (for example via passageway or channel between guides 542e and 542f) to at least one of the second fanning sliders 572b, 572c to move the connected at least one of the second fanning sliders 572b, 572c to increase tension levels in the various ones of the cables 573b when first fanning slider 572a is moved, for example, between the first activation position (e.g., position 571a) and the second activation position (e.g., position 571b) (e.g., as a consequence of movement of cover 520a). In some embodiments, various devices may be employed to delay a movement of one of the second fanning sliders 572b, 572c until another of the second fanning sliders 572b, 572c has moved by a desired amount or has moved to a desired location under the influence of a movement of first fanning slider 572a. Such delays may be used to move the expanded configuration of the manipulable portion 502 between the two fanned states in a series of staged movements. In some embodiments, a movement of one of the second fanning sliders 572b, 572c may stop before another of the second fanning sliders 572b, 572c does. In various embodiments, the respective sleeve 573a associated with each respective cable 573b maintains the respective cable 513b in a position suitable for applying the fanning force in a suitable direction during the tensioning of the cable 573b (e.g., which may be or may not be similar to a Bowden cable). Various ones of the elongate members 504 may be additionally physically coupled together by coupling members (similar to or the same as coupling members 2858 in co-assigned International Application No.: PCT/US2012/022061, which is incorporated herein by reference). In various example embodiments, each coupling member may allow movement of one of the elongate members 504 coupled by the coupling member to also cause movement of another of the elongate members 504 coupled by the coupling member. In some example embodiments, the coupling members are arranged to restrict or limit an amount of movement that an elongate member 504 undergoes as the portion of the device is moved into the second fanned configuration 537. For clarity, control element 513 is not shown in FIGS. 5M-1 and 5M-2. For clarity, the various control elements 573 are only shown in FIG. 5M-1. In some embodiments, actuator 572 forms part of the first actuator set 540.

In some embodiments, a locking device is selectively operable in a locked configuration which restricts cover 520a from moving at least in a direction away from the second position 570b (or, in some embodiments in which cover 520a forms part of actuator 572, from the second activation position 571b) and an unlocked configuration which permits cover 520a to move at least in the direction away from the second position 570b (or from the second activation position 571b). For example, in some embodiments, biasing member 520c (i.e., FIG. 5R-1) is arranged to provide a force on cover 520a that biases cover 520a downward or toward an upper surface of housing 520. When the cover 520a is moved from the first position 570a (i.e., FIG. 5S-1) to the second position 570b (i.e., FIG. 5S-2) (or from first activation position 571a to second activation position 571b), biasing member 520c forces the cover 520a downward to entrap a portion of the cover 520a against stop elements 520d (i.e., shown in FIG. 5S-1) and thereby locking cover 520a at second position 570b. In some embodiments, cover 520a is released from its locked state when a pulling force (for example as applied by a user) is applied upwardly to the cover 520a against the biasing action of biasing member 520c and out of unlocked engagement with stop elements 520d. When the cover 520a is released from it locked state, movement away from second position 570b or second activation position 571b is permitted. In some embodiments, the ability to lock actuator 572 (for example via cover 520a) advantageously enables the second fanned configuration 537 to be maintained.

The expanded configuration may be moved into other, different states in some embodiments. It is noted in various embodiments that, in any of the various states of the expanded configuration, the manipulable portion 502 may be sized too large for delivery through the lumen 512d of catheter sheath 512 (e.g., during percutaneous delivery of manipulable portion 502) or at least a part of the manipulable portion 502 may be too large to fit in the lumen 512d of catheter sheath 512. As compared between FIGS. 5S-2 and 5S-3, first particular actuator 540a is moved from a first activation position (e.g., position 574a shown in FIG. 5S-2) into a second activation position 574b shown in FIG. 5S-3) to vary a size, shape, or both size and shape of the expanded configuration of manipulable portion 502 from the second fanned configuration 537 exemplified in FIGS. 5M-1, 5M-2 into an enlarged expanded configuration 538 exemplified in FIG. 5N. In various embodiments, movement into the enlarged expanded configuration 538 may be caused by an increase in a radial spacing between various elongate members 504 in the circumferential distribution of the elongate members 504 associated with the second fanned configuration 537 (e.g., an increase in a radial distance of various ones of the elongate members 504 from a central axis of the circumferential distribution). In various embodiments, movement into the enlarged expanded configuration 538 may be caused by an increase in an overall size or dimension of the manipulable portion 502. In various embodiments, movement into the enlarged expanded configuration 538 may be caused by an increase in a distance between respective apexes of the two domed shaped portions 508a-1 and 508b-1. Changing the expanded configuration of the manipulable portion 502 into the enlarged expanded configuration 538 may be motivated for various reasons. For example, manipulable portion 502 may be manipulated into the enlarged expanded configuration 538 to create a conformance, or increase a level of conformance with a tissue surface within a bodily cavity into which the manipulable portion 502 is deployed. In some example embodiments, manipulable portion 502 may be further manipulated into the enlarged expanded configuration 538 to position various transducer elements 506 in closer proximity to an interior tissue surface within a bodily cavity.

In various example embodiments, first particular actuator 540a is moved from its respective first activation position 574a into its second activation position 574b to manipulate cable 513b to reduce a length of the portion 514 (not called out in FIG. 5N) of cable 513b that extends outwardly from sleeve 513a to manipulate the distal end of manipulable portion 502 into closer proximity to the sleeve 513a. This movement of cable 513b draws the domed distal portion 508b in closer proximity to sleeve 513a and increases or enlarges an overall size of the manipulable portion 502. With reference to FIG. 7, movement of the expanded configuration of manipulable portion 502 into the enlarged expanded configuration 538 accompanies a movement of forming slider 561 proximally along guide 542a to take up cable 513b. In FIG. 5S-3, handle 543a of first particular actuator 540a has been rotated (e.g., by a user manipulation) in rotational direction 576 to cause a locking device (e.g., locking device of FIG. 10) of first particular actuator 540a to move from an unlocked configuration to a locked configuration suitable for maintaining the first particular actuator 540a in the second activation position 574b. In this regard, first Bowden cable 552 (i.e., which includes sleeve 552a and cable 513b) is operable in various different configurations. For example, in various embodiments, at least one actuator is physically or operatively coupled to the first Bowden cable 552 to (a) move the sleeve 552a independently or separately from the cable 513b to cause the sleeve 552a to slide over the cable 513b during a first manipulation of the manipulable portion 502 to change, a size, a shape, or both thereof (e.g., as described above with respect to the manipulation of manipulable portion 502 in FIGS. 5H, 5I and 5J), and (b) move the cable 513b independently or separately from the sleeve 552a to cause the cable 513b to slide through the lumen of the sleeve 552a during a second manipulation of the manipulable portion 502 to change a size, a shape, or both thereof (e.g., as described above with respect to the manipulable portion 502 in FIG. 5N).

In some embodiments, the expanded configuration of manipulable portion 502 is manipulated into other states. For example, as compared between FIGS. 5S-3 and 5S-4, first particular actuator 540a is unlocked and moved from a first activation position (e.g., position 574b shown in FIG. 5S-3 and previously referred above in this disclosure as a second activation position associated with a transition into the enlarged expanded configuration 538) into a second activation position (e.g., position 574c shown in FIG. 5S-4) to vary a size, shape, or both size and shape of the expanded configuration of manipulable portion 502 from the enlarged expanded configuration 538 exemplified in FIG. 5N into a flattened expanded configuration 539 exemplified in FIG. 5O. As shown in FIG. 5O, at least some of the elongate members 504 are further manipulated (e.g., at least by the first particular actuator 540a in FIG. 7, among others) to distort at least one of the domed shapes 508a-1, 508b-1 of a respective one of the proximal and the distal portion 508a, 508b of manipulable portion 502. In this regard, in some embodiments, the first particular actuator 540a is selectively moveable into a respective activation position (e.g., 574b or 574c) to (a) act on the proximal portion 508a of the manipulable portion 502 when the manipulable portion 502 is in the expanded configuration to distort the first domed shape 508a-1, (b) act on the distal portion 508b of the manipulable portion 502 when the manipulable portion 502 is in the expanded configuration to distort the second domed shape 508b-1, or both (a) and (b). In some embodiments, manipulable portion 502 is manipulated to have a more oblate shape. Changing the expanded configuration of the manipulable portion 502 into the flattened expanded configuration 539 may be motivated for various reasons. For example, manipulable portion 502 may be manipulated into the flattened expanded configuration 539 to better fit within a particular shape of a bodily cavity into which the manipulable portion 502 is deployed.

In FIG. 5O, a control element 578 is provided to convert an input movement (e.g., an input movement of first particular actuator 540a) into an output movement suitable for manipulating the expanded configuration of manipulable portion 502 into the flattened expanded configuration 539. In FIG. 5O, the control element 578 includes a control cable 578b received in a lumen of sleeve 578a that is physically coupled to surface 518b of an elongate member 504. In various embodiments, sleeve 578a is sized to extend generally circumferentially along the manipulable portion 502 and terminate at a location proximate the distal ends 505 of the elongate members 504. From this termination location, the exiting cable 578b extends outwardly from the sleeve 578a and is physically coupled to the manipulable portion 502 at a location proximate a crossing location of various ones of the elongate members 504. In various embodiments, a first particular actuator 540a causes an amount of length of the cable 578b exiting sleeve 578a to decrease as the first particular actuator 540a is moved between the activation positions 574b and 574c. A reduction in the amount of length of the exiting portion of the cable 578b in turn flexes the expanded configuration of the manipulable portion 502 into the flattened expanded configuration 539. As noted above in this disclosure, first particular actuator 540a may be physically or operatively coupled to cable 513b in various embodiments. In some of these various embodiments, first particular actuator 540a includes a mechanism configured to decouple from or cease manipulating control element 513b as the first particular actuator 540a is moved between activation positions 574b and 574c. For clarity, control element 513 is not shown in FIG. 5O. For clarity, control element 578 is only shown in FIG. 5O.

In FIG. 5S-4, handle 543a of first particular actuator 540a has been rotated (e.g., by a user manipulation) in rotational direction 576 to cause a locking device (e.g., locking device of FIG. 10) of first particular actuator 540a to move from an unlocked configuration to a locked configuration suitable for maintaining the first particular actuator 540a in the second activation position 574c. It is noted that, in some embodiments, the first particular actuator 540a may be moved from some other first activation position (for example position 574a in FIG. 5S-2) as it is moved directly or continuously toward or to the second activation position (e.g., position 574c) to move into the flattened expanded configuration 539 without pausing or stopping at position 574b. That is, pausing or stopping at the enlarged expanded configuration 538 need not be required in some embodiments during a transition toward or to the flattened expanded configuration 539.

In some embodiments, the expanded configuration of manipulable portion 502 may be manipulated into yet other states. For example, as compared between FIGS. 5S-3 and 5S-5, second particular actuator 540b may be moved from a first activation position (e.g., position 575a shown in FIG. 5S-3) into a second activation position (e.g., position 575b shown in FIG. 5S-5) to vary a size, shape, or both size and shape of the expanded configuration of manipulable portion 502 from the enlarged expanded configuration 538 exemplified in FIG. 5N into an open clam shell configuration 544a exemplified in FIG. 5P. To arrive at the open clam shell configuration 544a, in some embodiments, the distal portion 508b of the manipulable portion 502 is pivoted, by selective movement of the second particular actuator 540b into a respective activation position (e.g., 575b), away from the proximal portion 508a of manipulable portion 502 to orient the respective domed shapes 508b-1, 508a-1 apart from one another.

For another example, as compared between FIGS. 5S-3 and 5S-6, second particular actuator 540b may additionally or alternatively be moved from a first activation position (e.g., position 575a shown in FIG. 5S-3) into a second activation position (e.g., position 575c shown in FIG. 5S-6) to vary a size, shape, or both size and shape of the expanded configuration of manipulable portion 502 from the enlarged expanded configuration 538 exemplified in FIG. 5N into a closed clam shell configuration 544b exemplified in FIG. 5Q as by way of another example. To arrive at the closed clam shell configuration 544*b*, the distal portion 508*b* of the manipulable portion 502 is pivoted by selective movement of the second particular actuator 540*b* into a respective activation position (e.g., 575*c*) toward or into the proximal portion 508*a* of manipulable portion 502, which may, in some embodiments, enclose the respective domed shapes 508*b*-1, 508*a*-1 at least partially within one another. In this regard, in some embodiments, the second particular actuator 540*b* is selectively moveable into a respective activation position (e.g., 575*b* or 575*c*) to pivot the proximal portion 508*a* and the distal portion 508*b* of the manipulable portion 502 with respect to one another when the manipulable portion 502 is in the expanded or deployed configuration.

Each of the open and closed clam shell configurations may be motivated for different reasons. For example, the open clam shell configuration 544*a* may be desired to increase an overall size of the manipulable portion 502, while the closed clam shell configuration 544*b* may be desired to decrease an overall size of the manipulable portion 502, thereby allowing the manipulable portion 502 to be accommodated in a various bodily cavities having a range of different sizes.

In various embodiments, a portion of control element 513 is manipulated by second particular actuator 540*b* to selectively transition the expanded configuration of the manipulable portion 502 into at least one of the open or closed clam shell configurations 544*a*, 544*b*. For example, with reference to FIG. 7, movement of the expanded configuration of manipulable portion 502 into the closed clam shell configuration 544*b* of FIG. 5Q accompanies a movement of the second particular actuator 540*b*'s sleeve slider 548*a* distally along guide 542*b* to manipulate control element 513 to cause an amount of length of at least the sleeve 513*a* extending outwardly from the distal end 510*b* of shaft 510 to increase and apply a "push" force on the distal portion 508*b* to move at least toward the proximal portion 508*a* in various embodiments. In some embodiments, an amount of length of the cable 513*b* extending outwardly from the distal end 510*b* of shaft 510 also increases as sleeve slider 548*a* is moved distally. In some embodiments, both sleeve 513*a* and cable 513*b* are moved concurrently. In some embodiments, both sleeve 513*a* and a portion of cable 513*b* within the lumen of sleeve 513*a* are moved with little or no relative movement therebetween.

In some embodiments, movement of the expanded configuration of manipulable portion 502 into the open clam shell configuration 544*a* of FIG. 5P accompanies a movement of sleeve slider 548*a* proximally along guide 542*b* to manipulate control element 513 to cause an amount of length of at least the cable 513*b* extending outwardly from the distal end 510*b* of shaft 510 to decrease and apply a "pull" force on the distal portion 508*b* to move away from the proximal portion 508*a*. In various embodiments, the extending portion of cable 513*b* is retracted into a notch or channel 547 positioned to allow for greater separation between the distal and proximal portions 508*a* and 508*b* in the open clam shell configuration. In some embodiments, sleeve 513*a* is additionally retracted proximally as sleeve slider 548*a* is moved proximally. In some embodiments, both sleeve 513*a* and cable 513*b* are moved concurrently. In some embodiments, both sleeve 513*a* and a portion of cable 513*b* within the lumen of sleeve 513*a* are moved with little or no relative movement therebetween. Channel 547 is shown only in FIGS. 5P and 5Q for clarity.

In each of FIGS. 5S-5 and 5S-6, handle 543*b* of second particular actuator 540*b* has been rotated (e.g., by a user manipulation) in rotational direction 577 to cause a locking device (e.g., locking device of FIG. 10) of second particular actuator 540*b* to move from an unlocked configuration to a locked configuration suitable for maintaining the second particular actuator 540*b* in respective ones of the second activation positions 575*b* and 575*c*.

As can be seen from FIG. 5S, in some embodiments, each of the respective actuators (e.g., 540*a*, 540*b*) in the first actuator set 540 comprises a handle (e.g., 543*a*, 543*b*) operatively coupled to a respective locking device (e.g., locking device of FIG. 10) to selectively move the respective locking device between an unlocked configuration and a locked configuration.

It is understood that in various embodiments, at least two of the actuators in the actuator set may be moved from their respective first activation positions into their second respective second activation positions to collectively change the size, the shape, or both a size and a shape of an expanded configuration of the manipulable portion 502 into a particular state. For example, both the first and second particular actuators 540*a* and 540*b* may be moved into various associated second activation positions to collectively change a size, a shape, or both a size and a shape of an expanded configuration of the manipulable portion 502 into combinations of the various states described above in this disclosure. In some embodiments, a user may choose the locations of the second activation positions and they need not occur at the end-of-travel. In some embodiments, the particular state includes, at least in part, a combination of the various states described above in this disclosure. The manipulable portion 502 has a size too large to be delivered percutaneously to the bodily cavity when the manipulable portion 502 is in the particular state, in some embodiments.

Multiple actuator sets may be associated with catheter system 500. In some embodiments, a first actuator set includes one or more actuators at least operatively coupled to manipulable portion 502 to change or vary a size, a shape, or both a size and a shape of an expanded configuration of the manipulable portion 502. In some embodiments, a first actuator set includes two or more actuators at least operatively coupled to the manipulable portion 502, each of the actuators in the first actuator set independently or separately moveable from the other actuators in the first actuator set from a respective first activation position into a respective second activation position to independently change a size, a shape, or both a size and a shape of an expanded configuration of the manipulable portion 502. As described above in this disclosure, at least two actuators in the first actuator set 540 may be moveable from their respective first activation positions into their respective second activation positions to collectively change the size, the shape, or both a size and a shape of the expanded configuration of the manipulable portion 502 into a particular state. In this regard, in some embodiments, the manipulable portion 502 is in the expanded configuration when the at least two actuators in the first actuator set 540 are in their respective first activation positions and when the at least two actuators in the first actuator set 540 are in their respective second activation positions. In some embodiments, the manipulable portion 502 has a size too large to be delivered percutaneously to the bodily cavity when the manipulable portion 502 is in the particular state.

For example, FIGS. 5W-1, 5W-2, 5W-3, and 5W-4 (collectively, FIG. 5W) each respectively show plan and elevation views of a portion of catheter system 500 according to some embodiments. In particular, FIG. 5W-1 shows a positioning of each of various actuators in first actuator set 540 including a positioning of first particular actuator 540*a* in respective second activation position 574c and a positioning of second particular actuator 540b in respective second activation position 575b. Cover 520a has been moved from its first position 570a (e.g., called out in FIGS. 5S-1 and 5W-4 but not shown in FIG. 5W-1) to its second position 570b to permit user access to actuators 540a and 540b so as to allow movement of actuators 540a and 540b into their respective second activation positions 574c, 575b from their respective first activation positions 574a, 575a (e.g., called out in FIG. 5S-2 but not called out in FIG. 5W-1). Additionally, third particular actuator 572 has been moved (e.g., via manipulation of cover 520a) into its respective second activation position 571b from its first activation position 571a (e.g., called out in FIGS. 5S-1 and 5W-4, but not called out in FIG. 5W-1). (Cover 520a has been sectioned in the respective plan view of each of FIGS. 5W-1, 5W-1, 5W-3 and 5W-4 for clarity of view of various features associated with cover 520a.) Accordingly, the positioning of these actuators into their respective second activation positions collectively changes the size, the shape, or both a size and a shape of the expanded configuration of the manipulable portion 502 into a particular state.

In some embodiments, the particular state of the expanded configuration corresponding to the various actuator positions shown in FIG. 5W-1 is collectively a combination of the flattened expanded configuration exemplified in FIG. 5O and the open clam shell configuration 544a exemplified in FIG. 5P. It is understood that other combinations of expanded configurations are provided in other embodiments. In various embodiments, manipulable portion 502 has a size too large for percutaneous delivery or a size too large to fit in the lumen 512d of catheter sheath 512 when the expanded configuration of the manipulable portion is moved into a particular state in response to the positioning of the various actuators into their respective second activation positions.

In FIG. 5W-1, handle 543a of first particular actuator 540a has been rotated (e.g., by a user manipulation) in rotational direction (e.g., rotational direction 576, not called out in FIG. 5W-1) to cause a locking device (e.g., locking device of FIG. 10) of first particular actuator 540a to move from an unlocked configuration to a locked configuration suitable for maintaining the first particular actuator 540a in its second activation position 574c. In FIG. 5W-1, handle 543b of second particular actuator 540b has been rotated (e.g., by a user manipulation) in a rotational direction (e.g., rotational direction 577, not called out in FIG. 5W-1) to cause a locking device (e.g., locking device of FIG. 10) of second particular actuator 540b to move from an unlocked configuration to a locked configuration suitable for maintaining the second particular actuator 540b in its second activation position 575b. In various embodiments, third particular actuator 572 is also locked in its respective second activation position 571b (for example as described above in this disclosure).

In some embodiments, a second actuator set is employed. The second actuator set may include a particular actuator moveable between two activation positions to cause at least two actuators in the first actuator set that are positioned in their respective second activation positions to move away from their respective second activation positions to cause the collectively changed size, the collectively changed shape, or both the collectively changed size and shape of the expanded configuration of the manipulable portion 502 to move away from a particular state corresponding to the positioning of the at least two actuators in the first actuator set in their respective second activation positions. For example, in various embodiments, actuator 572 is a particular actuator in a second actuator set 541 that is moveable between two activation positions to cause the at least two actuators (e.g., actuators 540a, 540b) in the first actuator set 540 that are positioned in their respective second activation positions (e.g., second activation positions 574c, 575b) to move away from their respective second activation positions to cause the collectively changed size, the collectively changed shape, or both the collectively changed size and shape of the expanded configuration of the manipulable portion 502 to move away from the particular state corresponding to the positioning of the at least two actuators in their respective second activation positions.

In some embodiments, first actuator set 540 does not include any actuator in the second actuator set 541. In some embodiments, the at least two actuators (e.g., actuators 540a, 540b) in the first actuator set 540 do not include any actuator (e.g., actuator 572) in the second actuator set 541. However, a particular actuator (e.g., actuator 572) in the second actuator set 541, in some embodiments, may also form part of the first actuator set 540. For example, recall that the first actuator set 540 may be defined to include one or more actuators (e.g., actuators 540a, 540b) at least operatively coupled to manipulable portion 502 to change or vary a size, a shape, or both a size and a shape of an expanded configuration of the manipulable portion 502. Also recall that the second actuator set 541 may be defined to include a particular actuator (e.g., actuator 572) moveable between two activation positions to cause at least two actuators (e.g., actuators 540a, 540b) in the first actuator set that are positioned in their respective second activation positions to move away from their respective second activation positions to cause the collectively changed size, the collectively changed shape, or both the collectively changed size and shape of the expanded configuration of the manipulable portion 502 to move away from a particular state corresponding to the positioning of the at least two actuators in the first actuator set in their respective second activation positions. In this case, in some embodiments, the particular actuator (e.g., actuator 572) may meet the definition or perform the functionalities of both the first actuator set 540 and the second actuator set 541. In such a case, the particular actuator (e.g., actuator 572) may be considered part of both the first actuator set 540 and the second actuator set 541.

For instance, if actuator 540a is a first particular actuator, actuator 540b is a second particular actuator, and actuator 572 is a third particular actuator 572, the third particular actuator 572: (a) may cause, according to a definition or functionality of the second actuator set 541, according to some embodiments, the first and second particular actuators 540a, 540b to move away from their respective second activation positions (e.g., respective ones of second activation positions 574c, 575b) when actuator 572 moves between its respective activation positions 571a, 571b, and (b) may, according to a definition or functionality of the first actuator set 540, according to some embodiments, be further independently or separately moveable from the other actuators in the first actuator set 540 from a respective first activation position 571a into a respective second activation position 571b to independently change a size, a shape, or both a size and a shape of the expanded configuration of the manipulable portion 502. Regarding (b), for example, the third particular actuator 572 may cause the expanded configuration of the manipulable portion 502 to change between a first fanned configuration 536 exemplified in FIGS. 5L-1 and 5L-2 and a second fanned configuration 537 exemplified in FIGS. 5M-1 and 5M-2. Accordingly, the third particular actuator 572, in some embodiments, may be considered part of both the first actuator set 540 and the second actuator set 541. However, whether or not the first actuator set 540 includes an actuator in the second actuator set 541 depends on the particular embodiment employed.

FIG. 5W show a movement of third particular actuator 572 at four successive points in time during a movement of third particular actuator 572 between two activation positions. In these illustrated embodiments, third particular actuator 572 is moved (e.g., via manipulation of cover 520a) from second activation position 571b (i.e., called out in FIG. 5W-1) toward or to first activation position 571a (i.e., called out in FIG. 5W-4). In some embodiments, a locking device associated with third particular actuator 572 (e.g., the locking device associated with cover 520a described above in this disclosure) is unlocked before the commencement of this movement. In various embodiments, the movement of third particular actuator 572 between the two activation positions 571a and 571b, and, in particular, from the second activation position 571b toward or to first activation position 571a, causes each of the first particular actuator 540a and the second particular actuator 540b to move away from their respective activation positions 574c, 575b as shown in FIGS. 5W-2, 5W-3 and 5W-4. For example, in some embodiments, third particular actuator 572 includes at least a first actuator override 520e and a second actuator override 520f. In various embodiments, first actuator override 520e is configured to override an operative state associated with first particular actuator 540a. In various embodiments, second actuator override 520e is configured to override an operative state associated with second particular actuator 540b. In some embodiments, first actuator override 520e is configured to override an operative positioning of first particular actuator 540a at its respective second activation position (e.g., second activation position 574c) and cause it to move away from its respective second activation position. In some embodiments, second actuator override 520f is configured to override an operative positioning of second particular actuator 540b its respective second activation position (e.g., second activation position 575b) and cause it to move away from its respective second activation position. In some embodiments, the first actuator override 520e, the second actuator override 520f, or each of the first and the second actuator overrides 520e, 520f is operatively coupled (for example via a linkage or other force transmission member or mechanism) to a respective one of first particular actuator 540a and second particular actuator 540b to cause movement thereof. In some embodiments, the first actuator override 520e, the second actuator override 520f, or each of the first and the second actuator overrides 520e, 520f is configured to be selectively brought into engagement or disengagement with a respective one of first particular actuator 540a and second particular actuator 540b. For example, in some embodiments, each of the first and the second actuator overrides 520e, 520f may include a slot, cavity, tunnel, or other receiver or engagement mechanism that includes one or more engagement surfaces that may be selectively brought into contact or engagement with a respective one of the first particular actuator 540a and second particular actuator 540b.

In some embodiments associated with FIG. 5W, each of the first and second overrides 520e, 520f is provided by, or forms part of third particular actuator 572. In some embodiments associated with FIG. 5W, each of the first and second overrides 520e, 520f of third particular actuator 572 is provided by, or forms part of the cover 520a, which may in turn, form part of third particular actuator 572 in some embodiments. In some embodiments, first actuator override

520e includes various engagement surfaces (e.g., engagement surfaces 520e-1 and 520e-2) configured to engage and subsequently manipulate a portion of first particular actuator 540a. In some embodiments, second actuator override 520f includes various engagement surfaces (e.g., engagement surfaces 520f-1 and 520f-2) configured to engage and subsequently manipulate a portion of second particular actuator 540b. It is noted that although surfaces 520e-1 and 520e-2 are called out separately, they may form part of a single or uniform surface in some embodiments. It is noted that although surfaces 520f-1 and 520f-2 are called out separately, they may form part of a single or uniform surface in some embodiments.

As third particular actuator 572 is moved from its second activation position 571b (e.g., FIG. 5W-1) toward or to its first activation position 571a (e.g., FIG. 5W-4), the engagement surface 520e-1 of first actuator override 520e is brought into contact, or otherwise engages with a portion of first particular actuator 540a (e.g., FIG. 5W-2). In some embodiments, the first engagement surface 520e-1 (or other engagement surface of first actuator override 520e) is brought into contact, or otherwise engages, with handle 543a of first particular actuator 540a. In some embodiments, engagement surface 520e-1 forms part of a cam (e.g., a linear cam) that is arranged to act on a cam follower (e.g., handle 543a) to move the cam follower in a desired manner. In some embodiments, engagement surface 520e-1 forms part of a cam that is arranged to act on a cam follower (e.g., handle 543a) to move the cam follower to move a locking device (e.g., locking device of FIG. 10) of first particular actuator 540a between a locked and unlocked configuration. For example, in FIG. 5W-2, handle 543a is oriented in a manner similar to, or the same as in FIGS. 5S-3, 5S-4, 5S-5 and 5S-6 corresponding to a locked configuration or state of a locking device (e.g., locking device of FIG. 10) that restricts movement (e.g., movement away from second activation position 574c) of first particular actuator 540a when handle 543a is positioned in the locked configuration or state. In some embodiments associated with FIG. 5W-2, engagement surface 520e-1 contacts handle 543a to rotate handle 543a in a direction (e.g., rotational direction 579) suitable for moving the locking device associated with first particular actuator 540a from the locked configuration to an unlocked configuration which allows for movement (e.g., movement away from second activation position 574c) of the first particular actuator 540a.

In various embodiments, once the first actuator 540a is free to move from its second activation position 574c, further or subsequent movement of third particular actuator 572 (e.g., by way of manipulation of cover 520a) causes movement of first particular actuator 540a away from its second activation position 574c. In some embodiments, this movement away from the second activation position 574c occurs when engagement surface 520e-2 of first actuator override 520e comes into contact, or otherwise engages, a portion of first actuator 540a (e.g., handle 543a) to cause movement of first actuator 540a away from its second activation position 574c, for example, as shown in FIG. 5W-3.

In some embodiments, the movement of third particular actuator 572 between the two activation positions 571a and 571b, (for example, from the second activation position 571b toward or to first activation position 571a) causes a first actuator (e.g., first particular actuator 540a) in the first actuator set 540 to move away from its respective second activation position (e.g., second activation position 574c) before a second actuator (e.g., second particular actuator 540*b*) in the first actuator set 540 is caused to move away from its respective second activation position (e.g., second activation position 575*b*) by the third particular actuator 572. In various embodiments, after the commencement of a movement of the first particular actuator 540*a* away from its respective second activation position 574*c*, engagement surface 520*f*-2 contacts, or otherwise engages a portion of second particular actuator 540*b* (e.g., handle 543*b*) to move second particular actuator 540*b* (e.g., in a direction away from second activation position 575*b*). For example, in FIG. 5W-3, after the commencement of a movement of the first particular actuator 540*a* away from its respective second activation position 574*c*, third particular actuator 572 has moved to a position where an engagement surface 520*f*-1 of second actuator override 520*f* contacts, or otherwise engages, a portion of second actuator 540*b* (e.g., handle 543*b*) to move (for example, by rotating handle 543*b* in rotational direction 580) a locking device (e.g., locking device of FIG. 10) from a locked configuration, which restricts movement of the second particular actuator 540*b*, to an unlocked configuration, which permits movement of second particular actuator 540*b*.

It is noted, that in some embodiments, the movement of third particular actuator 572 between the two activation positions 571*a* and 571*b* (e.g., from the second activation position 571*b* toward or to first activation position 571*a*) may cause a first actuator (e.g., first particular actuator 540*a*) in the first actuator set 540 to move away from its respective second activation position at the same time, or at approximately the same time as a second actuator (e.g., second particular actuator 540*b*) in the first actuator set 540 is caused to move away from its respective second activation position by the third particular actuator 572. For example, if first particular actuator 540*a* is positioned at second activation position 574*b* (i.e., instead of second activation position 574*c*) while second particular actuator 540*b* is positioned at second activation position 575*b* (e.g., in a manner similar to, or the same as that shown in FIG. 5S-5), initial engagement with each of the first and second particular actuators 540*a*, 540*b* by the third particular actuator 572 may occur at the same time, or at substantially the same time.

In various embodiments, third particular actuator 572 moves from its second activation position 571*b* (e.g., FIG. 5W-1) to a location at least proximate its respective first activation position 571*a* (e.g., FIG. 5W-4). In various embodiments, movement of the third particular actuator 572 between it respective activations positions 571*b*, 571*a* causes (a) the first particular actuator 540*a* to move from its second activation position (e.g., second activation position 574*c*) to a location at least proximate to its first activation position 574*a*, (b) the second particular actuator 540*b* to move from its second activation position (e.g., second activation position 574*b*) to a location at least proximate to its first activation position 575*a*, or both (a) and (b) as shown in FIG. 5W-4. In FIG. 5W-4, cover 520*a* has been moved from it second position 570*b* to its first position 570*a*. As described previously in this disclosure, cover 520*a* restricts access to the first and second actuators 540*a*, 540*b* when the cover 520*a* is in the first position 570*a*.

In various embodiments, when the third particular actuator 572 moves between its two activation positions (for example, from the second activation position 571*b* toward or to the first activation position 571*a*), each of the first and second particular actuators 540*a* and 540*b* move away from respective ones of their second activation positions (e.g., second activation positions 574*c*, 575*b*) to cause a size, a shape, or both a size and a shape of the expanded configuration of manipulable portion 502 to move away from the particular state that the expanded configuration of the manipulable portion 502 assumed when each of the first and second particular actuators 540*a* and 540*b* were in their respective second activation positions. In some of these embodiments, each of the first and second particular actuators 540*a* and 540*b* move away from respective ones of their second activation positions (e.g., second activation positions 574*c*, 575*b*) to cause the particular state of the expanded configuration of the manipulable portion 502 (i.e., when the first and second particular actuators 540*a* and 540*b* were positioned at respective ones of their second activation positions) to move toward or to the delivery configuration.

In various embodiments, associated with FIG. 5W, movement of the third particular actuator 572 from its second activation position 571*b* toward or to its first activation position 571*a* causes changes in various states or sub-states of the expanded configuration that were combined to impart the particular collective state or super-state onto the expanded configuration of the manipulable portion 502. For example, the positioning of each particular actuator (e.g., each actuator 540*a*, 540*b*, 572) imparts its own sub-state onto the configuration of the manipulable portion 502. For example, positioning of the actuator 540*b* into its second activation position 575*b* causes an open-clam shell sub-state effect on the expanded configuration of the manipulable portion 502 as shown, for example, in FIG. 5P, according to some embodiments. Positioning of the actuator 540*a* into its second activation position 574*c* causes a flattening sub-state effect on the expanded configuration of the manipulable portion 502 as shown, for example, in FIG. 5O, according to some embodiments. Positioning of the actuator 572 into its second activation position 571*b* causes a fanning sub-state effect on the expanded configuration of the manipulable portion 502, according to some embodiments. Accordingly, the combination of at least some of these individual sub-states is a collective state or super-state of the configuration of the manipulable portion 502. For instance, positioning of the actuator 540*b* into its second activation position 575*b*, positioning of the actuator 540*a* into its second activation position 574*c*, and positioning of the actuator 572 into its second activation position 571*b* cause a collective of super-state of the expanded configuration of the manipulable portion 502 that would appear like a combination of FIGS. 5O and 5P.

Accordingly, in various embodiments associated with FIG. 5W, changes in these collective or super-states may include a departure from the combined FIG. 5O-5P state when third particular actuator 572 moves the first and second particular actuators 540*a* and 540*b* away from their respective second activation positions 574*c*, 575*b*. For another example, in various embodiments associated with FIG. 5W, changes in these collective or super-states may include a departure from the second fanned configuration 537 (e.g., exemplified in FIGS. 5M-1, 5M-2) as the third particular actuator 572 moves from the second activation position 571*b* toward or to the first activation position 571*a*. In some of these embodiments, departure from these various states may cause the expanded configuration of the manipulable portion 502 to move, at least in part, toward or to the delivery configuration.

In this regard, changes in these collective or super-states may cause the collective or super-state of the configuration of the manipulable portion 502 to be changed from one state to another state. For instance, movement of the third particular actuator 572 from the second activation position 571*b* toward or to the first activation position 571*a* may cause the manipulable portion 502 to move from an expanded configuration state toward or to a delivery configuration state.

Accordingly, the expanded configuration of the manipulable portion 502 may undergo various changes as it transitions to a targeted or desired particular state (for example, a state suitable for a particular medical procedure having diagnostic aspects, treatment aspects, or combined diagnostic and treatment aspects) or transitions away from a previously targeted or desired particular state (e.g., during a transition toward or to a delivery configuration which may be motivated for various reasons including a desire to remove the manipulable portion 502 from the body upon which the medical procedure is performed). For example, as described above with respect to FIG. 5S, in some embodiments, each of at least two of the particular actuators (e.g., first particular actuator 540a, second particular actuator 540b) is moveable between its respective first activation position (e.g., a respective one of first activation positions 574a, 575a) and its respective second activation position (e.g., a respective one of second activation positions 574c, 575b) to collectively change a size, a shape or both a size and a shape of the expanded configuration of the manipulable portion 502 from a first particular (e.g., collective or super-) state to a second particular (e.g., collective or super-) state. In some embodiments, each actuator of the at least two actuators (e.g., the first actuator 540a or second actuator 540b) may include a user-accessible portion (e.g., a respective one of handles 543a, 543b) that is slideable relative to a surface of housing 520 by a user to move the actuator between its respective first and second activation positions and cause a size, a shape, or both a size and a shape of the expanded configuration of the manipulable portion 502 to be varied. The second particular state may be any of various configurations in various embodiments including the particular state described above in this disclosure in which the expanded configuration includes a combination of the forms shown in FIGS. 5O and 5P. In some embodiments, the first particular state is a preliminary or initial state of the expanded configuration. In other embodiments, the first state results from a transitioning of the expanded configuration from another state (e.g., a third state other than the second state).

In some embodiments, a particular actuator (e.g., actuator 572) in the second actuator set 541 is selectively moveable from one activation position (e.g., first activation position 571a) to another activation position (e.g., second activation position 571b) to independently change a size, a shape, or both a size and a shape of the expanded configuration of the manipulable portion 502 from a third state to the first state. For example, in some embodiments, manipulation of the third particular actuator 572 from first activation position 571a to second activation position 571b changes an expanded configuration of the manipulable portion 502 from a third state (e.g., first fanned configuration 536) to the first state (e.g., second fanned configuration 537) without engagement or coordinated movement of the actuators 540a, 540b in the first actuator set 540. Subsequent manipulation of various actuators in the first actuator set 540 may further transition the expanded configuration from the first state (e.g., second fanned configuration 537) to the second state (e.g., a combination of FIGS. 5O and 5P) as described above in this disclosure. When the collective or super-state of the configuration of the manipulable portion 502 is changed to the second state or some other state (e.g., the first or third states), it may be said that the collective or super-state to which the manipulable portion 502 is changed is a collectively changed size, a collectively changed shape, or both a collectively changed size and shape of the configuration of the manipulable portion 502.

In various embodiments, when the third particular actuator 572 is moved from its second activation position 571b toward or to its first activation position 571a, various actuators (e.g., first and second particular actuators 540a, 540b) in the first actuator set 540 may move from their respective second activation positions (e.g., second activation position 574c, 575b) to cause a size, a shape, or both a size and a shape of the expanded configuration of the manipulable portion 502 to move away from the second state to transition the manipulable portion at least in part toward or to the delivery configuration. In various embodiments, when the third particular actuator 572 is moved from its second activation position 571b toward or to its first activation position 571a, various actuators (e.g., first and second particular actuators 540a, 540b) in the first actuator set 540 may move from their respective second activation positions (e.g., second activation position 574c, 575b) to cause a size, a shape, or both a size and shape of the expanded configuration of the manipulable portion 502 to move away from the second state toward or to the third state (e.g., the first fanned configuration 536).

It is noted, in some embodiments, when the first and second actuators 540a, 540b are moved away from respective ones of their second activation positions (e.g., second activation positions 574c, 575b) to the respective ones of the first activation positions (e.g., first activation positions 574a, 575a), the expanded configuration of the manipulable portion 502 may have a different shape, size, or both size and shape than that possessed by the expanded configuration when the first and second actuators 540a, 540b were positioned at their respective first activation positions during a movement of the first and second actuators 540a, 540b from their respective first activation positions toward or to their respective second activation positions. In other words, the manipulable portion 502 may have a different shape, size, or both size and shape when in the same state (e.g., first activation positions 574a, 575a of first and second actuators 540a, 540b, even when the positioning of the actuator 572 is held constant) at two different times. This situation may happen for various reasons including friction and hysteresis in various portions of the catheter system 500. In some embodiments, the word "state" at least when used in the context of the configuration of the manipulable portion 502 may be understood to be a mode, condition, or characteristic of the configuration of the manipulable portion 502 and is not necessarily limited to an exact positioning, size, or shape of the manipulable portion 502. For example, in some embodiments, a particular collective state of the expanded configuration of the manipulable portion 502 may be a flattened state (e.g., FIG. 5O), as opposed to a precise position, size, and shape of the manipulable portion 502 in the flattened state. In some embodiments, a particular collective state of the expanded configuration of the manipulable portion 502 may be defined to include an absence of a particular sub-state, such as an absence of the flattening effects of FIG. 5O (e.g., due to the actuator 540a not being in its second activation position 574c) or an absence of the open clam shell effects of FIG. 5P (e.g., due to the actuator 540b not being in its second activation position 575b).

In various embodiments, a particular actuator (e.g., third particular actuator 572) in the second actuator set 541 is selectively moveable toward or to one particular activation position (e.g., first activation position 571a) while engaging at least two actuators (e.g., first and second particular actuators 540*a*, 540*b*) in first actuator set 540, and, consequently, causing the at least two actuators in the first actuator set 540 to move between their respective second and first activation positions (for example as described above with respect to FIG. 5W). In some of these various embodiments, the particular actuator (e.g., third particular actuator 572) in the second actuator set 541 is selectively moveable toward or to another particular activation position (e.g., second activation position 571*b*) while not engaging various actuators (e.g., first and second particular actuators 540*a*, 540*b* or any respective locking device (e.g., FIG. 10) thereof) in first actuator set 540, and while not causing each of the at least two actuators in the first actuator set 540 to move between their respective second and first activation positions (for example as described above with respect to FIGS. 5S-1 and 5S-2). In various embodiments, movement of the particular actuator (e.g., actuator 572) in the second actuator set 541 toward or to the one particular activation position (e.g., first activation position 571*a*) is in a different direction than movement of the particular actuator in the second actuator set 541 toward or to the another particular activation position (e.g., second activation position 571*b*).

In various embodiments, catheter system 500 includes an interlock device configured to restrict at least one actuator (e.g., at least first particular actuator 540*a*, second particular actuator 540*b*, or both) in the first actuator set 540 from being moved away from a respective first activation position (e.g., a respective one of first activation positions 574*a*, 575*a*) until at least a first actuator (e.g., third particular actuator 572) in the second actuator set 541 is moved in response to a user action. For example, the interlock device may be provided at least by a portion (e.g., the cover 520*a*) of the third particular actuator 572, such that the first particular actuator 540*a* and the second particular actuator 540*b* are restricted from moving away from their respective first activation positions 574*a*, 575*a* until the cover 520*a* is moved (e.g., FIGS. 5S-1 to 5S-2). In some embodiments, catheter system 500 includes an interlock device configured to restrict at least one actuator (e.g., at least one of first particular actuator 540*a*, second particular actuator 540*b*) in the first actuator set 540 from being moved between the respective first and second activation positions of the at least one actuator in the first actuator set 540 until at least one other actuator in the first actuator set 540 is moved into the respective second activation position of the at least one other actuator in the first actuator set 540. For example, when third particular actuator 572 forms part of the first actuator set 540, either of first and second particular actuators 540*a*, 540*b* is restricted from being moved between its respective first and second activation positions until the third particular actuator 572 is moved away from its first activation position 571*a* toward or to its second activation position 571*b*.

The use of an interlock device in various embodiments may be motivated for various reasons. For example, in some embodiments, a particular sequence in the activation of various ones of the actuators is desired. In some embodiments, an interlock device is employed to ensure that one particular actuator is activated to facilitate a subsequent activation of another actuator. For example, in some embodiments, an interlock device (e.g., cover 520*a*) is used to guide a user to activate actuator 572 to manipulate the expanded configuration of the manipulable portion 502 into the second fanned configuration 537 prior to an activation of any of actuators 540*a*, 540*b*. This sequence may be motivated for various reasons including circumventing a condition in which actuator 572, if activated after the activation of one or both of actuators 540*a* and 540*b*, could possibly need to apply potentially higher forces (e.g., forces that could damage or render a device of system 500 inoperable) to fan the elongate members 504 of the manipulable portion 502 into the second fanned configuration 537.

In some particular embodiments, cover 520*a* is configured (e.g., includes one or more suitably positioned engagement surfaces) to engage various ones of the actuators in the first actuation set 540 when the cover 520*a* is moved in a first direction (e.g., in a direction toward first position 570*a*) along a path between first and second positions 570*a*, 570*b*, but not engage various ones of the actuators in the first actuator set 540 when the cover 520*a* is moved in a second direction (e.g., in a direction toward second position 570*b*) along the path between first and second positions 570*a*, 570*b*, the second direction being different than the first direction. In some particular embodiments, cover 520*a* is configured (e.g., includes suitably positioned engagement surfaces) to engage various ones of the actuators in the first actuator set 540 to cause movement thereof when the cover 520*a* is moved in a first direction (e.g., in a direction toward first position 570*a*) along a path between first and second positions 570*a*, 570*b*, but not engage various ones (or, in some embodiments, any) of the actuators in the first actuation set 540 to cause movement thereof when the cover 520*a* is moved in a second direction (e.g., in a direction toward second position 570*b*) along the path between first and second positions 570*a*, 570*b*, the second direction being different than the first direction. For example in some embodiments, cover 520*a* does not engage actuators 540*a*, 540*b* and does not move them when the cover 520*a* moves from first position 570*a* toward or to second position 570*b* as described above in this disclosure with respect to various ones of FIG. 5S, but does engage actuators 540*a*, 540*b* to cause them to move when the cover 520*a* moves from second position 570*b* toward or to first position 570*a* as described above in this disclosure with respect to various ones of FIG. 5W. Movement of various ones of the actuators in the first actuation set 540 induced by an engagement by the cover 520*a* may cause, or lead to a change in a size, shape, or both, of an expanded configuration of the manipulable portion 502 away from a particular state. In various embodiments, cover 520*a* is operatively coupled to manipulable portion 502 to cause the manipulable portion 502 to move, at least partially, from the expanded configuration toward or to the delivery configuration when cover 520*a* moves from second position 570*b* toward or to first position 570*a*.

In various embodiments, catheter system 500 includes an actuator set that includes one or more actuators (e.g., first particular actuator 540*a*, second particular actuator 540*b* or both of the first and the second particular actuators 540*a*, 540*b*), each actuator in the actuator set selectively moveable into a respective activation position to cause a size, a shape, or both a size and a shape of the expanded configuration of the manipulable portion 502 to be varied. Cover 520*a* is selectively moveable between a first position (e.g., first position 570*a*) where user access to at least a respective part (e.g., handle 543*a*, 543*b*) of each of at least one actuator in the actuator set is restricted and a second position (e.g., second position 570*b*) where user access to at least the respective part of each of the at least one actuator in the actuator set is permitted. In some of these various embodiments, when cover 520*a* is moved from the second position toward or to the first position, the cover 520*a* engages each particular actuator in the actuator set that is positioned in the respective activation position of the particular actuator to move the particular actuator away from the respective activation position of the particular actuator.

In some embodiments, each actuator in the actuator set is selectively moveable into its respective activation position to cause a size, a shape or both a size and a shape of the expanded configuration of the manipulable portion 502 to be varied from an associated respective first (e.g., sub-) state to an associated respective second (e.g., sub-) state. For example, the actuator 540a is selectively moveable into its respective second activation position 574c to cause the expanded configuration of the manipulable portion 502 to include the flattened sub-state (e.g., characteristics of FIG. 5O), according to some embodiments. When the cover 520a is moved from the second position 570b toward or to the first position 570a, cover 520a engages each particular actuator in the actuator set that is positioned in the respective activation position of the particular actuator to move the particular actuator away from its respective activation position to cause, the size, the shape, or both of the expanded configuration of the manipulable portion to move from the respective second state associated with the particular actuator toward or to the respective first state associated with the particular actuator. For example, if movement of the actuator 540a into its respective second activation position 574c caused the expanded configuration of the manipulable portion 502 to change from a first state associated with the actuator 540a (e.g., a state not including the flattened sub-state effects such as shown in FIG. 5O) to a second state associated with the actuator 540a (e.g., a state including the flattened sub-state effects such as shown in FIG. 5O), the cover 520a may cause movement of the actuator 540b away from its respective second activation position 574c and, consequently, cause the expanded configuration to move from the second state (e.g., a state including the flattened sub-state effects such as shown in FIG. 5O) toward or to the first state (e.g., a state not including the flattened sub-state effects such as shown in FIG. 5O).

In some embodiments, the manipulable portion 502 has a size too large to fit in the lumen 512d of the catheter sheath 512 or a size too large to be percutaneously delivered to a bodily cavity when the expanded configuration of the manipulable portion 502 is in either of the respective first or second respective states associated with each actuator in the actuator set. In some embodiments, the catheter system 500 includes at least a first actuator (e.g., third particular actuator 572) that is selectively moveable into a respective activation position to cause a size, a shape, or both of the expanded configuration of the manipulable portion 502 to be varied, and cover 520a is operable to cause the first actuator to move (e.g., toward or to its respective activation position) when the cover 520a is moved between the first position 570a and the second position 570b (e.g., from the first position 570a toward or to the second position 570b). In some embodiments, the cover 520a is operable to cause the first actuator (e.g., third particular actuator 572) to move away from the respective activation position of the first actuator when the cover 520a is moved from the second position 570b toward or to the first position 570a.

In some embodiments, catheter system 500 includes at least a first actuator and a second actuator, each of the first and the second actuators independently or separately moveable with respect to one another into a respective activation position to cause a size, a shape, or both of the expanded configuration of the manipulable portion 502 to be varied from an associated respective first state to an associated respective second state. For example, in some embodiments, a first actuator 540a is moveable independently or separately with respect to a second actuator 540b into a respective second activation position 574c to cause the manipulable portion to be varied from a first state associated with the first actuator 540a (e.g., a state not including the flattened sub-state effects like FIG. 5O) to a second state associated with the first actuator 540a (e.g., a state including the flattened sub-state effects like FIG. 5O). Similarly, in some embodiments, the second actuator 540b is moveable independently or separately with respect to the first actuator 540a into a respective second activation position 575b to cause the manipulable portion to be varied from a first state associated with the second actuator 540b (e.g., a state not including the open-clam-shell sub-state effects like FIG. 5P) to a second state associated with the second actuator 540b (e.g., a state including the open-clam-shell sub-state effects like FIG. 5P).

In at least embodiments like these, cover 520a is moveable between a first position 570a where user access to at least a part of the second actuator is restricted and a second position 570b where user access to at least the part of the second actuator is permitted. In this regard, in some embodiments, cover 520a is operable to cause the first actuator to move away from the respective activation position of the first actuator when the cover 520a is moved from the second position 570b toward or to the first position 570a to cause the size, the shape, or both of the expanded configuration of the manipulable portion 502 to move from the respective second state associated with the first actuator toward or to the respective first state associated with the first actuator.

For example, in some embodiments, the second actuator is provided by one of the first and second particular actuators 540a and 540b (i.e., access to the one of the first and second particular actuators 540a and 540b being restricted when cover 520a is in first position 570a) and the first actuator is provided by another one of the first and the second particular actuators 540a and 540b, the another one of the first and the second particular actuators 540a and 540b being caused to move away from the respective activation state of the another one of the first and the second particular actuators 540a and 540b when the cover 520a is moved from the second position 570b toward or to the first position 570a to cause the size, the shape, or both of the expanded configuration of the manipulable portion 502 to move from the respective second state associated with the another one of the first and the second particular actuators 540a and 540b toward or to the respective first state associated with the another one of the first and the second particular actuators 540a and 540b.

In some embodiments, the second actuator is provided by one of the first and the second particular actuators 540a and 540b, and the first actuator is provided by the third particular actuator 572, the third particular actuator 572 being caused (e.g., by engagement) to move away from the respective activation state of the third particular actuator 572 when the cover 520a is moved from the second position 570b toward or to the first position 570a to cause the size, the shape, or both of the expanded configuration of the manipulable portion 502 to move from the respective second state associated with the third particular actuator 572 toward or to the respective first state associated with the third particular actuator 572. In some embodiments, cover 520a is physically coupled to and is a user-accessible portion of the first actuator (e.g., actuator 572) slideable along a surface of the housing 520 to cause the first actuator to move toward or to the respective activation position of the first actuator when the cover 520a is moved from the first position 570a to the second position 570b as described above in this disclosure.

In various embodiments, the second actuator (e.g., one of the first and the second particular actuators 540*a* and 540*b*) includes a user-accessible portion (e.g., handle 543*a* or 543*b*) slideable relative to a surface of housing 520 by a user to cause the size, the shape or both of the expanded configuration of the manipulable portion 502 to be varied from the respective first state associated with the second actuator to the respective second state associated with the second actuator. The user-accessible portion (e.g., handle 543*a* or 543*b*) may include a locking device (e.g., locking device of FIG. 10) as described above, at least a portion of which is rotatable by a user to prevent sliding of at least the user-accessible portion of the second actuator relative to the surface of the housing 520.

In various embodiments, the manipulable portion 502 has a size too large to fit in the lumen 512*d* of catheter sheath 512 or a size too large to be percutaneously delivered to a bodily cavity when the expanded configuration of the manipulable portion 502 is in (a) either of the respective first and second states associated with the first actuator, (b) either of the respective first and second states associated with the second actuator, or both (a) and (b). In various embodiments, the manipulable portion 502 is in the expanded configuration when the second actuator (e.g., one of the first and the second particular actuators 540*a* and 540*b*) is in its respective activation position. In various embodiments, the manipulable portion 502 is in the expanded configuration when the second actuator (e.g., one of the first and the second particular actuators 540*a* and 540*b*) is in its respective activation position and when the first actuator (e.g., third particular actuator 572 or another one of the first and the second particular actuators 540*a* and 540*b*) is in its respective activation position.

It should be noted that many of the various descriptions, above, refer to particular actuators in examples, such as actuators 540*a*, 540*b*, 572, etcetera, merely for illustration purposes. In this regard, it should be noted that the present invention is not limited to such particular actuators or their configurations, and different actuator sets or different actuator configurations may be implemented.

FIGS. 12A and 12B show a portion of a catheter system 1200, according to some embodiments. FIG. 12B shows a cross-section of a portion of a catheter system 1200, such as medical device system 500, according to some embodiments. The catheter system 1200 may include a catheter shaft 1210 (such as shaft 510), a control element 1213 (such as control element 513, 573, or 578), and a fluid-providing portion 1224 (which may be included as an element of fluid-providing portion 524, for example, at least in some embodiments where the fluid-providing portion 524 is considered a system not limited to flushing of the catheter sheath 512). Although only one control element 1213 is called out in FIG. 12A, additional control elements may be present and may have the same or similar constructions as the control element 1213. In various embodiments, the control element 1213 may include a Bowden cable, a push-pull rod, or a control wire, control line or control cable. In some embodiments, the control element 1213 or the control cable 1213*b* is flexible. In some embodiments, the control element 1213 includes a sleeve 1213*a* (such as sleeve 513*a*, 573*a*, or 578*a*) providing a control cable lumen 1213*d* (which may be lumen 511 in some embodiments) configured to receive a control cable 1213*b* (such as cable 513*b*, 573*b*, or 578*b*) therein. In some embodiments, the control element 1213 is located within a lumen 1211 of the catheter shaft 1210. In some embodiments, the control element 1213 includes a distal end 1213*e* (e.g., at a termination location (e.g., of the distal-most one of the control cable 1213*b* or control cable sleeve 1213*a*) on or within an end effector (e.g., manipulable portion 1202, which may be manipulable portion 502 in some embodiments)) and a proximal end 1213*f* (e.g., at a termination location at an actuator within an enclosure or housing (e.g., housing 520)). The catheter shaft 1210 may include a distal end at or near the distal end 1213*e* of the control element 1213, such as at distal end 510*b* in FIG. 5A. The catheter shaft 1210 may include a proximal end at or near the proximal end 1213*f* of the control element 1213, such as at proximal end 510*a* in FIG. 5A. In some embodiments, the control element 1213 and the fluid-providing portion 1224 are located in the lumen 1211 of the catheter shaft 1210. In some embodiments, the distal end 1213*e* of the control element 1213 and the distal end (e.g., 510*b*) of the catheter shaft 1210 are arranged to be percutaneously insertable into a body (i.e., of a patient) while the proximal end 1213*f* of the control element 1213 and the proximal end (e.g., 510*a*) of the catheter shaft 1210 remain outside of the body. At least an elongated portion of the control element 1213 extending between the proximal end 1213*f* and distal end 1213*e* may be located within a corresponding elongated portion (e.g., 510*c*) of catheter shaft 1210 within the lumen 1211.

In some embodiments, the fluid-providing portion 1224 includes a liquid supply port 1224*a* (which may also be referred to as a liquid entry port in some contexts) configured to provide liquid (e.g., saline originating from port 524*d* in FIGS. 5Y and 5Z) into lumen 1211 of the catheter shaft 1210. According to some embodiments, a conduit 1224*d* leads to or provides the liquid supply port 1224*a* that is arranged to provide liquid into lumen 1211. In some embodiments, an additional conduit within lumen 1211 (e.g., a conduit or tubular member 1224*d* provided by fluid-providing portion 1224) is not employed and liquid is introduced directly into a proximal end (e.g., at the enclosure 520) of catheter shaft lumen 1211 for example via port 524*e* in FIGS. 5Y and 5Z which is also a liquid entry port or a liquid intake port according to some embodiments. In some embodiments, the control element 1213 includes a liquid intake port 1213*c* arranged to receive the liquid provided by the liquid supply port 1224*a* into the control cable lumen 1213*d*. The liquid intake port 1213*c* may be provided at least in part by a notch, a small cut-out, a hole, channel, or other opening provided in the sleeve 1213*a* of the control element 1213 that allows fluid entry into the control cable lumen 1213*d*.

In some embodiments, the liquid intake port 1213*c* is located closer to a distal portion of the control element sleeve 1213*a* that provides the control cable lumen 1213*d*, a distal end (e.g., distal-termination end) of the control element sleeve 1213*a*, the distal end (e.g., distal-termination end) 1213*e* of the control element 1213, or the distal end (e.g., distal-termination end) of the catheter shaft (e.g., 510), than a proximal portion of the control element sleeve 1213*a* that provides the control cable lumen 1213*d*, a proximal end (e.g., proximal-termination end) of the control element sleeve 1213*a*, the proximal end (e.g., proximal-termination end) 1213*f* of the control element 1213, or the proximal end (e.g., proximal-termination end) of the catheter shaft. In some embodiments, the liquid intake port 1213*c* is located closer to the end effector of the catheter system (e.g., manipulable portion 1202, 502) than to the enclosure (e.g., housing 520) of the catheter system. In this configuration, as liquid from the catheter shaft lumen 1211 enters the liquid intake port 1213*c*, it spreads both distally toward distal end 1213*e* and proximally toward proximal end 1213*f* according to some embodiments. In flushing applications, by having the liquid intake port 1213c located toward the distal end 1213e, the distal portion of the control cable lumen 1213d between and including the liquid intake port 1213c and the distal end (e.g., distal-termination end) of the control element sleeve 1213a is flushed of air relatively quickly, so that the manipulable portion 502 can be inserted into the bodily cavity for patient treatment relatively promptly, while a proximal portion of the control cable lumen 1213d between and including the liquid intake port 1213c and the proximal end (e.g., proximal-termination end) of the control element sleeve 1213a may still be in the process of being flushed of air (e.g., in a direction toward the proximal end 1213f or a direction away from the manipulable portion or end effector 502), according to some embodiments.

It is noted that at least these embodiments can be particular advantageous at least in applications where the cross-sectional area of the control element lumen 1213d is particularly small or in which the control element lumen 1213d is partially occluded (for example, by control cable 1213b (such as cable 513b, 573b, or 578b) passing therethrough), both conditions being associated with high fluid drag or resistance effects that would lengthen the amount of time it takes to provide liquid if the liquid was forced directly through the control element lumen 1213d from the proximal end 1213f toward the distal end 1213e. By directing liquid distally through the larger, unobstructed lumen 1224b through most but not all of the fluid flow path, and then directing at least some of the liquid through a part of the control element lumen 1213d distal the liquid intake port 1213c, the overall time for the liquid travel is reduced. Further, the liquid directed proximally through control element lumen 1213d is directed away from the end effector and the patient, thereby enhancing the safety of the procedure. In some embodiments, the particular portions of the liquid that are directed proximally may not be subsequently directed back toward the manipulable portion 502 (and the patient in some cases), but rather may be directed into a container space or reservoir space, such as provided by, for example, interior cavity 520i of housing 520.

In this regard, in some flushing application embodiments, the liquid (e.g., saline) received in the control cable lumen 1213d flushes at least the distal portion of the control element sleeve 1213a that provides control cable lumen 1213d of a fluid (e.g., air) other than the liquid (e.g., saline). The distal portion of the control element sleeve 1213a that provides control cable lumen 1213d may include a region from the distal end (e.g., distal-termination end) of the sleeve 1213a (e.g., at or near the distal end 1213e of the control element 1213, depending on where the sleeve 1213a terminates distally with respect to the control cable 1213b) toward or to the liquid intake port 1213c. In some embodiments, the liquid supply port 1224a is arranged to provide liquid (e.g., saline) to flush the lumen 1211 of the catheter shaft 1210, the control cable lumen 1213d provided by sleeve 1213a of the control element 1213, or both. In some embodiments, the liquid flushes at least a distal portion of the catheter shaft lumen 1211 (such distal portion may include a distal end 1210b (which may correspond to the distal end 510b) of the catheter shaft 1210), the distal portion of the control element sleeve 1213a that provides control cable lumen 1213d, or both.

In this regard, in some embodiments, the liquid intake port 1213c of the control cable lumen 1213d provided by the sleeve 1213a of the control element 1213 is spaced along the sleeve 1213a from each of the proximal end of the sleeve 1213a and the distal end of the sleeve 1213a. In some embodiments, the liquid intake port 1213c is spaced along the control element sleeve 1213a at a particular distance from each of the proximal-termination end of the control element sleeve 1213a and the distal-termination end of the control element sleeve 1213a. (The proximal-termination end of the control element sleeve 1213a may, e.g., be located where the sleeve 1213a terminates in the rear or proximal wall 522a of the interior cavity 520g, according to some embodiments or where the sleeve 1213a couples with an actuator according to other embodiments, and the distal-termination end of the control element sleeve 1213a may, e.g., be located where the sleeve 1213a terminates within a region of the end effector, e.g., 1202 or 502, such as described above with respect to FIG. 5M-1 and control element sleeve 573a.) In some embodiments, the liquid intake port 1213c is spaced along the control element sleeve 1213a at a particular distance closer to the distal-termination end of the control element sleeve 1213a than the proximal-termination end of the control element sleeve 1213a. In some embodiments, the liquid intake port 1213c is arranged to receive the liquid provided by the liquid supply port 1224a and flush a proximal portion of the control cable lumen 1213d provided by the sleeve 1213a of the control element 1213. The proximal portion of the control cable lumen 1213d may include a region from the proximal end of the sleeve 1213a (e.g., at or near the proximal end 1213f of the control element 1213, depending on where the sleeve 1213a terminates proximally with respect to the control cable 1213b) toward or to the liquid intake port 1213c. The distal portions of the various lumens may be respectively mutually exclusive with the proximal portions. The distal portions of the various lumens may respectively terminate at a location along the respective lumen-providing member that is closer to the distal end of the lumen-providing member than the proximal end of the lumen-providing member. The proximal portions of the various lumens may respectively terminate at a location along the respective lumen-providing member that is closer to the proximal end of the lumen-providing member than the distal end of the lumen-providing member.

In some embodiments, the catheter shaft 1210 includes a first end portion proximate or at least including the distal end 1210b (which may correspond to the distal end 510b) of the shaft 1210, and a second end portion proximate or at least including the proximal end 1210a (which may correspond to the proximal end 510a) of the shaft 1210. The first end portion may be arranged to be percutaneously insertable or deliverable ahead of the second end portion through a bodily opening toward a bodily cavity. In some embodiments, the first end portion is arranged to be percutaneously insertable into the body while the second end portion remains outside of the body. The first end portion may be mutually exclusive with the second end portion. The first end portion may terminate at a location along the shaft 1210 that is closer to the distal end 1210b of the catheter shaft 1210 than to the proximal end 1210a of the catheter shaft 1210. The second end portion may terminate at a location along the shaft 1210 that is closer to the proximal end 1210a of the catheter shaft 1210 than to the distal end 1210b of the catheter shaft 1210. The end effector 502, 1202 may be located at least proximate the first end portion of the catheter shaft 1210. In some embodiments, the liquid supply port 1224a is located closer to the second end portion of the catheter shaft 1210 than the first end portion. Similarly, in some embodiments, the liquid supply port 1224a is located closer to the proximal end of the sleeve 1213a than the distal end of the sleeve 1213a. For example, the liquid supply port 1224a may be provided by port 524*e*. Of course, it should be noted that the above-mentioned first end portion and second end portion the catheter shaft 1210 could be flipped and, instead, be considered the proximal end portion and the distal end portion, respectively.

The catheter shaft 1210 may include at least two lumens within the catheter shaft 1210, each of which may be provided by a respective elongate tubular member. In this regard, the catheter shaft 1210 may be provided at least by an elongate tubular member. In some embodiments, each of the at least two lumens there may be provided by a respective elongate tubular member other than the catheter shaft 1210. In some embodiments, the control cable lumen 1213*d* is a first lumen within the catheter shaft 1210, and the fluid-providing portion lumen 1224*b* leading to the liquid supply port 1224*a* is a second lumen (to which the liquid supply port 1224*a* leads) within the catheter shaft 1210, each provided by a respective one of a first tubular member, conduit, or sleeve and a second tubular member, conduit, or sleeve of a group of two or more tubular members, conduits, or sleeves. In some embodiments, at least the catheter shaft lumen 1211 may be considered the second lumen. Other lumens may be considered the first lumen or the second lumen of the at least two lumens in other embodiments. In some embodiments, the first lumen (e.g., control cable lumen 1213*d* in some embodiments) is provided by the sleeve 1213*a* of control element 1213. In some embodiments, the second lumen (e.g., catheter shaft lumen 1211 or lumen 1224*b*) may be provided by the shaft 1210 or by conduit or tubular member 1224*d* of the fluid-providing portion 1224. In some embodiments, each conduit or sleeve providing each lumen of the at least two lumens includes a respective proximal end (e.g., which may be at or near proximal end 1210*a* of catheter shaft 1210, at or near proximal end 1213*f* of control element 1213, or at or near liquid intake port 1224*c* (shown in FIG. 5Z)) and a respective distal end (e.g., at or near distal end 1210*b* of the catheter shaft 1210, at or near distal end 1213*e* of control element 1213, or at or near liquid supply port 1224*a*). In some embodiments, each respective distal end is arranged to be percutaneously insertable into a body (i.e., of a patient) while each respective proximal end remains outside of the body. Each conduit or sleeve providing each lumen of the at least two lumens is arranged to be deliverable through a bodily opening leading toward a bodily cavity, according to some embodiments. For each conduit or sleeve providing each lumen of the at least two lumens, the respective distal end is arranged to be deliverable through the bodily opening ahead of the respective proximal end of the lumen, according to some embodiments. In some embodiments, the liquid supply port 1224*a* is located on the second sleeve (e.g., conduit or tubular member 1224*d* in some embodiments) closer to the proximal end of the second sleeve than to the distal end of the second sleeve. Of course, it should be noted that the above-mentioned first lumen and second lumen could be flipped and, instead, be considered the second lumen and first lumen, respectively. The same applies to the above-discussed first tubular member, conduit, or sleeve and a second tubular member, conduit, or sleeve.

In some embodiments, each of the at least two lumens is provided by a respective tubular member or conduit (e.g., sleeve 1213*a* for control cable lumen 1213*d*, outer wall of shaft 1210 for catheter shaft lumen 1211, or conduit 1224*d* of fluid-providing portion 1224 for lumen 1224*b*). In some embodiments, at least a first one of the at least two lumens is located within a second one of the at least two lumens. For example, if the first one of the at least two lumens is the control cable lumen 1213*d*, and if the second one of the at least two lumens is the lumen 1211 of the shaft 1210, then the control cable lumen 1213*d* is located within the lumen 1211 in some embodiments. In some embodiments, one conduit (e.g., sleeve 1213*a*) is located in another conduit (e.g., the shaft 1210). In some embodiments, at least a first one (e.g., control cable lumen 1213*d*) of the at least two lumens is provided by a tubular member or conduit (e.g., sleeve 1213*a*) located in the second lumen (e.g., lumen 1211).

Per the discussions above, the catheter system 1200 may include two or more lumens, including at least a first lumen (e.g., control cable lumen 1213*d*) and a second lumen (e.g. catheter shaft lumen 1211 or the fluid-providing portion lumen 1224*b*). (Other lumens may be such first lumen or second lumen in other embodiments.) In some embodiments, each of the first and second lumens (as well as each of the tubular members or conduits that form such lumens) has a respective longitudinal axis extending (e.g., each of the respective axes going into and coming out of the page in FIG. 12B) between (a) a respective proximal end (e.g., which may be at or near proximal end 1210*a* of catheter shaft 1210, at or near proximal end 1213*f* of control element 1213, or at or near liquid intake port 1224*c*) of the respective sleeve that provides the respective lumen and (b) a respective distal end (e.g., which may be at or near distal end 1210*b* of the catheter shaft 1210, at or near distal end 1213*e* of control element 1213, or at or near liquid supply port 1224*a*) of the respective sleeve that provides the respective lumen. In this regard, in some embodiments, each of such respective longitudinal axes may extend between the first end portion of the catheter shaft 1210 and the second end portion of the catheter shaft 1210, discussed above. Each of the first and second lumens (as well as each of the tubular members or conduits that form such lumens) may further include a respective cross-sectional area having a bounding circumference as viewed along the respective longitudinal axis (e.g., circumference of inner wall of sleeve 1213*a* in FIG. 12B, for lumen 1213*d*; lumens 1211 and 1224*b* would have corresponding bounding circumferences from the inner wall of the shaft 1210 and the inner wall of a conduit 1224*d* of fluid-providing portion 1224, respectively). In some embodiments, the respective cross-sectional areas are circumferentially bounded by at least one surface (e.g., surfaces of the aforementioned inner walls). In various embodiments, the at least one surface forms a surface of the respective lumen. In some embodiments, the cross-sectional areas of the first lumen and the second lumen (as well as the tubular members or conduits that form such lumens) are different (e.g., the cross-sectional area of lumens 1213*d*, 1211, and 1224*b* in FIG. 12B are all different). In some embodiments, the cross-sectional area of one of the first and second lumens is larger than the other of the first and second lumens. For example the first lumen (e.g., catheter shaft lumen 1211 or the fluid-providing portion lumen 1224*b*) is larger than the cross-sectional area of the second lumen (e.g. control cable lumen 1213*d*) according to some embodiments. In some embodiments, the cross-sectional area of the tubular member or conduit that forms the second lumen is larger than the cross-sectional area of the tubular member or conduit that forms the first lumen. Of course, what is referred to as the first lumen and what is referred to as the second lumen may be flipped, according to some embodiments.

In some embodiments, the catheter system 1200 includes an end effector 1202 (e.g., manipulable portion 502) located proximate the distal end 1213*e* of the control element 1213.

In some embodiments, the end effector 1202 includes a plurality of elongate members (e.g., elongate members 304 or 504) arranged in a stacked array in a delivery configuration for delivery to a bodily cavity through the lumen 1211 of the catheter shaft 1210 (e.g., in a delivery configuration shown in FIGS. 3A, 5G). In some embodiments, the catheter shaft 1210 may be the catheter sheath, and the catheter sheath may be provided by a tubular shaft. In this regard, in some embodiments, the end effector 1202 may reside within the same lumen as at least the liquid intake port 1213c at least in the delivery configuration.

As discussed above, in some embodiments, the end effector 1202 is biased to transition from a delivery configuration to an expanded configuration as the end effector 1202 advances through the distal end 1213e of the catheter shaft 1210. In some embodiments, the control element 1213 is physically or at least operatively coupled to the end effector 1202 to enable a particular end effector function of the end effector 1202. The end effector function may be selectively executed or performed, at least in part, at least in response to a relative movement or repositioning between a portion of the control cable 1213b and a portion of the sleeve 1213a (an example of an elongate member of a control element) in which the portion of the control cable 1213b is located. In some embodiments, the catheter system 1200 includes at least one actuator (e.g. actuators 540 shown in the embodiments of various FIG. 5) provided in an enclosure (e.g. housing 520 shown in the embodiments of various FIG. 5). In some embodiments, the catheter shaft 1210 extends between the end effector 1202 and at least one actuator. The control cable 1213b may be physically or at least operatively coupled between the actuator and the end effector 1202 to selectively effect movement of at least a portion of a control element (e.g., 1213) and to enable a particular end effector function of the end effector 1202 (e.g., 502). The at least one actuator may be provided at least in part with the enclosure 520, which is physically coupled to the shaft member 1210, at a location proximate the second end portion of the shaft 1210. In some embodiments, the control cable 1213b and an elongate member (e.g., at least a portion of the control cable sleeve 1213a) of the control element 1213 each extends outwardly (e.g., distally toward end effector 502, in some embodiments) from an interior cavity (e.g. interior cavity 520g shown in the embodiments of various FIG. 5) of the enclosure (e.g., 520). In some embodiments, the liquid supply port (which may also be referred to as a liquid entry port) 1224a is arranged to receive the liquid from the interior cavity 520g. In some embodiments, the catheter system 1200 corresponds to the catheter system 500, and various portions of the catheter system 1200 not shown in FIGS. 12A and 12B correspond to various portions of the catheter system 500 shown in the embodiments of various FIG. 5 collectively.

In some embodiments, the fluid-providing portion 1224 includes a liquid intake port (e.g., a first liquid intake port) 1224c (FIG. 5Z) in a wall of the enclosure 520 arranged to receive at least a first part or portion of the liquid provided by the liquid entry of inlet port 524d into the interior cavity 520g. The liquid intake port 1224c is fluidly coupled via conduit 1224d to liquid supply port 1224a, according to some embodiments. In some embodiments, the liquid intake port 1224c is an opening in a proximal bulkhead 1225a (pointed to in FIG. 5Z, and may have the same appearance and construction as a distal bulkhead 1225b shown in FIG. 12A, described below) in the front or distal wall of the interior cavity 520g. The bulkhead 1225a, in some embodiments, allows entry of fluid from the interior cavity 520g into the liquid intake port 1224c, while allowing the control lines (e.g., 513, 573, 578) to pass through it, and while preventing or restricting liquid, other than the liquid that passes into liquid intake port 1224c, from entering the lumen (e.g., 1211) of the catheter shaft (e.g., 1210 or 510) from the interior cavity 520g. In this regard, in some embodiments, the liquid intake port 1224c and the port 524e may be the same. In some embodiments, greater fluid pressure exists on the distal side of the proximal bulkhead 1225a, e.g., from fluid moving proximally through the lumen 1211 from liquid supply port 1224a, than on the proximal side of the proximal bulkhead 1225a, e.g., from fluid moving from the liquid inlet port 524d into the interior cavity 520g. Such an arrangement allows some fluid to enter proximally through the proximal bulkhead 1225a from the lumen 1211 to the interior cavity 520g and correspondingly prevents liquid from moving from the interior cavity 520g to the lumen 1211 via the proximal bulkhead 1225a. In some of these embodiments, liquid may be supplied to liquid supply port 1224a from a source other than interior cavity 520g. For example, in some embodiments, liquid is supplied from liquid entry port 524d directly to conduit 1224d (e.g., by some interconnecting conduit fluidly coupling port 524d to conduit 1224d) rather than flowing into and wetting interior cavity 520g before flowing into conduit 1224d. In this regard, interior cavity 520g may be considered to be return chamber for the liquid rather than a supply chamber for the liquid. Also in this regard, the liquid intake port 1224c of the fluid-providing portion may be located closer to the proximal end of conduit 1224d of fluid-providing portion 1224 than to the distal end (e.g., liquid supply port 1224a) of the conduit of fluid-providing portion 1224. Similarly, in some embodiments, the liquid intake port 1224c is located closer to the proximal portion of the control cable sleeve 1213a, the proximal end of the control cable sleeve 1213a, or the proximal end 1213f of the control element 1213 than to the distal portion of the control cable sleeve 1213a, the distal end of the control cable sleeve 1213a, or the distal end 1213e of the control element 1213. However, as shown in FIG. 12A, the liquid supply port 1224a may be located closer to a distal portion of the control cable sleeve 1213a, a distal end of the control element sleeve 1213a, or the distal end 1213e of the control element 1213 than to a proximal portion of the control cable sleeve 1213a, a proximal end of the control element sleeve 1213a, or the proximal end 1213f of the control element 1213.

In some embodiments, the first part of the liquid provided by the liquid entry or inlet port 524d from the interior cavity 520g that enters the liquid intake port 1224c proceeds distally through the conduit 1224d, then out of the liquid supply port 1224a and into the catheter shaft lumen 1211 (e.g. a first lumen in some contexts). In other words, the liquid intake port 1224c may also be considered a liquid supply port and may be arranged to receive (or have introduced therein) at least the first part of the liquid from the interior cavity 520g provided by the liquid entry port 524d to distribute at least the first part of the liquid (or provide a flow of the liquid) through the fluid-providing portion lumen 1224b (an example of a first lumen or conduit in some contexts, or a second lumen in other contexts) at least toward the respective distal end (e.g., the liquid supply port 1224a) of the fluid-providing portion conduit 1224d. In some embodiments, the adding of the liquid into the catheter shaft lumen 1211 via liquid supply port 1224a includes providing a flow of the liquid through the fluid-providing portion lumen 1224b toward the respective distal end (e.g., the liquid supply port 1224a) of the fluid-providing portion 1224 (e.g., a sleeve that provides the lumen 1224b). In some embodiments, the first liquid intake port 1224c is arranged to distribute a part of the liquid provided by the liquid entry port 524d toward or to the respective proximal end or portion of the fluid-providing portion 1224.

According to some embodiments, as liquid continues to fill the catheter shaft lumen 1211 entering from the liquid supply port 1224a via the liquid intake port 1224c, at least a portion (e.g., at least a portion located proximate the end effector 1202, 502) of the control element 1213 located in the control cable lumen 1213d is wetted by the liquid, and the liquid intake port 1213c (e.g., a second liquid intake port, which is located in the catheter shaft 1210) of the control cable lumen 1213d (an example of a second lumen) is arranged to receive at least a second part of the liquid provided by the liquid supply port 1224a to distribute it through the control cable lumen 1213d at least toward the respective proximal end 1213f and respective distal end 1213e of the control element sleeve 1213a. In this regard, in some embodiments, the second liquid intake port 1213c may also be arranged to distribute a part of the liquid provided by the liquid entry port 524d toward (a) the respective distal end of the second lumen, toward (b) the respective proximal end of the second lumen, or toward both (a) and (b). In some embodiments, the second liquid intake port 1213c may be arranged to distribute a part of the liquid provided by the liquid entry port 524d toward the respective distal end of the second lumen to, for example, flush the distal portion of the control cable lumen 1213d of a fluid (e.g., air) other than the liquid (e.g., saline). In this regard, the liquid intake port 1213c for the control cable lumen 1213d may be located closer (e.g., along a length of the control cable lumen 1213d) to the respective distal end 1213e of the control element sleeve 1213a than the respective proximal end 1213f of the control element sleeve 1213a, for example, to facilitate prompt provision of liquid to the distal portion of the control cable lumen 1213d for treatment or flushing of a fluid (e.g., air) other than the liquid (e.g., saline). In some embodiments, the second liquid intake port 1213c may be located at a location along the control element sleeve 1213a that is spaced a particular distance from the respective distal end of the control element sleeve 1213a. In some embodiments, provision of liquid into the control cable lumen 1213d causes a portion of the control cable 1213b located within the second lumen 1213d to be wetted by the liquid (e.g., saline). In some embodiments, the portion of the control cable 1213b wetted by the liquid is located proximate the end effector 1202, such as in a region of the distal portion (e.g., at least distal of port 1213c) of the control cable 1213b. Because fluid from the fluid-providing portion 1224 enters the control cable lumen 1213d via liquid intake port 1213c, according to some embodiments, it may be said that at least the fluid-providing portion lumen 1224b and the control cable lumen 1213d are fluidly coupled to the allow for fluid flow between such lumens.

In some embodiments, the liquid provided by entry port 524d and received by the first liquid intake port 1224c corresponds to a first part of the liquid provided by the entry port 524d. In some embodiments, at least a portion of the first part of the liquid received by the first liquid intake port 1224c is received by the second liquid intake port 1213c. In some embodiments, the liquid received by the second liquid intake port 1213c corresponds to a second part of the liquid provided by the entry port 524d. The second part of the liquid received by the second liquid intake port 1213c includes at least a portion of the first part of the liquid received by the first liquid intake port 1224c according to some embodiments. In some embodiments, the second liquid intake port 1213c is arranged to receive the second part of the liquid provided by the liquid entry port 524d and to distribute the second part of the liquid through the lumen 1213d toward both the distal end and proximal end of the second lumen 1213d.

In some embodiments, a distal bulkhead 1225b is provided to allow passage of all conduits (e.g., sleeve 1213a, conduit 1224d, among others) within the lumen 1211 of the catheter shaft 1210 through the bulkhead 1225b, while blocking or inhibiting the flow of fluid present in the lumen 1211 (but not present in the conduits within the lumen 1211) from passing from a distal region 1225d of the lumen 1211 distal of the bulkhead 1225b to a proximal region 1225c of the lumen 1211 proximal of the bulkhead 1225b, and vice versa. In some embodiments, the proximal region 1225c may be hermetically sealed in conjunction with proximal bulkhead 1225a shown in FIG. 5Z. The distal bulkhead 1225b may expedite the provision of fluid distally within the catheter shaft lumen 1211 and other lumens (e.g., via port 1213c) by eliminating the need to flush the proximal region 1225c.

In some embodiments, the conduit 1224d and the distal bulkhead 1225b are not provided, and the liquid supply port 1224a and the liquid intake port 1224c are the same and present at the location of the liquid intake port 1224c shown in FIG. 5Z. In some of these embodiments, liquid from the inlet port 524d enters the liquid intake port/liquid supply port 1224c/1224a and then enters the catheter shaft lumen 1211 at the proximal end (e.g., 510a) of the catheter shaft (e.g., 1210, 510). The catheter shaft lumen 1211 is then filled proximally toward distally, according to at least some of these embodiments. In this regard, the liquid intake port/liquid supply port 1224c/1224a, according to at least some of these embodiments, may be located closer to the respective proximal ends of the lumens (or tubular members or conduits that form such lumens) in the catheter shaft 1210 than the respective distal ends of the lumens (or tubular members or conduits that form such lumens) in the catheter shaft 1210. Further in this regard, it may be considered that the liquid intake port 1224c (which also may be considered a liquid supply port), liquid supply port 1224a, or both the liquid intake port 1224c and liquid supply port 1224a is/are located within the interior cavity 520g of the enclosure 520 in some embodiments. In some embodiments, the liquid supply ports 1224c and 1224a may be located adjacently about the front/distal wall 522a of the interior cavity 520g, such that the supply port 1224c is located on or adjacent a side of such wall 522a facing the interior cavity 520g, and the supply port 1224a is located on or adjacent the opposing side of such wall 522a facing into the interior of the catheter shaft lumen 1211, with a relatively short connecting lumen therebetween. In this regard, in some embodiments, the liquid supply port 1224c is arranged to provide a flow of the liquid through a lumen (e.g., a shorter version of the illustrated fluid-providing portion lumen 1224b) toward the port 1224a.

In some embodiments, the distal bulkhead 1225b, the proximal bulkhead 1225a, or both, need not be present even when the conduit 1224d is provided. In some embodiments where the proximal bulkhead 1225a is not provided, there may be an exchange of fluid directly via port 524e between the interior cavity 520g and the catheter shaft lumen 1211 at the proximal end (e.g., 510a) of the shaft (e.g., 1210, 510), and vice versa, while other fluid passes into the conduit 1224d via liquid intake port 1224c toward liquid supply port 1224a. In some of these embodiments, the liquid intake port 1224c may be located in another portion of the front or distal wall of the interior cavity 520g than the port 524e. Embodiments such as these may be beneficial at least by allowing the catheter shaft lumen 1211 to fill from both a distal location (e.g., via liquid supply port 1224a) and a proximal location (e.g., via port 524e), while allowing undesired fluid (e.g., air) to escape the catheter shaft lumen 1211 proximally (e.g., via port 524e) and exit the catheter system (e.g., via outlet port 524c).

A discussion is now made regarding methods of controlling various catheter systems according to various embodiments. Although reference is made to catheter system 500 for ease of discussion, it is understood that the methods may be associated with other catheter devices or systems in other embodiments. In some of these embodiments, a catheter system controlled by various ones of the described methods includes a catheter sheath (e.g., catheter sheath 512) a proximal end (e.g., proximal end 512a), a distal end (e.g., distal end 512b), and a lumen (e.g., first lumen 512d) extending between the proximal end of the catheter sheath and the distal end of the catheter sheath. The catheter system may further include a shaft (e.g., shaft 510) comprising a proximal end (e.g., proximal end 510a), a distal end (e.g., distal end 510b), and an elongated portion (e.g., elongated portion 510c) extending between the proximal end of the shaft and the distal end of the shaft, at least part of the shaft sized for delivery through the lumen of the catheter sheath, and the distal end of the shaft arranged to be delivered through the lumen of the catheter sheath prior to at least the elongated portion of the shaft. The catheter system may further include a manipulable portion (e.g., manipulable portion 502) coupled to the shaft and located at least proximate the distal end of the shaft, the manipulable portion shaped for delivery through the lumen of the catheter sheath. The catheter system may further include a control element (e.g., control element 513) physically coupled to the manipulable portion, the control element receivable in the lumen of the catheter sheath. The catheter system may further include an elongated fluid-providing member receivable in the lumen of the catheter sheath. In some embodiments, the manipulable portion is selectively moveable between a delivery configuration in which the manipulable portion is shaped to be delivered though the lumen of the catheter sheath and an expanded configuration in which the manipulable portion is shaped too large for delivery through the lumen of the catheter sheath, for example as described above with respect to manipulable portion 502. In some embodiments, the elongated fluid-providing member is configured to provide fluid for treatment or flushing of the lumen of the catheter sheath.

In some embodiments, each of various ones of the methods described in this disclosure is implemented under the guidance of a control system (e.g., control system 545 described later in this disclosure, or one or more components of system 100 or control system 322, such as controller 324). The control system may be a controller-based control system, a mechanical-based control system or a combination of the two. In some embodiments, each of various ones of the methods described in this disclosure may be implemented at least in part by manual input from an operator or user. It is understood that the methods described in this disclosure are not exhaustive and various aspects from different ones of the described methods may be combined to form at least one other method. Additionally, different sequences of steps or additional or alternate steps may be employed by at least some of the described methods. In some embodiments, each of various ones of the methods is employed to achieve a particular desired outcome of a portion of the catheter system (for example, a required control line tension adjustment that is the same or similar to that described above in this disclosure). In some embodiments, each of various ones of the methods is employed to achieve a particular deployment state of the catheter system operated in a medical treatment or diagnostic procedure.

A flow chart representing a method 900A for controlling the catheter system according to various embodiments is provided in FIG. 9A. In block 902 of method 900A, at least a shape of the manipulable portion is modulated at least in a state where at least a part of the manipulable portion and a part of the control element extend outside the distal end of the catheter sheath. In some embodiments, a portion of shaft is located in a lumen of the sheath. The modulation of the manipulable portion may occur in a manner that is the same or similar to the modulation of the manipulable portion 502 in the sequence depicted in FIGS. 5I and 5J by way of non-limiting example. In various embodiments, the part of the manipulable portion extending outside the distal end of the catheter sheath has a shape during or throughout the modulation that is too large to fit in the lumen of the catheter sheath. In block 904 of method 900A, the control element is manipulated to cause a length of the part of the control element extending outside the distal end of the catheter sheath to increase and subsequently decrease during or throughout the modulation of the manipulable portion. The manipulation of the control element may occur in a manner that is the same or similar to the manipulation of cable 513b in the sequence depicted in FIGS. 5H, 5I and 5J by way of non-limiting example.

A flow chart representing a method 900B for controlling the catheter system according to various embodiments is provided in FIG. 9B. In Block 912 of method 900B, the manipulable portion is transitioned at least partially between the expanded configuration and the delivery configuration. In block 914, a manipulation of the control element causes the control element to have a first amount of length located outside the distal end of the catheter sheath when a particular amount of the manipulable portion is located outside the distal end of the catheter sheath during a transition toward or to the expanded configuration. In block 916, a manipulation of the control element causes the control element to have a second amount of length located outside of the distal end of the catheter sheath, when the same particular amount of the manipulable portion is located outside the distal end of the catheter sheath during a transition toward or to the delivery configuration. In various embodiments, the second amount of length is different than the first amount of length. The transitioning of the manipulable portion at least partially between the expanded configuration and the delivery configuration may occur in a different manner in other embodiments. For example, an exploded view of block 912 is provided in FIG. 9C according to some embodiments. In block 912a the manipulable portion is transitioned toward or to the expanded configuration as the manipulable portion is advanced out of the distal end of the catheter sheath. In block 912b, the manipulable portion is transitioned toward or to the delivery configuration as the manipulable portion is retracted into the distal end of the catheter sheath.

A flow chart representing a method 900C for controlling the catheter system according to various embodiments is provided in FIG. 9D. In block 922 of method 900C, the manipulable portion is transitioned at least partially between the expanded configuration and the delivery configuration. In block 924, a manipulation of the control element causes the control element to have a first amount of length located outside of the distal end of the catheter sheath when a particular relative positioning exists between the catheter sheath and the shaft received in the lumen of the catheter sheath during the transition toward or to the expanded configuration. In block 926, a manipulation of the control element causes the control element to have a second amount of length located outside of the distal end of the catheter sheath when the same particular relative positioning exists between the catheter sheath and the shaft received in the lumen of the catheter sheath during the transition toward or to the delivery configuration. In various embodiments, the second amount of length is different than the first amount of length. In various embodiments, the particular relative positioning between the catheter sheath and the shaft received in the lumen of the catheter sheath is a relative longitudinal positioning.

A flow chart representing a method 900D for controlling the catheter system according to various embodiments is provided in FIG. 9E. In block 928 of method 900D, a first relative movement is provided to cause a distance between a location on the part of the shaft received in the lumen of the catheter sheath and a location on the catheter sheath to decrease. In block 930 of method 900D, a second relative movement is provided to cause a distance between a location on the part of the shaft received in the lumen of the catheter sheath and a location on the catheter sheath to increase. Each of the first or second relative movements may be provided by a manipulation of the shaft, the catheter sheath or both the shaft and the catheter sheath. In block 932, in response to the first relative movement, a shape of at least a part of the manipulable portion extending outside the distal end of the catheter sheath is varied to, at least in part, cause the distal end of the manipulable portion to move along a first trajectory during the first relative movement. In block 934, in response to the second relative movement, a shape of at least a part of the manipulable portion extending outside the distal end of the catheter sheath is varied to, at least in part, cause the distal end of the manipulable portion to move along a second trajectory during the second relative movement. In various embodiments, the second trajectory is different than the first trajectory.

A flow chart representing a method 1100 of operating a medical device system (e.g., at least 500, 1200) according to various embodiments is provided in FIG. 11. The method 1100 is beneficial for, among other things, promptly providing liquid for treatment or sufficiently flushing required portions of the catheter shaft (e.g., 510, 1210) of air or other undesirable to allow such portions to begin being inserted into body (i.e., of a patient) toward a bodily cavity for treatment, even while other portions of the catheter shaft are still receiving the liquid. In some embodiments where the liquid is not needed in such other portions, liquid flow may be blocked, e.g., by a bulkhead. The method 1100 also is beneficial for, among other things, safely removing the end effector or manipulable portion (e.g., 502, 1202) from the bodily cavity even in a failure state. It should be noted that the ordering of blocks in method 1100 (and the other methods described herein) are provided to, among other things, facilitate an ordering of discussion. However, the actual sequencing of the actions described in these blocks may occur in a different order, and various embodiments are not limited to the particular ordering of blocks pictured. In addition, unless explicitly stated or otherwise required by context, blocks of methods described herein should not be interpreted as being required in at least some embodiments of the present invention. In addition, the blocks of method 1100 include references characters of various elements (e.g., inlet port 524*d*, interior cavity 520*g*, etc.). It should be noted that these reference characters are merely provided as one example of the respective element for ease of discussion, but the method 1100 is not limited to those particularly cited elements.

The method 1100 may operate in a state in which the medical device system (e.g., at least 500, 1200) is provided with a particular end effector function of the end effector (e.g., 502) enabled at least by way of a physical or at least an operative coupling between one or more control elements (e.g., 513, 573, 578) and the end effector (e.g., 502). The particular end effector function may be any of those described above or otherwise within the scope of the present invention.

According to block 1102 of method 1100, a liquid, such as a treatment liquid, an expansion liquid, or a flushing liquid (e.g., saline), is provided into the interior cavity 520*g* of housing or enclosure 520 via inlet port 524*d* shown in FIGS. 5X, 5Y, and 5Z, while enclosure lid 520*h* is in a closed state. In some embodiments, such liquid may be included as part of the medical device system (e.g., at least 500, 1200). The medical device system (e.g., at least 500, 1200) may be provided with one or more indicators, such as instructions 1101, which may be instructions provided in a digital operating manual stored in memory device system 130 and displayed or otherwise presented (e.g., audibly) via a display device of input-output device system 120, instructing a user or operator to direct liquid from the inlet port 524*d* into the interior cavity 520*g* of the enclosure 520.

As described with block 1104, as the liquid fills the interior cavity 520*g*, fluid, which may be an undesirable fluid such as air, that was originally present in the interior cavity 520*g* exits the outlet port 524*c* in various embodiments. In addition, various portions of the control elements (e.g., 513, 573, 578) (and, consequently, sleeves or elongate members and cables thereof) within the interior cavity 520*g* of the enclosure 520 become submerged in and wetted by the liquid, according to some embodiments. In this regard, the medical device system (e.g., at least 500, 1200) may be provided with one or more indicators, such as instructions 1103, which may be instructions provided in a digital operating manual stored in memory device system 130 and displayed or otherwise presented (e.g., audibly) via a display device of input-output device system 120, instructing a user or operator to submerge or wet a portion of a control element (e.g., 513, 573, or 578) in the liquid within the interior cavity 520*g* of the enclosure 520, according to some embodiments.

As described at block 1106, as the liquid continues to fill the interior cavity 520*g* from inlet port 524*d*, a part or some of the liquid enters the liquid intake port 1224*c* of the fluid-providing portion 1224 and travels distally within the lumen 1224*b*, according to some embodiments. In some embodiments, as described at block 1108, such liquid then exits the liquid supply port 1224*a* and enters the catheter shaft lumen 1211. As the catheter shaft lumen 1211 begins and continues to fill with the liquid, various portions of the control elements (e.g., 513, 573, 578, 1213) within the catheter shaft lumen 1211 become wetted by the liquid, according to some embodiments. As described at block 1110, liquid continues to be added into the catheter shaft via lumen 1211 via the liquid supply port 1224*a* at least until a sufficient amount of the liquid has been added into the catheter shaft via lumen 1211 to enter the liquid intake port 1213*c* of sleeve (e.g., a first sleeve) 1213*a* leading to control cable lumen 1213*d* and fills the lumen 1213*d* both distally and proximately, according to some embodiments.

In embodiments that deal with flushing applications, the flushing of undesired fluid (e.g., fluid other than the liquid) distally from the control cable lumen 1213*d* causes an exit or flushing of the undesired fluid from a distal portion of the control cable lumen 1213*d*, the distal portion extending from and including a distal end (e.g., at the end effector 502, 1202) of the control element sleeve 1213*a* to the liquid intake port 1213*c*, according to some embodiments.

In some embodiments, the flushing of undesired fluid proximally from the control cable lumen 1213*d* causes an exit of the undesired fluid from the proximal portion of the control cable lumen 1213*d*. The proximal portion may extend from and include a proximal end (e.g., within or adjacent the rear or proximal wall 522*a* of the interior cavity 520*g* or within the interior cavity 520*i*) of the control element sleeve 1213*a*, according to some embodiments. In this regard, the proximal portion of the control cable lumen 1213*d* may be located closer to the proximal end of the sleeve 1213*a* than to the distal portion of the control cable lumen 1213*d*. In some embodiments, the proximal portion of the control cable lumen 1213*d* may extend from the proximal end of the control element sleeve 1213*a* to the liquid intake port 1213*c*, according to some embodiments. Because the space between the control cable sleeve 1213*a* and the control cable 1213*b* is small in various embodiments, only a relatively small volume of flushing liquid may progress proximally through the control cable lumen 1213*d* and into the interior cavity 520*i*. Accordingly, the storage or subsequent handling of the flushing liquid into the interior cavity 520*i* in this manner is not particularly onerous. Further, by depositing flushing fluid from the control cable lumen 1213*d* into the interior cavity 520*i*, there is no contamination of or interaction with the flushing fluid in the interior cavity 520*g* which acts as a supply of fresh flushing liquid, thereby reducing the occurrences of reintroducing any flushed contamination back into the system.

In some embodiments where the liquid intake port 1213*c* is located toward the distal end 1213*e* of the control element 1213, the distal portion of the control element 1213 (e.g., all or some of the portion of the control element 1213 distal from the liquid intake port 1213*c* including the distal end of the control element sleeve 1213*a*) is filled quicker than the proximal portion of the control element 1213 (e.g., all or some of the portion of the control element 1213 proximal from the liquid intake port 1213*c* including the proximal end of the control element sleeve 1213*a*). Such a configuration may allow the end effector (e.g., 1202, 502) to be inserted into the body (i.e., of the patient) toward the bodily cavity for treatment at an earlier time as compared to fluid-filling mechanisms that flush catheter shafts proximally-to-distally. In this regard, as shown at block 1112, at least when the distal portion of the catheter shaft lumen 1211 and relevant lumens therein are wetted or filled with liquid (e.g., treatment liquid, or flushing liquid that flushes undesired fluid, such as air), the end effector (e.g., 1202, 502) may be inserted into the body toward the bodily cavity for treatment, according to some embodiments. Functions of the end effector (e.g., 1202, 502) may be enabled or executed by operation of the various control cables (e.g., 513, 573, 578, 1213) via associated actuators, and diagnosis, treatment or both diagnosis and treatment may be performed, as described at block 1116.

In some embodiments, one or more of the control elements (e.g., 513, 573, 578, 1213) can be operated to execute or perform a particular end effector function at least by increasing or decreasing tension in the respective control cable therein. In some embodiments, one or more of the control elements (e.g., 513, 573, 578, 1213) may be operated to execute or perform a particular end effector function at least by moving the one or more control elements in a particular direction. Instructions for increasing or decreasing tension in the respective control cable may be provided according to instructions, like instructions 1101, 1103. Instructions for moving the respective control cable in a particular direction may be provided according to instructions, like instructions 1101, 1103.

In this regard, filling of proximal portions of the catheter shaft lumen 1211 and relevant lumens therein, such as at least control cable lumen 1213*d*, may continue while diagnosis or treatment is being performed according to block 1116. In embodiments where the flow of liquid in the proximal portions is not desired, such flow may be blocked or restricted, e.g., via a bulkhead. As described at block 1114, however, the interior cavity 520*g*, the catheter shaft lumen 1211, and the relevant lumens therein are eventually filled with liquid (e.g., treatment liquid or flushing liquid, which may flush undesired fluid (e.g., air)). In this regard, complete filling of the interior cavity 520*g*, the catheter shaft lumen 1211, and relevant lumens therein with liquid may be performed prior to insertion of any portion of the medical device system (e.g., at least 500, 1200) into a body (i.e., of a patient), according to some embodiments.

In some embodiments, during performance of the diagnosis or treatment according to block 1116, a failure condition may be detected. The failure condition may be that a tension on one or more control cables (e.g., cable 513*b*, 573*b*, 578*b*, 1213*b*) exceeds or does not achieve a predefined threshold in a particular state of the end effector (e.g., 502, 1202), a condition that indicates that an associated actuator has become inoperable for reliably performing an activation, or any other condition indicating that the end effector may be in an unintended state, such as in an unsafe state or a state difficult to withdraw from the bodily cavity. The detection of such a failure condition may be manually performed or may be performed in conjunction with the assistance of one or more mechanical or electronic devices. For example, one or more force or tension gauges (e.g., 525 in FIG. 5Z) may be provided that indicate an amount of force on or tension in one or more of the control elements (e.g., cable 513, 573, 578, 1213) and various sensors may be employed to detect the operability of various actuators. In some embodiments, such one or more gauges or sensors may be part of the input-output device system 120 that provide information to the data processing device system 110, so that the data processing device system 110 may provide a visual, audible, or visual and audible warning when a failure condition is detected. It should be noted, however, that the present invention is not limited to the details of any particular technique for detecting a failure condition.

In some embodiments, the medical device system (e.g., at least 500, 1200) may be provided with one or more indicators, such as instructions 1115 in a digital operating manual stored in memory device system 130 and displayed or otherwise presented (e.g., audibly) via a display device of input-output device system 120, that instruct a user or operator to detect the above-discussed failure condition associated with a particular end effector function. The particular end effector function may be a function of retracting, deploying, or otherwise manipulating a size or shape of the end effector (e.g., 502, 1202), for example, into various ones of the positions shown in one or more of FIGS. 5G-5Q, 3A, 3B.

As described at block 1116, upon or in response to detection of the failure condition, the enclosure lid 520*h* may be opened and a portion of each of one or more control elements or lines (e.g., control elements 513, 573, 578, 1213) (e.g., the sleeve (e.g., elongate member in some embodiments) and cable thereof) within the interior cavity 520g may be severed, cut, or otherwise disabled to facilitate safe removal of the end effector (e.g., 502, 1202) from the bodily cavity. During the severing, cutting, or otherwise disabling, liquid may continue to be provided or directed into the interior cavity 520g of the enclosure 520 via inlet port 524d. In some embodiments, at least the control element 513 (which controls coiling and clam shelling) is cut, but the control element 578 (which controls flattening) is not.

In some embodiments, one or more indicators may be provided, such as the instructions 1115, which may include instructions to detect a condition indicating a failure associated with the end effector 502 or particular end effector function thereof, and in response to detecting such failure condition, to open the enclosure lid 520h providing access to a region of the control element(s) in the enclosure 520 via an access port made accessible by the opening of the enclosure lid 502h and then to sever, cut, or otherwise disable the region of each of one or more of the control elements (e.g., 513, 573, 578, 1213) located within the interior cavity 520g of the enclosure 520 in response to the detected failure condition. In this regard, the one or more indicators, which may be the instructions 1115, may include instructions to sever, cut, or otherwise disable the region of each of one or more of the control elements at least by passing at least a portion of at least one tool through the access port made accessible by the opening of the enclosure lid. In some embodiments, the medical device system 500 includes at least one visual representation of at least part of the instructions, such as a visual representation of one or more indicators, such as text, graphics, or both, to sever a region of a control element within the interior cavity 520g of enclosure 520. In some embodiments, the above discussed one or more indicators, which may be provided by instructions 1101, 1103, 1115, may be coded as a processor-accessible file in a format compatible with visual or audible presentation or representation by the data processing device system 110 via an input-output device system 120 communicatively connected to the data processing device system 110. In some embodiments, the instructions 1115 include instructions to sever, cut, or otherwise disable one or more regions of one or more control elements (e.g., control element 513, 573, 578, 1213) at least by passing a portion of at least one tool (e.g., sterile cutters) through an access port made accessible by opening the enclosure lid 520h.

The portion or portions of the one or more control elements severed, cut, or otherwise disabled according to block 1116 may be wet by or submerged in the liquid in the interior cavity 520g according to various embodiments. In this regard, the opening of the enclosure lid 520h may provide access to a submerged portion of one or more of the control elements in the interior cavity 520g of the enclosure 520 via the access port made accessible by the opening of the enclosure lid 520h. The severing, cutting, or otherwise disabling may inhibit or prevent a particular end effector function of the end effector (e.g., 502, 1202) that would occur under operating or intended conditions. In some embodiments, the particular end effector function is inhibited or prevented due to loss of at least partial controllability of the end effector (e.g., 502, 1202) by loss or degradation of the coupling between the end effector and one or more actuators coupled to the severed, cut, or otherwise disabled control element(s). In some embodiments, severing, cutting, or otherwise disabling of one or more of the control elements (e.g., 513, 573, 578, 1213) (e.g., sleeve and cable thereof) releases tension in the respective control element (e.g., sleeve and cable thereof), thereby facilitating safe removal of the end effector from the bodily cavity.

When presenting the one or more indicators, such as instructions 1101, 1103, and 1115, the data processing device system 110 may be configured by one or more programs, such as an operating system and one or more application programs stored in the memory device system 130, to open, for example, one or more processor-accessible files stored in the memory device system 130. The one or more files may be in a format compatible with visual presentation, audible presentation, or both by the data processing device system 110 via the input-output device system 120, such as a Portable Document Format (PDF) format or other document format, known in the art. In this regard, the one or more files may represent an operation manual for the medical device system (e.g., at least 500, 1200) stored in PDF format or other document format, known in the art. Upon opening one or more of the one or more files, the data processing device system 110 may be configured, e.g. by the above-discussed on or more programs and by reading the opened file(s), to cause presentation (e.g., visually via a display device, such as display device system 320, audibly, e.g., via speaker device system 334, or both visually and audibly) of textual, graphical, audible, or a combination thereof, of the various instructions associated with instructions 1101, 1103, and 1115 via input-output device system. For example, the data processing device system 110 may cause the display device system 320 to visually present one or more pages of an operation manual, the page(s) including text, graphics, or both that instruct a user to submerge or wet a portion of a control element (e.g., 1213) in a liquid within an interior cavity (e.g., 520g) of an enclosure (e.g., 520); detect a failure condition associated with an end effector (e.g., 502) or a function thereof; open an enclosure lid (e.g., 520h) to provide access to a region of the control element in the enclosure via an access port made accessible by the opening of the enclosure lid; sever a region of the control element located within the enclosure in response to the detected failure condition, at least by passing at least a portion of at least one tool through the access port made accessible by the opening of the enclosure lid; or a combination of some or all of such instructions, according to various embodiments. Of course, other forms of indicators or instructions may be provided.

While some of the embodiments disclosed above are suitable for cardiac mapping, the same or similar embodiments may be used for mapping other bodily organs, for example gastric mapping, bladder mapping, arterial mapping and mapping of any bodily lumen, bodily chamber or bodily cavity into which the devices of the present invention may be introduced.

While some of the embodiments disclosed above are suitable for cardiac ablation, the same or similar embodiments may be used for ablating other bodily organs or any bodily lumen, bodily chamber or bodily cavity into which the devices of the present invention may be introduced.

While some of the embodiments disclosed above are described in the context of flushing of fluid, such as air, from one or more lumens, the same or similar embodiments may be used for providing cryogenic fluid for cryogenic ablation or for providing fluid to expand or inflate an expandable structure, such as a balloon catheter. For example, in some embodiments, the end effector (e.g., 502, 1202) is an inflatable member that receives cryogenic coolant to ablate tissue in a bodily cavity. In some of these embodiments, the cryogenic coolant is supplied from the liquid supply port 1224*a* to an interior of the inflatable member, and the liquid intake port 1213*c* (e.g., a second liquid intake port) is located at a distal end of the sleeve 1213*a* at a location within the inflatable member (e.g., an end effector). In some of these embodiments, a control element is provided in a conduit (e.g., sleeve 1213*a*) through which the cryogenic coolant flows. The cryogenic coolant in the inflatable member may enter the liquid intake port 1213*c* and be recirculated back to the fluid source (e.g., via outlet port 524*c* and then back in via inlet port 524*d*), according to some embodiments. In some of these embodiments, the control cable sleeve 1213*a* may terminate at the front/distal wall 522*b* of the interior cavity 520*g*, instead of terminating at the rear/proximal wall 522*a* of the interior cavity 520*g* as in some other embodiments described above.

Subsets or combinations of various embodiments described above can provide further embodiments.

These and other changes can be made to the invention in light of the above-detailed description. In general, in the following claims, the terms used should not be construed to limit the invention to the specific embodiments disclosed in the specification and the claims, but should be construed to include other catheter systems including all medical treatment catheter systems and medical diagnostic catheter systems in accordance with the claims. Accordingly, the invention is not limited by the disclosure, but instead its scope is to be determined entirely by the following claims.

What is claimed is:

1. A method of operating a medical device system, the medical device system comprising an end effector, an enclosure, a catheter shaft extending between the end effector and the enclosure, and a control element operatively coupled to the end effector and at least one actuator to selectively enable a particular end effector function of the end effector, the control element spanning at least a portion of an interior of the catheter shaft between the end effector and a portion of the enclosure, the method comprising:

inhibiting the particular end effector function at least by severing the control element within a region of the control element located within the enclosure, wherein the particular end effector function is a retracting, deploying, or otherwise manipulating a size or shape of the end effector.

2. The method of claim 1, wherein the severing comprises severing the control element within the region of the control element while the region of the control element is submerged in a liquid in an interior cavity of the enclosure.

3. The method of claim 1, wherein the severing comprises severing the control element within the region of the control element while a portion of the control element in an interior cavity of the enclosure is wetted by a liquid.

4. The method of claim 1, wherein the control element comprises a flexible control cable, the control cable spanning at least the portion of the interior of the catheter shaft between the end effector and the portion of the enclosure.

5. The method of claim 4, wherein, in a state of the medical device system, the control cable includes tension by way of at least the operative coupling of the control element to the end effector and the at least one actuator, and wherein the severing releases the tension in the control cable.

6. The method of claim 4, wherein the severing comprises severing a portion of the control cable while the portion of the control cable is submerged in a liquid in an interior cavity of the enclosure.

7. The method of claim 1, wherein the control element comprises a control cable and an elongate member, the elongate member comprising a first end, a second end, and an elongated portion extending between the first end and the second end, the elongate member providing at least a control cable lumen extending between the first end and the second end, the control cable lumen including the control cable therein, each of the control cable lumen and the control cable spanning at least the portion of the interior of the catheter shaft between the end effector and the portion of the enclosure.

8. The method of claim 7, wherein, in a state of the medical device system, the control cable includes tension by way of at least the operative coupling of the control element to the end effector and the at least one actuator, and wherein the severing releases the tension in the control cable.

9. The method of claim 7, wherein the severing comprises severing a portion of the control cable while the portion of the control cable is submerged in a liquid in an interior cavity of the enclosure.

10. The method of claim 9, wherein the severing comprises severing a portion of the elongate member while the portion of the elongate member is submerged in the liquid in the interior cavity of the enclosure.

11. The method of claim 7, wherein a portion of the control cable and a portion of the elongate member are located in an interior cavity of the enclosure, at least the portion of the elongate member submerged in a liquid in the interior cavity of the enclosure.

12. The method of claim 11, wherein the control cable lumen and the control cable each extends outwardly from the interior cavity of the enclosure through each of at least two spaced-apart openings provided in at least one wall of the enclosure.

13. The method of claim 12, wherein the elongate member is sealed to at least a particular wall of the at least one wall of the enclosure at each of at least one of the at least two spaced-apart openings to restrict an egress of the liquid from the enclosure at the at least one of the at least two spaced-apart openings.

14. The method of claim 11, wherein each particular part of the elongate member that is submerged in the liquid in the interior cavity of the enclosure lacks an inlet in the interior cavity of the enclosure, the inlet suitable to allow an ingress of the liquid from the interior cavity of the enclosure into the control cable lumen.

15. The method of claim 11, comprising wetting the portion of the control cable with the liquid prior to the severing.

16. The method of claim 2, wherein the enclosure comprises an inlet port, and the method comprises directing a first portion of the liquid from the inlet port into the interior cavity of the enclosure during the severing.

17. The method of claim 2, wherein the enclosure comprises an inlet port and an outlet port, and the method comprises directing a first portion of the liquid from the inlet port into the interior cavity of the enclosure while expelling a fluid other than the liquid from the outlet port.

18. The method of claim 7, wherein the first end of the elongate member is arranged to be delivered ahead of the second end of the elongate member during percutaneous delivery of at least a portion of the catheter shaft, and the method comprises providing a flow of liquid through a portion of the control cable lumen while a portion of the control cable is located in the portion of the control cable lumen, the flow of liquid flowing through the portion of the control cable lumen toward the first end.

19. The method of claim 7, wherein the first end of the elongate member is arranged to be delivered ahead of the second end of the elongate member during percutaneous delivery of at least a portion of the catheter shaft, and the method comprises providing a flow of liquid through a portion of the control cable lumen while a portion of the control cable is located in the portion of the control cable lumen, an inlet of the flow of liquid into the portion of the control cable lumen located along the elongate member at a location spaced from each of the first end and the second end of the elongate member.

20. The method of claim 1, comprising opening an enclosure lid providing access to an interior cavity of the enclosure via an access port made accessible by the opening of the enclosure lid, and wherein the severing comprises severing the control element within the region of the control element located within the enclosure with at least a first tool, the severing occurring at least by passing at least a portion of the at least the first tool through the access port made accessible by the opening of the enclosure lid.

21. The method of claim 1, comprising opening an enclosure lid providing access to an interior cavity of the enclosure via an access port made accessible by the opening of the enclosure lid, and wherein the severing comprises severing the control element within the region of the control element with at least a first tool while the region of the control element is submerged in a liquid in the interior cavity of the enclosure.

22. The method of claim 1, comprising detecting a failure condition, wherein the severing occurs in response to the detected failure condition.

* * * * *